US011426461B2

(12) United States Patent
Wallace

(10) Patent No.: US 11,426,461 B2
(45) Date of Patent: Aug. 30, 2022

(54) METHODS FOR PREVENTING DENGUE AND HEPATITIS A

(71) Applicant: Takeda Vaccines, Inc., Cambridge, MA (US)

(72) Inventor: Derek Wallace, Brookline, MA (US)

(73) Assignee: Takeda Vaccines, Inc., Cambridge, MA (US)

( * ) Notice: Subject to any disclaimer, the term of this patent is extended or adjusted under 35 U.S.C. 154(b) by 0 days.

(21) Appl. No.: 16/809,268

(22) Filed: Mar. 4, 2020

(65) Prior Publication Data

US 2021/0023204 A1 Jan. 28, 2021

Related U.S. Application Data

(63) Continuation-in-part of application No. 16/561,953, filed on Sep. 5, 2019.

(30) Foreign Application Priority Data

| Sep. 5, 2018 | (EP) | 18192701 |
| Sep. 5, 2018 | (EP) | 18192711 |
| Sep. 5, 2018 | (EP) | 18192717 |
| Sep. 5, 2018 | (EP) | 18192776 |
| Sep. 5, 2018 | (EP) | 18192787 |
| Sep. 5, 2018 | (EP) | 18192793 |
| Sep. 5, 2018 | (EP) | 18192800 |
| Sep. 5, 2018 | (EP) | 18192814 |
| Jan. 29, 2019 | (EP) | 19154334 |
| Mar. 7, 2019 | (EP) | 19161184 |

(51) Int. Cl.

| *A61K 39/295* | (2006.01) |
| *A61K 39/29* | (2006.01) |
| *A61K 39/39* | (2006.01) |
| *A61P 31/14* | (2006.01) |
| *A61K 9/00* | (2006.01) |

(52) U.S. Cl.
CPC .......... *A61K 39/295* (2013.01); *A61K 9/0019* (2013.01); *A61K 39/29* (2013.01); *A61K 39/39* (2013.01); *A61P 31/14* (2018.01)

(58) Field of Classification Search
None
See application file for complete search history.

(56) References Cited

U.S. PATENT DOCUMENTS

| 4,810,092 A | 3/1989 | Auth |
| 5,021,347 A | 6/1991 | Yasui et al. |
| 5,229,293 A | 7/1993 | Matsuura et al. |
| 5,494,671 A | 2/1996 | Lai et al. |
| 5,514,375 A | 5/1996 | Paoletti et al. |
| 6,165,477 A | 12/2000 | Ivy et al. |
| 6,184,024 B1 | 2/2001 | Lai et al. |
| 6,660,273 B2 | 12/2003 | Pletnev et al. |
| 7,094,411 B2 | 8/2006 | Kinney et al. |
| 8,673,316 B2 | 3/2014 | Kinney et al. |
| 2006/0062803 A1 | 3/2006 | Kinney et al. |
| 2010/0303860 A1 | 12/2010 | Stinchcomb et al. |
| 2011/0311579 A1 | 12/2011 | Mason et al. |
| 2014/0302088 A1 | 10/2014 | Stinchcomb et al. |
| 2015/0150961 A1 | 6/2015 | Stinchcomb et al. |
| 2015/0265695 A1 | 9/2015 | Yao et al. |
| 2017/0304426 A1 | 10/2017 | Tornieporth et al. |
| 2019/0381163 A1 | 12/2019 | Wallace et al. |
| 2020/0069751 A1 | 3/2020 | Wallace |

FOREIGN PATENT DOCUMENTS

| EP | 2353609 A1 | 8/2011 |
| JP | H05276941 A | 10/1993 |
| JP | 2003-523189 A | 8/2003 |
| JP | 2016-513970 A | 5/2016 |
| WO | 1990001946 A1 | 3/1990 |
| WO | 1992003545 A1 | 3/1992 |
| WO | 1993006214 A1 | 4/1993 |
| WO | 1996040933 A1 | 12/1996 |
| WO | 1998037911 A1 | 9/1998 |
| WO | 1999063095 A1 | 12/1999 |
| WO | 2001060847 A2 | 8/2001 |
| WO | 2001060847 A3 | 4/2002 |
| WO | 2002072036 A2 | 9/2002 |
| WO | 2002072036 A3 | 5/2003 |
| WO | 2010/141386 A1 | 12/2010 |
| WO | 2013/188315 A1 | 12/2013 |
| WO | 2014016360 A1 | 1/2014 |
| WO | 2014074912 A1 | 5/2014 |
| WO | 2014093182 A1 | 6/2014 |
| WO | 2014150939 A2 | 9/2014 |
| WO | 2016034629 A1 | 3/2016 |
| WO | 2017005652 A1 | 1/2017 |
| WO | 2017005654 A1 | 1/2017 |
| WO | 2017179017 A1 | 10/2017 |

OTHER PUBLICATIONS

Thisyakorn and Tantawichien, Dengue vaccine: a key for prevention, Expert Review of Vaccines, 2020, vol. 19, No. 6, pp. 499-506.*
O'Leary and Kimberlin, ACIP Update: Update From the Advisory Committee on Immunization Practices, 2017, Journal of the Pediatric Infectious Diseases Society, vol. 6, No. 4, pp. 311-316.*
Beatty et al., "Dengue virus NS1 triggers endothelial permeability and vascular leak that is prevented by NS1 vaccination," Sci. Transl. Med. Sep. 9, 2015, vol. 7, No. 304, pp. 1-13.
Bhamarapravati et al., "Immunization with a live attenuated dengue-2-virus candidate vaccine (?16681-PDK 53 : clinical, immunological and biological responses in adult volunteers," Bulletin of the World Health Organization, 1987, vol. 65, No. 2, pp. 189-195.

(Continued)

*Primary Examiner* — Benjamin P Blumel
(74) *Attorney, Agent, or Firm* — Honigman LLP; Fernando Alberdi; Jonathan P. O'Brien

(57) ABSTRACT

The invention relates to a method for preventing dengue disease and hepatitis A in a subject or subject population by simultaneously administering a unit dose of a dengue vaccine composition and a hepatitis A vaccine on the same day. The unit dose of a dengue vaccine composition includes constructs of each dengue serotype, such as TDV-1, TDV-2, TDV-3 and TDV-4, at various concentrations in order to improve protection from dengue infection.

40 Claims, 6 Drawing Sheets

Specification includes a Sequence Listing.

(56) References Cited

OTHER PUBLICATIONS

Bhatt et al., "The global distribution and burden of dengue," Nature, Apr. 25, 2013, vol. 496 (7446), pp. 504-507.
Biswal et al., "Efficacy of a Tetravalent Dengue Vaccine in Healthy Children and Adolescents," New England Journal of Medicine, Nov. 21, 2019, vol. 381, No. 21.
Butrapet et al., "Attenuation markers of a candidate dengue type 2 vaccine virus, strain 16681 (PDK-53), are defined by mutations in the 5' noncoding region and nonstructural proteins 1 and 3," J. Virol., Apr. 2000, vol. 74, No. 7, pp. 3111-3119.
Capeding et al., "Clinical efficacy and safety of a novel tetravalent dengue vaccine in healthy children in Asia: a phase 3, randomised, observer-masked, placebo-controlled trial," Lancet, 2014, vol. 384, pp. 1358-1365.
DeLaBarrera et al., "Comparative Evaluation of Three Assays for Measurement of Dengue Virus Neutralizing Antibodies," Dengue Virus NS1 Disrupts the Endothelial Glycocalyx, Leading to Hyperpermeability, Jul. 1, 2008, vol. 79, No. 1, pp. 115-122.
Endy, "Dengue Human Infection Model Performance Parameters," Journal Infectious Diseases, 2014, vol. 209 (Suppl. 2), pp. S56-S60.
Gentry et al., "Identification of distinct antigenic determinants on dengue-2 virus using monoclonal antibodies," May 1982, Am. J. Trop. Med. Hyg., vol. 31, No. 3, Pt. 1, pp. 548-555.
Glasner et al., "Dengue virus NS1 cytokine-independent vascular leak is dependent on endothelial glycocalyx components," PloS Pathog., Nov. 9, 2017, vol. 13, No. 11, pp. 1-22.
Hadinegoro et al., "Efficacy and Long-Term Safety of a Dengue Vaccine in Regions of Endemic Disease," New England Journal of Medicine, Sep. 24, 2015, vol. 373, No. 13, p. 1195-1206.
Henchal et al., "Dengue virus-specific and flavivirus group determinants identified with monoclonal antibodies by indirect immunofluorescence," Jul. 13, 1982, Am. J. Trop. Med. Hyg., vol. 31, No. 4, pp. 830-836.
Henchal et al., "Epitopic Analysis of Antigenic Determinants on the Surface of Dengue-2 Virions Using Monoclonal Antibod-ies," Am. J. Trop. Med. Hyg., 1985, vol. 34, No. 1, pp. 162-169.
Huang et al "Chimeric Dengue Type 2 (Vaccine Strain PDK-53)/Dengue Type 1 Virus as a Potential Candidate Dengue Type 1 Virus Vaccine" Journal Of Virology, Apr. 2000, vol. 74, No. 7, pp. 3020-3028.
Huang et al., "Dengue 2 PDK-53 virus as a chimeric carrier for tetravalent dengue vaccine development," J. Virology, Nov. 2003, vol. 77, No. 21, pp. 11436-11447.
Huang et al., "Genetic and Phenotypic Characterization of Manufacturing Seeds for a Tetravalent Dengue Vaccine (DEN-Vax)," PLOS Neglected Dis, May 2013, vol. 7, No. 5, e2243, 11 pages.
Kinney et al. "Construction of Infectious cDNA Clones for Dengue 2 Virus: Strain 16681 and Its Attenuated Vaccine Deriva-tive, Strain PDK-531" Virology, 1997, vol. 230, No. 2, pp. 300-308.
Mullard, "Sanofi's dengue vaccine rounds final corner," Nature Reviews Drug Discovery, Nov. 2014, vol. 13, pp. 801-802.
NCT02993757 "Immunogenicity and Safety of a Tetravalent Dengue Vaccine Administered Concomitantly or Sequentially With Gardasil," ClinicalTrials.gov, Apr. 5, 2018, Retrieved from the Internet Oct. 25, 2018, 10 pages.
Pinheiro-Michelsen et al., "Anti-dengue Vaccines: From Development to Clinical Trials," Frontiers in Immunology, Jun. 18, 2020, vol. 11, pp. 1-18.
Puerta-Guardo et al., "Dengue Virus NS1 Disrupts the Endothelial Glycocalyx, Leading to Hyperpermeability," PloS Pathog, Jul. 14, 2016, vol. 12, No. 7, pp. 1-29.
Sridhar et al., "Effect of Dengue Serostatus on Dengue Vaccine Safety and Efficacy," New England Journal of Medicine, Jul. 26, 2018, vol. 379, No. 4, pp. 327-340.
Stanaway et al., "The global burden of dengue: an analysis from the Global Burden of Disease Study 2013," Lancet Infect Dis., Jun. 16, 2016, vol. 16, No. 6, pp. 712-723.
Villar et al., "Safety and immunogenicity of a recombinant tetravalent dengue vaccine in 9-16 year olds: a randomized, controlled, phase II trial in Latin America," Pediatr Infect Dis J, Oct. 2013, vol. 32, No. 10, pp. 1102-1109.
Wallace Presentation Session: Vaccines (Developpers), "Takeda's dengue vaccine candidate in children: one or two dos-es?," Apr. 20-23, 2016, p. 86.
World Health Organization, Recommendations for all immunization programmes, Aug. 1, 2018, Retrieved from the Internet, 10 pages.
World Health Organization, Wkly Epidemiol Rec, "Dengue vaccine: WHO position paper—Sep. 2018," Sep. 7, 2018, vol. 93, pp. 457-476.
Biswal et al., "Efficacy of a Tetravalent Dengue Vaccine in Healthy Children Aged 4-16 years: a randomised, placebo-controlled, phase 3 trial," Lancet, Mar. 17, 2020, vol. 395, pp. 1423-1433.
López-Medina et al., "Effcacy of a Dengue Vaccine Candidate (TAK-003) in Healthy Children and Adolescents 2 Years after Vaccination," The Journal of Infectious Diseases, 2021, pp. 1-12.
Press Release: "Potential Impact of Takeda's Dengue Vaccine Candidate Reinforced by Long-Term Safety and Efficacy Results," May 22, 2021, 5 pages.
Press Release: "Takeda Begins Regulatory Submissions for Dengue Vaccine Candidate in EU and Dengue-Endemic Countries," Mar. 25, 2021, 4 pages.
Press Release: "Takeda's Pipeline Has Potential to Contribute Significantly to Revenue Growth Over Next Decade," Dec. 9, 2020, 4 pages.
European Search Report dated Feb. 12, 2019 for corresponding EP application 18192701.3.
European Search Report dated Nov. 13, 2018 for corresponding EP application 18192701.3.
European Search Report dated May 3, 2019 for corresponding EP application 19161184.7.
European Search Report dated Nov. 13, 2018 for corresponding EP application 18192711.2.
European Search Report dated Nov. 13, 2018 for corresponding EP application 18192717.9.
European Search Report dated Nov. 29, 2018 for corresponding EP application 18192776.5.
European Search Report dated Nov. 13, 2018 for corresponding EP application 18192800.3.
European Search Report dated Nov. 13, 2018 for corresponding EP application 18192793.0.
European Search Report dated Nov. 13, 2018 for corresponding EP application 18192787.2.
European Search Report dated Nov. 13, 2018 for corresponding EP application 18192814.4.
Saez-Llorens, X. et al., "Immunogenicity and safety of one versus two doses of tetravalent dengue vaccine in healthy children aged 2-17 years in Asia and Latin America: 18-month interim data from a phase 2, randomised, placebo-controlled study", The Lancet Infectious Diseases, Feb. 2018, pp. 162-170, vol. 18.
World Health Organization, "Guidelines for plaque reduction neutralization testing of human antibodies to dengue viruses", Jul. 2007.
Takeda Vaccines, "Immunogenicity and Safety of Tetravalent Dengue Vaccine (TDV) Co-administered With an Hepatitis A Virus Vaccine", ClinicalTrials.gov, May 15, 2018.
World Health Organization, "Table 3: Recommendations for Interrupted or Delayed Routine Immunization—Summary of WHO position papers", Aug. 2018.
Brewoo, J. N. et al., "Immunogenicity and efficacy of chimeric dengue vaccine (DENVax) formulations in interferon-deficient AG129 mice", Vaccine, 2012, pp. 1513-1520, vol. 30(8).
Chokephaibulkit, K., "Combination Vaccines", Journal of the Medical Association of Thailand, Aug. 2002, pp. 694-699, vol. 85 suppl. 2.
Crevat, D., et al. "First Experience of Concomitant Vaccination Against Dengue and MMR in Toddlers", The Pediatric Infectious Disease Journal, Aug. 2015, pp. 884-892, vol. 34, No. 8.

(56) References Cited

OTHER PUBLICATIONS

Putnak, J.R. et al., "Comparative Evaluation of Three Assays for Measurement of Dengue Virus Neutralizing Antibodies", The American Journal of Tropical Medicine and Hygiene, 2008, pp. 115-122, vol. 79(1).
Dubey, A.P. et al., "Immunogenicity and safety of a tetravalent dengue vaccine in healthy adults in India: A randomized, observer-blind, placebo-controlled phase II trial", Human Vaccines & Immunotherapeutics, Feb. 2016, pp. 512-518, vol. 12 No. 2.
George, S. L. et al., "Safety and Immunogenicity of a Live Attenuated Tetravalent Dengue Vaccine Candidate in Flavivirus-Naive Adults: A Randomized, Double-Blinded Phase 1 Clinical Trial", The Journal of Infectious Diseases, Oct. 1, 2015, pp. 1032-1041, vol. 212(7).
Huang, L. et al., "Concomitant administration of live attenuated Japanese encephalitis chimeric virus vaccine (JE-CV) and measles, mumps, rubella (MMR) vaccine: Randomized study in toddlers in Taiwan", Vaccine, 2014, pp. 5363-5369, vol. 32(41).
King, G.E., et al., "Simultaneous administration of childhood vaccines: an important public health policy that is safe and efficacious", The Pediatric Infectious Disease Journal, May 1994, pp. 394-407, vol. 13 No. 5.
Lopez, P. et al., "Immunogenicity and Safety of Yellor Fever Vaccine (Stamaril) When Administered Concomitantly With a Tetravalent Dengue Vaccine Candidate in Healthy Toddlers at 12-13 Months of Age in Colombia and Peru", The Pediatric Infectious Disease Journal, Oct. 2016, pp. 1140-1147, vol. 35 No. 10.
Osorio, J. E. et al., "A recombinant, chimeric tetravalent dengue vaccine candidate based on a dengue virus serotype 2 backbone", Expert Review of Vaccines, 2016, pp. 497-508, vol. 15, No. 4.
Osorio, J. E. et al., "Development of DENVax: A chimeric dengue-2 PDK-53-based tetravalent vaccine for protection against dengue fever", Vaccine, 2011, pp. 7251-7260, vol. 29(42).
Osorio, J. E. et al., "Safety and immunogenicity of a recombinant live attenuated tetravalent dengue vaccine (DENVax) in flavivirus-naive healthy adults in Colombia: a randomised, placebo-controlled, phase 1 study", The Lancet Infectious Diseases, Sep. 2014, pp. 830-838, vol. 14(9).
Roehrig, J. T. et al., "Guidelines for Plaque-Reduction Neutralization Testing of Human Antibodies to Dengue Viruses", Viral Immunology, 2008, pp. 123-132, vol. 21 No 2.
Rupp, R. et al., "Safety and immunogenicity of different doses and schedules of a live attenuated tetravalent dengue vaccine (TDV) in healthy adults: A Phase 1b randomized study", Vaccine, 2015, pp. 6351-6359, vol. 33.
Saez-Llorens, X. et al., "Safety and immunogenicity of one versus two doses of Takeda's tetravalent dengue vaccine in children in Asia and Latin America: interim results from a phase 2, randomised, placebo-controlled study", The Lancet Infectious Diseases, Jun. 2017, pp. 615-625, vol. 17(6).
Rinderknecht, S. et al., "Immunogenicity and Safety of an Inactivated Hepatitis A Vaccine When Coadministered with Measles-mumps-rubella and Varicella Vaccines in Children Less Than 2 years of Age", The Pediatric Infectious Disease Journal, Oct. 2011, pp. e179-e185, vol. 30, No. 10.
Sirivichayakul, C. et al., "Safety and Immunogenicity of a Tetravalent Dengue Vaccine Candidate in Healthy Children and Adults in Dengue-Endemic Regions: A Randomized, Placebo-Controlled Phase 2 Study", The Journal of Infectious Diseases, May 15, 2016, pp. 1562-1572, vol. 213(10).
Timiryasova, T. M. et al., "Optimization and Validation of a Plaque Reduction Neutralization Test for the Detection of Neutralizing Antibodies to Four Serotypes of Dengue Virus Used in Support of Dengue Vaccine Development", The American Journal of Tropical Medicine and Hygiene, 2013, pp. 962-970, vol. 88(5).
Wichmann, O. et al., "Live-attenuated tetravalent dengue vaccines: The needs and challenges of post-licensure evaluation of vaccine safety and effectiveness", Vaccine, 2017, pp. 5535-5542, vol. 35(42).
Wilder-Smith, A. et al., "Age specific differences in efficacy and safety for the CYD-tetravalent dengue vaccine", Expert Review of Vaccines, 2016, pp. 437-441, vol. 15 No. 4.
Vesikari, T. et al., "Safety and Immunogenicity of a Booster Dose of the 10-Valent Pneumococcal Nontypeable Haemophilus influenzae Protein D Conjugate Vaccine Coadministered With Measles-Mumps-Rubella-Varicella Vaccine in Children Aged 12 to 16 Months", The Pediatric Infectious Disease Journal, Jun. 2010, pp. e47-e56, vol. 29, No. 6.
Rodriguez Melo, F. I. et al., "Immunogenicity and Safety of a Booster Injection of DTap-IPV//Hib (Pentaxim) Administered Concomitantly With Tetravalent Dengue Vaccine in Healthy Toddlers 15-18 Months of Age in Mexico: A Randomized Trial", The Pediatric Infectious Disease Journal, Jun. 2017, pp. 602-608, vol. 36, No. 6.
Schilling, A. et al., "Coadministration of a 9-Valent Human Papillomavirus Vaccine with Meningococcal and Tdap Vaccines", Pediatrics, Sep. 2015, pp. e563-e572, vol. 136, No. 3.
ALAPE 2018. Takeda vacuna contra el dengue. McIntosh Sep. 5, 2018.
Haiyan Chu, et al., "CD8+ T-cell Responses in Flavivirus-Naïve Individuals Following Immunization with a Live-Attenuated Tetravalent Dengue Vaccine Candidate"—Major Article JID 2015:212 (Nov. 15).
Lisa A. Jackson, et al., "A phase 1 study of safety and immunogenicity following intradermal administration of a tetravalent dengue vaccine candidate"—Vaccine 36 (2018) p. 3976-3983—May 19, 2018.
Medical Director Clinical Science Study Director Takeda: "Safety and Immunogenicity With Two Different Serotype 2 Potencies of Takeda's Tetravalent Dengue Vaccine Candidate (TDV) in Adults in Singapore"—Clinical Trials Jul. 16, 2019—DEN 205.
Jorge Osorio et al: "Efficacy of a Tetravalent Chimeric Dengue Vaccine (DENVax) in Cynomolgus Macaques", Am J. Trop. Med. Hyg., 84(6), 2011, pp. 978-987—The American Society of Tropical Medicine and Hygiene.
Presentation Biswal Asia Dengue Summit (2016) DEN-204.
Presentation Lorenzato Medtrop (2018) DEN-204.
Presentation Wallace(2016) DEN-204 (p. 86).
Press Release: "Takeda's Dengue Vaccine Candidate Meets Primary Endpoint in Pivotal Phase 3 Efficacy Trial"—Jan. 29, 2019.
Takeda Press Release: "Takeda Completes Enrollment of More Than 20,000 Children and Adolescents in Global Phase 3 Trial of Dengue Vaccine Candidate"—Apr. 5, 2017—DEN-301.
Derek Wallace: "Persistence of neutralizing antibodies one year after two doses of a candidate recombinant tetravalent dengue vaccine in subjects aged from 1.5 to 45 years"—ASTMH Oct. 27, 2015 DEN-203.
Hashimoto et al., "Molecular Cloning and Complete Nucleotide Sequence of the Genome of Japanese Encephalitis Virus Beijing-1 Strain," Virus Genes, 1988, vol. 1, No. 3, pp. 305-317.
Heinz et al., "Flaviviruses" Immunochemistry of viruses II, The basis for serodiagnosis and vaccines, (edited by von Regenmortel and Neurath), Elsevier Science Publishers B.V., Chapter 14, 1990 pp. 289-305.
Hennessy et al., "Effectiv ness of live-attenuated Japanese encephalitis vaccine (SA14-14-2): a case-control study" The Lancet, vol. 347, Jun. 8, 1996, pp. 1583-1586.
Ho et al., "DNA vaccination induces a long-term antibody response and protective immunity against pseudorabies virus in mice" Archives of Virology, 1998, vol. 143, pp. 115-125.
Hsiang-Chi et al., "Dengue Type 4 Live-Attenuated Vaccine Viruses Passaged in Vero Cells Affect Genetic Stability and Dengue-Induced Hemorrhaging in Mice," PLOS ONE, Oct. 28, 2011 (Oct. 28, 2011), vol. 6, No. 10, p. e25800.
Hubálek et al., "West Nile Fever—a Reemerging Mosquito-Borne Viral Disease in Europe" Emerging Infectious Diseases, Sep.-Oct. 1999, vol. 5, No. 5, pp. 643-650.
Hunt et al., "Relationships of Bunyamwera Group Viruses by Neutralization" Am. J. Trop. Med. Hyg. 1979, vol. 28, No. 4, pp. 740-749.
Jia et al., "Genetic analysis of West Nile New York 1999 encephalitis virus" The Lancet, Dec. 4, 1999, vol. 354, pp. 1971-1972.

(56) References Cited

OTHER PUBLICATIONS

Jirakanjanakit et al., "Dynamics of Susceptibility and Transmissibility of The Live Attenuated, Candidate Vaccines Dengue-1 PDK-13, Dengue-3 PGMK30F3, and Dengue-4 PDK-48 after Oral Infection in Aedes Aegypti," Am. J. Trop. Med. Hyg. 1999, vol. 61, No. 4, pp. 672-676.
Johnson et al., "Detection of Anti-Arboviral Immunoglobulin G by Using a Monoclonal Antibody-Based Capture Enzyme-Linked Immunosorbent Assay," Journal of Clinical Microbiology, May 2000, vol. 38, No. 5, pp. 1827-1831.
Johnson et al., "Growth Characteristics of ChimeriVax-DEN2 Vaccine Virus in Aedes Aegypti and Aedes Albopictus Mosquitoes," Am. J. Trop Med. Hyg., 2002, vol. 67, No. 3, pp. 260-265.
Kanesa-Thasan et al., "Safety and immunogenicity of attenuated dengue virus vaccines (Aventis Pasteur) in human volunteers," Vaccine, 2001 vol. 19 pp. 3179-3188.
Kawano et al., "Genetic Determinants of Dengue Type 4 Virus Neurovirulence for Mice," Journal of Virology, Nov. 1993, vol. 67, No. 11, pp. 6567-6575.
Kelly et al., "Evolution of attenuating mutations in dengue-2 strain S16803 PDK50 vaccine and comparison of growth kinetics with parent virus," Virus Genes, 2011, vol. 43, pp. 18-26.
Khin et al., "Infection, Dissemination, Transmission, and Biological Attributes of Dengue-2 PDK53 Candidate Vaccine Virus after Oral Infection in Aedes Aegypti," Am. J. Trop Med. Hyg., 1994, vol. 51, No. 6, pp. 864-869.
Kimura-Kuroda et al., "Antigenic Comparison of Envelope Protein E between Japanese Encephalitis Virus and Some Other Flaviviruses Using Monoclonal Antibodies," J. Gen. Virol., 1986, vol. 67, pp. 2663-1672.
Kimura-Kuroda et al., "Topographical Analysis of Antigenic Determinants on Envelope Glycoprotein V3 (E) of Japanese Encephalitis Virus, Using Monoclonal Antibodies" Journal of Virology, Jan. 1983, vol. 45, No. 1, pp. 124-132.
Kinney et al., "Development of New Vaccines against Dengue Fever and Japanese Encephalitis," Intervirology, 2001, vol. 44, pp. 176-197.
Klinman et al., "CpG motifs as immune adjuvants," Vaccine, 1999, vol. 17, pp. 19-25.
Kochel Tadeusz et al., "Inoculation of plasmids expressing the dengue-2 envelope gene elicit neutralizing antibodies in mice," Vaccine. 1997, vol. 15, No. 5, pp. 547-552.
Kohler et al., "Continuous cultures of fused cells secreting antibody of predefined specificity," Nature, Aug. 7, 1975, vol. 256, pp. 495-497.
Konishi et al., "Avipox virus-vectored Japanese encephalitis virus vaccines: use as vaccine candidates in combination with purified subunit immunogens," Vaccine, 1994, vol. 12, No. 7, pp. 633-638.
Konishi et al., "Comparison of Protective Immunity Elicited by Recombinant Vaccinia Viruses That Synthesize E or NS1 of Japanese Encephalitis Virus," Virology, 1991, vol. 185, pp. 401-410.
Konishi et al., "Generation and Characterization of a Mammalian Cell Line Continuously Expressing Japanese Encephalitis Virus Subviral Particles," Journal of Virology, Mar. 2001, vol. 75, No. 5, pp. 2204-2212.
Konishi et al., "Induction of Protective Immunity against Japanese Encephalitis in Mice by Immunization with a Plasmid Encoding Japanese Encephalitis Virus Premembrane and Envelope Genes," Journal of Virology, Jun. 1998, vol. 72, No. 6, pp. 4925-4930.
Konishi et al., "Mice Immunized with a Subviral Particle Containing the Japanese Encephalitis Virus prM/M and E Proteins Are Protected from Lethal JEV Infection," Virology, 1992, vol. 188, pp. 714-720.
Kozak "Circumstances and Mechanisms of Inhibition of Translation by Secondary Structure in Eucaryotic mRNAs," Molecular and Cellular Biology, Nov. 1989, vol. 9, No. 11, pp. 5134-5142.
Kuno et al., "Phylogeny of the Genus Flavivirus," Journal of Virology, Jan. 1998, vol. 72, No. 1, pp. 73-83.
Laemmli U.K. "Cleavage of Structural Proteins during the Assembly of the Head of Bacteriophage T4," Nature, Aug. 15, 1970, vol. 227, pp. 680-685.
Lai et al., "Evaluation of molecular strategies to develop a live dengue vaccine," Clinical and Diagnostic Virology, 1998, vol. 10, pp. 173-179.
Lai et al., "Immunization of Monkeys with Baculovirus Recombinant-expressed Dengue Envelope and NS1 Glycoproteins Induces Partial Resistance to Challenge with Homotypic Dengue Virus," Vaccines 90: Modern approaches to New Vaccines including Prevention of AIDS, Cold Spring Harbor, NY, 1990, pp. 119-124.
Lanciotti R. et al., "Origin of the West Nile Virus Responsible for an Outbreak of Encephalitis in the Northeastern United States," Science, Dec. 17, 1999, vol. 286, pp. 2333-2337.
Liljeström et al., "In Vitro Mutagenesis of a Full-Length eDNA Clone of Semliki Forest Virus: the Small 6,000-Molecular-Weight Membrane Protein Modulates Virus Release," Journal of Virology, Aug. 1991, vol. 65, No. 8, pp. 4107-4113.
Lin et al., "DNA Immunization with Japanese Encephalitis Virus Nonstructural Protein NS1 Elicits Protective Immunity in Mice," Journal of Virology, Jan. 1998, vol. 72, No. 1, pp. 191-200.
Mackow et al., "The Nucleotide Sequence of Dengue Type 4 Virus: Analysis of Genes Coding for Nonstructural Proteins," Virology, 1987, vol. 159, pp. 217-228.
Mandl et al., "Complete Genomic Sequence of Powassan Virus: Evaluation of Genetic Elements in Tick-Borne versus Mosquito-Borne Flaviviruses," Virology, 1993, vol. 194, pp. 173-184.
Martin et al., "Standardization of Immunoglobulin M Capture Enzyme-Linked Immunosorbent Assays for Routine Diagnosis of Arboviral Infections," Journal of Clinical Microbiology, May 2000, vol. 38, No. 5, pp. 1823-1826.
Mason et al., "Japanese Encephalitis Virus-Vaccinia Recombinants Produce Particulate Forms of the Structural Membrane Proteins and Induce High Levels of Protection against Lethal JEV infection," Virology, 1991, vol. 180, pp. 294-305.
Mason et al., "Sequence of the Dengue-1 Virus Genome in the Region Encoding the Three Structural Proteins and the Major Nonstructural Protein NS1," Virology,1987, vol. 161, pp. 262-267.
Men et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," Journal of Virology, Jun. 1996, vol. 70, No. 6, pp. 3930-3937.
Mir et al., "High-efficiency gene transfer into skeletal muscle mediated by electric pulses," Applied Biological Sciences, Proc. Natl. Acad. Sci. USA, Apr. 1999, vol. 96, pp. 4262-4267.
Monath et al., "Recombinant, chimeric live, attenuated vaccine (ChimeriVax) incorporating the envelope genes of Japanese encephalitis (SA14-14-2) virus and the capsid and nonstructural genes of yellow fever (17D) virus is safe, immunogenic and protective in non-human primates," Vaccine, 1999, vol. 17 pp. 1869-1882.
Nitayaphan et al., "Nucleotide Sequence of the Virulent SA-14 Strain of Japanese Encephalitis Virus and Its Attenuated Vaccine Derivative, SA-14-14-2," Virology, 1990, vol. 177, pp. 541-552.
Novello et al., "Update: West Nile Virus Activity—Northeastern United States, 2000," http://www.cdc.gov/mmwr/preview/mmwrhtml/mm4936a4.htm MMWR Weekly Sep. 15, 2000 / vol. 49, No. 36, pp. 820-822.
Nowak et al., "Analysis of the Terminal 4 Sequences of West Nile Virus Structural Proteins and of the in Vitro Translation of these Proteins Allow the Proposal of a Complete Scheme of the Proteolytic Cleavages Involved in Their Synthesis," Virology, Academic Press. Orlando, Apr. 1, 1989, vol. 169, No. 2, pp. 365-376.
Osatomi et al., "Complete Nucleotide Sequence of Dengue Type 3 Virus Genome RNA," Virology, 1990, vol. 176, pp. 643-647.
Osatomi et al., "Nucleotide Sequence of Dengue Type 3 Virus Genomic RNA Encoding Viral Structural Proteins," Virus Genes, Oct. 1988, vol. 2, No. 1, pp. 99-108. Abstract Only.
Phillpotts et al., "Immunisation with DNA polynucleotides protects mice against lethal challenge with St. Louis encephalitis virus." Arch Virol., 1996, vol. 141, pp. 743-749.

(56) References Cited

OTHER PUBLICATIONS

Pletnev et al., "Construction and characterization of chimeric tick-borne encephalitis/ dengue type 4 viruses." Proc. Nat. Acad. Sci. USA, Medical Sciences, Nov. 1992, vol. 89: pp. 10532-10536.
Pletnev, et al., "Chimeric Tick-Borne Encephalitis and Dengue Type 4 Viruses: Effects of Mutations on Neurovirulence in Mice." J. Virol., Aug. 1993, vol. 67, No. 8, pp. 4956-4963.
Aberle et al., "A DNA Immunization Model Study with Constructs Expressing the Tick-Borne Encephalitis Virus Envelope Protein E in Different Physical Forms," Journal of Immunology, 199, vol. 163, pp. 6756-6761.
*AK Steel Corporation v. Sollac and Ugine*; United States Court of Appeals for the Federal Circuit; http://laws.lp.findlaw.com/fed/031074.html (Sep. 24, 2003), 8 pages.
Allison et al., "Synthesis and Secretion of Recombinant Tick-Borne Encephalitis Virus Protein E in Soluble and Particulate Form," Journal of Virology, Sep. 1995, vol. 69, No. 9, pp. 5816-5820.
Alvarez et al., "A Phase I Study of Recombinant Adenovirus Vector-Mediated Delivery of an Anti-erbB-2 Single-Chain (sFv) Antibody Gene for Previously Treated Ovarian and Extraovarian Cancer Patients," Mary Ann Liebert, Inc., Human Gene Therapy, Jan. 20, 1997, vol. 8, pp. 229-242.
Anderson et al., "Isolation of West Nile Virus from Mosquitoes, Crows, and a Cooper's Hawk in Connecticut", Ovid: Anderson: Science, vol. Dec. 17, 1999, vol. 286(5448), pp. 2331-2333.
Anonymous, "Guidelines for plaque reduction neutralization testing of human antibodies to dengue viruses," Sep. 21, 2007 (Sep. 21, 2007), p. 1-36,; Retrieved from the Internet:; URL:http://apps.who.int/iris/bitstream/handle/10665/69687/who_ivb_07.07_eng.pdf;jsessionid=E54172674C933124415AFC5BB972E6B9?sequence=1; XP055519586.
Arnon Ruth "Synthetic Vaccines vol. I" CRC Press, Inc. Boca Raton, Florida pp. 83-92.
Arroyo et al., Molecular Basis for Attenuation of Neurovirulence of a Yellow Fever Virus/Japanese Encephalitis Virus Chimera Vaccine (ChimeriVax-JE), Journal of Virology, Jan. 2001, vol. 75, No. 2, pp. 934-942.
Asnis et al., "The West Nile Virus Outbreak of 1999 in New York: The Flushing Hospital Experience," Clinical Infectious Diseases, 2000, vol. 30, pp. 413-418.
Azevedo et al., "Main features of DNA-based immunization vectors," Brazilian Journal of Medical and Biological Research 1999, vol. 32, No. 2, pp. 147-153.
Benjamin, Sarah, "Optimization and analysis of live attenuated denvax-4 constructs," Masters Thesis: Colorado State University, Summer 2013, 97 pages.
Bhamarapravati et al., "Live attenuated tetravalent dengue vaccine," Cab International, Wallingford, OX, UK, 1997, Dengue and Dengue Hamorrhagic Fever, D.J. Gubler and G. Kuno (ed), Chapter 17, pp. 367-377.
Bhamarapravati et al., "Live attenuated tetravalent dengue vaccine," Vaccine, 2000, vol. 18, pp. 44-47.
Bhatt et al., "Growth characteristics of the chimeric Japanese encephalitis virus vaccine candidate, chimeriVax-je (YF/JE SA14-14-2), in culex tritaeniorhynchus, aedes albopictus, and aedes aegypti mosquitoes," Am. J. Trop. Med. Hyg., 2000, vol. 62, No. 4, pp. 480-484.
Blok et al., "Comparison of a Dengue-2 Virus and Its Candidate Vaccine Derivative: Sequence Relationships with the Flaviviruses and Other Viruses," Virology, 1992, vol. 187, pp. 573-590.
Bray et al., "Construction of intertypic chimeric dengue viruses by substitution of structural protein genes," Proc. Nat. Acad. Sci. USA, Medical Sciences, Nov. 1991, vol. 88, pp. 10342-10346.
Bray et al., "Mice Immunized with Recombinant Vaccinia Virus Expressing Dengue 4 Virus Structural Proteins with or without Nonstructural Protein NS1 are Protected against Fatal Dengue Virus Encephalitis," Journal of Virology, Jun. 1989, vol. 63, No. 6, pp. 2853-2856.
Bray et al., "Monkeys Immunized with Intertypic Chimeric Dengue Viruses Are Protected against Wild-Type Virus Challenge," Journal of Virology, Jun. 1998, vol. 70, No. 6, pp. 4162-4166.
Butrapet et al., "Chimeric Dengue Type 2/Type 1 Viruses Induce Immune Responses in Cynomolgus Monkeys," Southeast Asian J. Trap. Med. Public Health, Sep. 2002, vol. 33, No. 3, pp. 589-599.
Butrapet et al., "Determining genetic stabilities of chimeric dengue vaccine candidates based on dengue 2 PDK-53 virus by sequencing and quantitative TaqMAMA," Journal of Virological Methods, 2006, vol. 131, No. 1, pp. 1-9.
Cahour et al., "Growth-Restricted Dengue Virus Mutants Containing Deletions in the 5' Noncoding Region of the RNA Genome," Virology, 1995, vol. 207, pp. 68-76.
Calvert et al., "Non-structural proteins of dengue 2 virus offer limited protection to interferon-deficient mice after dengue 2 virus challenge,", Journal of General Virology, vol. 87, 2006, pp. 339-346.
Caufour et al., "Construction, characterization and immunogenicity of recombinant yellow fever 17D-dengue type 2 viruses," Virus Research, 2011, vol. 79, pp. 1-14.
Chambers et al., "Flavivirus Genome Organization, Expression, and Replication," Annu. Rev. Microbiol. 1990, vol. 44, pp. 649-688.
Chambers et al., "Yellow Fever Virus/Dengue-2 Virus and Yellow Fever Virus/Dengue-4 Virus Chimeras: Biological Characterization, Immunogenicity, and Protection against Dengue Encephalitis in the Mouse Model," Journal of Virology, Mar. 2003. vol. 77, No. 6, pp. 3655-3668.
Chambers et al., "Yellow Fever/Japanese Encephalitis Chimeric Viruses: Construction and Biological Properties," Journal of Virology, Apr. 1999, vol. 73, No. 4, pp. 3095-3101.
Chang et al., "A Single Intramuscular Injection of Recombinant Plasmid DNA Induces Protective Immunity and Prevents Japanese Encephalitis in Mice," Journal of Virology, May 2020, vol. 74, No. 9, pp. 4244-4252.
Chen et al., "Construction of Intertypic Chimeric Dengue Viruses Exhibiting Type 3 Antigenicity and Neurovirulence for Mice," Journal of Virology, Aug. 1995, vol. 69, No. 8, pp. 5186-5190.
Clarke et al., "Techniques for Hemagglutination and Hemagglutination-Inhibition with Arthropod-Borne Viruses," The Rockefeller Foundation Virus Laboratories, New York, N.Y., Am. J. Trop. Med. Hyg., 1958, p. 561-573.
Cooper et al., "Update: Surveillance for West Nile Virus in Overwintering Mosquitoes—New York, 2000," 3 pages.
Database UniProt Accession No. Q9WLZ7, XP-002731515, http://ibis/exam/dbfetch.jsp?id=UNIPROT%3AQ9WLZ7, 2 pages.
Database UniProt accession No. D2KQW7 Database UniProt SubName: Full=Polyprotein (ECO:0000313 EMBL:ADA00411.1); XP002731516, retrieved from EBI accession No. UNIPROT:D2KQW7, http://ibis/exam/dbfetch.jsp?d=UNIPROT:D2KQW7 Feb. 9, 2010, 2 pages.
Database UniProt Accession No. P29991 "RecName: Full=Genome polyprotein; Contains: RecName: Full=Capsid protein C; AltName: Full=Core protein; Contains: RecName: Full=prM; Contains," XP002731514, retrieved from EBI accession No. Uniprot: P29991; Apr. 1, 1993 http://ibis/exam/dbfetch.jsp?id=UNIPROT%3AP29991 .6 pages.
Davis et al., "West Nile Virus Recombinant DNA Vaccine Protects Mouse and Horse from Virus Challenge and Expresses In Vitro a Noninfectious Recombinant Antigen That Can Be Used in Enzyme-Linked Immunosorbent Assays," Journal of Virology, May 2001, vol. 75, No. 9, pp. 4040-4047.
Deubel et al., "Nucleotide Sequence and Deduced Amino Acid Sequence of the Nonstructural Proteins of Dengue Type 2 Virus, Jamaica Genotype: Comparative Analysis of the Full-Length Genome" Virology, 1988, vol. 165, pp. 234-244.
Deubel et al., "Nucleotide Sequence and Deduced Amino Acid Sequence of the Structural Proteins of Dengue Type 2 Virus, Jamaica Genotype," Virology, 1986, vol. 155, pp. 365-377.
Dharakul et al., "Dengue Virus-Specific Memory T Cell Responses in Human Volunteers Receiving a Live Attenuated Dengue Virus Type 2 Candidate Vaccine," JID Jul. 1994, vol. 170, pp. 27-33.
Dmitriev et al., "Immunization with recombinant vaccinia viruses expressing structural and part of the nonstructural region of tick-

(56) References Cited

OTHER PUBLICATIONS borne encephalitis virus eDNA protect mice against lethal encephalitis," Journal of Biotechnology, 1996, vol. 44, pp. 97-103.

Duarte Dos Santos et al., "Complete nucleotide sequence of yellow fever virus vaccine strains 17DD and 17D-213," Virus Research 1995, vol. 35, pp. 35-41.

Durbin et al., "Attenuation and Immunogenicity in Humans of a Live Dengue Virus Type-4 Vaccine Candidate with a 30 Nucleotide Deletion in its 3'—Untranslated Region," Am. J Trop. Med. Hyg. 2001, vol. 65(5), pp. 405-413.

Falgout et al., "Immunization of Mice with Recombinant Vaccinia Virus Expressing Authentic Dengue Virus Nonstructural Protein NS1 Protects against Lethal Dengue Virus Encephalitis," Journal of Virology, Sep. 1990, vol. 64, No. 9, pp. 4356-4363.

Falgout et al., "Proper Processing of Dengue Virus Nonstructural Glycoprotein NS1 Requires the N-Terminal Hydrophobic Signal Sequence and the Downstream Nonstructural Protein NS2a," Journal of Virology, May 1989, vol. 63, No. 5, pp. 1852-1860.

Garmendia et al., "Recovery and Identification of West Nile Virus from a Hawk in Winter," Journal of Clinical Microbiology, Aug. 2000, vol. 38, No. 8, pp. 3110-3111.

Gruenberg et al., "Partial Nucleotide Sequence and Deduced Amino Acid Sequence of the Structural Proteins of Dengue Virus Type 2, New Guinea C and PUO-218 Strains" J. gen. Virol., 1988, vol. 69, pp. 1391-1398.

Guirakhoo et al., "Construction, Safety, and Immunogenicity in Nonhuman Primates of a Chimeric Yellow Fever-Dengue Virus Tetravalent Vaccine" Journal of Virology, Aug. 2001, vol. 75, No. 16, pp. 7290-7304.

Guirakhoo et al., "Immunogenicity, Genetic Stability, and Protective Efficacy of a Recombinant, Chimeric Yellow Fever-Japanese Encephalitis Virus (ChimeriVax-JE) as a Live, Attenuated Vaccine Candidate against Japanese Encephalitis," Virology, 1999, vol. 257, pp. 363-372.

Guirakhoo et al., "Recombinant Chimeric Yellow Fever-Dengue Type 2 Virus Is Immunogenic and Protective in Nonhuman Primates" Journal of Virology, The American Society for Microbiology, Jun. 1, 2000, vol. 74, No. 12, pp. 5477-5485.

Guirakhoo et al., "Viremia and Immunogenicity in Nonhuman Primates of a Tetravalent Yellow Fever-Dengue Chimeric Vaccine: Genetic Reconstructions, Dose Adjustment, and Antibody Responses against Wild-type Dengue Virus Isolates" Virology, 2002, vol. 298, pp. 146-159.

Hahn et al., "Nucleotide Sequence of Dengue 2 RNA and Comparison of the Encoded Proteins with Those of Other Flaviviruses," Virology, 1988, vol. 162, pp. 167-180.

Halstead et al., Observations related to the pathogenesis of dengue hemorrhagic fever. II. Antigenic and Biologic Properties of Dengue Viruses and their Association with disease in the host; Yale Journal of Biology and Medicine, Apr. 1970, vol. 42, pp. 276-292.

Puri et al., "Molecular analysis of dengue virus attenuation after serial passage in primary in dog kidney cells." J. Gen Virol., 1997, vol. 78, pp. 2287-2291.

Rice et al., "Nucleotide Sequence of Yellow Fever Virus: Implications for Flavivirus Gene Expression and Evolution," Science, 1985, vol. 229, pp. 726-733.

Rice et al., "Transcription of Infectious Yellow Fever RNA From Full-Length eDNA Templates Produced by In Vitro Ligation," The New Biologist, Dec. 1989, vol. 1, No. 3, pp. 285-296.

Roehrig et al., "Identification of Epitopes on the E Glycoprotein of Saint Louis Encephalitis Virus Using Monoclonal Antibodies." Virology, 1986, vol. 128, pp. 118-126.

Roehrig et al., "Synthetic Peptides Derived from the Deduced Amino Acid Sequence of the E-Glycoprotein of Murray Valley Encephalitis Virus Elicit Antiviral Antibody," Virology, 1989, vol. 171, pp. 49-60.

Sabchareon, et al., "Protective efficacy of the recombinant, live-attenuated, CYD tetravalent dengue vaccine in Thai schoolchildren: a randomised, controlled phase 2b trial," The Lancet, Nov. 3, 2021, vol. 380, pp. 1559-1567.

Sato et al., "Immunostimulatory DNA Sequences Necessary for Effective Intradermal Gene Immunization," Science, Jul. 19, 1996, vol. 273, No. 5273, pp. 352-354.

Seeger et al., "The cloned genome of ground squirrel hepatitis virus is infectious in the animal," Proc. Nat. Acad. Sci. USA, Medical Sciences, Sep. 1984, vol. 81, pp. 5849-5852.

Sela, Michael, "The Choice of Carrier." In Synthetic Vaccines vol. I, R. Amon, (ed) CRC Press Inc., Boca Raton, FL. Chapter 6, 1987, pp. 83-92.

Smithburn et al., "A Neurotropic Virus Isolated From The Blood Of a Native Of Uganda," Am. J. Trop. Med. Hyg., 1940, vol. 20, pp. 471-492.

Stocks et al: "Signal Peptidase Cleavage at the Flavivirus C-prM Junction: Dependence on the Viral NS2B-3 Protease for Efficient Processing Requires Determinants in C, the Signal Peptide, and prM," Journal Of Virology, LNKDPUBMED: 9499070, Mar. 1998, Mar. 1998 (Mar. 1998), vol. 72, No. 3, pp. 2141-2149.

Sumiyoshi et al., "Complete Nucleotide Sequence of Japanese Encephalitis Virus Genome RNA," Virology, 1987, vol. 161, pp. 497-510.

Tardei et al., "Evaluation of Immunoglobulin M (IgM) and IgG Enzyme Immunoassays in Serologic Diagnosis of West Nile Virus Infection," J. Clin. Microbiol. Jun. 2000, vol. 38, No. 6, pp. 2232-2239.

Trent Dennis W. et al., "Partial Nucleotide Sequence of St. Louis Encephalitis Virus RNA: Structural Proteins, NS1, ns2a, and ns2b," Virology, 1987, vol. 156, pp. 293-304.

Trent Dennis W. et al., "Recombinant dengue virus vaccines." In: Dengue and Dengue Hemorrhagic Fever. D.J. Gubler and G. Kuno (eds). CAB International, New York, NY Chapter 18, 1997, pp. 379-403.

Troyer et al., "A Live Attenuated Recombinant Dengue-4 Virus Vaccine Candidate With Restricted Capacity For Dissemination In Mosquitoes And Lack Of Transmission From Vaccinees To Mosquitoes," Am. J. Trop. Med. Hyg., 2001, vol. 65, No. 5, pp. 414-419.

Tsai et al "Japanese Encephalitis Vaccines," In Vaccines, (3rd edition) Plotkin and Orenstein (eds), W.B. Saunders Company, Philadelphia, PA. Chapter 27, 1999, pp. 672-710.

Tsai et al., "Japanese Encephalitis Vaccines," In Vaccines, (2nd edition), Plotkin and Mortimer (eds.), W.B. Saunders Co., Philadelphia, PA. Chapter 24, 1994, pp. 671-713.

Update: "Surveillance for Weste Nile Virus in Overwintering Mosquitoes—New York, 2000," Morb. Mortal. Wkly. Rep., Mar. 10, 2000, vol. 49, No. 09, pp. 178-179.

Update: "West Nile Virus Activity—Northeastern United States, 2000," Morb. Mortal. Wkly. Rep., Sep. 15, 2000, vol. 49, No. 36, pp. 820-822.

Van Der Most et al., "Chimeric yellow fever/dengue virus as a candidate dengue vaccine: quantification of the dengue virus-specific CD8 T-cell response," Journal of Virology, Sep. 1, 2000 2(Sep. 1, 2000), vol. 74. No. 17, pp. 8094-8101.

Vaughn et al., "Testing of dengue 2 live-attenuated vaccine (strain 16681 PDK 53) in ten American volunteers," Vaccine 1996, vol. 14 No. 4, pp. 329-336.

Venugopal et al., "Immunity to St. Louis encephalitis virus by sequential immunization with recombinant vaccinia and baculovirus derived PrM/E proteins," Vaccine, 1995, vol. 13, No. 11, pp. 1000-1005.

Wang et al., "Immune Response to Neonatal Genetic Immunization," Virology, 1997, vol. 228, pp. 278-284.

Wolff et al., "Long-term persistence of plasmid DNA and foreign gene expression in mouse muscle," Hum. Mol. Genet., 1992, vol. 1, No. 6, pp. 363-369.

World Health Organization, "Dengue vaccine research: Immunization, Vaccines and Biologicals" www.who.int/immunization/research/development/dengue_vaccines/en/, Sep. 12, 2018, 3 pages.

World Health Organization, Dengue Vaccine Research, website page at www.who.int/immunuzation/research/development/dengue_vaccines/en, last updated Dec. 5, 2017, 3 pages.

World Health Organization, Updated Questions and Answers related to the dengue vaccine Dengvaxia and its use, website page at www.who.int/immunization/diseases/dengue/q_and_a_dengue_vaccine_dengvaxia_use/en/published Dec. 22, 2017, 7 pages.

(56) References Cited

OTHER PUBLICATIONS

Xie et al., "Membrane Topology and Function of Dengue Virus NS2A Protein," Journal of Virology, Apr. 2013, vol. 87, No. 8, pp. 4609-4622.

Yamshchikov et al., "Processing of the Intracellular Form of the West Nile Virus Capsid Protein by the Viral NS2B-NS3 Protease: an In Vitro Study," Journal of Virology, LNKDPUBMED:8057458, Sep. 1994, vol. 68, No. 9, pp. 5765-5771.

Yang et al., "A p300/CBP-associated factor that competes with the adenoviral oncoprotein E1A," Nature, Jul. 25, 1996, vol. 382.

Yoksan et al., "Dengue Virus Vaccine Development: Study on Biological Markers of Uncloned Dengue 1-4 Viruses Serially Passaged in Primary Kidney Cells," Arbovirus Research in Australia—Proceedings 4th Symposium, T. D. St. George, B.H. Kay, and J. Blok (eds.), CSIRO/QIMR, Brisbane 1986, pp. 35-38.

Zhang et al., "Immunization of Mice with Dengue Structural Proteins and Nonstructural Protein NS1 Expressed by Baculovirus Recombinant Induces Resistance to Dengue Virus Encephalitis," J. Viro., Aug. 1988, vol. 62, No. 8, pp. 3027-3031.

Zhang et al., "Passive Protection of Mice, Goats, and Monkeys Against Japanese Encephalitis With Monoclonal Antibodies," 1989, J. Med. Virol., vol. 29, pp. 133-138.

Zhao et al., "Cloning Full-Length Dengue Type 4 Viral DNA Sequences: Analysis of Genes Coding for Structural Proteins," Virology, 1986, vol. 155, pp. 77-88.

Zhao et al., "Expression of Dengue Virus Structural Proteins and Nonstructural Protein NS1 by a Recombinant Vaccinia Virus," Journal of Virology, Dec. 1987, vol. 61, No. 12, pp. 4019-4022.

\* cited by examiner

Figure 1

Figure 4
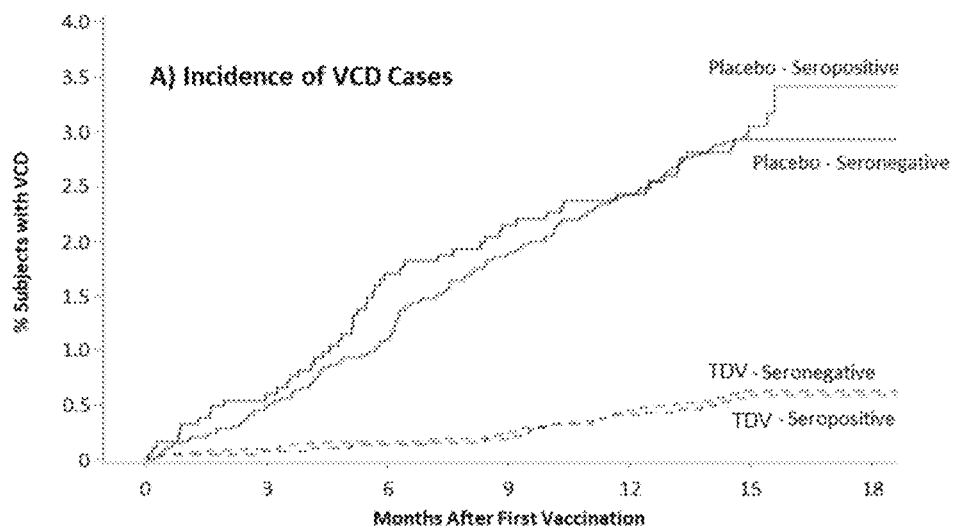
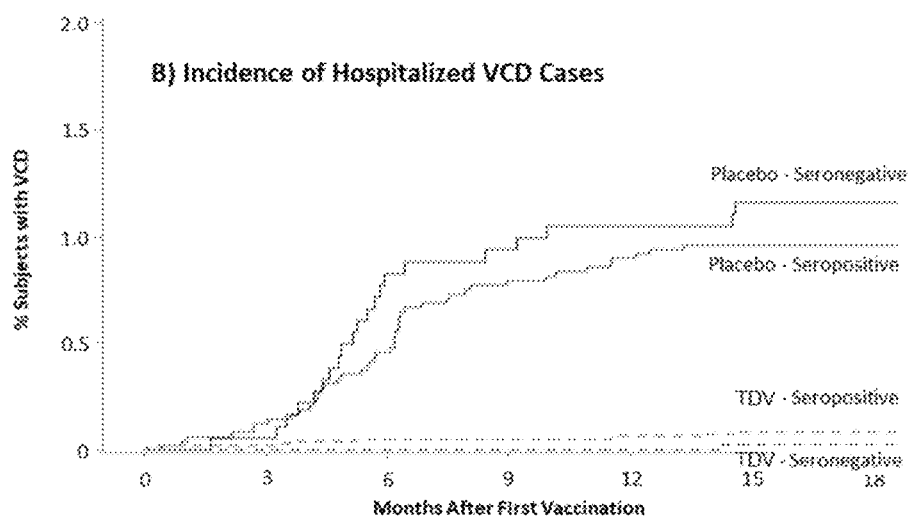

METHODS FOR PREVENTING DENGUE AND HEPATITIS A

SEQUENCE LISTING

The sequence listing submitted in text format (.txt) filed on Oct. 16, 2020, "36429US3_ST25.txt (created Oct. 9, 2020 and having 345 KB of data), is incorporated herein by reference.

FIELD OF INVENTION

The present invention relates to a method for administering a unit dose of a dengue vaccine composition to a subject or a subject population simultaneously on the same day with a hepatitis A vaccine. The unit dose according to this invention provides immune responses against all serotypes of dengue virus, i.e. DENV-1, DENV-2, DENV-3 and DENV-4 and against hepatitis A virus.

BACKGROUND OF THE INVENTION

Vaccines for protection against viral infections have been effectively used to reduce the incidence of human disease. One of the most successful technologies for viral vaccines is to immunize animals or humans with a weakened or attenuated virus strain (a "live attenuated virus"). Due to limited replication after immunization, the attenuated virus strain does not cause disease. However, the limited viral replication is sufficient to express the full repertoire of viral antigens and can generate potent and long-lasting immune responses to the virus. Thus, upon subsequent exposure to a pathogenic virus strain, the immunized individual is protected from the disease. These live attenuated viral vaccines are among the most successful vaccines used in public health.

Dengue disease is a mosquito-borne disease caused by infection with a dengue virus. Dengue virus infections can lead to debilitating and painful symptoms, including a sudden high fever, headaches, joint and muscle pain, nausea, vomiting and skin rashes. To date, four serotypes of dengue virus have been identified: dengue-1 (DENV-1), dengue-2 (DENV-2), dengue-3 (DENV-3) and dengue-4 (DENV-4). Dengue virus serotypes 1-4 can also cause dengue hemorrhagic fever (DHF) and dengue shock syndrome (DSS). In the most severe cases, DHF and DSS can be life threatening. Dengue viruses cause 50-100 million cases of debilitating dengue fever, 500,000 cases of DHF/DSS, and more than 20,000 deaths each year, a large portion of which are children. All four dengue virus serotypes are endemic throughout the tropical regions of the world and constitute the most significant mosquito-borne viral threat to humans there. Dengue viruses are transmitted to humans primarily by *Aedes aegypti* mosquitoes, but also by *Aedes albopictus* mosquitoes. Infection with one dengue virus serotype results in life-long protection from re-infection by that serotype, but does not prevent secondary infection by one of the other three dengue virus serotypes. In fact, previous infection with one dengue virus serotype may lead to an increased risk of severe disease (DHF/DSS) upon secondary infection with a different serotype.

To date, only one vaccine, a tetravalent dengue vaccine based on a yellow fever backbone, CYD-TDV (Dengvaxia®, Sanofi Pasteur, Lyon, France), has been licensed in several countries based on the clinical demonstration of an overall vaccine efficacy (VE) against virologically-confirmed dengue (VCD) of 56-61% in children in Asia and Latin America (Capeding M R et al. Clinical efficacy and safety of a novel tetravalent dengue vaccine in healthy children in Asia: a phase 3, randomised, observer-masked, placebo-controlled trial. Lancet 2014, 384:1358-65; Villar L A et al. Safety and immunogenicity of a recombinant tetravalent dengue vaccine in 9-16 year olds: a randomized, controlled, phase II trial in Latin America. Pediatr Infect Dis J 2013, 32:1102-9). However, clinical trials have shown that Dengvaxia® can enhance, rather than reduce, the risk of severe disease due to dengue infection in individuals who had not been previously infected by a dengue virus (seronegative populations). Therefore, Dengvaxia® is only recommended for use in individuals who had been previously infected with at least one dengue virus serotype (seropositive populations). More specifically, according to the European Medicine Agencys European Public Assessment report (EPAR) for the product, Dengvaxia® is only for use in people from 9 to 45 years of age who have been infected with dengue virus before and who live in areas where this infection is endemic. Endemic areas are areas where the disease occurs regularly throughout the year. See also Sridhar S et al. Effect of Dengue Serostatus on Dengue Vaccine Safety and Efficacy. N Engl J Med 2018, 379:327-40; and World Health Organization. Dengue vaccine: WHO position paper—September 2018. Wkly. Epidemiol. Rec. 2018, 93:457-476. S. R. Hadinegoro et al. report in the New England Journal of Medicine, Vol. 373, page 1195, in "Efficacy and Long-Term Safety of a Dengue Vaccine in Regions of Endemic Disease" a pooled risk of hospitalization for virologically-confirmed dengue disease among those under the age of 9 years of 1.58 indicating an increased risk for the vaccinated group with respect to severe dengue. This leaves a substantial unmet need for an effective vaccine with a good safety profile in both dengue-naïve and seropositive individuals, including those dengue-naïve populations living in endemic areas, younger individuals who may not have developed any seropositive response to dengue or been exposed to dengue, and travelers and individuals from non-endemic regions. There is also a need for outbreak control or travel vaccination, offering a reduction in the risk of dengue after only one dose.

One further disadvantage of the only currently approved dengue vaccine, Dengvaxia®, is that it must only be given to people who have had a positive test result showing a previous infection with dengue virus (EPAR), i.e. individuals with known serostatus for dengue. Thus, individuals with unknown serostatus for dengue cannot be vaccinated with Dengvaxia®.

There is hence a need for a dengue vaccine and corresponding method of inoculation that stimulates an immune response to all dengue serotypes, preferably a balanced immune response to all serotypes, and protects against dengue disease of any severity (including DSS, DHF), both in seronegative and seropositive populations, which is safe for a larger group of ages, in particular also for subjects of 9 years and younger. The development of a safe and effective vaccine capable of protecting all populations, including both seronegative and seropositive populations, and in particular children and young adults and elderly subjects in endemic settings and for the purpose of traveling, represents an important approach to the prevention and control of this global disease.

There is thus a medical need for a dengue vaccine and corresponding method of inoculation which, as well as being safe and efficacious irrespective of serostatus and in a broad age group. There is a need for a dengue vaccine and corresponding method of inoculation that avoids costly and time consuming serostatus tests or seroprevalence considerations. There is a need for a dengue vaccine and corresponding method of inoculation that can be used in an outbreak situation. Furthermore there is a medical need for a dengue vaccine which as well as being safe and effective can also be administered to individuals with unknown dengue serostatus, children under 9 years and seronegative individuals.

There is also a need for a vaccine that is administered in fewer doses than the current Dengvaxia® dosing schedule of 3 doses, 6 months apart, such as a vaccine that can be administered in only two doses or one dose to be efficacious.

The above objects are commensurate with the research priorities provided by the WHO in the Dengue Vaccine: WHO position paper—September 2018 (Wkly. Epidemiol. Rec. 2018, 93:457-476).

Hepatitis A is a liver disease caused by the hepatitis A virus (HAV). The virus is primarily spread when an uninfected (and unvaccinated) person ingests food or water that is contaminated with the feces of an infected person. The disease is closely associated with unsafe water or food, inadequate sanitation and poor personal hygiene. The virus can also be transmitted through close physical contact with an infectious person. Unlike hepatitis B and C, hepatitis A infection does not cause chronic liver disease and is rarely fatal, but it can cause debilitating symptoms and fulminant hepatitis (acute liver failure), which is often fatal. Hepatitis A occurs sporadically and in epidemics worldwide, with a tendency for cyclic recurrences.

The hepatitis A virus is one of the most frequent causes of foodborne infection. Epidemics related to contaminated food or water can erupt explosively, such as the epidemic in Shanghai in 1988 that affected about 300,000 people. Hepatitis A viruses persist in the environment and can withstand food-production processes routinely used to inactivate and/ or control bacterial pathogens. The disease can lead to significant economic and social consequences in communities. It can take weeks or months for people recovering from the illness to return to work, school, or daily life. The impact on food establishments identified with the virus, and local productivity in general, can be substantial. In developing countries with poor sanitary conditions and hygienic practices, most children (90%) have been infected with the hepatitis A virus before the age of 10 years.

The number of people traveling internationally has grown substantially in recent decades. According to the United Nations World Tourism Organization (UNWTO), over 1.1 billion tourists travelled abroad in 2014. The risk of becoming ill during international travel depends on many factors, such as the region of the world visited, the length of the trip, and the diversity of planned activities. Vaccine recommendations are a prominent part of health preparations before international travel. Vaccination against hepatitis A virus is commonly recommended for travelers to at-risk areas around the world including Asia, Africa, and Latin America.

For routine hepatitis A vaccination, a two-dose schedule is recommended, particularly in travelers at substantial risk of contracting hepatitis A and in immunocompromised individuals. However, in healthy individuals, comparable effectiveness has been achieved with a single dose. The vaccination schedule for children/adolescents (12 months through 18 years of age) as well as for adults (?19 years of age) consists of a primary dose administered intramuscularly, and a further booster dose administered intramuscularly 6 to 18 months later.

Available hepatitis A vaccines include HAVRIX® and VAQTA®.

Hence, there is a need for a safe and effective method of simultaneously preventing dengue disease and hepatitis A. In particular, there is a need for hepatitis A and dengue vaccines which provide non-inferiority when administered simultaneously to a subject or subject population and a suitable administration schedule for achieving synergy.

Furthermore, there is a need of effectively and safely preventing dengue disease and hepatitis A in subjects being unaware of their hepatitis A and/or dengue serostatus, in particular in subjects from non-endemic countries which travel into dengue and hepatitis A endemic countries.

OBJECTS AND SUMMARY

It is an object of the present invention to provide a safe and effective protection against dengue disease and hepatitis A.

It is an object of the present invention to provide a method of administration for preventing hepatitis A and dengue disease which is useful in typical vaccination settings wherein the subjects are unaware of their serostatus for dengue and/or hepatitis A and a corresponding serotest is unavailable, unpractical or unreliable.

It is an object of the present invention to provide a safe and effective protection against dengue disease and hepatitis A for travelers from hepatitis A and dengue non-endemic countries, in particular for travelers being vaccinated in travel clinics. In this context it is beneficial if multiple during the same medical appointments are avoided and vaccination can be conducted simultaneously for more than one disease.

It is an object of the present invention to provide a safe and effective vaccine for preventing hepatitis A and dengue disease in a subject or subject population and a corresponding method of preventing hepatitis A and dengue disease in a subject or a subject population from a dengue-endemic and dengue non-endemic region and for a broad range of ages, in particular for subjects between 2 to 60 years of age, preferably for subjects between 18 and 60 years of age, and independent of previous exposure to any dengue virus serotype and/or to hepatitis A virus and independent of corresponding seropositivity or seronegativity with respect to dengue and/or hepatitis A before vaccination.

It is an object of the invention to provide vaccines and a corresponding method of preventing hepatitis A and dengue disease which avoids testing for individual dengue and/or hepatitis A serostatus before individual administration of a hepatitis A and a dengue vaccine to a subject or subject population, or analysis of seroprevalence rates of dengue and/or hepatitis A in subjects or subject populations to be vaccinated.

It is an object of the present invention to provide a dengue vaccine and a hepatitis A vaccine which can be safely co-administered with TDV as travel vaccines before an international travel of a subject to HAV and dengue endemic countries and a method of safely administering these vaccines.

Therefore, the present invention is directed to a method of preventing dengue disease as well as hepatitis A.

The present invention is further directed to a method of preventing hepatitis A and dengue disease in a subject or subject population, the method comprising simultaneously on the same day administering a hepatitis A vaccine and a unit dose of a dengue vaccine composition, wherein said unit dose comprises a tetravalent dengue virus composition including four live, attenuated dengue virus strains.

Definitions

In describing the present invention, the following terms are to be used as indicated below. As used herein, the singular forms "a," "an," and "the" include plural references unless the context clearly indicates otherwise.

As used herein, the terms "unit dose of a dengue vaccine composition", "unit dose" and "unit dose of the invention as described herein" refer to the amount of a dengue vaccine which is administered to a subject in a single dose. In one embodiment, one unit dose is present in a vial and this unit dose is administered to a subject, e.g. optionally after reconstitution. In one embodiment, more than one unit dose of the dengue vaccine composition may be present in a vial so that with the content of one vial more than one subject can be vaccinated.

A "lyophilized unit dose" or "unit dose in lyophilized form" refers to the unit dose that is obtained by subjecting a given volume of the liquid dengue vaccine composition, such as 0.5 mL, to lyophilization. Thus, the aqueous formulations of the dengue vaccine composition being produced by combining the pharmaceutically acceptable excipients and the dengue virus composition comprising the four dengue virus strains, preferably TDV-1 to TDV-4, is subjected to lyophilization to obtain the lyophilized unit dose.

A "reconstituted unit dose" or "unit dose in reconstituted form" is obtained from the lyophilized dose by reconstitution with a pharmaceutically acceptable diluent. The diluent does not contain dengue virus. The reconstituted unit dose is a liquid which can be administered to a subject, for example by injection, such as subcutaneous injection.

As used herein, the term "upon reconstitution with 0.5 mL" is not limiting the reconstitution to be performed using 0.5 mL of the diluent, but refers to the concentration of the dengue viruses that will be present in the reconstituted unit dose when 0.5 mL diluent are used for reconstitution. While using a different volume for reconstitution (e.g. 0.8 mL) will result in a different concentration of dengue viruses in the reconstituted unit dose, the administration of the total volume of the unit dose (e.g. 0.8 mL) will result in the same total amount of dengue virus being administered.

As used herein, a "concentration of at least X log 10 pfu/0.5 mL" refers to the concentration of a dengue serotype in 0.5 mL, but is not limiting the unit dose to be 0.5 mL. If the unit dose has a volume different than 0.5 mL, or is lyophilized from a volume different than 0.5 mL, or is reconstituted with a volume different than 0.5 mL, said concentration will differ from the "concentration of at least X log 10 pfu/0.5 mL". However, if the unit dose has a volume of 0.5 mL, or is lyophilized from a volume of 0.5 mL, or is reconstituted with a volume of 0.5 mL, said concentration will be the "concentration of at least X log 10 pfu/0.5 mL". Thus, while the concentration may differ, the total amount of virus in the unit dose remains the same.

As used herein, the term "dengue serotype" refers to a species of dengue virus which is defined by its cell surface antigens and therefore can be distinguished by serological methods known in the art. At present, four serotypes of dengue virus are known, i.e. dengue serotype 1 (DENV-1), dengue serotype 2 (DENV-2), dengue serotype 3 (DENV-3) and dengue serotype 4 (DENV-4).

As used herein, the term "tetravalent dengue virus composition" refers to a dengue virus composition comprising four different immunogenic components from the four different dengue serotypes DENV-1, DENV-2, DENV-3 and DENV-4, preferably comprising four different live, attenuated dengue viruses, each representing one dengue serotype, and which aims to stimulate immune responses to all four dengue serotypes.

As used herein, the term "live attenuated dengue virus" refers to a viable dengue virus which is mutated to provide reduced virulence. The live attenuated dengue virus can be a dengue virus in which all components are derived from the same dengue serotype or it can be a chimeric dengue virus having parts from two or more dengue serotypes or a mixed chimeric dengue virus having parts from other flaviviruses.

A "virus strain" and in particular a "dengue virus strain" is a genetic subtype of a virus, in particular of a dengue virus, which is characterized by a specific nucleic acid sequence. A dengue serotype may comprise different strains with different nucleic acid sequences which have the same cell surface antigens. A dengue virus strain can be a dengue virus in which all components are derived from the same dengue serotype or it can be a chimeric dengue virus having parts from two or more dengue serotypes.

As used herein, "TDV-2" refers to a molecularly characterized and cloned dengue serotype 2 strain derived from the live attenuated DEN-2 PDK-53 virus strain. The PDK-53 strain is described for example in Bhamarapravati et al. (1987) Bulletin of the World Health Organization 65(2): 189-195. In one embodiment, the TDV-2 strain served as a backbone for the chimeric TDV-1, TDV-3 and TDV-4 strains into which parts from the TDV-1, TDV-3 and TDV-4 strains were introduced.

A "non-chimeric dengue virus" or "non-chimeric dengue serotype strain" or "non-chimeric dengue strain" comprises only parts from one dengue serotype. In particular, a non-chimeric dengue virus does not include parts from a different flavivirus such as yellow fever virus, Zika virus, West Nile virus, Japanese encephalitis virus, St. Louis encephalitis virus, tick-borne encephalitis virus. TDV-2 is an example of a non-chimeric dengue virus.

A "chimeric dengue virus" or "chimeric dengue serotype strain" or "chimeric dengue strain" comprises parts from at least two different dengue serotypes. As used herein, the chimeric dengue virus does not include parts from a different flavivirus such as yellow fever virus, Zika virus, West Nile virus, Japanese encephalitis virus, St. Louis encephalitis virus, tick-borne encephalitis virus. In particular, the chimeric dengue virus described herein does not include parts from the yellow fever virus. As used herein, a "chimeric dengue serotype 2/1 strain" or "DENV-2/1 chimera" or "TDV-1" refers to a dengue virus chimeric construct which comprises parts from both DENV-2 and DENV-1. In particular, in the chimeric dengue serotype 2/1 strain the prM and E proteins from DENV-1 replace the prM and E proteins from DENV-2 as detailed below. As used herein, a "chimeric dengue serotype 2/3 strain" or "DENV-2/3 chimera" or "TDV-3" refers to a dengue virus chimeric construct which comprises parts from both DENV-2 and DENV-3. In particular, in the chimeric dengue serotype 2/3 strain the prM and E proteins from DENV-3 replace the prM and E proteins from DENV-2 as detailed below. As used herein, a "chimeric dengue serotype 2/4 strain" or "DENV-2/4 chimera" or "TDV-4" refers to a dengue virus chimeric construct which comprises parts from both DENV-2 and DENV-4. In particular, in the chimeric dengue serotype 2/4 strain the prM and E proteins from DENV-4 replace the prM and E proteins from DENV-2 as detailed below. A mixed chimeric dengue virus has parts from other flaviviruses.

As used herein, "TDV" refers to a tetravalent live attenuated dengue vaccine that comprises a mixture of the four live attenuated dengue virus strains TDV-1, TDV-2, TDV-3 and TDV-4 expressing surface antigens from the four dengue serotypes DENV-1, DENV-2, DENV-3 and DENV-4, respectively. In one embodiment (e.g. also in the examples), TDV-1 has the nucleotide sequence according to SEQ ID No. 1 and/or the amino acid sequence according to SEQ ID No. 2. In one embodiment, TDV-2 has the nucleotide sequence according to SEQ ID No. 3 and/or the amino acid sequence according to SEQ ID No. 4. In one embodiment, TDV-3 has the nucleotide sequence according to SEQ ID No. 5 and/or the amino acid sequence according to SEQ ID No. 6. In one embodiment, TDV-4 has the nucleotide sequence according to SEQ ID No. 7 and/or the amino acid sequence according to SEQ ID No. 8.

As used herein, the term "dengue disease" refers to the disease which is caused by infection with dengue virus. Symptoms of dengue disease include sudden high fever, headaches, joint and muscle pain, nausea, vomiting and skin rashes. The term dengue disease also includes the more severe forms of dengue hemorrhagic fever (DHF) and dengue shock syndrome (DSS). Symptoms of DHF include increased vascular permeability, hypovolemia and abnormal blood clotting mechanisms. Subjects with DHF may present with severe manifestations of plasma leakage and hemorrhage. When a subject with DHF experiences shock he or she will be categorized as having DSS. Symptoms of DSS include bleeding that may appear as tiny spots of blood on the skin and larger patches of blood under the skin. Prolonged shock is the main factor associated with complications including massive gastrointestinal hemorrhage that can lead to death. As used herein, DHF cases are defined as VCD cases meeting WHO 1997 DHF criteria. In the context of preventing dengue disease in elderly subjects, the term "preventing dengue disease" preferably includes preventing DHF and/or DSS. In the context of preventing dengue disease in elderly subjects, the term "preventing dengue disease" preferably includes preventing severe end-organ manifestations of dengue such as hepatomegaly and acute renal failure.

As used herein, "preventing dengue disease" refers to preventing a subject from developing one or more symptoms of dengue disease because of an infection with a dengue virus. In particular, preventing dengue disease is achieved by vaccinating or inoculating a subject with a dengue vaccine composition, such as the reconstituted unit dose described herein. As used herein, the term "prophylactically treating dengue disease" is equivalent to "preventing dengue disease". In a particular embodiment, preventing dengue disease includes preventing DHS and/or DSS.

As used herein, the terms "virologically-confirmed dengue disease", "VCD case", or "VCD fever" refer to febrile illness or illness clinically suspected to be dengue disease with a positive serotype-specific reverse transcriptase polymerase chain reaction (RT-PCR). The term "virologically confirmable dengue" disease refers to a subject having febrile illness or illness clinically suspected to be dengue disease, wherein testing the subject, e.g. using RT-PCR, would confirm the presence of at least one dengue serotype. Severe forms of VCD fever will be identified as follows: Dengue Hemorrhagic Fever (DHF) was defined according to the WHO 1997 criteria. Severe dengue was defined through an assessment of an independent Dengue Case Adjudication Committee which will assess all hospitalized VCD cases (severe/non-severe) based on criteria redefined in a charter. All non-hospitalized cases are considered non-severe.

As used herein, the term "febrile illness" is defined as temperature≥38° C. on any 2 of 3 consecutive days.

As used herein, the terms "virologically-confirmed dengue disease with hospitalization", is considered to be a surrogate for severe dengue and the "incidence of virologically-confirmed dengue disease with hospitalization" is used as a safety parameter. As used herein, the "relative risk with respect to virologically-confirmed dengue disease with hospitalization" means the number of events of virologically confirmed dengue disease with hospitalization divided by the number of subjects treated with the unit dose as disclosed herein over the number of events of virologically confirmed dengue disease with hospitalization divided by the number of subjects treated with placebo. If the "relative risk with respect to virologically-confirmed dengue disease with hospitalization" is 1 or lower the vaccine provides for the same or less risk for virologically-confirmed dengue disease with hospitalization as placebo and is considered "safe". In this context the risk of virologically-confirmed dengue disease with hospitalization may be also 0.9 or less, 0.8 or less, 0.7 or less, 0.6 or less, 0.5 or less, 0.4 or less, 0.3 or less, 0.2 or less, or 0.1 or less, in particular when determined from 30 days after a second administration until 12 months after a second administration, in particular when determined in age groups selected from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects.

As used herein, alternatively a vaccine is considered "safe" when the vaccine efficacy (VE) with respect to virologically-confirmed dengue disease with hospitalization is 0% or higher. This means that the vaccine provides for the same likelihood or less for virologically-confirmed dengue disease with hospitalization as placebo. In particular considered "safe" is the combined vaccine efficacy against virologically-confirmed dengue with hospitalization against all four serotypes with a 2-sided 95% confidence interval, wherein the lower bound is more than 25%, in particular when measured against placebo in a subject population of at least 1,500 or at least 2,000 healthy subjects (in particular when measured in age groups selected in particular from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects) being seronegative against all serotypes at baseline or being seropositive against at least one serotype at baseline, in particular when said unit dose or said placebo is administered at least twice within less than 6 months, such as within 3 months, about from first administration or from 30 days after the second or last administration of the administration schedule until at least 12 months, until 12 to 18 months, until 12 months, or until 18 months after the second or last administration of the administration schedule. In particular, the lower bound may be more than 30%, more than 40%, more than 50%, more than 60%, more than 65%, more than 66%, more than 67%, more than 68% more than 70%, or more than 75%. In particular, the 2-sided 95% confidence interval of the combined vaccine efficacy against virologically-confirmed dengue with hospitalization against all four serotypes when comparing seropositive and seronegative subjects provides for lower bounds of the 2-sided confidence interval which are within 10% points or within 15% points or within 20% points. In a particular embodiment "safe" means providing a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline from first administration of the administration schedule until 12 to 18 months after the last administration of the administration schedule.

If one of the criteria as defined above for the term "safe" is fulfilled, the vaccine is considered safe within the meaning of this invention. In this context, safe in particular refers to a vaccine that is safe for all subjects irrespective of their serostatus at baseline. This means that the vaccine can be administered without the need to determine the occurrence of a previous dengue infection in the subject before administration. Preferably, the vaccine is safe as defined above with respect to all age groups starting from 4 years of age and preferably irrespective of the serostatus, in particular from 4 years of age to 60 years of age, or 4 years of age to 16 years of age. Relevant subgroups in this context are under 9 years of age, from 2 years of age to under 9 years of age, from 4 years of age to under 9 years of age, 4 to 5 years of age, 6 to 11 years of age and 12 to 16 years of age or any age group within 4 to 16 years of age. For further definitions of VE against virologically-confirmed dengue disease with hospitalization reference is made to the disclosure below with respect to certain methods of treatment.

As used herein, "vaccine efficacy" or "VE" measure the proportionate reduction in cases among vaccinated persons. Vaccine efficacy (VE) is measured by calculating the risk of disease among vaccinated and unvaccinated persons and determining the percentage reduction in risk of disease among vaccinated persons relative to unvaccinated persons. The greater the percentage reduction of illness in the vaccinated group, the greater the vaccine efficacy. For example, a VE of 90% indicates a 90% reduction in disease occurrence among the vaccinated group, or a 90% reduction from the number of cases you would expect if they have not been vaccinated. The vaccine efficiency is calculated by the formula: $100*(1-HR)$, wherein HR is the Hazard Ratio which is defined as the Hazard rate of vaccine ($\lambda v$) divided by the Hazard rate of placebo ($\lambda c$), i.e. $HR=\lambda v/\lambda c$. $\lambda v$ denote the hazard rate for the subjects vaccinated with a tetravalent dengue vaccine composition as disclosed herein and $\lambda c$ denote the hazard rate for unvaccinated subjects, i.e. subjects receiving placebo. The hazard rate ratio HR is estimated from a Cox proportional hazard model with study vaccine as a factor, adjusted for age, and stratified by region. As used herein the term "combined vaccine efficacy against all four serotypes" is defined as the vaccine efficacy in relation to the risk of dengue disease irrespective of the serotype being responsible for the virologically-confirmed dengue disease and the subject baseline serostatus. A vaccine is considered "effective" in case the combined vaccine efficacy is above 30%. In this context the combined vaccine efficacy may be also 40% or more, 50% or more, 60% or more, 70% or more, 72% or more, or 80% or more, in particular when determined from 30 days after a second administration until 12 months after a second administration or 18 months after a second vaccination, in particular when determined in age groups selected from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects. In this context, effective in particular refers to a vaccine that is effective for all subjects irrespective of their serostatus at baseline. Preferably, the vaccine is effective with respect to all age groups starting from 4 years of age and preferably irrespective of the serostatus, in particular from 4 years of age to 60 years of age or from 4 years of age to 16 years of age and irrespective of the serostatus. Relevant subgroups in this context are under 9 years of age, from 2 years of age to under 9 years of age, from 4 years of age to under 9 years of age, 4 to 5 years of age, 6 to 11 years of age and 12 to 16 years of age or any age group within 4 to 16 years of age. In certain embodiments "effective" means providing a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects irrespective of serostatus at baseline and 4 to 16 years of age, from the first administration of the administration schedule until 18 months after the last administration of the administration schedule. Further specific efficacies can be defined. As used herein, "combined vaccine efficacy against all four serotypes in seronegative subjects" refers to the efficacy measured in subjects which are seronegative at baseline. As used herein, "vaccine efficacy against a specific serotype, e.g. serotype 1" refers to the efficacy in relation to a specific serotype being responsible for the virologically-confirmed dengue disease. As used herein, "combined vaccine efficacy against all four serotypes against virologically-confirmed dengue with hospitalization" refers to the efficacy wherein only virologically-confirmed dengue cases with hospitalization are considered. Such vaccine efficacies can be determined with respect to subjects being seronegative or seropositive at baseline and for different age groups.

As used herein, the "relative risk" means the number of events of virologically confirmed dengue disease divided by the number of subjects treated with the unit dose as disclosed herein over the number of events of virologically confirmed dengue disease divided by the number of subjects treated with placebo. As used herein the term "combined relative risk against all four serotypes" is defined as the relative risk in relation to the risk of dengue disease irrespective of the serotype being responsible for the virologically-confirmed dengue disease and the subject baseline serostatus.

As used herein, "vaccinating" or "inoculating" refers to the administration of a vaccine to a subject, with the aim to prevent the subject, from developing one or more symptoms of a disease. As used herein, "vaccinating against dengue disease" or "inoculating against dengue disease" refers to the administration of a dengue vaccine composition to a subject, with the aim to prevent the subject, from developing one or more symptoms of dengue disease. In principle the method comprises a primary vaccination and optionally one or more booster vaccinations. The primary vaccination is defined as the primary administration schedule for administering the composition or unit dose as disclosed herein to establish a protective immune response and e.g. consists of two administrations e.g. within three months. Whenever an administration is mentioned within this disclosure such administration refers to the primary vaccination unless it is specified as booster vaccination. The booster vaccination refers to an administration or administration schedule which takes place after the primary vaccination e.g. at least 1 year, or 4 to 4.5 years, or even 5 or 10 years after the last administration, e.g. the second administration, of the primary vaccination schedule. The booster administration attempts at enhancing or reestablishing the immune response of the primary vaccination.

As used herein, the terms "subject" or "subjects" are limited to human subjects (e.g. infants, children or adults).

The terms "elderly subject" or "elderly subjects" refer to subjects with an age of more than 60 years, such as 61 years to 100 years, 61 years to 90 years, 61 years to 80 years, 61 years to 75 years, or 61 years to 70 years.

As used herein, "subject population" refers to a group of subjects. The subject population may refer to least 40 subjects, at least 50 subjects, at least 60 subjects, at least 100 subjects or at least 1000 subjects and is defined by certain parameters. The parameters that may be used to define a subject population include, but are not limited to, the age of the subjects, whether the subjects are from a dengue endemic region or from a dengue non-endemic region and the serostatus of the subjects.

As used herein, "endemic region" refers to a region where a disease or infectious agent is constantly present and/or usually prevalent in a population within this region. As used herein, "non-endemic region" refers to a region from which the disease is absent or in which it is usually not prevalent. Accordingly, a "dengue endemic region" refers to geographic areas in which an infection with dengue virus is constantly maintained at a baseline level. A "dengue non-endemic region" is a geographic area in which an infection with dengue virus is not constantly maintained at a baseline level. Accordingly, subject populations or subjects "from a dengue endemic region" or "from a dengue non-endemic region" refer to subject populations or subjects living in geographic areas as defined above. Whether a geographic area or a subject population is dengue-endemic or not can be determined by different calculatory methods such as the ones described in Bhatt et al. (2013) Nature 496 (7446): 504-507 and supplementary material and in Stanaway et al. (2016) Lancet Infect Dis. 16(6): 712-723 and supplementary material. Overviews of dengue endemic regions and dengue epidemiology are regularly published, for example, by the WHO or CDC. Typical dengue-endemic regions are in Latin America, Southeast Asia and the Pacific islands and dengue endemic countries include, but are not limited to, Australia, Brazil, Bangladesh, Colombia, China, Dominican Republic, Indonesia, India, Mexico, Malaysia, Nicaragua, Nigeria, Pakistan, Panama, Philippines, Puerto Rico, Singapore, Sri Lanka, Thailand and Vietnam. The area's force of infection is measured by seroprevalence surveys provided as seroprevalence rate. Areas with very high force of infection are considered to have a seroprevalence rate of more than 80%. As used herein the term "region" when it concerns seroprevalence rates refers to a geographic area where the seroprevalence rate could be determined or is known, e.g. a village, a town, a city, a region, a county, a state, a province or parts of the foregoing or a whole country.

As used herein, "serostatus" refers to the amount of antibodies a subject has with respect to a certain infectious agent, in particular dengue virus. As used herein, "seronegative" or "seronaïve" means that the subject does not have neutralizing antibodies against any one of dengue serotypes DENV-1, DENV-2, DENV-3 and DENV-4 in the serum. A seronegative or seronaïve subject or subject population is defined by a neutralizing antibody titer of less than 10 for each one of the four dengue serotypes. A subject or subject population having a neutralizing antibody titer of equal to or more than 10 for at least one dengue serotype is defined as being "seropositive" with respect to said dengue serotype. Serostatus at baseline refers to the serostatus before the administration of a dengue vaccine composition as described herein.

As used herein, a "neutralizing antibody titer" refers to the amount of antibodies in the serum of a subject that neutralize the respective dengue serotype. The neutralizing antibody titer against DENV-1, DENV-2, DENV-3 and DENV-4 is determined in a serum sample of the subject using known methods such as the plaque reduction neutralization test (PRNT) as described in the WHO Guidelines (World Health Organization Department of Immunization Vaccines Biologicals (2007) Guidelines for plaque reduction neutralization testing of human antibodies to dengue viruses, WHO/IVB/07.07) or a microneutralization (MNT50) assay as described herein. As used herein, the "ratio of not more than 20 for the neutralizing antibody titer of dengue serotype 2 to the neutralizing antibody titer of dengue serotype 4" means that the neutralizing antibody titer of dengue serotype 2 is divided by the neutralizing antibody titer of dengue serotype 4 and that the ratio obtained hereby is no more than 20. In other words, the neutralizing antibody titer of dengue serotype 2 is not more than 20-times higher than the neutralizing antibody titer of dengue serotype 4 in the subject.

As used herein, the terms "geometric mean neutralizing antibody titer" and "GMT" refer to the geometric mean value of the titer of neutralizing antibodies against the corresponding dengue serotype in the serum of subjects in a subject population. The geometric mean value is calculated by a well-known formula. As used herein, the "ratio of not more than 20 for the GMT of dengue serotype 2 to the GMT of dengue serotype 4" means that the geometric mean neutralizing antibody titer of dengue serotype 2 (GMT DENV-2) is divided by the geometric mean neutralizing antibody titer of dengue serotype 4 (GMT DENV-4) and that the ratio obtained hereby is no more than 20. In other words, the geometric mean neutralizing antibody titer of dengue serotype 2 is not more than 20-times higher than the geometric mean neutralizing antibody titer of dengue serotype 4 in the subject population.

As used herein, an "immune response" refers to a subject's response to the administration of the dengue vaccine. In particular, the immune response includes the formation of neutralizing antibodies to one or more dengue serotypes. It may also include the stimulation of a cell-mediated response or the formation of antibodies to non-structural proteins such as NS1. An immune response is stimulated by the administration of a unit dose of the invention as described herein, if the titer of neutralizing antibodies against at least one dengue virus serotype and preferably against all four dengue virus serotypes is increased after said administration of said unit dose. An immune response is stimulated by the administration of a unit dose of the invention as described herein, if the secretion of interferon gamma by peripheral blood mononuclear cells stimulated with peptides from dengue virus proteins is increased after said administration of said unit dose. An immune response is stimulated by the administration of a unit dose of the invention as described herein, if the titer of antibodies to non-structural proteins such as NS1 is increased after said administration of said unit dose. In a particular embodiment, the administration of a reconstituted unit dose of the present invention as described herein stimulates the formation of neutralizing antibodies to one or more dengue serotypes, a cell-mediated response and the formation of antibodies to non-structural proteins such as NS1.

As used herein, a "balanced immune response" means that the immune response to the four dengue serotypes is sufficient to provide protection against infection by all four dengue serotypes and preferably the immune response to the four dengue serotypes has a similar strength. In particular, the neutralizing antibody titer against the four dengue serotypes at day 180 or day 365 after administration of a first reconstituted unit dose of the invention as described herein is similar, i.e. it differs by less than factor 30, by less than factor 25 or by less than factor 20.

The "total concentration in pfu/0.5 ml" which serves as a base value for the calculation of the percentage concentration for each individual component of a tetravalent dengue vaccine is shown for one exemplary tetravalent vaccine composition comprising dengue serotype 1 in a concentration of 3.60 log 10 pfu/0.5 ml, a dengue serotype 2 concentration of 4.00 log 10 pfu/0.5 ml, a dengue serotype 3 concentration of 4.60 log 10 pfu/0.5 ml and a dengue serotype 4 concentration of 5.11 log 10 pfu/0.5 ml.

Primarily, the logarithmic values of the concentrations are converted into numerical values. The results of this conversion are $4 \times 10^3$ pfu/0.5 ml for serotype 1, $1 \times 10^4$ pfu/0.5 ml for serotype 2, $4 \times 10^4$ pfu/0.5 ml for serotype 3 and $1.3 \times 10^5$ pfu/0.5 ml for serotype 4. The total concentration in pfu/0.5 ml is the sum of the preceding numerical values resulting in $1.84 \times 10^5$ pfu/0.5 ml.

The "percentage concentration" for each of the serotypes 1, 2, 3 and 4 is obtained by dividing the numerical concentration value (expressed as pfu/0.5 ml) of an individual serotype by the total concentration (expressed in pfu/0.5 ml) and multiplying the result by 100 i.e.:

Percentage concentration of serotype 1=($4 \times 10^3$ pfu/0.5 ml÷$1.84 \times 10^5$ pfu/0.5 ml)×100=2%

Percentage concentration of serotype 2=($1 \times 10^4$ pfu/0.5 ml÷$1.84 \times 10^5$ pfu/0.5 ml)×100=5%

Percentage concentration of serotype 3=($4 \times 10^4$ pfu/0.5 ml÷$1.84 \times 10^5$ pfu/0.5 ml)×100=22%

Percentage concentration of serotype 4=($1.3 \times 10^5$ pfu/0.5 ml÷$1.84 \times 10^5$ pfu/0.5 ml)×100=71%.

The percentage concentrations are rounded to whole numbers.

As used herein "simultaneous" administration means an administration of at least two different vaccines such as a dengue vaccine and a hepatitis A vaccine on the same day. "On the same day" has the ordinary meaning of within 24 hours, such as e.g. within one calendar day. The simultaneous administration may be administered by the same medical practitioner, such as during the same medical appointment.

As used herein "sequential" administration means an administration of at least two different vaccines, such as a dengue vaccine and a yellow fever vaccine, or a dengue vaccine and a hepatitis A vaccine on different or subsequent days, such as within 90 days, but in a combined administration schedule.

As used herein, the term "chronic disease or condition" includes those diseases and conditions which persist in an elderly subject for three months or more. In particular, it includes diabetes, hypertension, allergies, previous strokes, ischemic heart disease, chronic renal impairment and chronic obstructive pulmonary disease.

As used herein, the term "impaired immune system" means that at least one function of at least one component of the immune system is weaker than in younger subjects, i.e. in subjects with an age of less than 60 years. These functions include a lower antioxidant response of monocytes against oxidative stress induced by dengue virus and lower T cell responses and cytokine production in response to dengue virus infection.

As used herein, "solicited systemic adverse events" in children under 6 years are defined as fever, irritability/fussiness, drowsiness and loss of appetite that occurred within 14 days after each vaccination, and in children of 6 years or more are defined as fever, headache, asthenia, malaise and myalgia that occurred within 14 days after each vaccination.

As used herein, "solicited local adverse events" are injection site pain, injection site erythema and injection site swelling that occurred within 7 days after each vaccination.

As used herein, "unsolicited adverse events" are any adverse events (AEs) that are not solicited local or systemic AEs, as defined above.

As used herein, a "serious adverse event" or "SAE" is any untoward medical occurrence or effect that at any dose results in death, is life-threatening, requires inpatient hospitalization or prolongation of existing hospitalization, results in persistent or significant disability/incapacity, is a congenital anomaly/birth defect or is medically important due to other reasons than the above mentioned criteria.

The relationship of each AE, including solicited systemic AEs (solicited local AEs are considered as related) to trial vaccine(s) will be assessed using the following categories: As used herein, "IP-Related AE" or "vaccine related AE" means that there is suspicion that there is a relationship between the vaccine and the AE (without determining the extent of probability); there is a reasonable possibility that the vaccine contributed to the AE. As used herein, "Non-IP Related" or "non-vaccine related" means that there is no suspicion that there is a relationship between the vaccine and the AE; there are other more likely causes and administration of the vaccine is not suspected to have contributed to the AE.

As used herein, a subject or subject population being "2 to 60 years of age" "or 18 to 60 years of age" refers to a subject or subject population being 2 to 60 years of age or 18 to 60 years of age on the first day of the administration of the dengue vaccine composition as described herein.

As used herein "%-points" refers to the difference of two %-values in a %-value. For example two values in % which are within 5%-points refers to e.g. one value at 1% and a second value at 6%.

As used herein, the term "determination of the previous dengue infection in the subject before administration" means that a previous dengue infection has to be assessed before vaccination in that there is a laboratory confirmed history of dengue or through an appropriately validated serological test e.g. by the method as disclosed herein such as the MNT50 test described in Example 2 or any serotesting with adequate performance in terms of specificity and cross reactivity based on the locale disease epidemiology.

As used herein % w/v refers to % mg/ml wherein e.g. 150 mg/ml are 15% w/v.

As used herein, the term "hepatitis A virus" may be abbreviated as "HAV".

As used herein, the term "placebo" may be abbreviated as "Pbo".

As used herein, "hepatitis A seronegative at baseline" or "hepatitis A naïve (at baseline)" each mean that a subject does not have a predefined amount of anti-hepatitis A antibodies in the serum. Quantitatively, the hepatitis A seronegativity of a subject is defined as an anti-hepatitis A antibody level of <10 mIU/ml. When anti-hepatitis A antibody levels are determined by ELISA, the lower level of quantification is 12.5 mIU/ml which is effectively the lower anti-HAV antibody level for determining seronegativity. Subjects having anti-hepatitis A antibody levels of ≥12.5 mIU/ml are defined as hepatitis A seropositive. An ELISA for determining the anti-hepatitis A antibodies is for example disclosed in Beck et al. J Travel Med 2004; 11:201-207.

As used herein, "at baseline" refers to the time point of the last measurement of a subject's serostatus prior to the first vaccination.

As used herein, the unit "mIU/ml" refers to milli-international unit per milliliter. This concentration unit refers to a quantity of anti-hepatitis A antibodies in a subject's serum (e.g. when measured prior or after vaccination). As used herein, the "viral antigen activity of hepatitis A vaccines" of the present invention is expressed in terms of a standard recommendation of the WHO using an enzyme-linked immunosorbent assay (ELISA). According to this recommendation of the WHO (see WHO Information Sheet "Observed Rate of Vaccine Reactions—Hepatitis A Vaccine", published June 2012), the viral antigen activity of a hepatitis A vaccine is expressed in terms of ELISA Units (EL.U.). The viral antigen activity of a hepatitis A vaccine can for example be determined by an ELISA according to Andre F E., Hepburn A. D'Hondt E., "Inactivated candidate vaccines for hepatitis", A. Prog Med Virol 1990; 37:72-95.

As used herein, the term "CCID" refers to the quantity of virus (e.g. vaccinal virus) infecting 50% of the cell culture. The CCID50 assay is a limit dilution assay with statistical titer calculation (Morrison D et al, J Infect Dis. 2010; 201(3):370-7)).

"Non-inferiority", as used herein, with respect to a simultaneous on the same day administration of a hepatitis A vaccine and a tetravalent dengue vaccine is in particular concluded, if the seroprotection rate (SPR) difference between the SPR of a subject group receiving HAV and placebo (simultaneously on the same day, i.e. control subject population) and the SPR of a subject group receiving HAV and TDV (simultaneously on the same day) has an upper bound of a two-sided 95% confidence interval which is lower than the non-inferiority margin set at 10%, wherein seroprotection rates are based on measurements on day 30 after the simultaneous administration on day 1, calculated using the Newcombe score method. A non-inferiority clinical study is a study designed to provide a comparison between at least two methods of treatments, in the present case between a simultaneous administration of a dengue vaccine and a hepatitis A vaccine and a mono-administration of either a dengue vaccine or a hepatitis A vaccine.

As used herein, the term "seroprotection rate", abbreviated "SPR", is defined by the proportion/percentage of HAV or DEN-naive subjects at baseline who are seroprotected against HAV or DENV, respectively, at day 30 (month 1) after the first vaccination.

As used herein, the term "control subject population" refers to a group of subjects which does not receive a simultaneous administration of a hepatitis A vaccine and a unit dose of a dengue vaccine composition, but a single verum (such as a hepatitis A vaccine or a unit dose of a dengue vaccine composition) and a placebo on the same day in a clinical study setting as e.g. in a non-inferiority clinical study.

As used herein, the term "synergism" or "synergy" is defined as an effect of simultaneously on the same day administering the hepatitis A vaccine and the unit dose of the dengue vaccine composition to a subject or subject population, wherein said administering provides a higher anti-hepatitis A antibody concentration and/or a higher mean titer of neutralizing antibodies against each of the dengue virus serotypes than the corresponding simultaneous administration of a hepatitis A vaccine and a placebo on the same day and/or the simultaneous administration of a unit dose of the dengue vaccine composition and a placebo on the same day (mono-administrations). Such higher antibody concentrations after simultaneous administration in comparison to the mono-administrations are signs in favor of the simultaneous administration.

BRIEF DESCRIPTION OF THE DRAWINGS

FIG. 1: Genetic structure of the four dengue strains contained in TDV. The solid red triangles indicate the three attenuating mutations present in the 5'NCR, NS1 and NS3 proteins. The TDV-1, TDV-3 and TDV-4 strains are chimeric viruses where the prM and E genes from dengue serotype 1, 3 and 4, respectively, are inserted into the TDV-2 backbone.

FIG. 4: Cumulative incidence of A) virologically-confirmed dengue cases and B) hospitalized virologically-confirmed dengue cases over time during Part 1 study period by baseline serostatus (safety set data; data presented truncated at Month 18). Tables show numbers of participants under follow-up at various time points to end of Part 1 study period.

DETAILED DESCRIPTION

Dengue Virus Strains

Figure 2:
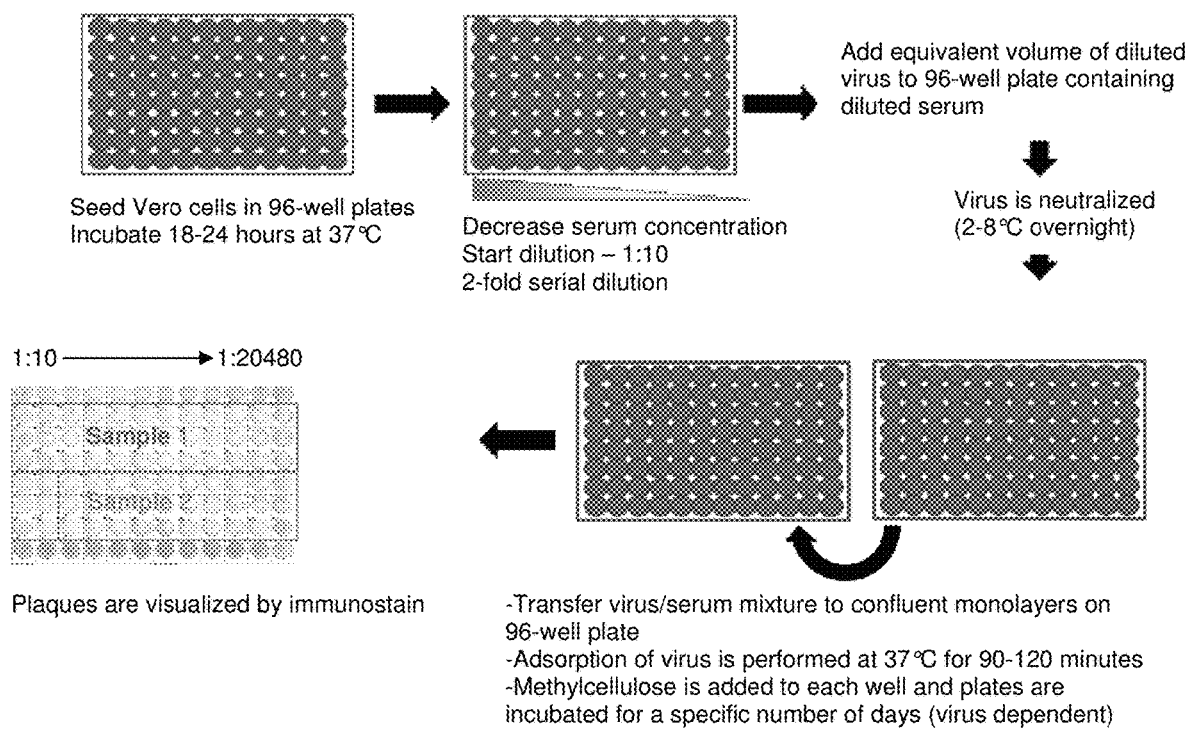
FIG. 2: Schematic drawing illustrating the microneutralization test (MNT) used to determine the titer of neutralizing antibodies.

The dengue virus is a single stranded, positive sense RNA virus of the family flaviviridae. The taxonomy is outlined in Table 1. The family flaviviridae includes three genera, flavivirus, hepacivirus and pestivirus. The genus flavivirus contains highly pathogenic and potentially hemorrhagic fever viruses, such as yellow fever virus and dengue virus, encephalitic viruses, such as Japanese encephalitis virus, Murray Valley encephalitis virus and West Nile virus, and a number of less pathogenic viruses.

TABLE 1

| Dengue Virus Taxonomy of the GMO Parental Strain | |
|---|---|
| Family | Flaviviridae |
| Genus | Flavivirus |
| Species | Dengue virus |
| Strains | Dengue Serotype 2 (Strain 16681), Strain DEN-2 PDK-53 |
| GMO parent | TDV-2 |

Figure 1:
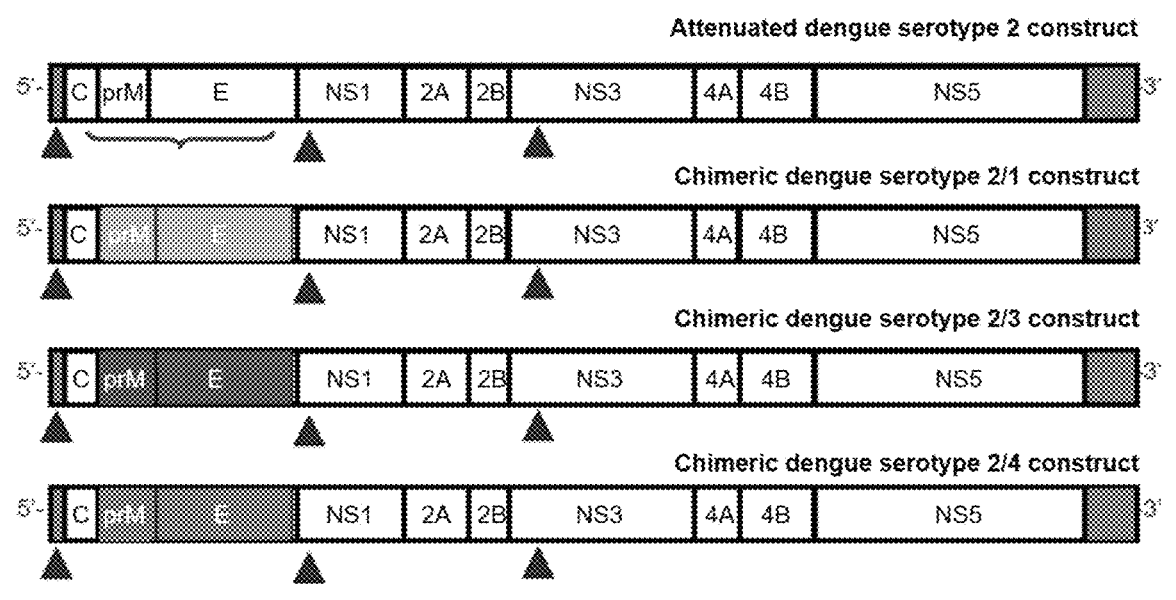

The flavivirus genome comprises in 5' to 3' direction (see FIG. 1):
 a 5'-noncoding region (5'-NCR),
 a capsid protein (C) encoding region,
 a pre-membrane protein (prM) encoding region,
 an envelope protein (E) encoding region,
 a region encoding nonstructural proteins (NSI, NS2A, NS2B, NS3, NS4A, NS4B, NS5) and
 a 3' noncoding region (3'-NCR).

The viral structural proteins are C, prM and E, and the nonstructural proteins are NSI to NS5. The structural and nonstructural proteins are translated as a single polyprotein and processed by cellular and viral proteases.

The unit dose of the invention as described herein comprises a dengue virus composition that comprises four live attenuated dengue virus strains (tetravalent dengue virus composition) representing dengue serotype 1, dengue serotype 2, dengue serotype 3 and dengue serotype 4. Preferably the composition comprises chimeric dengue viruses and optionally at least one non-chimeric dengue virus, in particular a molecularly characterized and cloned dengue serotype 2 strain derived from the live attenuated DEN-2 PDK-53 virus strain (TDV-2), and three chimeric dengue strains derived from the TDV-2 strain by replacing the structural proteins prM and E from TDV-2 with the corresponding structural proteins from the other dengue serotypes, resulting in the following chimeric dengue strains:

a DENV-2/1 chimera (TDV-1),
a DENV-2/3 chimera (TDV-3) and
a DENV-2/4 chimera (TDV-4).

The genetically modified tetravalent dengue vaccine TDV is based on a molecularly characterized and cloned dengue-2 virus strain (TDV-2). This attenuated TDV-2 strain was generated by cDNA cloning of the attenuated laboratory-derived DEN-2 PDK-53 virus strain that was originally isolated at Mahidol University, Bangkok, Thailand (Kinney et al. (1997) Virology 230(2): 300-308). DEN-2 PDK-53 was generated by 53 serial passages in primary dog kidney (PDK) cells at 32° C. (Bhamarapravati et al. (1987) Bull. World Health Organ. 65(2): 189-195).

The attenuated DEN-2 PDK-53 strain (the precursor of TDV-2) was derived from the wild type virus strain DEN-2 16681 (SEQ ID NO 11) and differs in nine nucleotides from the wild type as follows (Kinney et al. (1997) Virology 230(2): 300-308):

(i) 5'-noncoding region (NCR)-57 (nt-57 C-to-T): major attenuation locus
(ii) prM-29 Asp-to-Val (nt-524 A-to-T)
(iii) nt-2055 C-to-T (E gene) silent mutation
(iv) NS1-53 Gly-to-Asp (nt-2579 G-to-A): major attenuation locus
(v) NS2A-181 Leu-to-Phe (nt-4018 C-to-T)
(vi) NS3-250 Glu-to-Val (nt-5270 A-to-T): major attenuation locus
(vii) nt-5547 (NS3 gene) T-to-C silent mutation
(viii) NS4A-75 Gly-to-Ala (nt-6599 G-to-C)
*nt-8571 C-to-T (NS5 gene) silent mutation The three nucleotide changes located in the 5' noncoding region (NCR) (nucleotide 57) (mutation (i)), the NS-1 (amino acid 828 of SEQ ID NO. 4) (mutation (iv)) and NS-3 genes (amino acid 1725 of SEQ ID NO. 4) (mutation (vi)) form the basis for the attenuation phenotype of the DEN-2 PDK-53 strain (Butrapet et al. (2000) J. Virol. 74(7): 3111-3119) (Table 2). These three mutations are referred to herein as the "attenuating mutations" and are comprised in TDV-1, TDV-2, TDV-3 and TDV-4.

TABLE 2

Attenuating mutations in the common genetic backbone of all TDV strains

| Location of Mutation | Nucleotide Change in TDV-2 | Amino Acid Change in TDV-2 |
|---|---|---|
| 5' Noncoding Region (5'NCR) | 57 C to T | Not applicable (silent) |
| Nonstructural Protein 1 (NS1) | 2579 G to A | 828 Gly to Asp |
| Nonstructural Protein 3 (NS3) | 5270 A to T | 1725 Glu to Val |

In one embodiment, TDV-2 comprises in addition to the three attenuating mutations one or more mutations selected from:

a) a mutation in the prM gene at nucleotide 524 from adenine to thymidine resulting in an amino acid change at position 143 from asparagine to valine, and/or b) a silent mutation in the E gene at nucleotide 2055 from cytosine to thymidine, and/or c) a mutation in the NS2A gene at nucleotide 4018 from cytosine to thymidine resulting in an amino acid change at position 1308 from leucine to phenylalanine, and/or d) a silent mutation in the NS3 gene at nucleotide 5547 from thymidine to cytosine, and/or e) a mutation in the NS4A gene at nucleotide 6599 from guanine to cytosine resulting in an amino acid change at position 2168 from glycine to alanine, and/or f) a silent mutation in the prM gene at nucleotide 900 from thymidine to cytosine.

The silent mutation in the NS5 gene at nucleotide 8571 from cytosine to thymidine of DEN-2 PDK-53 is not present in the TDV-2 strain.

In another embodiment, TDV-2 comprises in addition to the three attenuating mutations one or more mutations selected from:

g) a mutation in the prM gene at nucleotide 592 from adenine to guanine resulting in an amino acid change at position 166 from lysine to glutamine, and/or h) a mutation in the NS5 gene at nucleotide 8803 from adenine to guanine resulting in an amino acid change at position 2903 from isoleucine to valine.

In another embodiment, TDV-2 comprises in addition to the three attenuating mutations the mutations a) and g), preferably the mutations a), g), c), e) and h), more preferably the mutations a), g), c), e), h) and b), even more preferably the mutations a), g), c), e), h), b) and d), and most preferably the mutations a) to h). The nucleotide positions and amino acids positions of TDV-2 refer to the nucleotide sequence as shown in SEQ ID NO. 3 and amino acid sequence as shown in SEQ ID NO. 4.

The dengue virus structural envelope (E) protein and pre-membrane (prM) protein have been identified as the primary antigens that elicit a neutralizing protective antibody response (Plotkin 2001). For creation of the tetravalent dengue vaccine (TDV), TDV-2 was modified by replacing the nucleic acid sequence encoding the DENV-2 prM and E glycoproteins with the nucleic acid sequence encoding the corresponding wild type prM and E glycoproteins from the DENV-1, DENV-3, and DENV-4 wild type strains DENV-1 16007, DENV-3 16562 or DENV-4 1036 virus, respectively, (see Table 3) using standard molecular genetic engineering methods (Huang et al. (2003) J. Virol. 77(21): 11436-11447).

TABLE 3

Viral origin of prM/E gene regions of the TDV virus strains

| Virus | Strain | Origin | Source | Reference | Nucleotide sequence | Amino acid sequence |
|---|---|---|---|---|---|---|
| DENV-1 | 16007 | Thailand, 1964 | DHF/DSS patient | Halstead and Simasthien, 1970 | SEQ ID NO. 9 | SEQ ID NO. 10 |
| DENV-2 | 16681 | Thailand, 1964 | DHF/DSS patient | Halstead and Simasthien, 1970 | SEQ ID NO. 11 | SEQ ID NO. 12 |
| DENV-3 | 16562 | Philippines, 196 | DHF patient | Halstead and Simasthien, 1970 | SEQ ID NO. 13 | SEQ ID NO. 14 |
| DENV-4 | 1036 | Indonesia, 1976 | DF patient | Gubler et al., 1979 | SEQ ID NO. 15 | SEQ ID NO. 16 |

A diagram of the four TDV strains comprised in the dengue vaccine composition is shown in FIG. 1.

The chimeric dengue strains TDV-1, TDV-3 and TDV-4 express the surface antigens prM and E of the DENV-1, DENV-3 or DENV-4 viruses, as depicted in Table 3 respectively, and retain the genetic alterations responsible for the attenuation of TDV-2. Thus, each of the TDV-1, TDV-3 and TDV-4 strains comprises the attenuating mutations described in Table 2.

In one embodiment, TDV-1 comprises in addition to the three attenuating mutations one or more mutations selected from:

c) a mutation in the NS2A gene at nucleotide 4018 from cytosine to thymidine resulting in an amino acid change at position 1308 from leucine to phenylalanine, and/or d) a silent mutation in the NS3 gene at nucleotide 5547 from thymidine to cytosine, and/or e) a mutation in the NS4A gene at nucleotide 6599 from guanine to cytosine resulting in an amino acid change at position 2168 from glycine to alanine, and/or i) a silent mutation in the E gene at nucleotide 1575 from thymidine to cytosine, and/or j) a silent mutation in the junction site between the prM-E gene and the DEN-2 PDK-53 backbone at nucleotide 453 from adenine to guanine, and/or k) a mutation in the junction site between the prM-E gene and the DEN-2 PDK-53 backbone at nucleotides 2381/2382 from thymidine-guanine to cytosine-cytosine resulting in an amino acid change at position 762 from valine to alanine.

In another embodiment, TDV-1 comprises in addition to the three attenuating mutations one or more mutations selected from:

l) a mutation in the NS2A gene at nucleotide 3823 from adenine to cytosine resulting in an amino acid change at position 1243 from isoleucine to leucine, and/or m) a mutation in the NS2B gene at nucleotide 4407 from adenine to thymidine resulting in an amino acid change at position 1437 from glutamine to asparagine, and/or n) a silent mutation in the NS4B gene at nucleotide 7311 from adenine to guanine.

In another embodiment, the TDV-1 strain comprises in addition to the three attenuating mutations the mutations l) and m), preferably the mutations l), m), c) and e), even more preferably the mutations l), m), c), e), d) and n), and most preferably the mutations l), m), c), e), d), n), i), j) and k). The nucleotide positions and amino acids positions of TDV-1 refer to the nucleotide sequence as shown in SEQ ID NO. 1 and amino acid sequence as shown in SEQ ID NO. 2.

In one embodiment, TDV-3 comprises in addition to the three attenuating mutations one or more mutations selected from:

c) a mutation in the NS2A gene at nucleotide 4012 from cytosine to thymidine resulting in an amino acid change at position 1306 from leucine to phenylalanine, and/or d) a silent mutation in the NS3 gene at nucleotide 5541 from thymidine to cytosine, and/or e) a mutation in the NS4A gene at nucleotide 6593 from guanine to cytosine resulting in an amino acid change at position 2166 from glycine to alanine, and/or j) a silent mutation in the junction site between the prM-E gene and the DEN-2 PDK-53 backbone at nucleotide 453 from adenine to guanine, and/or k) a mutation in the junction site between the prM-E gene and the DEN-2 PDK-53 backbone at nucleotides 2375/2376 from thymidine-guanine to cytosine-cytosine resulting in an amino acid change at position 760 from valine to alanine, and/or o) a silent mutation in the prM gene at nucleotide 552 from cytosine to thymidine, and/or p) a mutation in the E gene at nucleotide 1970 from adenine to thymidine resulting in an amino acid change at position 625 from histidine to leucine.

In another embodiment, TDV-3 comprises in addition to the three attenuating mutations one or more mutations selected from:

q) a mutation in the E gene at nucleotide 1603 from adenine to thymidine resulting in an amino acid change at position 503 from threonine to serine, and/or r) a silent mutation in the NS5 gene at nucleotide 7620 from adenine to guanine.

In another embodiment, TDV-3 comprises in addition to the three attenuating mutations the mutations p) and q), preferably the mutations p), q), c) and e), even more preferably the mutations p), q), c), e), d) and r), and most preferably the mutations p), q), c), e), d), r), j), k) and o). The nucleotide positions and amino acids positions of TDV-3 refer to the nucleotide sequence as shown in SEQ ID NO. 5 and amino acid sequence as shown in SEQ ID NO. 6.

In one embodiment, TDV-4 comprises in addition to the three attenuating mutations one or more mutations selected from:

c) a mutation in the NS2A gene at nucleotide 4018 from cytosine to thymidine resulting in an amino acid change at position 1308 from leucine to phenylalanine, and/or d) a silent mutation in the NS3 gene at nucleotide 5547 from thymidine to cytosine, and/or e) a mutation in the NS4A gene at nucleotide 6599 from guanine to cytosine resulting in an amino acid change at position 2168 from glycine to alanine, and/or j) a silent mutation in the junction site between the prM-E gene and the DEN-2 PDK-53 backbone at nucleotide 453 from adenine to guanine, and/or k) a mutation in the junction site between the prM-E gene and the DEN-2 PDK-53 backbone at nucleotides 2381/2382 from thymidine-guanine to cytosine-cytosine resulting in an amino acid change at position 762 from valine to alanine, and/or s) a mutation in the C gene at nucleotide 396 from adenine to cytosine resulting in an amino acid change at position 100 from arginine to serine, and/or t) a silent mutation in the E gene at nucleotide 1401 from adenine to guanine, and/or u) a mutation in the E gene at nucleotide 2027 from cytosine to thymidine resulting in an amino acid change at position 644 from alanine to valine, and/or v) a mutation in the E gene at nucleotide 2275 from adenine to cytosine resulting in an amino acid change at position 727 from methionine to leucine.

In another embodiment, TDV-4 comprises in addition to the three attenuating mutations one or more mutations selected from:

w) a silent mutation in the C gene at nucleotide 225 from adenine to thymidine, and/or x) a mutation in the NS2A gene at nucleotide 3674 from adenine to guanine resulting in an amino acid change at position 1193 from asparagine to glycine, and/or y) a mutation in the NS2A gene at nucleotide 3773 from adenine to an adenine/guanine mix resulting in an amino acid change at position 1226 from lysine to a lysine/asparagine mix, and/or z) a silent mutation in the NS3 gene at nucleotide 5391 from cytosine to thymidine, and/or aa) a mutation in the NS4A gene at nucleotide 6437 from cytosine to thymidine resulting in an amino acid change at position 2114 from alanine to valine, and/or bb) a silent mutation in the NS4B gene at nucleotide 7026 from thymidine to a thymidine/cytosine mix, and/or cc) a silent mutation in the NS5 gene at nucleotide 9750 from adenine to cytosine.

In another embodiments, TDV-4 comprises in addition to the three attenuating mutations the mutation s), u) and v), preferably the mutations s), u), v), c), e), x), y) and aa), even more preferably the mutations s), u), v), c), e), x), y), aa) and w), even more preferably the mutations s), u), v), c), e), x), y), aa), w), d), z), bb) and cc), and most preferably the mutations s), u), v), c), e), x), y), aa), w), d), z), bb), cc), j), k) and t). The nucleotide positions and amino acids positions of TDV-4 refer to the nucleotide sequence as shown in SEQ ID NO. 7 and amino acid sequence as shown in SEQ ID NO. 8.

In a preferred embodiment, TDV-1 has the nucleotide sequence of SEQ ID NO. 1, TDV-2 has the nucleotide sequence of SEQ ID NO. 3, TDV-3 has the nucleotide sequence of SEQ ID NO. 5, and/or TDV-4 has the nucleotide sequence of SEQ ID NO. 7. In a further preferred embodiment, TDV-1 has the amino acid sequence of SEQ ID NO. 2, TDV-2 has the amino acid sequence of SEQ ID NO. 4, TDV-3 has the amino acid sequence of SEQ ID NO. 6, and TDV-4 has the amino acid sequence of SEQ ID NO. 8. In a further preferred embodiment, TDV-1 has a nucleotide sequence encoding the amino acid sequence of SEQ ID NO. 2, TDV-2 has a nucleotide sequence encoding the amino acid sequence of SEQ ID NO. 4, TDV-3 has a nucleotide sequence encoding the amino acid sequence of SEQ ID NO. 6, and TDV-4 has a nucleotide sequence encoding the amino acid sequence of SEQ ID NO. 8.

TABLE 4

Sequences of the TDV virus strains

| SEQ ID NO. | dengue virus strain | sequence type |
|---|---|---|
| SEQ ID NO. 1 | TDV-1 | nucleotide sequence |
| SEQ ID NO. 2 | TDV-1 | amino acid sequence |
| SEQ ID NO. 3 | TDV-2 | nucleotide sequence |
| SEQ ID NO. 4 | TDV-2 | amino acid sequence |
| SEQ ID NO. 5 | TDV-3 | nucleotide sequence |
| SEQ ID NO. 6 | TDV-3 | amino acid sequence |
| SEQ ID NO. 7 | TDV-4 | nucleotide sequence |
| SEQ ID NO. 8 | TDV-4 | amino acid sequence |

Thus, in a particularly preferred embodiment, the unit dose of the invention as described herein comprises the live attenuated dengue virus strains TDV-1, TDV-2, TDV-3 and TDV-4, wherein TDV-1, TDV-3 and TDV-4 are based on TDV-2 and comprise the prM and E regions of DENV-1, -3 and -4, respectively. In another particularly preferred embodiment, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The E protein of DENV-3 has two fewer amino acids than the E protein of DENV-2. Therefore, the nucleotides and encoded amino acid backbone of TDV-2 starting after the E region of DENV-3 at nucleotide 2374 of SEQ ID NO. 5 and amino acid 760 of SEQ ID NO. 6 are 6 nucleotides less and 2 amino acids less than the original TDV-2 nucleotide and amino acid positions, respectively.

Dengue Vaccine Composition

The present invention is in part directed to a unit dose of a dengue vaccine composition as described. The dengue vaccine composition comprises a tetravalent dengue virus composition, also referred to as dengue virus composition, and pharmaceutically acceptable excipients.

Dengue Virus Composition, Virus Concentrations and %-Concentrations

The present invention is in part directed to a unit dose of a dengue vaccine composition, wherein the dengue vaccine composition comprises a tetravalent dengue virus composition including four live attenuated dengue virus strains:
(i) a dengue serotype 1 preferably in a concentration of at least 3.3 log 10 pfu/0.5 mL,
(ii) a dengue serotype 2 preferably in a concentration of at least 2.7 log 10 pfu/0.5 mL,
(iii) a dengue serotype 3 preferably in a concentration of at least 4.0 log 10 pfu/0.5 mL, and
(iv) a dengue serotype 4 preferably strain in a concentration of at least 4.5 log 10 pfu/0.5 mL.

In one embodiment, the dengue vaccine composition comprises a tetravalent dengue virus composition including four live attenuated dengue virus strains:
(i) a dengue serotype 1 preferably in a concentration of at least 3.3 log 10 pfu/0.5 mL to 3.8 log 10 pfu/0.5 mL,
(ii) a dengue serotype 2 preferably in a concentration of at least 2.7 log 10 pfu/0.5 mL, (iii) a dengue serotype 3 preferably in a concentration of at least 4.0 log 10 pfu/0.5 mL, and (iv) a dengue serotype 4 preferably strain in a concentration of at least 4.5 log 10 pfu/0.5 ml or 4.6 log 10 pfu/0.5 mL, optionally to 6.2 log 10 pfu/0.5 ml.

The present invention is further in part directed to a unit dose of a dengue vaccine composition, wherein the dengue vaccine composition comprises a tetravalent dengue virus composition including four live attenuated dengue virus strains:

(i) a chimeric dengue serotype 2/1 strain in a concentration of at least 3.3 log 10 pfu/0.5 mL, (ii) a dengue serotype 2 strain in a concentration of at least 2.7 log 10 pfu/0.5 mL, (iii) a chimeric dengue serotype 2/3 strain in a concentration of at least 4.0 log 10 pfu/0.5 mL, and (iv) a chimeric dengue serotype 2/4 strain in a concentration of at least 4.5 log 10 pfu/0.5 mL.

In one embodiment, the dengue vaccine composition comprises a tetravalent dengue virus composition including four live attenuated dengue virus strains:

(i) a chimeric dengue serotype 2/1 strain in a concentration of at least 3.3 log 10 pfu/0.5 mL to 3.8 log 10 pfu/0.5 ml, (ii) a dengue serotype 2 strain in a concentration of at least 2.7 log 10 pfu/0.5 mL, (iii) a chimeric dengue serotype 2/3 strain in a concentration of at least 4.0 log 10 pfu/0.5 mL, and (iv) a chimeric dengue serotype 2/4 strain in a concentration of at least 4.5 log 10 pfu/0.5 mL or at least 4.6 log 10 pfu/0.5 mL to optionally 6.2 log 10 pfu/0.5 ml.

Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In one embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.3 log 10 pfu/0.5 mL to 5.3 log 10 pfu/0.5 mL, (ii) the dengue serotype 2 (e.g. dengue serotype 2 strain) has a concentration of 2.7 log 10 pfu/0.5 mL to 5.0 log 10 pfu/0.5 mL, (iii) the dengue serotype 3 (e.g. chimeric dengue serotype 2/3 strain) has a concentration of 4.0 log 10 pfu/0.5 mL to 6.0 log 10 pfu/0.5 mL, and (iv) the dengue serotype 4 (e.g. chimeric dengue serotype 2/4 strain) has a concentration of 4.5 log 10 pfu/0.5 mL to 6.5 log 10 pfu/0.5 mL.

In one such embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.3 log 10 pfu/0.5 mL to 5.0 log 10 pfu/0.5 mL, (ii) the dengue serotype 2 (e.g. dengue serotype 2 strain) has a concentration of 2.7 log 10 pfu/0.5 mL to 4.9 log 10 pfu/0.5 mL, (iii) the dengue serotype 3 (e.g. chimeric dengue serotype 2/3 strain) has a concentration of 4.0 log 10 pfu/0.5 mL to 5.7 log 10 pfu/0.5 mL, and (iv) the dengue serotype 4 (e.g. chimeric dengue serotype 2/4 strain) has a concentration of 4.5 log 10 pfu/0.5 mL to 6.2 log 10 pfu/0.5 mL.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/dose to 5.0 log 10 pfu/dose, (ii) a dengue serotype 2 (e.g. dengue serotype 2 strain) has a concentration of 2.7 log 10 pfu/dose to 4.9 log 10 pfu/dose, (iii) a dengue serotype 3 (e.g. chimeric dengue serotype 2/3 strain) has a concentration of 4.0 log 10 pfu/dose to 5.7 log 10 pfu/dose, and (iv) a dengue serotype 4 (e.g. chimeric dengue serotype 2/4 strain) has a concentration of 4.5 log 10 pfu/dose to 5.5 log 10 pfu/dose.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/dose to 4.1 log 10 pfu/dose, (ii) a dengue serotype 2 (e.g. dengue serotype 2 strain) has a concentration of 2.7 log 10 pfu/dose to 3.6 log 10 pfu/dose, (iii) a dengue serotype 3 (e.g. chimeric dengue serotype 2/3 strain) has a concentration of 4.0 log 10 pfu/dose to 4.7 log 10 pfu/dose, and (iv) a dengue serotype 4 (e.g. chimeric dengue serotype 2/4 strain) has a concentration of 4.5 log 10 pfu/dose to 5.3 log 10 pfu/dose.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/0.5 mL to 3.6 log 10 pfu/0.5 mL, (ii) a dengue serotype 2 (e.g. dengue serotype 2 strain) has a concentration of 2.7 log 10 pfu/0.5 mL to 4.0 log 10 pfu/0.5 mL, (iii) a dengue serotype 3 (e.g. chimeric dengue serotype 2/3 strain) has a concentration of 4.0 log 10 pfu/0.5 mL to 4.6 log 10 pfu/0.5 mL, and (iv) a dengue serotype 4 (e.g. chimeric dengue serotype 2/4 strain) has a concentration of 4.5 log 10 pfu/0.5 ml or 4.6 log 10 pfu/0.5 mL to 5.1 log 10 pfu/0.5 mL.

In another embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 4.3 log 10 pfu/0.5 mL to 4.4 log 10 pfu/0.5 mL, (ii) the dengue serotype 2 (e.g. dengue serotype 2 strain) has a concentration of 3.7 log 10 pfu/0.5 mL to 3.8 log 10 pfu/0.5 mL, (iii) the dengue serotype 3 (e.g. chimeric dengue serotype 2/3 strain) has a concentration of 4.5 log 10 pfu/0.5 mL to 5.0 log 10 pfu/0.5 mL, and (iv) the dengue serotype 4 (e.g. chimeric dengue serotype 2/4 strain) has a concentration of 5.5 log 10 pfu/0.5 mL to 5.6 log 10 pfu/0.5 mL.

In a particularly preferred embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 4.4 log 10 pfu/0.5 mL, (ii) the dengue serotype 2 (e.g. dengue serotype 2 strain) has a concentration of 3.8 log 10 pfu/0.5 mL,
(iii) the dengue serotype 3 (e.g. chimeric dengue serotype 2/3 strain) has a concentration of 4.5 log 10 pfu/0.5 mL, and
(iv) the dengue serotype 4 (e.g. chimeric dengue serotype 2/4 strain) has a concentration of 5.6 log 10 pfu/0.5 mL.

In another particularly preferred embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 3.6 log 10 pfu/0.5 mL,
(ii) the dengue serotype 2 (e.g. dengue serotype 2 strain) has a concentration of 4.0 log 10 pfu/0.5 mL,
(iii) the dengue serotype 3 (e.g. chimeric dengue serotype 2/3 strain) has a concentration of 4.6 log 10 pfu/0.5 mL, and
(iv) the dengue serotype 4 (e.g. chimeric dengue serotype 2/4 strain) has a concentration of 5.1 log 10 pfu/0.5 mL.

In another preferred embodiment, the dengue vaccine composition comprises a tetravalent dengue virus composition including four live attenuated dengue virus strains wherein the arithmetic sum of all four serotypes is less than 6.7 log 10 pfu/0.5 mL, preferably less than 5.5 log 10 pfu/0.5 mL. In certain such embodiments, the arithmetic sum of all four serotypes is at least 4.6 log 10 pfu/0.5 mL. In a preferred embodiment, the dengue vaccine composition comprises a tetravalent dengue virus composition including four live attenuated dengue virus strains wherein the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The present invention is in part directed to a unit dose of a dengue vaccine composition, wherein the dengue vaccine composition comprises a tetravalent dengue virus composition including four live attenuated dengue virus strains:
(i) a dengue serotype 1 (e.g. chimeric dengue serotype 2/1 strain) in a concentration of at least 3.3 log 10 pfu/dose,
(ii) a dengue serotype 2 (e.g. dengue serotype 2 strain) in a concentration of at least 2.7 log 10 pfu/dose,
(iii) a dengue serotype 3 (e.g. chimeric dengue serotype 2/3 strain) in a concentration of at least 4.0 log 10 pfu/dose, and
(iv) a dengue serotype 4 (e.g. chimeric dengue serotype 2/4 strain) in a concentration of at least 4.5 log 10 pfu/dose.

In one embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 3.3 log 10 pfu/dose to 5.3 log 10 pfu/dose,
(ii) the dengue serotype 2 (e.g. dengue serotype 2 strain) has a concentration of 2.7 log 10 pfu/dose to 5.0 log 10 pfu/dose,
(iii) the dengue serotype 3 (e.g. chimeric dengue serotype 2/3 strain) has a concentration of 4.0 log 10 pfu/dose to 6.0 log 10 pfu/dose, and
(iv) the dengue serotype 4 (e.g. chimeric dengue serotype 2/4 strain) has a concentration of 4.5 log 10 pfu/dose to 6.5 log 10 pfu/dose.

In one such embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 3.3 log 10 pfu/dose to 5.0 log 10 pfu/dose,
(ii) the dengue serotype 2 (e.g. dengue serotype 2 strain) has a concentration of 2.7 log 10 pfu/dose to 4.9 log 10 pfu/dose,
(iii) the dengue serotype 3 (e.g. chimeric dengue serotype 2/3 strain) has a concentration of 4.0 log 10 pfu/dose to 5.7 log 10 pfu/dose, and
(iv) the dengue serotype 4 (e.g. chimeric dengue serotype 2/4 strain) has a concentration of 4.5 log 10 pfu/dose to 6.2 log 10 pfu/dose.

In a further such embodiment, the dengue vaccine composition comprises a tetravalent dengue virus composition including four live attenuated dengue virus strains wherein:
(i) a dengue serotype 1 (e.g. chimeric dengue serotype 2/1 strain) has a concentration of 3.3 log 10 pfu/dose to 5.0 log 10 pfu/dose,
(ii) a dengue serotype 2 (e.g. dengue serotype 2 strain) has a concentration of 2.7 log 10 pfu/dose to 4.9 log 10 pfu/dose,
(iii) a dengue serotype 3 (e.g. chimeric dengue serotype 2/3 strain) has a concentration of 4.0 log 10 pfu/dose to 5.7 log 10 pfu/dose, and
(iv) a dengue serotype 4 (e.g. chimeric dengue serotype 2/4 strain) has a concentration of 4.5 log 10 pfu/dose to 5.5 log 10 pfu/dose.

In a further such embodiment, the dengue vaccine composition comprises a tetravalent dengue virus composition including four live attenuated dengue virus strains wherein:
(i) a dengue serotype 1 (e.g. chimeric dengue serotype 2/1 strain) has a concentration of 3.3 log 10 pfu/dose to 4.1 log 10 pfu/dose,
(ii) a dengue serotype 2 (e.g. dengue serotype 2 strain) has a concentration of 2.7 log 10 pfu/dose to 3.6 log 10 pfu/dose,
(iii) a dengue serotype 3 (e.g. chimeric dengue serotype 2/3 strain) has a concentration of 4.0 log 10 pfu/dose to 4.7 log 10 pfu/dose, and
(iv) a dengue serotype 4 (e.g. chimeric dengue serotype 2/4 strain) has a concentration of 4.5 log 10 pfu/dose to 5.3 log 10 pfu/dose.

In a further such embodiment, the dengue vaccine composition comprises a tetravalent dengue virus composition including four live attenuated dengue virus strains wherein:
(i) a dengue serotype 1 (e.g. chimeric dengue serotype 2/1 strain) has a concentration of 3.3 log 10 pfu/dose to 3.6 log 10 pfu/dose,
(ii) a dengue serotype 2 (e.g. dengue serotype 2 strain) has a concentration of 2.7 log 10 pfu/dose to 4.0 log 10 pfu/dose,
(iii) a dengue serotype 3 (e.g. chimeric dengue serotype 2/3 strain) has a concentration of 4.0 log 10 pfu/dose to 4.6 log 10 pfu/dose, and (iv) a dengue serotype 4 (e.g. chimeric dengue serotype 2/4 strain) has a concentration of 4.5 log 10 pfu/dose 4.6 log 10 pfu/dose to 5.1 log 10 pfu/dose.

In another embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 4.3 log 10 pfu/dose to 4.4 log 10 pfu/dose,
(ii) the dengue serotype 2 (e.g. dengue serotype 2 strain) has a concentration of 3.7 log 10 pfu/dose to 3.8 log 10 pfu/dose,
(iii) the dengue serotype 3 (e.g. chimeric dengue serotype 2/3 strain) has a concentration of 4.5 log 10 pfu/dose to 5.0 log 10 pfu/dose, and
(iv) the dengue serotype 4 (e.g. chimeric dengue serotype 2/4 strain) has a concentration of 5.5 log 10 pfu/dose to 5.6 log 10 pfu/dose.

In a particularly preferred embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 4.4 log 10 pfu/dose,
(ii) the dengue serotype 2 (e.g. dengue serotype 2 strain) has a concentration of 3.8 log 10 pfu/dose,
(iii) the dengue serotype 3 (e.g. chimeric dengue serotype 2/3 strain) has a concentration of 4.5 log 10 pfu/dose, and
(iv) the dengue serotype 4 (e.g. chimeric dengue serotype 2/4 strain) has a concentration of 5.6 log 10 pfu/dose.

In another particularly preferred embodiment, the dengue vaccine composition comprises a tetravalent dengue virus composition including four live attenuated dengue virus strains wherein:
(i) the dengue serotype 1 (e.g. chimeric dengue serotype 2/1 strain) has a concentration of 3.6 log 10 pfu/dose,
(ii) the dengue serotype 2 (e.g. dengue serotype 2 strain) has a concentration of 4.0 log 10 pfu/dose,
(iii) the dengue serotype 3 (e.g. chimeric dengue serotype 2/3 strain) has a concentration of 4.6 log 10 pfu/dose, and
(iv) the dengue serotype 4 (e.g. chimeric dengue serotype 2/4 strain) has a concentration of 5.1 log 10 pfu/dose.

In another preferred embodiment, the dengue vaccine composition comprises a tetravalent dengue virus composition including four live attenuated dengue virus strains wherein the arithmetic sum of all four serotypes is less than 6.7 log 10 pfu/dose, preferably less than 5.5 log 10 pfu/dose. In certain such embodiments, the arithmetic sum of all four serotypes is at least 4.6 log 10 pfu/dose. In a preferred embodiment, the dengue vaccine composition comprises a tetravalent dengue virus composition including four live attenuated dengue virus strains wherein the arithmetic sum of all four serotypes is in the range of 4.6 log 10 pfu/dose to 6.7 log 10 pfu/dose, preferably in the range of 4.6 log 10 pfu/dose to 5.5 log 10 pfu/dose.

In one embodiment in the composition (i), (ii), (iii), and (iv) provide a total concentration of pfu/0.5 mL and based on said concentration, the concentration of (iii) at least 10% of the total concentration in pfu/0.5 mL.

In one embodiment in the composition (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 6%, or at least 8%, or at least 10%, or at least 12%, or at least 14%, or at least 16%, or at least 18%.

It is preferred that the concentration in the reconstituted unit dose of (iii) in pfu/0.5 mL is at least 10%.

In one embodiment in the composition (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The concentration of the different dengue viruses is preferably determined by an immuno-focus assay known in the art. For example, the concentration may be determined by an immuno-focus assay wherein serial dilutions of dengue virus are applied to monolayers of adherent cells, such as Vero cells. After a period of time which allows infectious viruses to bind to the cells and to be taken up by the cells, an overlay containing thickening agents, such as agarose or carboxymethylcellulose, is added to prevent diffusion of viruses so that progeny viruses can only infect cells adjacent to the original infected cells. After a period of incubation to allow viral replication, cells are fixed and stained using serotype-specific anti-dengue monoclonal antibodies and a secondary antibody such as an antibody labeled with alkaline phosphatase. The foci are stained by adding a suitable substrate for the enzyme attached to the secondary antibody, such as 5-bromo-4-chloro-3-indolyl-phosphate/nitro blue tetrazolium phosphatase substrate. The number of plaques on the plate corresponds to the plaque forming units of the virus in the solutions applied to the cells. For example, a concentration of 1,000 pfu/µl indicates that 1 µl of the solution applied to the cells contains enough viruses to produce 1,000 plaques in a cell monolayer.

The dengue vaccine composition comprises a tetravalent dengue virus composition including four live attenuated dengue virus strains, wherein a chimeric dengue serotype 2/1 strain, a dengue serotype 2 strain, a chimeric dengue serotype 2/3 strain, and a chimeric dengue serotype 2/4 strain provide a total concentration in pfu/0.5 mL. The term "total concentration in pfu/0.5 mL" or "total concentration in pfu/dose" is the sum of the concentrations of the dengue serotype 1 (e.g. chimeric dengue serotype 2/1 strain), dengue serotype 2 (e.g. the dengue serotype 2 strain), the dengue serotype 3 (e.g. chimeric dengue serotype 2/3 strain) and the dengue serotype 4 (e.g. chimeric dengue serotype 2/4 strain), preferably the sum of the concentrations of TDV-1, TDV-2, TDV-3 and TDV-4, and is defined as 100% of the dengue virus concentration as determined by pfu (plaque forming units) in 0.5 mL or in a dose.

In one embodiment, the dengue vaccine composition comprises a tetravalent dengue virus composition including four live attenuated dengue virus strains, wherein a dengue serotype 1 (e.g. chimeric dengue serotype 2/1 strain), a dengue serotype 2 (e.g. dengue serotype 2 strain), a dengue serotype 3 (e.g. chimeric dengue serotype 2/3 strain), and a dengue serotype 4 (e.g. chimeric dengue serotype 2/4 strain) provide a total concentration in pfu/0.5 mL, wherein based on said total concentration the concentration of a dengue serotype 2 (e.g. dengue serotype 2 strain) measured in pfu/0.5 mL is less than 10% of the total concentration, or less than 8%, or less than 6% of the total concentration, and wherein the concentration of a dengue serotype 4 (e.g. chimeric dengue serotype 2/4 strain) measured in pfu/0.5 mL is at least 50% or at least 60% or at least 65% of the total concentration. In one embodiment, based on said total concentration the concentration of a dengue serotype 2 (e.g. dengue serotype 2 strain) measured in pfu/0.5 mL is 0.3 to 10% or 0.5 to 8% of the total concentration and the concentration of a dengue serotype 4 (e.g. chimeric dengue serotype 2/4 strain) measured in pfu/0.5 mL is 50% to 90% or 60% to 88% of the total concentration. This means that the concentration of the dengue serotype 2 (e.g. dengue serotype 2 strain) is lower than the concentration of the dengue serotype 4 (e.g. chimeric dengue serotype 2/4 strain).

In one such embodiment, the concentration of a dengue serotype 1 (e.g. chimeric dengue serotype 2/1 strain) measured in pfu/0.5 mL is at least 1% of the total concentration, and/or the concentration of a dengue serotype 3 (e.g. chimeric dengue serotype 2/3 strain) measured in pfu/0.5 mL is at least 6% of the total concentration, or at least 7% or 8%, 10%, 12%, 14%, 16% or 18% of the total concentration. In one such embodiment, the concentration of a dengue serotype 2 (e.g. chimeric dengue serotype 2/1 strain) measured in pfu/0.5 mL is 1% to 7% or 2% to 6% or 2.0% to 5.0% of the total concentration, and/or the concentration of a dengue serotype 3 (e.g. chimeric dengue serotype 2/3 strain) measured in pfu/0.5 mL is 6% to 25% or 7% to 25% or 10% to 25% or 18% to 25% of the total concentration. This means that the concentration of the dengue serotype 1 (e.g. chimeric dengue serotype 2/1 strain) is lower than the concentration of the dengue serotype 3 (e.g. chimeric dengue serotype 2/3 strain).

In a preferred embodiment, the concentration of a dengue serotype 2 strain, such as TDV-2, measured in pfu/0.5 mL is less than 10% of the total concentration, preferably less than 6% or less than 2%, the concentration of a dengue serotype 4 (e.g. chimeric dengue serotype 2/4 strain), such as TDV-4, measured in pfu/0.5 mL is at least 50% of the total concentration, preferably at least 65%, the concentration of a dengue serotype 1 (e.g. chimeric dengue serotype 2/1 strain), such as TDV-1, measured in pfu/0.5 mL is at least 1% of the total concentration, preferably between 1% and 7% or 2.0% to 5.0%, and the concentration of a dengue serotype 3 (e.g. chimeric dengue serotype 2/3 strain), such as TDV-3, measured in pfu/0.5 mL is at least 6% of the total concentration, preferably between 6% and 25% or 10% to 25% or 18% to 25%.

In a further preferred embodiment, a dengue virus composition comprising a dengue serotype 1 (e.g. chimeric dengue serotype 2/1 strain), a dengue serotype 2 (e.g. dengue serotype 2 strain), a dengue serotype 1 (e.g. chimeric dengue serotype 2/3 strain), and a dengue serotype 4 (e.g. chimeric dengue serotype 2/4 strain), such as TDV-1, TDV-2, TDV-3 and TDV-4, is provided, wherein the concentration of the dengue serotype 1 (e.g. chimeric dengue serotype 2/1 strain) measured in pfu/0.5 mL is at least 1% of the total concentration, preferably between 1% and 7% or 2.0% and 5.0%, the concentration of the dengue serotype 2 (e.g. dengue serotype 2 strain) measured in pfu/0.5 mL is less than 10% of the total concentration, preferably less than 6% or less than 2% and the concentration of the dengue serotype 3 (e.g. chimeric dengue serotype 2/3 strain) measured in pfu/0.5 mL is at least 6% of the total concentration, preferably between 6% and 25% or 10% to 25% or 18% to 25%. It is particularly preferred that the dengue serotype 4 (e.g. chimeric dengue serotype 2/4 strain) has the highest concentration of all four dengue serotypes.

In a further preferred embodiment, the dengue vaccine composition comprises a tetravalent dengue virus composition including four live attenuated dengue virus strains, wherein the concentration of the dengue serotype 1 (e.g. chimeric dengue serotype 2/1 strain) measured in pfu/0.5 mL is 1% to 7% of the total concentration, the concentration of the dengue serotype 2 (e.g. dengue serotype 2 strain) measured in pfu/0.5 mL is less than 8% of the total concentration, such as in the range of 1% to 8% of the total concentration, the concentration of the dengue serotype 3 (e.g. chimeric dengue serotype 2/3 strain) measured in pfu/0.5 mL is at least 10% of the total concentration, and the concentration of the dengue serotype 4 (e.g. chimeric dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

In a further preferred embodiment the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

According to a further embodiment, the chimeric dengue serotype 2/4 strain, preferably TDV-4, has the highest concentration in the dengue vaccine composition, followed by the chimeric dengue serotype 2/3 strain, preferably TDV-3, followed by the chimeric dengue serotype 2/1 strain, preferably TDV-1, followed by the dengue serotype 2 strain, preferably TDV-2. It is particularly preferred that the dengue serotype 2 strain has the lowest concentration of the four strains present in the dengue vaccine composition.

Whenever reference is made to a concentration/0.5 ml, this does not limit the volume of the unit dose described herein to 0.5 ml. 0.5 ml is the reference volume for the determination of the concentrations of the virus strains in the composition in pfu/ml. The volume and/or amount per unit dose is described in the respective chapter.

Pharmaceutically Acceptable Excipients

The present invention is in part directed to a unit dose of a dengue vaccine composition, wherein the dengue vaccine composition comprises one or more pharmaceutically acceptable excipients. In one embodiment, the dengue vaccine composition comprises a non-reducing sugar, a surfactant, a protein and an inorganic salt. Preferably, the non-reducing sugar is trehalose, the surfactant is poloxamer 407, the protein is human serum albumin and the inorganic salt is sodium chloride.

In one embodiment, the unit dose of a dengue vaccine composition comprises the following pharmaceutically acceptable excipients:

- from about 10% w/v to about 20% w/v α,α-trehalose dihydrate or an equimolar amount of other forms of α,α-trehalose,
- from about 0.5% w/v to about 1.5% w/v poloxamer 407,
- from about 0.05% w/v to about 2% w/v human serum albumin, and
- from about 70 mM to 140 mM sodium chloride.

In one embodiment, the unit dose of a dengue vaccine composition comprises the following pharmaceutically acceptable excipients when measured in 0.5 ml:

- from about 10% w/v to about 20% w/v α,α-trehalose or an equimolar amount of other forms of α,α-trehalose,
- from about 0.5% w/v to about 1.5% w/v poloxamer 407,
- from about 0.05% w/v to about 2% w/v human serum albumin, and
- from about 70 mM to 140 mM sodium chloride, and preferably
- has a pH of 7 to 8.5.

In one embodiment, the unit dose of a dengue vaccine composition comprises the following pharmaceutically acceptable excipients when measured in 0.5 ml:

- from about 143 mg/ml to about 185 mg/ml α,α-trehalose dihydrate or an equimolar amount of other forms of α,α-trehalose,
- from about 9.1 mg/ml to about 12.4 mg/ml poloxamer 407,
- from about 0.88% mg/ml to about 1.32 mg/ml human serum albumin, and
- from about 70 mM to 140 mM sodium chloride, and preferably
- has a pH of 7 to 8.5.

In a preferred embodiment, the lyophilized unit dose of the invention as described herein comprises the following pharmaceutically acceptable excipients:

- about 15% w/v α,α-trehalose dihydrate,
- about 1% w/v poloxamer 407,
- about 0.1% w/v human serum albumin, and
- about 100 mM sodium chloride.

In a preferred embodiment, the lyophilized unit dose of the invention as described herein comprises the following pharmaceutically acceptable excipients when measured in 0.5 ml:

- about 15% w/v α,α-trehalose,
- about 1% w/v poloxamer 407,
- about 0.1% w/v human serum albumin, and
- about 100 mM sodium chloride.

In a preferred embodiment, the lyophilized unit dose of the invention as described herein comprises the following pharmaceutically acceptable excipients:

- about 82.9 mg α,α-trehalose dihydrate,
- about 5 mg poloxamer 407,
- about 0.5 mg human serum albumin, and
- about 50 μmoles sodium chloride.

In a preferred embodiment, the reconstituted unit dose of the invention as described herein comprises the following pharmaceutically acceptable excipients:

- about 15% w/v α,α-trehalose dihydrate,
- about 1% w/v poloxamer 407,
- about 0.1% w/v human serum albumin, and
- about 137 mM sodium chloride, and preferably
- has a pH of 7 to 8.5

In a preferred embodiment, the reconstituted unit dose of the invention as described herein comprises the following pharmaceutically acceptable excipients when measured in 0.5 ml:

- about 15% w/v α,α-trehalose,
- about 1% w/v poloxamer 407,
- about 0.1% w/v human serum albumin, and preferably
- about 137 mM sodium chloride and preferably
- has a pH of 7 to 8.5.

In a preferred embodiment, the reconstituted unit dose of the invention as described herein comprises the following pharmaceutically acceptable excipients:

- about 82.9 mg α,α-trehalose dihydrate,
- about 5 mg poloxamer 407,
- about 0.5 mg human serum albumin, and preferably
- about 68.5 μmoles sodium chloride, and preferably
- has a pH of 7 to 8.5.

The human serum albumin may be a native or recombinant human serum albumin (rHSA). The poloxamer 407 may be e.g. Pluronic F127.

In one embodiment, the unit dose further comprises a buffer. The buffer may be phosphate buffered saline (PBS). The buffer may include at least one of sodium chloride (NaCl), monosodium dihydrogen phosphate ($NaH_2PO_4$), disodium hydrogen phosphate ($Na_2HPO_4$), potassium chloride (KCl), and potassium dihydrogen phosphate ($KH_2PO_4$). In a preferred embodiment, the buffer may include disodium hydrogen phosphate ($Na_2HPO_4$), potassium chloride (KCl), and potassium dihydrogen phosphate ($KH_2PO_4$). The buffer may have a pH in the range of 7.0 to 8.5 at 25° C.

Unit Dose

The present invention is directed in part to a unit dose of a dengue vaccine composition comprising a tetravalent dengue virus composition as described herein and pharmaceutically acceptable excipients as described herein.

The present invention is directed in part to a unit dose of a dengue vaccine composition as described above e.g. of (i) a dengue serotype 1 (e.g. chimeric dengue serotype 2/1 strain) with a concentration of at least 3.3 log 10 pfu/0.5 mL,
(ii) a dengue serotype 2 (e.g. dengue serotype 2 strain) with a concentration of at least 2.7 log 10 pfu/0.5 mL,
(iii) a dengue serotype 3 (e.g. chimeric dengue serotype 2/3 strain) with a concentration of at least 4.0 log 10 pfu/0.5 mL, and
(iv) a dengue serotype 4 (e.g. chimeric dengue serotype 2/4 strain) with a concentration of at least 4.5 log 10 pfu/0.5 mL.

Preferably, the chimeric dengue serotype 2/1 strain is TDV-1, the dengue serotype 2 strain is TDV-2, the chimeric dengue serotype 2/3 strain is TDV-3, and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In one embodiment, the unit dose is lyophilized. In one such embodiment, the lyophilized unit dose is obtained by subjecting a volume of 0.5 mL of the aqueous dengue vaccine composition produced by combining pharmaceutically acceptable excipients as described herein and the dengue vaccine composition as described herein comprising the four dengue virus strains, in particular TDV-1 to TDV-4, to lyophilization. In a preferred embodiment the residual moisture content as determined by Karl Fischer Determination is equal to or less than 5.0%, preferably equal to or less than 3%.

In another embodiment, the unit dose is reconstituted. The reconstituted unit dose is obtained by subjecting the lyophilized unit dose to reconstitution with a pharmaceutically acceptable diluent, preferably before administration of the dengue vaccine. In one such embodiment, reconstitution will be accomplished by adding a pharmaceutically acceptable diluent, such as water for injection, phosphate buffered saline or an aqueous sodium chloride solution, to the lyophilized unit dose. In one embodiment, an aqueous sodium chloride solution, such as a 37 mM aqueous sodium chloride solution, is added to the lyophilized unit dose for reconstitution. In one such embodiment, the lyophilized unit dose will be reconstituted with 0.3 to 0.8 mL, or 0.4 to 0.7 mL, or 0.5 mL of diluent. In a preferred embodiment, the lyophilized unit dose is reconstituted with 0.3 to 0.8 mL, 0.4 to 0.7 mL or 0.5 mL of 37 mM aqueous sodium chloride solution. In a more preferred embodiment, the lyophilized unit dose is reconstituted with 0.5 mL of 37 mM aqueous sodium chloride solution. The reconstituted unit dose can subsequently be administered subcutaneously.

It is preferred that the unit dose in lyophilized form is the final product after manufacture of the unit dose and the storage form of the unit dose, wherein the unit dose in reconstituted form is prepared before administration of the unit dose to a subject.

The present invention is, moreover, directed in part to a unit dose of a dengue vaccine composition comprising:
a tetravalent virus composition including four live attenuated dengue virus strains, wherein the unit dose is lyophilized and upon reconstitution with 0.5 mL of a pharmaceutically acceptable diluent comprises:

(i) a dengue serotype 1, such as a chimeric dengue serotype 2/1 strain, in a concentration of at least 3.3 log 10 pfu/0.5 ml,
(ii) a dengue serotype 2, such as a dengue serotype 2 strain, in a concentration of at least 2.7 log 10 pfu/0.5 ml,
(iii) a dengue serotype 3, such as a chimeric dengue serotype 2/3 strain, in a concentration of at least 4.0 log 10 pfu/0.5 ml, and
(iv) a dengue serotype 4, such as a chimeric dengue serotype 2/4 strain, in a concentration of at least 4.5 log 10 pfu/0.5 ml.

In one embodiment, the reconstituted unit dose has a volume of e.g. 0.5 mL, wherein upon reconstitution with a pharmaceutically acceptable diluent (i), (ii), (iii), and (iv) provide a total concentration of pfu/0.5 mL and based on said concentration, the concentration of (iii) at least 10% of the total concentration in pfu/0.5 mL.

In another embodiment the reconstituted unit dose has a volume of e.g. 0.5 mL, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 6%, or at least 8%, or at least 10%, or at least 12%, or at least 14%, or at least 16%, or at least 18%.

It is preferred that the concentration in the reconstituted unit dose of (iii) in pfu/0.5 mL is at least 10%.

In one embodiment the reconstituted unit dose has a volume of e.g. 0.5 mL, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%.

In one embodiment, the present invention is directed to a lyophilized unit dose of a dengue vaccine composition comprising upon reconstitution with 0.5 mL of a pharmaceutically acceptable diluent a dengue serotype 1 (e.g. chimeric dengue serotype 2/1 strain) with a concentration of at least 3.3 log 10 pfu/0.5 mL, a dengue serotype 2 (e.g. dengue serotype 2 strain) with a concentration of at least 2.7 log 10 pfu/0.5 mL, a dengue serotype 3 (e.g. chimeric dengue serotype 2/3 strain) with a concentration of at least 4.0 log 10 pfu/0.5 mL, and a dengue serotype 4 (e.g. chimeric dengue serotype 2/4 strain) with a concentration of at least 4.5 log 10 pfu/0.5 mL and pharmaceutically acceptable excipients as described herein, wherein the unit dose is preferably formulated in 0.5 mL before lyophilization. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In one such embodiment, the lyophilized unit dose is obtained by lyophilizing 0.5 mL of a dengue vaccine composition comprising a dengue serotype 1 (e.g. chimeric dengue serotype 2/1 strain) in a concentration of 3.3 log 10 pfu/dose to 5.0 log 10 pfu/0.5 mL, a dengue serotype 2 (e.g. dengue serotype 2 strain) in a concentration of 2.7 log 10 pfu/dose to 4.9 log 10 pfu/0.5 mL, a dengue serotype 3 (e.g. chimeric dengue serotype 2/3 strain) in a concentration of 4.0 log 10 pfu/dose to 5.7 log 10 pfu/0.5 mL, and a dengue serotype 4 (e.g. chimeric dengue serotype 2/4 strain) in a concentration of 4.5 log 10 pfu/dose to 5.5 log 10 pfu/0.5 mL and pharmaceutically acceptable excipients as described herein. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In one such embodiment, the lyophilized unit dose is obtained by lyophilizing 0.5 mL of a dengue vaccine composition comprising a dengue serotype 1 (e.g. chimeric dengue serotype 2/1 strain) in a concentration of 3.3 log 10 pfu/0.5 mL to 3.6 log 10 pfu/0.5 mL, a dengue serotype 2 (e.g. dengue serotype 2 strain) in a concentration of 2.7 log 10 pfu/0.5 mL to 4.0 log 10 pfu/0.5 mL, a dengue serotype 3 (e.g. chimeric dengue serotype 2/3 strain) in a concentration of 4.0 log 10 pfu/0.5 mL to 4.6 log 10 pfu/0.5 mL, and a dengue serotype 4 (e.g. chimeric dengue serotype 2/4 strain) in a concentration of 4.5 log 10 pfu/0.5 mL or 4.6 log 10 pfu/0.5 mL to 5.1 log 10 pfu/0.5 mL and pharmaceutically acceptable excipients as described herein. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In certain embodiments, the lyophilized unit dose refers to 0.5 mL before lyophilization, wherein TDV-2 and TDV-4 are present in certain relative amounts, based on the total concentration of TDV-1, TDV-2, TDV-3 and TDV-4 in pfu/0.5 mL, and the concentration of TDV-2 measured in pfu/0.5 mL is less than 10% or less than 8% or less than 6%, and the concentration of TDV-4 measured in pfu/0.5 mL is at least 50% or at least 65%. In some of these embodiments, the concentration of TDV-1 measured in pfu/0.5 mL is at least 1% and/or the concentration of TDV-3 measured in pfu/0.5 mL is at least 6%, 7%, 8%, 10%, 12%, 14%, 16% or at least 18%.

In certain embodiments, the reconstituted unit dose has a volume of 0.5 mL and TDV-2 and TDV-4 are present in certain relative amounts, based on the total concentration of TDV-1, TDV-2, TDV-3 and TDV-4 in pfu/0.5 mL, and the concentration of TDV-2 measured in pfu/0.5 mL is less than 10% or less than 8% or less than 6%, and the concentration of TDV-4 measured in pfu/0.5 mL is at least 50% or at least 65%. In some of these embodiments, the concentration of TDV-1 measured in pfu/0.5 mL is at least 1% and/or the concentration of TDV-3 measured in pfu/0.5 mL is at least 6%, 7%, 8%, 10%, 12%, 14%, 16% or at least 18%.

In a further preferred embodiment, the reconstituted unit dose has a volume of 0.5 mL and comprises a tetravalent dengue virus composition including four live attenuated dengue virus strains, wherein the concentration of the dengue serotype 1 (e.g. dengue serotype 2/1 strain) measured in pfu/0.5 mL is 1% to 7% of the total concentration, the concentration of the dengue serotype 2 (e.g. dengue serotype 2 strain) measured in pfu/0.5 mL is less than 8% of the total concentration, such as in the range of 1% to 8% of the total concentration, the concentration of the dengue serotype 3 (e.g. chimeric dengue serotype 2/3 strain) measured in pfu/0.5 mL is at least 10% of the total concentration, and the concentration of the dengue serotype 4 (e.g. dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

In a further preferred embodiment, the reconstituted unit dose has a volume of 0.5 mL and comprises a tetravalent dengue virus composition including four live attenuated dengue virus strains, wherein the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

The lyophilized unit dose reconstituted in 0.5 mL will provide the above concentrations for the four dengue serotypes. While the unit dose of a dengue vaccine composition as described herein refers to the concentrations of the dengue serotypes in 0.5 mL, the lyophilized unit dose can be reconstituted with other volumes of a pharmaceutically acceptable diluent, such as an aqueous sodium chloride solution, without changing the absolute virus amount administered or the ratios of the viruses to one another.

In certain embodiments, the lyophilized unit dose of the invention is prepared from a solution comprising a non-reducing sugar, a surfactant, a protein and an inorganic salt.

In certain embodiments, the lyophilized unit dose of the invention is prepared from a solution comprising trehalose, poloxamer 407, human serum albumin and sodium chloride.

In certain embodiments, the lyophilized unit dose of the invention is prepared from a solution comprising about 10% w/v to about 20% w/v α,α-trehalose dihydrate or an equimolar amount of other forms of α,α-trehalose, from about 0.5% w/v to about 1.5% w/v poloxamer 407, from about 0.05% w/v to about 2% w/v human serum albumin, and about 70 mM to about 120 mM sodium chloride.

In preferred embodiments, the lyophilized unit dose of the invention as described herein is prepared from a solution comprising about 15% w/v α,α-trehalose dihydrate, about 1% w/v poloxamer 407, about 0.1% w/v human serum albumin and about 100 mM sodium chloride.

In one embodiment, the solution from which the lyophilized unit dose is prepared further comprises a buffer. The buffer may be phosphate buffered saline (PBS). The buffer may include at least one of sodium chloride (NaCl), monosodium dihydrogen phosphate ($NaH_2PO_4$), disodium hydrogen phosphate ($Na_2HPO_4$), potassium chloride (KCl), and potassium dihydrogen phosphate ($KH_2PO_4$). In a preferred embodiment, the buffer may include disodium hydrogen phosphate ($Na_2HPO_4$), potassium chloride (KCl), and potassium dihydrogen phosphate ($KH_2PO_4$). The buffer may have a pH in the range of about 7.0 to about 8.5 at 25° C. or a pH of about 6.8 to about 7.6 at 25° C., preferably a pH of about 7.2 at 25° C.

In preferred embodiments, the reconstituted unit dose of the invention as described herein comprising about 15% w/v α,α-trehalose dihydrate, about 1% w/v poloxamer 407, about 0.1% w/v human serum albumin and about 137 mM sodium chloride. The reconstituted unit dose may have a pH of about 7.0 to about 8.5 at 25° C., preferably a pH of about 7.2 at 25° C.

The unit dose of the invention as described herein activates multiple arms of the immune system-neutralizing antibodies, cellular immunity and anti-NS1 antibodies—in both seronegative and seropositive subject populations or in both seronegative and seropositive subjects. Thus, the unit dose of the invention as described herein protects both dengue seronegative and dengue seropositive subject populations or subjects against dengue disease.

In one embodiment, one unit dose is present in a container, preferably a vial, and said unit dose is administered to a subject after reconstitution. In one embodiment, more than one unit dose of the dengue vaccine composition may be present in a container, preferably a vial, so that with the content of one container, preferably a vial, more than one subject can be vaccinated. In one embodiment, the container comprising more than one unit doses of the invention as described herein is used for providing the reconstituted unit dose to be used in the methods of the invention as described herein.

The certain embodiments, the container comprising the unit dose of the invention is part of a kit. Thus, the invention is directed in part to a kit for preparing a reconstituted unit dose comprising a lyophilized unit dose of the present invention as described herein, and a pharmaceutically acceptable diluent for reconstitution.

In certain embodiments, the diluent for reconstitution provided in a container, preferably a vial, or a pre-filled syringe. In some embodiments, the diluent for reconstitution is selected from water for injection, phosphate buffered saline or an aqueous sodium chloride solution. In a preferred embodiment, the diluent for reconstitution is 30 to 40 mM sodium chloride, such as 37 mM sodium chloride.

In certain embodiments, the kit may further comprise a hepatitis A vaccine, such as HAVRIX® or VAQTA®. In some embodiments, the hepatitis A vaccine may be in a separate container, such as a vial. In another embodiment, the hepatitis A vaccine and the unit dose of the invention may be in the same container. Thus, the invention is directed in part to a combined dengue/hepatitis A vaccine, wherein the unit dose of the invention as described herein is combined with a hepatitis A vaccine. Such a combined dengue/hepatitis A vaccine comprises the unit dose of the invention as described herein and a hepatitis A vaccine, such as HAVRIX® or VAQTA®, in the same formulation. In certain embodiments, the invention is directed to a kit comprising such a combined dengue/hepatitis A vaccine and a unit dose of the invention as described herein.

Hepatitis a Vaccine

In certain embodiments, the hepatitis A vaccine is an inactivated hepatitis A vaccine.

In certain embodiments, the hepatitis A vaccine comprises a hepatitis A virus derived from a hepatitis A virus strain HM-175.

In certain embodiments, wherein the hepatitis A vaccine comprises an inactivated hepatitis A virus and the inactivated hepatitis A virus is derived from a wild-type hepatitis A virus strain HM-175.

In certain embodiments, the inactivated hepatitis A virus is adsorbed on a carrier aluminum. In some of these embodiments, the aluminum is aluminum hydroxide or aluminum hydroxyphosphate sulfate.

In certain embodiments, wherein the hepatitis A vaccine comprises a phosphate-buffered saline solution and excipients dissolved therein in the form of an amino acid and in the form of polysorbate. In such embodiments, the amino acid is present at a concentration of 0.2 to 0.8% w/v and/or the polysorbate is present at a concentration of 0.01 to 0.09 mg/ml.

In certain embodiments, the hepatitis A vaccine includes a hepatitis A virus expressing a viral antigen in a concentration ranging from 500 ELISA Units (EL.U.) to 2000 ELISA Units (EL.U.), preferably from 700 EL.U. to 1600 EL.U., most preferably from 1300 to 1550 EL.U. Alternatively, the concentration ranges from 500 EL.U. to 900 EL.U. In a further embodiment, the concentration ranges from 200 to 400 EL.U.

In certain embodiments, the hepatitis A vaccine is included in a liquid 1 ml dose or in a 0.5 ml dose.

An example of such an hepatitis A vaccine is HAVRIX®, from GlaxoSmithKline, which is a sterile suspension of inactivated virus for intramuscular administration. HAVRIX® makes use of the hepatitis A virus strain HM-175 which is derived from a wild-type hepatitis A virus (HAV) HM-175 of which the complete nucleotide sequence is disclosed in Cohen et al., Journal of Virology, Vol. 61, No. 1, published January 1987, p. 50 to 59 (in particular, the entire sequence of the wild-type hepatitis A virus HM-175 is provided in FIG. 1 of said publication).

The virus (strain HM175) is propagated in MRC-5 human diploid cells. After removal of the cell culture medium, the cells are lysed to form a suspension. This suspension is purified through ultrafiltration and gel permeation chromatography procedures. Treatment of this lysate with formalin ensures viral inactivation. Viral antigen activity is referenced to a standard using an enzyme linked immunosorbent assay (ELISA), and is therefore expressed in terms of ELISA Units (EL.U.). Each 1-mL dose for adults (≥18 years of age) of vaccine contains 1440 EL.U. of viral antigen, adsorbed on 0.5 mg of aluminum as aluminum hydroxide. Each 0.5-mL dose for children and adolescents (12 months through 18 years of age) of vaccine contains 720 EL.U. of viral antigen, adsorbed onto 0.25 mg of aluminum as aluminum hydroxide. HAVRIX® contains the following excipients: Amino acid supplement (0.3% w/v) in a phosphate-buffered saline solution and polysorbate 20 (0.05 mg/mL). From the manufacturing process, HAVRIX® also contains residual MRC-5 cellular proteins (not more than 5 μg/mL), formalin (not more than 0.1 mg/mL), and neomycin sulfate (not more than 40 ng/mL), an aminoglycoside antibiotic included in the cell growth media. HAVRIX® is formulated without preservatives.

Another useful hepatitis A vaccine is VAQTA® from Merck Sharp & Dohme Corp., which is an inactivated whole virus vaccine derived from hepatitis A virus grown in cell culture in human MRC-5 diploid fibroblasts. It contains inactivated virus of a strain, which was originally derived by further serial passage of a proven attenuated strain. The virus is grown, harvested, purified by a combination of physical and high performance liquid chromatographic techniques developed at the Merck Research Laboratories, formalin inactivated, and then adsorbed onto amorphous aluminum hydroxyphosphate sulfate. VAQTA® is a sterile suspension for intramuscular injection. One milliliter of the vaccine contains approximately 50 U of hepatitis A virus antigen, which is purified and formulated without a preservative. Within the limits of current assay variability, the 50 U dose of VAQTA® contains less than 0.1 µg of non-viral protein, less than $4 \times 10^{-6}$ µg of DNA, less than $10^{-4}$ µg of bovine albumin, and less than 0.8 µg of formaldehyde. Other process chemical residuals are less than 10 parts per billion (ppb), including neomycin. Each 0.5-mL pediatric dose contains 25 U of hepatitis A virus antigen and adsorbed onto approximately 0.225 mg of aluminum provided as amorphous aluminum hydroxyphosphate sulfate, and 35 µg of sodium borate as a pH stabilizer, in 0.9% sodium chloride. Each 1-mL adult dose contains 50 U of hepatitis A virus antigen and adsorbed onto approximately 0.45 mg of aluminum provided as amorphous aluminum hydroxyphosphate sulfate, and 70 µg of sodium borate as a pH stabilizer, in 0.9% sodium chloride.

Yellow Fever Vaccine

YF-VAX®, a yellow fever vaccine from Sanofi, for subcutaneous use, is prepared by culturing the YF-17D strain of yellow fever virus in living avian leukosis virus-free (ALV-free) chicken embryos. The vaccine contains sorbitol and gelatin as a stabilizer and is lyophilized. No preservative is added. YF-VAX is formulated to contain not less than 4.74 $\log_{10}$ pfu per 0.5 mL dose throughout the life of the product.

Combined Vaccine Composition

The present invention is also directed in part to a combined vaccine composition comprising a hepatitis A antigen as in HAVRIX® or VAQTA®, and a dengue antigen such as the tetravalent dengue vaccine, TDV, as disclosed herein or any other suitable tetravalent live attenuated dengue virus vaccine.

In certain embodiments, the invention is directed to the combined vaccine composition, wherein the dengue vaccine composition comprises a tetravalent dengue virus composition including four live attenuated dengue virus strains:
  (i) a dengue serotype 1 preferably in a concentration of at least 3.3 log 10 pfu/0.5 mL,
  (ii) a dengue serotype 2 preferably in a concentration of at least 2.7 log 10 pfu/0.5 mL,
  (iii) a dengue serotype 3 preferably in a concentration of at least 4.0 log 10 pfu/0.5 mL, and
  (iv) a dengue serotype 4 preferably strain in a concentration of at least 4.5 log 10 pfu/0.5 mL.

In certain embodiments, the invention is directed to the combined vaccine composition, wherein the dengue vaccine composition comprises a tetravalent dengue virus composition including four live attenuated dengue virus strains:
  (i) a chimeric dengue serotype 2/1 strain in a concentration of at least 3.3 log 10 pfu/0.5 mL to 3.8 log 10 pfu/0.5 ml,
  (ii) a dengue serotype 2 strain in a concentration of at least 2.7 log 10 pfu/0.5 mL,
  (iii) a chimeric dengue serotype 2/3 strain in a concentration of at least 4.0 log 10 pfu/0.5 mL, and
  (iv) a chimeric dengue serotype 2/4 strain in a concentration of at least 4.5 log 10 pfu/0.5 mL or at least 4.6 log 10 pfu/0.5 mL to optionally 6.2 log 10 pfu/0.5 ml.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In certain embodiments, the invention is directed to the combined vaccine composition, wherein upon reconstitution of the dengue vaccine composition with a pharmaceutically acceptable diluent (i), (ii), (iii), and (iv) provide a total concentration of pfu/0.5 mL and based on said total concentration of pfu/0.5 ml the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 6%, at least 8%, or at least 10%, or at least 12%, or at least 14%, or at least 16%, or at least 18%.

In certain embodiments, the invention is directed to the combined vaccine composition, wherein the dengue vaccine composition comprises one or more pharmaceutically acceptable excipients. In one embodiment, the dengue vaccine composition comprises a non-reducing sugar, a surfactant, a protein and an inorganic salt. Preferably, the non-reducing sugar is trehalose, the surfactant is poloxamer 407, the protein is human serum albumin and the inorganic salt is sodium chloride.

Furthermore, any vaccine excipients or combinations thereof known to the person skilled in the art, e.g. disclosed in WO 2018/027075 A1, can be used for the combined vaccine composition.

In one embodiment, the unit dose of a dengue vaccine composition comprises the following pharmaceutically acceptable excipients:
  from about 10% w/v to about 20% w/v α,α-trehalose dihydrate or an equimolar amount of other forms of α,α-trehalose,
  from about 0.5% w/v to about 1.5% w/v poloxamer 407,
  from about 0.05% w/v to about 2% w/v human serum albumin, and
  from about 70 mM to 140 mM sodium chloride.

In certain embodiments, the invention is directed to the combined vaccine composition, wherein the dengue vaccine composition comprises other dengue vaccines such as Dengvaxia®. Dengvaxia® is a tetravalent dengue vaccine with mixed chimeric dengue viruses based on a yellow fever backbone, CYD-TDV (Dengvaxia®, Sanofi Pasteur, Lyon, France), and has been licensed in several countries based on the clinical demonstration of an overall vaccine efficacy (VE) against virologically-confirmed dengue (VCD) of 56-61% in children in Asia and Latin America (Capeding M R et al. Clinical efficacy and safety of a novel tetravalent dengue vaccine in healthy children in Asia: a phase 3, randomised, observer-masked, placebo-controlled trial. Lancet 2014, 384:1358-65; Villar L A et al. Safety and immunogenicity of a recombinant tetravalent dengue vaccine in 9-16 year olds: a randomized, controlled, phase II trial in Latin America. Pediatr Infect Dis J 2013, 32:1102-9). The preparation of these particular strains CYD1, CYD2, CYD3 and CYD4 has been described in detail in international patent applications WO 98/37911, WO 03/101397, WO07/021672, WO 08/007021, WO 08/047023 and WO 08/065315, to which reference may be made for a precise description of the processes for their preparation. The corresponding nucleotide sequences of the prM-E regions of CYD1, CYD2, CYD3 and CYD4 are provided in WO2016034629 and SEQ ID NOs are set out in Table 16 of this reference.

In certain embodiments, the invention is directed to the combined vaccine composition, wherein the quantity of a chimeric dengue virus within CYD-TDV comprised in a vaccine composition of the present invention lies within a range of about $10^5$ CCID50 to about $10^6$ CCID50. The quantity of a live attenuated chimeric dengue virus of each of serotypes 1 to 4 comprised in the CYD dosage form, e.g. Dengvaxia®, is preferably equal.

In such embodiments, the CYD-TDV is dissolved/dissolvable in a solution containing 0.4% NaCl.

In certain embodiments, the invention is directed to the combined vaccine composition, wherein the dengue vaccine composition comprises other dengue vaccines such as TV003 or TV005. TV003, developed by the U.S. National Institute of Allergy and Infectious Diseases, comprises vaccine components rDEN1Δ30, rDEN2/4Δ30, rDEN3Δ30/31 and rDEN4Δ30, wherein each of these components is present at a concentration of 3 $\log_{10}$ PFU. TV005 is similar to TV003 with the difference that the concentration of rDEN2/4Δ30 in TV005 is 4 $\log_{10}$ PFU. The vaccines TV003 and TV005 and their vaccine components as well as their production are described in more detail in WO 2008/022196 A2 and S. S. Whitehead, Expert Rev Vaccines, 2016, 15(4): 509 to 517. Using recombinant DNA technology, two attenuation strategies were utilized for the vaccine components of TV003 or TV005: deletions in the 3' untranslated region and structural gene chimerization. For example, the component rDEN4Δ30 contains all the structural and non-structural proteins of a wild type DENV-4, but is attenuated by a 30-nucleotide deletion in the 3' untranslated region (denoted "Δ30"). The other vaccine components are also attenuated due to the 30-nucleotide deletion in the 3' untranslated region. In addition, rDEN3Δ30/31 includes a 31 nucleotide deletion in the 3' untranslated region (shown in detail in FIG. 1c and FIG. 13 of WO 2008/022196 A2). The rDEN2/4Δ30 component was created by substituting the prM and E genes of DENV-2 into the rDEN4Δ30 genome. The complete genomic sequences of dengue strains which can be used to produce TV003 or TV005 are available under the Genbank accession numbers in Table A of WO 2008/022196 A1.

In certain embodiments, the invention is directed to the combined vaccine composition, wherein the hepatitis A vaccine is an inactivated hepatitis A vaccine.

In certain embodiments, wherein the hepatitis A vaccine comprises a hepatitis A virus derived from a hepatitis A virus strain HM-175.

In certain embodiments, the invention is directed to the combined vaccine composition, wherein the hepatitis A vaccine comprises an inactivated hepatitis A virus and the inactivated hepatitis A virus is derived from a wild-type hepatitis A virus strain HM-175.

In certain embodiments, the invention is directed to the combined vaccine composition, the inactivated hepatitis A virus is adsorbed on a carrier aluminum. In some of these embodiments, the aluminum is aluminum hydroxide or aluminum hydroxyphosphate sulfate.

In certain embodiments, the invention is directed to the combined vaccine composition, wherein the hepatitis A vaccine comprises a phosphate-buffered saline solution and excipients dissolved therein in the form of an amino acid and in and in the form of polysorbate. In such embodiments, the amino acid is present at a concentration of 0.2 to 0.8% w/v and/or the polysorbate is present at a concentration of 0.01 to 0.09 mg/ml.

In certain embodiments, the invention is directed to the combined vaccine composition, wherein the hepatitis A vaccine includes a hepatitis A virus expressing a viral antigen in a concentration ranging from 500 ELISA Units (EL.U.) to 2000 ELISA Units (EL.U.), preferably from 700 EL.U. to 1600 EL.U., most preferably from 1300 to 1550 EL.U. Alternatively, the concentration ranges from 500 EL.U. to 900 EL.U. In a further embodiment, the concentration ranges from 200 to 400 EL.U.

In certain embodiments, the invention is directed to the combined vaccine composition, wherein the combined vaccine is included in a dose comprising a liquid, wherein the liquid has a volume of 0.5 ml, 1 ml, or 1.5 ml.

In certain embodiments, the combined vaccine composition is provided in one single vial in a liquid form or in a dehydrated form, such as a lyophilized form.

In certain embodiments, the combined vaccine composition is obtained from mixing a unit dose of a dengue vaccine composition and a dose of a hepatitis A vaccine in a syringe.

The invention is also directed in part to a method of administering any of the above combined vaccine compositions to a subject or subject population.

In certain embodiments, the invention is directed to said methods, wherein the combined vaccine composition is administered subcutaneously or intramuscularly.

Method of Preventing Dengue Disease and Hepatitis A, Corresponding Uses, and Corresponding Kit The present invention is directed to a method of preventing hepatitis A and dengue disease.

The present invention is directed in part to a method of preventing hepatitis A and dengue disease in a subject or subject population, the method comprising simultaneously on the same day administering a hepatitis A vaccine, such as HAVRIX® or VAQTA®, and a unit dose of a dengue vaccine composition, wherein said unit dose comprises a tetravalent dengue virus composition including four live, attenuated dengue virus strains.

In certain embodiments, the invention is directed to said method, wherein the hepatitis A vaccine, such as HAVRIX®, comprises an inactivated virus. Preferably, the hepatitis A vaccine comprises an inactivated hepatitis A virus and the inactivated hepatitis A virus is derived from a hepatitis A virus strain HM-175.

In certain embodiments, the hepatitis A vaccine, such as HAVRIX®, is derived from a hepatitis A virus strain HM-175.

In certain embodiments, the invention is directed to said methods, wherein the hepatitis A vaccine, such as HAVRIX®, which is preferably a virus derived from a hepatitis A virus strain HM-175, is adsorbed on aluminum.

According to some of these embodiments, the aluminum is aluminum hydroxide or aluminum hydroxyphosphate sulfate.

In certain embodiments, the invention is directed to said method, wherein the hepatitis A vaccine, such as HAVRIX®, which is preferably derived from a hepatitis A virus strain HM-175, comprises a phosphate-buffered saline solution and excipients dissolved therein in the form of an amino acid and in and in the form of polysorbate.

In certain embodiments, the invention is directed to said method, wherein the hepatitis A vaccine, such as HAVRIX®, includes a hepatitis A virus expressing a viral antigen in a concentration ranging from 500 ELISA Units (EL.U.) to 2000 ELISA Units (EL.U.), preferably from 700 EL.U. to 1600 EL.U., most preferably from 1300 to 1550 EL.U. Alternatively, the concentration ranges from 500 EL.U. to 900 EL.U. In a further embodiment, the concentration ranges from 200 to 400 EL.U.

For example, viral antigen activity of a hepatitis A vaccine can be measured according to a method disclosed in Andre F E., Hepburn A., D'Hondt E., "Inactivated candidate vaccines for hepatitis", A. Prog Med Virol 1990; 37:72-95.

In certain embodiments, the invention is directed to said method, wherein the dengue vaccine composition upon reconstitution with 0.5 mL of a pharmaceutically acceptable diluent comprises
(i) a chimeric dengue serotype 2/1 strain in a concentration of at least 3.3 log 10 pfu/0.5 mL,
(ii) a dengue serotype 2 strain in a concentration of at least 2.7 log 10 pfu/0.5 mL,
(iii) a chimeric dengue serotype 2/3 strain in a concentration of at least 4.0 log 10 pfu/0.5 mL, and (iv) a chimeric dengue serotype 2/4 strain in a concentration of at least 4.5 log 10 pfu/0.5 mL.

According to some of these embodiments, upon reconstitution of the dengue vaccine composition with a pharmaceutically acceptable diluent, (i), (ii), (iii), and (iv) provide a total concentration of pfu/0.5 mL and based on said total concentration of pfu/0.5 ml the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 6%, at least 8%, or at least 10%, or at least 12%, or at least 14%, or at least 16%, or at least 18%.

In certain embodiments, the invention is directed to said methods, wherein the subject population or subject is seronegative with respect to all dengue serotypes. According to some of these embodiments, the subject population or subject is seronegative with respect to hepatitis A at baseline.

In certain embodiments the invention is directed to said methods, wherein the unit dose of the invention as described herein and the hepatitis A vaccine, such as HAVRIX® or VAQTA®, are administered on day 0/1.

In certain embodiments, the invention is directed to said methods, wherein the unit dose of the invention as described herein is administered by subcutaneous injection and wherein the hepatitis A vaccine, such as HAVRIX® or VAQTA®, is administered by intramuscular injection. According to some embodiments, the injections are administered to the arm, preferably to the deltoid region of the arm. According to some of these embodiments, the subcutaneous injection of the unit dose of the invention as described herein and the intramuscular injection of the hepatitis A vaccine, such as HAVRIX® or VAQTA®, are administered to different anatomical sites, such as to opposite arms.

In certain embodiments, the invention is directed to said methods, wherein two unit doses of the dengue vaccine composition of the invention as described herein are administered. In some embodiments, the two unit doses of the invention as described herein are administered within 12 month or more, or within 6 month, or within three months, such as at day 0/1 and day 90. According to some of these embodiments, a further third unit dose of the invention as described herein is administered after the second administration. Such a third administration may be administered between 6 to 12 months after the first administration, such as 12 months after the first administration, or later than 12 month after the first administration, such as 12 months (1 year) after the second administration or even 5 years or longer after the first or second administration and may act as a booster.

In certain embodiments, the invention is directed to said methods, wherein two unit doses of the invention as described herein and one dose of a hepatitis A vaccine, such as HAVRIX® or VAQTA®, are administered, in particular according to the following schedule
a first simultaneous administration of the first unit dose and said hepatitis A vaccine on day 0/1, and
a second administration of the second unit dose after said first simultaneous administration, such as about 3 months later such as on day 90.

In certain embodiments, the invention is directed to said method, wherein the unit dose of the invention as described herein is administered subcutaneously to a subject or subject population and the hepatitis A vaccine, such as HAVRIX® or VAQTA®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said method, wherein the unit dose of the invention as described herein and the hepatitis A vaccine, such as HAVRIX® or VAQTA®, are administered to a subject or subject population from a dengue endemic region. In certain embodiments, the unit dose of the invention as described herein is administered subcutaneously and the hepatitis A vaccine, such as HAVRIX® or VAQTA®, is administered intramuscularly to a subject or subject population from a dengue endemic region.

In certain embodiments, the invention is directed to said method, wherein the subject or subject population is from a dengue non-endemic region, preferably from a dengue non-endemic and a hepatitis A non-endemic region.

According to some embodiments, a second dose of a hepatitis A vaccine, such as HAVRIX® or VAQTA®, is administered. The second dose of the hepatitis A vaccine may be administered after the first administration of the hepatitis A vaccine. Such a second administration may act as a booster and may be administered 6 to 12 months or 6 to 18 months, such as 9 months after the first administration of the hepatitis A vaccine, such as on day 270.

In certain embodiments, the invention is directed to said method, wherein the unit dose of the invention as described herein is administered subcutaneously and wherein the hepatitis A vaccine, such as HAVRIX® or VAQTA®, is administered intramuscularly to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and a hepatitis A non-endemic region. According to certain embodiments, the subject or subject population is seronegative for all four dengue serotypes.

In certain embodiments, the invention is directed to said method, wherein the method does not include a step of determination whether there was a previous dengue infection and/or a previous hepatitis A infection in the subject population or in the subject before the administration of the hepatitis A vaccine and before the administration of the unit dose of the dengue vaccine composition or wherein the hepatitis A serostatus and/or the dengue serostatus of the subject population or of the subject is unknown before the administration of the hepatitis A vaccine and before the administration of the unit dose of the dengue vaccine composition. According to certain embodiments, the method does not include a step of determination whether there was a previous dengue infection and/or a previous hepatitis A infection in the subject population or in the subject at any time before, during and after the steps of administration of the hepatitis A vaccine and of the unit dose of the dengue vaccine composition or wherein the hepatitis A serostatus and/or the dengue serostatus of the subject population or of the subject is unknown at any time before, during or after the steps of administration of the hepatitis A vaccine and of the unit dose of the dengue vaccine composition.

In certain embodiments, the invention is directed to said method, wherein the method comprises a primary vaccination consisting of the steps of:
(A) selecting a subject for administration of the unit doses of the tetravalent dengue virus composition and the hepatitis A vaccine in need for protection against dengue infection and hepatitis A infection without determination whether there was a previous dengue infection and/or a previous hepatitis A infection, and
(B) administering simultaneously on the same day a first unit dose of the tetravalent dengue virus composition and a hepatitis A vaccine to the subject, and optionally
(C) administering at least one further unit dose of the tetravalent dengue virus composition to the subject within 3 to 12 months of administration of the first unit dose and optionally
(D) administering at least one further dose of the hepatitis A vaccine to the subject within 6 to 18 months of administration of the first unit dose.

In certain embodiments, the invention is directed to said method, the method comprises a primary vaccination consisting of the steps of:
(A) selecting a subject for administration of the unit doses of the tetravalent dengue virus composition and the hepatitis A vaccine in need for protection against dengue infection and hepatitis A infection, and
(B) administering simultaneously on the same day a first unit dose of the tetravalent dengue virus composition and a hepatitis A vaccine to the subject, and
(C) administering two further unit doses of the tetravalent dengue virus composition to the subject at about 6 and about 12 months of administration of the first unit dose and administering a further hepatitis A vaccine to the subject at either about 6 or about 12 months of administration of the first unit dose. In some of these embodiments, step (A), the selecting of the subject, is carried out without determination whether there was a previous hepatitis A infection.

In certain embodiments, the invention is directed to said method, wherein upon reconstitution of the unit dose with a pharmaceutically acceptable diluent (i), (ii), (iii), and (iv) provide a total concentration of pfu/0.5 mL and based on said total concentration of pfu/0.5 ml the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 6%, at least 8%, or at least 10%, or at least 12%, or at least 14%, or at least 16%, or at least 18%.

In certain embodiments, the method provides compatibility between the dengue vaccine composition and the hepatitis A vaccine. Compatibility means in particular that the immune response after simultaneous administration is not inferior in comparison with a mono-administration of these vaccines.

In certain embodiments, the method provides synergy between the dengue vaccine composition and the hepatitis A vaccine. Synergy means in particular that the immune response after simultaneous administration is better for one or both vaccines in comparison with a mono administration of these vaccines.

In certain embodiments, the invention is directed to said method, wherein the method provides non-inferiority in a non-inferiority clinical study including at least 60 or at least 120 healthy subjects divided into one subject population and into one control subject population, wherein the subject population receives simultaneously on the same day the hepatitis A vaccine and the unit dose of the dengue vaccine composition and the control subject population receives simultaneously on the same day a hepatitis A vaccine and a placebo administration In certain embodiments, the invention is directed to said methods, wherein the hepatitis A vaccine provides a hepatitis A seroprotection rate of at least 95% or of at least 98% on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline and being seronegative with respect to all dengue virus serotypes at baseline.

In certain embodiments, the invention is directed to said method, wherein the method provides a hepatitis A seroprotection rate difference with respect to a hepatitis A mono-administration, the difference being determined in a non-inferiority clinical study including at least 60 or at least 120 healthy subjects being seronegative with respect to hepatitis A at baseline and seronegative with respect to all dengue virus serotypes at baseline,
  the healthy subjects being divided into
  a) a subject population of at least 30 or at least 50 healthy subjects receiving simultaneously on the same day an administration (on day 0/1) of the hepatitis A vaccine and the unit dose of the dengue vaccine composition, and
  b) a control subject population of at least 30 or at least 50 healthy subjects receiving simultaneously on the same day an administration (on day 0/1) of a hepatitis A vaccine and a placebo,
  wherein the difference is determined between the hepatitis A seroprotection rate of the control subject population on day 30 after the administration (on day 0/1) and the hepatitis A seroprotection rate of the subject population on day 30 after the administration (on day 0/1), and
  wherein the difference has an upper bound within a two-sided 95% confidence interval which is lower than 10%.

In certain embodiments, the invention is directed to said method, wherein the hepatitis A vaccine provides a hepatitis A seroprotection rate of at least 95% or of at least 98% or of at least 99% on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline, wherein the healthy subjects include healthy subject(s) which are seropositive with respect to at least one dengue virus serotype at baseline and healthy subject(s) which are seronegative with respect to all dengue virus serotypes at baseline.

In certain embodiments, the invention is directed to said method, wherein the method provides a hepatitis A seroprotection rate difference with respect to a hepatitis A mono-administration, the difference being determined in a non-inferiority clinical study including at least 60 or at least 120 healthy subjects being seronegative with respect to hepatitis A at baseline, wherein the healthy subjects include healthy subject(s) which are seropositive with respect to at least one dengue virus serotype at baseline and healthy subject(s) which are seronegative with respect to all dengue virus serotypes at baseline,
the healthy subjects being divided into
a) a subject population of at least 30 or at least 50 healthy subjects receiving simultaneously on the same day an administration (on day 0/1) of the hepatitis A vaccine and the unit dose of the dengue vaccine composition, wherein the subject population includes healthy subject(s) which are seropositive with respect to at least one dengue virus serotype at baseline and healthy subject(s) which are seronegative with respect to all dengue virus serotypes at baseline, and
b) a control subject population of at least 30 or at least 50 healthy subjects receiving simultaneously on the same day an administration (on day 0/1) of a hepatitis A vaccine and a placebo, wherein the control subject population includes healthy subject(s) which are seropositive with respect to at least one dengue virus serotype at baseline and healthy subject(s) which are seronegative with respect to all dengue virus serotypes at baseline,
wherein the difference is determined between the hepatitis A seroprotection rate of the control subject population on day 30 after the administration (on day 0/1) and the hepatitis A seroprotection rate of the subject population on day 30 after the administration (on day 0/1), and
wherein the difference has an upper bound within a two-sided 95% confidence interval which is lower than 10%.

In certain embodiments, the invention is directed to said method, wherein the subject or subject population is exposed to a hepatitis A virus outbreak and/or a dengue virus outbreak.

In certain embodiments, the invention is directed to said method, wherein the method provides an anti-hepatitis A virus antibody Geometric Mean Concentration (GMC) of at least 70 mIU/ml or at least 80 mIU/ml or at least 90 mIU/ml on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline and being seronegative with respect to all dengue virus serotypes at baseline.

An ELISA for determining the anti-hepatitis A antibodies is for example disclosed in Beck et al. J Travel Med 2004; 11:201-207.

In certain embodiments, the invention is directed to said method, wherein the simultaneous administration of the hepatitis A vaccine and the unit dose of the dengue vaccine composition to the subject or the subject population does not provide serious adverse events related to the simultaneous administration. Additionally, there are no deaths related to the simultaneous administration.

In certain embodiments, the invention is directed to said methods, wherein the method provides the Geometric Mean Titer (GMT) of neutralizing antibodies measured by MNT50 of
at least 110 or at least 140 or at least 150 for dengue serotype 1,
at least 3000 or at least 3500 or at least 3900 for dengue serotype 2,
at least 100 or at least 120 or at least 140 for dengue serotype 3, and/or
at least 80 or at least 110 or at least 140 for dengue serotype 4,
on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline and being seronegative with respect to all dengue virus serotypes at baseline.

In some embodiments, the geometric mean neutralizing antibody titers (GMTs) of a subject population or the neutralizing antibody titers of a subject are determined in accordance with a microneutralization test, for example according to the method described in Example 2.

The present invention is directed in part to a method of preventing hepatitis A and dengue disease in a subject or subject population, the method comprising simultaneously on the same day administering a hepatitis A vaccine, and a unit dose of a dengue vaccine composition, wherein said unit dose comprises a tetravalent dengue virus composition including four live, attenuated dengue virus strains, wherein the four live, attenuated dengue virus strains are different from the ones used in the unit dose as defined above.

In one embodiment of the invention, the method is directed to a simultaneous on the same day administration of a hepatitis A vaccine with other dengue vaccines such as Dengvaxia®. Dengvaxia® is a tetravalent dengue vaccine based on a yellow fever backbone, CYD-TDV (Dengvaxia®, Sanofi Pasteur, Lyon, France), and has been licensed in several countries based on the clinical demonstration of an overall vaccine efficacy (VE) against virologically-confirmed dengue (VCD) of 56-61% in children in Asia and Latin America (Capeding M R et al. Clinical efficacy and safety of a novel tetravalent dengue vaccine in healthy children in Asia: a phase 3, randomised, observer-masked, placebo-controlled trial. Lancet 2014, 384:1358-65; Villar L A et al. Safety and immunogenicity of a recombinant tetravalent dengue vaccine in 9-16 year olds: a randomized, controlled, phase II trial in Latin America. Pediatr Infect Dis J 2013, 32:1102-9). The preparation of these particular strains CYD1, CYD2, CYD3 and CYD4 has been described in detail in international patent applications WO 98/37911, WO 03/101397, WO07/021672, WO 08/007021, WO 08/047023 and WO 08/065315, to which reference may be made for a precise description of the processes for their preparation. The corresponding nucleotide sequences of the prM-E regions of CYD1, CYD2, CYD3 and CYD4 are provided in WO2016034629 and SEQ ID NOs are set out in Table 16 of this reference.

In one such embodiment, the method comprises a vaccination consisting of the steps of:
(A) selecting a subject for administration of the equal doses of the CYD-TDV composition, such as Dengvaxia®, and the hepatitis A vaccine, such as HAVRIX® or VAQTA®, in need for protection against dengue infection and hepatitis A infection, and
(B) administering a first dose of the CYD-TDV composition, such as Dengvaxia®, and the hepatitis A vaccine, such as HAVRIX® or VAQTA® to the subject at month 0,
(C) administering a further dose of the CYD-TDV composition, such as Dengvaxia®, and optionally the hepatitis A vaccine, such as HAVRIX® or VAQTA® to the subject within 3 to 11 months, in particular at about month 6 of the administration of the first CYD-TDV dose, and
(D) administering a final dose of the CYD-TDV, such as Dengvaxia®, and optionally the hepatitis A vaccine, such as HAVRIX® or VAQTA® to the subject at about month 12.

In certain embodiments, the subject is from 2 to 60 years of age.

In particular embodiments, the subject is 2 to 18 years of age, or 4 to 16 years of age, or 18 to 60 years of age.

Preferably, the exact quantity of each component of the CYD-TDV to be administered may vary according to the age and the weight of the subject being vaccinated, the frequency of administration as well as the other ingredients in the composition. The quantity of a chimeric dengue virus within CYD-TDV comprised in a dose of a vaccine composition lies within a range of about $10^5$ CCID50 to about $10^6$ CCID50. The quantity of a live attenuated chimeric dengue virus of each of serotypes 1 to 4 comprised in the CYD dosage form, e.g. Dengvaxia®, is preferably equal. Advantageously, a vaccine composition, as described in this section, comprises an effective amount of a dengue antigen as defined herein.

In certain embodiments, the invention is directed to said method, wherein the dengue vaccine composition comprises other dengue vaccines such as TV003 or TV005. TV003, developed by the U.S. National Institute of Allergy and Infectious Diseases, comprises vaccine components rDEN1Δ30, rDEN2/4Δ30, rDEN3Δ30/31 and rDEN4Δ30, wherein each of these components is present at a concentration of 3 $\log_{10}$ PFU. TV005 is similar to TV003 with the difference that the concentration of rDEN2/4Δ30 in TV005 is 4 $\log_{10}$ PFU. The vaccines TV003 and TV005 and their vaccine components as well as their production are described in more detail in WO 2008/022196 A2 and S. S. Whitehead, Expert Rev Vaccines, 2016, 15(4): 509 to 517. Using recombinant DNA technology, two attenuation strategies were utilized for the vaccine components of TV003 or TV005: deletions in the 3' untranslated region and structural gene chimerization. For example, the component rDEN4Δ30 contains all the structural and non-structural proteins of a wild type DENV-4, but is attenuated by a 30-nucleotide deletion in the 3' untranslated region (denoted "Δ30"). The other vaccine components are also attenuated due to the 30-nucleotide deletion in the 3' untranslated region. In addition, rDEN3Δ30/31 includes a 31 nucleotide deletion in the 3' untranslated region (shown in detail in FIG. 1c and FIG. 13 of WO 2008/022196 A2). The rDEN2/4Δ30 component was created by substituting the prM and E genes of DENV-2 into the rDEN4Δ30 genome. The complete genomic sequences of dengue strains which can be used to produce TV003 or TV005 are available under the Genbank accession numbers in Table A of WO 2008/022196 A1.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, and Dengvaxia® disclosed herein and the hepatitis A vaccine disclosed herein are simultaneously on the same day administered to the subject or to the subject population.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, and the hepatitis A vaccine disclosed herein are simultaneously on the same day administered to the subject or to the subject population on day 0/1 as a first administration and Dengvaxia® disclosed herein is subsequently administered to the subject or to the subject population within three months from the first administration, such as on day 90 from the first administration, as a second administration. Alternatively, Dengvaxia® disclosed herein and the hepatitis A vaccine disclosed herein are simultaneously on the same day administered to the subject or to subject population on day 0/1 as a first administration and the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, is administered subsequently to the subject or to the subject population within three months from the first administration, such as on day 90 from the first administration, as a second administration.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, and TV003 or TV005 disclosed herein and the hepatitis A vaccine disclosed herein are simultaneously on the same day administered to the subject or to the subject population.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, and the hepatitis A vaccine disclosed herein are simultaneously on the same day administered to the subject or the subject population on day 0/1 as a first administration and wherein TV003 or TV005 disclosed herein is subsequently administered to the subject or to the subject population within three months from the first administration, such as on day 90 from the first administration, as a second administration. Alternatively, TV003 or TV005 disclosed herein and the hepatitis A vaccine disclosed herein are simultaneously on the same day administered to the subject or to the subject population on day 0/1 as a first administration and the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, is administered subsequently to the subject or to the subject population within three months from the first administration, such as on day 90 from the first administration, as the second administration.

The above method is also to be considered in the context of a use of the unit dose of dengue vaccine as disclosed herein for such methods of preventing dengue disease and hepatitis A or in the context of the use of the unit dose of dengue vaccine for the manufacture of a medicament for such methods of preventing dengue disease and hepatitis A.

Furthermore, the present invention is directed to a kit against hepatitis A and dengue disease comprising a box containing at least (a) a first container holding a hepatitis A vaccine, as defined above such as HAVRIX®, and (b) a second container holding a unit dose of a dengue vaccine composition as defined above, wherein said unit dose comprises a tetravalent dengue virus composition including four live, attenuated dengue virus strains.

Method of Preventing Dengue Disease and Yellow Fever and Uses

The present invention is directed in part to a method of preventing dengue disease as well as yellow fever in a subject. Thus, in certain embodiments the invention is directed to a method of preventing dengue disease in a subject, comprising administering to the subject a reconstituted unit dose of the invention as described herein, wherein the method further comprises preventing yellow fever in the subject by concomitant administration of a yellow fever vaccine, in particular YF-17D, to the subject.

The present invention is directed in part to a method of preventing dengue disease as well as yellow fever in a subject population. Thus, in certain embodiments the invention is directed to a method of preventing dengue disease in a subject population, comprising administering to the subject population a reconstituted unit dose of the invention as described herein, wherein the method further comprises preventing yellow fever in the subject population by concomitant administration of a yellow fever vaccine, in particular YF-17D, to the subject population.

In certain embodiments the invention is directed to said methods, wherein the unit dose of the invention as described herein and the yellow fever vaccine, in particular YF-17D, are administered simultaneously. In some of these embodiments the simultaneous administration is on day 0 or day 90, preferably on day 0. In other embodiments the administration of the unit dose of the invention as described herein and the yellow fever vaccine, in particular YF-17D, are done sequentially such as wherein the yellow fever vaccine is administered before or after the unit dose of dengue vaccine as described herein, such as within about 6 weeks, or such as within about 4 weeks, or such as within about 2 weeks, or such as about within 1 week.

In certain embodiments the invention is directed to said methods, wherein the reconstituted unit dose of the invention as described herein is administered and the yellow fever vaccine, in particular YF-17D, are administered by subcutaneous injection. According to some embodiments, the subcutaneous injections are administered to the arm, preferably to the deltoid region of the arm. According to some of these embodiments the subcutaneous injections of the unit dose of the invention as described herein and yellow fever vaccine, in particular YF-17D, are administered to different anatomical sites, such as to opposite arms, in particular when the vaccines are administered simultaneously.

In certain embodiments the invention is directed to said methods, wherein two unit doses of the invention as described herein are administered. In some embodiments the two unit doses of the invention as described herein are administered within 12 month or more, or within 6 month, or within three months, such as at day 0/1 and day 90. According to some of these embodiments a further third unit dose of the invention as described herein is administered after the second. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said methods, wherein two reconstituted unit doses of the invention as described herein and one dose of a yellow fever vaccine, in particular YF-17D, are administered, in particular according to the following schedule an administration of said yellow fever vaccine on day 0, a first administration of the first reconstituted unit dose after said yellow fever vaccine administration, such as 3 months later and preferably on day 90, and a second administration of the second reconstituted unit dose after said first administration of the reconstituted unit dose, such as 3 months later and preferably on day 180.

In certain embodiments the invention is directed to said methods, wherein two reconstituted unit doses of the invention as described herein and one dose of a yellow fever vaccine, in particular YF-17D, are administered, in particular according to the following schedule a first administration of the first reconstituted unit dose on day 0, a second administration of the second reconstituted unit dose after said first administration of the reconstituted unit dose, such as 3 months later and preferably on day 90, and an administration of said yellow fever vaccine after said second administration of the reconstituted unit dose, such as 3 months later and preferably on day 180.

In certain embodiments the invention is directed to said methods, wherein two reconstituted unit doses of the invention as described herein and one dose of a yellow fever vaccine, in particular YF-17D, are administered, in particular according to the following schedule a simultaneous administration of the first reconstituted unit dose and said yellow fever vaccine on day 0, and a second administration of the second reconstituted unit dose after said simultaneous administration, such as 3 months later and preferably on day 90.

In a preferred embodiment, the yellow fever vaccine and unit dose of the invention as described herein are administered simultaneously on day 0 or simultaneously on day 90.

In certain embodiments, the invention is directed to said methods, wherein the subject or subject population is seronegative to all dengue serotypes. In certain embodiments, the invention is directed to said methods, wherein the reconstituted unit dose of the invention as described herein is administered subcutaneously to a subject or subject population and the yellow fever vaccine, in particular YF-17D vaccine, is administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the yellow fever vaccine, in particular YF-17D, are administered to a subject or subject population from a dengue endemic region. In certain embodiments, the reconstituted unit dose of the invention as described herein and the yellow fever vaccine, in particular YF-17D, are administered subcutaneously to a subject or subject population from a dengue endemic region. In other embodiments, the subject or subject population is from a dengue non-endemic region. Such a subject population or such a subject may be vaccinated according to the present invention in the context of traveling to a dengue endemic region and yellow fever endemic region.

In certain embodiments the invention is directed to said methods, wherein the reconstituted unit dose of the invention as described herein and of the yellow fever vaccine, in particular YF-17D, are administered subcutaneously to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and yellow fever non-endemic region. According to some of these embodiments, the subject or subject population are seronegative for all four dengue serotypes.

The above method is also to be considered in the context of a use of the unit dose of dengue vaccine as disclosed herein for such methods or in the context of the use of the unit dose of dengue vaccine for the manufacture of a medicament for such methods.

Method of Preventing and Uses. Method of Inoculating Against Dengue Disease and Uses The present invention is directed in part to a method of preventing dengue disease (in particular virologically confirmable dengue, VCD) in a subject. Thus, in certain embodiments the invention is directed to a method of preventing dengue disease in a subject, comprising administering to the subject, a unit dose/tetravalent dengue virus composition, in particular a reconstituted unit dose of the invention as described herein.

The present invention is directed in part to a method of preventing dengue hemorrhagic fever (DHF) and dengue shock syndrome (DSS). Thus, in certain embodiments the invention is directed to a method of preventing dengue hemorrhagic fever (DHF) and dengue shock syndrome (DSS), comprising administering to the subject a reconstituted unit dose/tetravalent dengue virus composition of the invention as described herein.

The present invention is therefore directed to a method of inoculating a subject against virologically confirmable dengue disease with a tetravalent dengue virus composition including four live attenuated dengue virus strains representing serotype 1, serotype 2, serotype 3 and serotype 4, wherein in particular the tetravalent dengue virus composition includes a chimeric dengue serotype 2/1 strain and a dengue serotype 2 strain and a chimeric dengue serotype 2/3 strain and a chimeric dengue serotype 2/4 strain, wherein in particular the dengue serotype 2 strain is derived from the wild type virus strain DEN-2 16681 (SEQ ID NO 11) and differs in at least three nucleotides from the wild type as follows:

a) 5'-noncoding region (NCR)-57 (nt-57 C-to-T): major attenuation locus b) NS1-53 Gly-to-Asp (nt-2579 G-to-A): major attenuation locus c) NS3-250 Glu-to-Val (nt-5270 A-to-T): major attenuation locus; and wherein the three chimeric dengue strains are derived from the serotype 2 strain by replacing the structural proteins prM and E from serotype 2 strain with the corresponding structural proteins from the other dengue serotypes, resulting in the following chimeric dengue strains:

a DENV-2/1 chimera, a DENV-2/3 chimera and a DENV-2/4 chimera.

Further information regarding the serotypes of the tetravalent composition can be derived from section "Dengue virus strains" above.

The tetravalent dengue virus composition for such a method may be in the form of a unit dose comprising:

(i) a dengue serotype 1 in a concentration of at least 3.3 log 10 pfu/0.5 ml, (ii) a dengue serotype 2, in a concentration of at least 2.7 log 10 pfu/0.5 ml, (iii) a dengue serotype 3, in a concentration of at least 4.0 log 10 pfu/0.5 ml, and (iv) a dengue serotype 4, in a concentration of at least 4.5 log 10 pfu/0.5 ml.

The present invention is in particular directed to such a method wherein the unit dose is lyophilized and upon reconstitution with 0.5 mL of a pharmaceutically acceptable diluent comprises:

(i) a dengue serotype 1 in a concentration of at least 3.3 log 10 pfu/0.5 ml, (ii) a dengue serotype 2, in a concentration of at least 2.7 log 10 pfu/0.5 ml, (iii) a dengue serotype 3, in a concentration of at least 4.0 log 10 pfu/0.5 ml, and (iv) a dengue serotype 4, in a concentration of at least 4.5 log 10 pfu/0.5 ml.

Further information regarding the tetravalent composition or the unit dose can be derived from section "Dengue vaccine composition" and "Unit dose" above.

The present invention is therefore directed to a method and corresponding use, the method comprising a primary vaccination with only two administrations of the unit dose comprising the steps of:

(A) administering a first unit dose of the tetravalent dengue virus composition to the subject, and (B) administering a second unit does of the tetravalent dengue virus composition to the subject within 3 months of administration of the first unit dose.

According to this embodiment the administration of only two doses within 3 months is sufficient to provide effective protection against a subsequent dengue infection.

Such method preferably provides a combined vaccine efficacy against all four serotypes in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the second administration of the administration schedule.

Such method also preferably provides a combined vaccine efficacy against all four serotypes, in preventing virologically confirmable dengue disease with a 2-sided 95% confidence interval, wherein the lower bound is more than 45%, when measured against placebo in a subject population of at least 1,500 or at least 2,000 healthy subjects seronegative against all serotypes at baseline and 14 to 16 years of age, from 30 days after the second administration of the administration schedule until 18 months after the second administration of the administration schedule.

According to certain embodiments the method of inoculation against the virologically confirmable dengue disease is due to a dengue serotype 2, and/or due to a dengue serotype 1. The method has very high efficacy against dengue serotype 2 and dengue serotype 1 and the highest efficacy against dengue serotype 2.

In certain embodiments, the invention is directed to said methods having a vaccine efficacy against serotype 1, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 30%, is more than 35% is more than 40%, is more than 45%, is more than 50%, or is more than 54%. In certain such embodiments the subject population of at least 1,500 is seronegative against all serotypes at base line and the lower bound is more than 35%. In certain such embodiments the seronegative and seropositive population each provide a vaccine efficacy against serotype 1 with a 2-sided 95% confidence interval, wherein the lower bounds are within 10%-points.

In certain embodiments, the invention is directed to said methods having a vaccine efficacy against serotype 1, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 40%, is more than 50%, is more than 60%, or is more than 65%. In certain such embodiments the subject population of at least 1,500 is seronegative against all serotypes at base line. In certain such embodiments the seronegative and seropositive population each provide a vaccine efficacy against serotype 1 which are within 5%-points.

In certain embodiments, the invention is directed to said methods having a vaccine efficacy against serotype 2, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 50%, is more than 60%, is more than 70%, is more than 80%, or is more than 85%. In certain such embodiments the subject population of at least 1,500, is seronegative against all serotypes. In certain such embodiments the seronegative and seropositive population each provide a vaccine efficacy against serotype 2 with a 2-sided 95% confidence interval, wherein the lower bounds are within 5%-points.

In certain embodiments, the invention is directed to said methods having a vaccine efficacy against serotype 2, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 60%, is more than 70%, is more than 80%, or is more than 90%. In certain such embodiments the subject population of at least 1,500 is seronegative against all serotypes at base line. In certain such embodiments the seronegative and seropositive population each provide a vaccine efficacy against serotype 2 which are within 5%-points.

The efficacy of the method is further described in more detail below in this the section.

In certain embodiments the unit dose is reconstituted and administered by subcutaneous injection. According to some of these embodiments, the subcutaneous injection is administered to the arm, preferably to the deltoid region of the arm.

According to one embodiment such a method does not include a step of determination whether there was a previous dengue infection in the subject before administration of the unit dose or wherein the serostatus of the subject is unknown before administration of the unit dose.

According to one embodiment such a method does not include a step of determination of a previous dengue infection in the subjects preferably at any time before, during or after the steps of administration or wherein the serostatus of the subject is unknown preferably at any time before, during or after the steps of administration.

The method according to the invention does not require the testing of the serostatus before vaccination and thus allows immediate treatment and outbreak control. According to certain embodiments the use is for a method wherein the subject is exposed to a dengue outbreak. In certain such embodiments the outbreak is due to a dengue serotype 2, and/or due to a serotype 1.

According to one embodiment such a method the subject is from a region wherein the seroprevalence rate is unknown and/or wherein the seroprevalence rate is below 80%, or below 70%, or below 60%.

According to one embodiment of such a method the subject is seronegative at baseline and is from a region or travels to a region wherein the seroprevalence rate is high with respect to serotype 1 and/or serotype 2 i.e. 80%, or 90% or above.

According this embodiment the vaccine and corresponding method is safe for seronegative and seropositive subjects and thus does not require an analysis of the serostatus or a determination of a previous dengue infection or a high seroprevalence rate in the region. Such a method preferably provides a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline, preferably in at least 1,500 healthy 4 to 16 year old subjects seronegative at baseline, from first administration of the administration schedule until 12 to 18 months after the second administration of the administration schedule. Preferably, the 2-sided 95% confidence interval of the combined vaccine efficacy against virologically-confirmed dengue with hospitalization against all four serotypes when comparing seropositive and seronegative subjects provides for lower bounds of the 2-sided confidence interval which are within 10% points or within 15% points or within 20% points. The method is preferably safe with respect to serotype 1 and serotype 2 which may therefore be used in outbreak situations due to serotype 1 and/or serotype 2 or even for seronegative subjects (e.g. travelers) or subjects with unknown serostatus in regions with very high seroprevalence rates (>80%) due to serotype 1 and/or serotype 2.

The safety of the method is further described in more detail in the section "method of preventing, method of inoculating".

According to one embodiment such a method does not include the active surveillance with respect to febrile illness of the subject after the administration of the first- and second-unit dose. During active surveillance any subject with febrile illness (defined as fever≥38° C. on any 2 of 3 consecutive days) will be asked to return to the site for dengue fever evaluation by the Investigator. Subjects/guardians will be contacted at least weekly to ensure robust identification of febrile illness by reminding subjects/guardians of their obligation to return to the site in case of febrile illness. This contact will be implemented through appropriate methods that may differ in each trial site (eg, phone calls, text messaging, home visits, school-based surveillance).

According to one embodiment such a method does not include vaccine immunogenicity analysis including GMTs for dengue neutralizing antibodies.

According to one embodiment such a method does not include a reactogenicity analysis. Such a reactogenicity analysis relates to solicited local AEs (injection site pain, injection site erythema, and injection site swelling) and solicited systemic AEs (child<6 years: fever, irritability/fussiness, drowsiness and loss of appetite; child≥6 years: asthenia, fever, headache, malaise and myalgia) which will e.g. be assessed for 7 days and 14 days, respectively, following each vaccination (vaccination day included) via collection of diary cards.

According to one embodiment the method does not include an active surveillance, an immunogenicity analysis and a reactogenicity analysis.

According to such embodiments the vaccine and the corresponding method of inoculation are safe and therefore do not require further steps of surveillance or analysis.

In view of the above the method according to one embodiment comprises a primary vaccination consisting of the steps of:
(A) selecting a subject for administration of the unit doses of the tetravalent dengue virus composition in need for protection against dengue infection without determination of a previous dengue infection, and
(B) administering a first unit dose of the tetravalent dengue virus composition to the subject, and
(C) administering a second unit dose of the tetravalent dengue virus composition to the subject within 3 months of administration of the first unit dose.
Therefore the method of inoculating is finalized without determination of a previous dengue infection. The method further optionally comprises at least 1 years after the administration of the second unit dose a booster dose of the unit dose.

Selecting the subject may include all types of considerations but preferably not the determination of a previous dengue infection. The selection may include consideration of the age, health conditions, and threat of infection. The threat of infection includes consideration of the seroprevalence rate in the region in which the subject normally lives or intends to travel, the serotype specific seroprevalence rate and an outbreak situation or serotype specific outbreak situations. The subject may be selected due to its exposure to serotype 1 and/or serotype 2 or due to the fact it requires protection against a specific dengue serotype, i.e. serotype 1 and/or serotype 2.

According to the invention the method is applicable to subjects of all kinds of ages. According to one embodiment the subject is under 9 years of age, or 4 to 5 years of age, or 6 to 11 years of age or 12 to 16 years, or 6 to 16 years of age or 4 to 16 years of age, or 2 to 17 years of age, or 9 years of age, or over 9 years of age, or 9 to 17 years of age, or 18 to 45 years of age, or 46 to 60 years of age, or over 60 years of age.

In particular the present invention is directed to such a method wherein the method which is safe.

In particular the present invention is directed to such a method providing a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline from first administration of the administration schedule until 12 to 18 months after the last administration of the administration schedule.

In particular the present invention is directed to such a method wherein the method which is effective.

In particular the present invention is directed to such a method providing a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the last administration of the administration schedule.

In certain embodiments, the invention is directed to said methods, wherein the subject is seronegative to all dengue serotypes.

The present invention is directed in part to a method of preventing dengue disease (in particular virologically confirmable dengue, VCD) in a subject population. Thus, in certain embodiments the invention is directed to a method of preventing dengue disease in a subject population, comprising administering to the subject population a unit dose, in particular a reconstituted unit dose of the invention as described herein.

The present invention is in part directed to said method for preventing dengue disease (in particular virologically confirmable dengue, VCD) in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease (in particular virologically confirmable dengue, VCD) in a subject comprising administering to the subject at least a first reconstituted unit dose of the invention as described herein, wherein certain ratios of neutralizing antibody titers at day 180 or 365 after administration of said first unit dose to the subject are achieved. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for GMT DENV-4 of not more than 50, or not more than 40, or not more than 30, or not more than 20. In some of these embodiments, the ratio of the neutralizing antibody titers of DENV-2: DENV-1 is not more than 20, or not more than 18, or not more than 15 at day 180 or 365 after administration of said first reconstituted unit dose, and/or the ratio of the neutralizing antibody titers of DENV-2: DENV-3 is not more than 20, or not more than 18, or not more than 15 at day 180 or 365 after administration of said first reconstituted unit dose.

The geometric mean neutralizing antibody titers (GMTs) of a subject population or the neutralizing antibody titers of a subject are determined in accordance with the microneutralization test disclosed herein, for example according to the method described in Example 2. Without wishing to be bound to any theory, it is presently understood that a method inducing a more balanced immune response due to the administration of the reconstituted unit dose of the invention as described herein, in terms of less differences between the geometric mean neutralizing antibody titers (GMTs) against the four dengue serotypes or the neutralizing antibody titers against the four dengue serotypes, is beneficial to the subject or subject population to be vaccinated. In particular, it is understood that a much greater response to any one of the four serotypes, such as to DENV-2 in comparison to the other serotypes, is less beneficial.

The present invention is in part directed to said method for preventing dengue disease (in particular virologically confirmable dengue, VCD) in a subject or subject population wherein the method provides a seropositivity rate in a subject population of at least 50 subjects including the administration of two unit doses subcutaneously at day 1 and at day 90, wherein the subjects of the subject population are seronegative to all dengue serotypes at baseline. In certain such embodiments, at least 80% of the subject population are seropositive for all four dengue serotypes at least one month after administration of the first unit dose, such as at day 30, and/or at least 80% of the subject population are seropositive for all four dengue serotypes before or at the time of the administration of the second unit dose, such as at day 90, and/or at least 80%, or at least 85%, or at least 90%, or at least 95% of the subject population are seropositive for all four dengue serotypes after the administration of the second unit dose, such as at day 120, and/or at least 80%, or at least 85%, or at least 90% of the subject population are seropositive for all four dengue serotypes after the administration of the second unit dose, such as at day 270.

The present invention is in part directed to said method for preventing dengue disease (in particular virologically confirmable dengue, VCD) in a subject or subject population wherein the method provides a seropositivity rate in a subject population of at least 100 subjects including administration of two unit doses subcutaneously at day 1 and at day 90, wherein the subjects of the subject population comprises from 20% to 40% subjects who are seronegative to all dengue serotypes and from 60% to 80% subjects who are seropositive to at least one dengue serotype at base line, wherein at day 120 and/or day 270 the seropositivity rate for all four dengue serotypes in the seronegative part of the subject population and the seropositivity rate for all four dengue serotypes in the seropositive part of the subject population do not deviate more than 10%-points and/or wherein at day 120 the seropositivity rate for all four dengue serotypes in the seronegative part of the subject population and the seropositivity rate for all four dengue serotypes in the seropositive part of the subject population do not deviate more than 5%-points.

The present invention is in part directed to a method of preventing virologically confirmable dengue disease in a subject or subject population comprising administering to the subject or subject population a reconstituted unit dose of a tetravalent dengue virus composition including four live, attenuated dengue serotypes, in particular the virus strains as described herein.

The present invention is in part directed to a method of preventing virologically confirmable dengue disease with hospitalization in a subject or subject population comprising administering to the subject or subject population a reconstituted unit dose of a tetravalent dengue virus composition including four live, attenuated dengue serotypes, in particular the virus strains as described herein.

In certain embodiments, the method includes a reconstituted unit dose/tetravalent dengue virus composition of a dengue vaccine composition administered for preventing dengue disease in a subject or a subject population, the reconstituted unit dose comprising: a tetravalent virus composition including four live attenuated dengue virus strains, wherein a unit dose is lyophilized and upon reconstitution with 0.5 mL of a pharmaceutically acceptable diluent the reconstituted unit dose is obtained which comprises:
(i) a dengue serotype 1, such as a chimeric dengue serotype 2/1 strain, in a concentration of at least 3.3 log 10 pfu/0.5 ml,
(ii) a dengue serotype 2, such as a dengue serotype 2 strain, in a concentration of at least 2.7 log 10 pfu/0.5 ml,
(iii) a dengue serotype 3, such as a chimeric dengue serotype 2/3 strain, in a concentration of at least 4.0 log 10 pfu/0.5 ml, and
(vi) a dengue serotype 4, such as a chimeric dengue serotype 2/4 strain, in a concentration of at least 4.5 log 10 pfu/0.5 ml.

It is preferred that the reconstituted unit dose/tetravalent dengue virus composition is used in the method of preventing dengue disease of the present invention, wherein upon reconstitution of the unit dose with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6% and wherein the subject or subject population is of 18 to 60 years of age.

In another preferred embodiment, the reconstituted unit dose/tetravalent dengue virus composition is used in the method of preventing dengue disease of the present invention, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8% and wherein the subject or subject population is of 2 to 17 years of age.

In certain embodiments, the invention is directed to said methods, wherein said unit dose comprises a tetravalent dengue virus composition including four live attenuated dengue serotypes, in particular the virus strains described herein wherein the serotypes have certain concentrations as described herein with respect to the virus composition and unit dose such as:
  (i) a dengue serotype 1 (e.g. chimeric dengue serotype 2/1 strain) has a concentration of 3.3 log 10 pfu/dose to 5.0 log 10 pfu/dose, or 3.3 log 10 pfu/0.5 mL to 5.0 log 10 pfu/0.5 mL
  (ii) a dengue serotype 2 (e.g. dengue serotype 2 strain) has a concentration of 2.7 log 10 pfu/dose to 4.9 log 10 pfu/0.5 dose, or 2.7 log 10 pfu/0.5 ml to 4.9 log 10 pfu/0.5 ml
  (iii) a dengue serotype 3 (e.g. chimeric dengue serotype 2/3 strain) has a concentration of 4.0 log 10 pfu/dose to 5.7 log 10 pfu/0.5 dose, or 4.0 log 10 pfu/0.5 mL to 5.7 log 10 pfu/0.5 mL and
  (iv) a dengue serotype 4 (e.g. chimeric dengue serotype 2/4 strain) has a concentration of 4.5 log 10 pfu/dose to 5.5 log 10 pfu/0.5 dose, or 4.5 log 10 pfu/0.5 mL to 5.5 log 10 pfu/0.5 mL.

In preferred such embodiments, the subject or subject population is of 2 to 17 years of age, such as 4 to 16 years of age, and preferably less than 9 years of age. In other preferred embodiments, the subject or subject population is 4-5 years of age, 6-11 years of age or 12-16 years of age.

In certain embodiments, the invention is directed to said methods, wherein said unit dose upon reconstitution with 0.5 mL of a pharmaceutically acceptable diluent has a concentration of 3.3 log 10 pfu/0.5 mL to 3.6 log 10 pfu/0.5 mL for dengue serotype 1 (e.g. chimeric dengue serotype 2/1 strain), has a concentration of 2.7 log 10 pfu/0.5 mL to 4.0 log 10 pfu/0.5 mL for dengue serotype 2 (e.g. dengue serotype 2 strain), has a concentration of 4.0 log 10 pfu/0.5 mL to 4.6 log 10 pfu/0.5 mL for dengue serotype 3 (e.g. chimeric dengue serotype 2/3 strain) and has a concentration of 4.5 log 10 pfu/0.5 mL or 4.6 log 10 pfu/0.5 mL to 5.1 log 10 pfu/0.5 mL for dengue serotype 4 (e.g. chimeric dengue serotype 2/4 strain). In preferred such embodiments, the subject or subject population is of 2 to 17 years of age, such as 4 to 16 years of age, and preferably less than 9 years of age. In other preferred embodiments, the subject or subject population is 4-5 years of age, 6-11 years of age or 12-16 years of age.

In certain embodiments, the invention is directed to said methods, wherein the concentration of the dengue serotype 1 (e.g. chimeric dengue serotype 2/1 strain) measured in pfu/0.5 mL is 1% to 7% of the total concentration, the concentration of the dengue serotype 2 (e.g. dengue serotype 2 strain) measured in pfu/0.5 mL is less than 8% of the total concentration, such as in the range of 1% to 8% of the total concentration, the concentration of the dengue serotype 3 (e.g. chimeric dengue serotype 2/3 strain) measured in pfu/0.5 mL is at least 10% of the total concentration, and the concentration of the dengue serotype 4 (e.g. chimeric dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL Preferably, in said embodiments the subject or subject population is of 2 to 17 years of age, such as 4 to 16 years of age, and even more preferably less than 9 years of age. In other preferred embodiments, the subject or subject population is 4-5 years of age, 6-11 years of age or 12-16 years of age.

In a further preferred embodiment, the invention is directed to said methods, wherein the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In certain embodiments, the invention is directed to said methods, wherein the reconstituted unit dose of the invention as described herein is administered by subcutaneous injection. According to some of these embodiments, the subcutaneous injection is administered to the arm, preferably to the deltoid region of the arm.

In certain embodiments, the invention is directed to said methods, wherein the reconstituted unit dose is administered to a subject of unknown serostatus and/or wherein no test has been carried out to determine whether the subject is seropositive or seronegative (before) the unit dose as described herein is administered. In certain embodiments, the invention is directed to said methods which do not include a step of determination of a previous dengue infection in the subject or subjects. In certain embodiments, the invention is directed to said methods which do not include the analysis of the seroprevalence rate in the region or is conducted in a region with a seroprevalence of below 80%, below 70% or below 60%. In certain embodiments the invention is directed to a method wherein the serostatus of the subject is unknown. In such embodiments the serostatus is not determined at any time before and after administration in relation to this method. In certain embodiments of the invention the method is used in an outbreak situation. In certain embodiments, the invention is directed to said methods being conducted outside a clinical trial In certain embodiments, the invention is directed to said methods, wherein the subject, or subject population is seronegative to all dengue serotypes.

In certain embodiments, the invention is directed to said methods, wherein two unit doses of the invention as described herein are administered. In some embodiments the two unit doses are administered within 12 months or more, or within six months, or within three months, and optionally at least 4 weeks apart such as at day 0 and day 90 or at day 1 and day 90. According to some of these embodiments, a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments, the method of the invention comprises or consists of a single unit dose of the invention being administered.

In certain embodiments, the invention is directed to said methods, wherein the reconstituted unit dose of the invention as described herein is administered subcutaneously to a subject or subject population that is seronegative with respect to all dengue serotypes. In other embodiments, the subject or subject population is seropositive with respect to at least one dengue serotype.

In certain embodiments, the invention is directed to said methods, wherein the unit dose of the invention as described herein is administered to a subject or subject population from a dengue endemic region. In some of these embodiments, the subject or subject population is from Singapore, Dominican Republic, Panama, Philippines, Colombia, Puerto Rico or Thailand, in particular from Singapore, Dominican Republic, Panama, or Philippines. In a preferred embodiment, the subject or subject population is from Asia Pacific or from Latin America. In some other of these embodiments, the subject or subject population is from Thailand, Sri Lanka, Philippines, Panama, Nicaragua, Dominican Republic, Colombia or Brazil. In other embodiments, the subject, or subject population is from a dengue non-endemic region. Such a subject population or such a subject may be vaccinated according to the present invention in the context of traveling to a dengue endemic region. In certain embodiments, the reconstituted unit dose of the invention as described herein is administered subcutaneously to a subject, or subject population that is from a dengue endemic region or a dengue non-endemic region.

In certain embodiments, the invention is directed to said methods, wherein the reconstituted unit dose of the invention as described herein is administered subcutaneously to a subject or subject population of 2 to 60 years of age. In some embodiments, the subjects or subject population are adults of more than 17 years, or more than 18 years, or 18 to 60 years. In further specific embodiments, the subjects or subject population are adults of more than 21 years, or 21 to 60 years, or 21 to 45 years of age.

In certain embodiments, the invention is directed to said methods, wherein the reconstituted unit dose of the invention as described herein is administered subcutaneously to children and adolescents of 2 to 17 years of age. In some embodiments, the subjects or subject population are less than 9 years of age, or less than 4 years of age. In some embodiments, the subjects or subject population are from 2 to 9 years of age, or from 2 to 5 years of age, or from 4 to 9 years of age or from 6 to 9 years of age. In other embodiment, the subject or subject population is 4 to 16 years of age. In some such embodiments, the subject or subject population is 4-5 years of age, 6-11 years of age or 12-16 years of age. Optionally, the subject or subject population is seronegative with respect to all dengue serotypes.

In certain embodiments, the invention is directed to said methods, wherein the unit dose of the invention as described herein is administered to a pediatric subject or pediatric subject population of less than 2 years of age, preferably of 2 months to 2 years or 2 months to 1.5 years or 2 months to 1 year. According to some of these embodiments, the pediatric subject or pediatric subject population is seronegative and from a dengue endemic region.

In certain embodiments, the invention is directed to said methods, wherein the reconstituted unit dose of the invention as described herein is administered to a pediatric subject or pediatric subject population of less than 2 years of age, preferably of 2 months to 2 years or 2 months to 1.5 years or 2 months to 1 year, preferably by subcutaneous injection. According to some of these embodiments, the pediatric subject or pediatric subject population is seronegative and from a dengue endemic region.

In a certain embodiments, the invention is directed to said methods, wherein the subject or subject population is 4-5 years of age and from Asia Pacific, 6-11 years of age and from Asia Pacific, or 12-16 years of age and from Asia Pacific. In other embodiments, the subject or subject population is 4-5 years of age and from Latin America, 6-11 years of age and from Latin America, or 12-16 years of age and from Latin America.

In a certain embodiments, the invention is directed to said methods, wherein the subject or subject population is 4-5 years of age and seropositive for at least 1 dengue serotype, 6-11 years of age and seropositive for at least 1 dengue serotype, or 12-16 years of age and seropositive for at least 1 dengue serotype. In other embodiments, the subject or subject population is 4-5 years of age and seronegative for all dengue serotypes, 6-11 years of age and seronegative for all dengue serotypes, or 12-16 years of age and seronegative for all dengue serotypes.

In a certain embodiments, the invention is directed to said methods, wherein the subject or subject population is from Asia Pacific or Latin America and seropositive for at least one dengue serotype at baseline. In other embodiments, the subject or subject population is from Asia Pacific or Latin America and seronegative for at all dengue serotype at baseline.

In certain embodiments, the invention is directed to said methods, wherein the subject or subject population is from Asia Pacific, seropositive for at least one dengue serotype at baseline and 4-5 years of age, 6-11 years of age, or 12-16 years of age. In other embodiments, the subject or subject population is from Asia Pacific, seronegative for all dengue serotypes at baseline and 4-5 years of age, 6-11 years of age, or 12-16 years of age. In yet other embodiments, the subject or subject population is from Latin America, seropositive for at least one dengue serotype at baseline and 4-5 years of age, 6-11 years of age, or 12-16 years of age. In other embodiments, the subject or subject population is from America, seronegative for all dengue serotypes at baseline and 4-5 years of age, 6-11 years of age, or 12-16 years of age.

In certain embodiments, the invention is directed to said methods, wherein the subject or subject population had prior vaccination against Yellow Fever. In other embodiments, the subject or subject population had prior vaccination against Japanese Encephalitis. In yet other embodiments, the subject or subject population had no prior vaccination against Yellow Fever. In other embodiments, the subject or subject population had no prior vaccination against Japanese Encephalitis. Prior vaccination indicates a vaccination prior to 30 days after a second administration, such as within 4 months after the first administration, with the reconstituted unit dose as described herein. For example for vaccine efficacy (VE) as determined in Example 6 from 30 days post-second vaccination, a prior vaccination of Yellow Fever is defined as a Yellow Fever vaccination occurring before 30 days post-second vaccination. In certain embodiments, the subject or subject population received Dengvaxia® within the administration regimen as described herein or within 4.5 years after administration of the first dose.

Particularly unbalanced titers of neutralizing antibodies against the four dengue serotypes are observed in seronegative populations or subjects after administration of the commercially available dengue vaccine. The present invention shows that in particular seronegative subjects show a more balanced immune response to the four dengue serotypes after administration of the reconstituted unit dose of the invention as described herein. It is therefore contemplated that the unit dose of the invention as described herein and methods of the present invention as described herein may provide a more robust immune response in a subject population including both seropositive and seronegative subjects. This balanced response and balanced efficacy and safety is required to allow inoculation without prior serostatus analysis which is a major advantage in vaccination programs and in particular in outbreak situations.

The present invention is directed in part to a method of preventing virologically confirmable dengue disease in a subject comprising administering to the subject a tetravalent dengue virus composition including four dengue virus strains representing serotype 1, serotype 2, serotype 3 and serotype 4, wherein the virus strains are optionally live, attenuated dengue virus strains.

The present invention is directed in part to a method of preventing virologically confirmable dengue disease in a subject consisting of administering to the subject a tetravalent dengue virus composition including four dengue virus strains representing serotype 1, serotype 2, serotype 3 and serotype 4, wherein the virus strains are optionally live, attenuated dengue virus strains.

In certain embodiments, the invention is directed to said methods, wherein there is no step of determining the serostatus of the subject at baseline, in other words, said methods do not comprise a determination of a previous dengue infection of the subject at baseline before the administration of the tetravalent dengue virus composition. In particular, such methods are safe and effective. Thus, in certain such embodiments, the subject has not been tested for the presence a previous dengue infection.

In certain embodiments, the invention is directed to said methods, wherein the vaccine administration is safe irrespective of whether there is a determination that the subject had a previous dengue infection before the administration of the tetravalent dengue virus composition. In particular, such methods are also effective.

In certain embodiments, the invention is directed to said methods, wherein the method is safe and/or effective.

In certain embodiments, the invention is directed to said methods, wherein the composition includes at least one chimeric dengue virus. In certain such embodiments, the invention is directed to said methods, wherein the composition includes at least one non-chimeric dengue virus and at least one chimeric dengue virus, in particular a chimeric dengue serotype 2/1 strain and a dengue serotype 2 strain and a chimeric dengue serotype 2/3 strain and a chimeric dengue serotype 2/4 strain. The details of the composition are described above.

Therefore, in certain embodiments, the invention is directed to said methods having a vaccine efficacy, preferably a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline and e.g. 14 to 16 years of age, wherein a reconstituted unit dose/tetravalent dengue virus composition as described herein or placebo is administered e.g. at least twice within less than 6 months, such as within 3 months, after first administration or 30 days after the second/last administration until at least 12 to 18 months (e.g. at 12 or at 18 months) after the second/last administration. In embodiments, the invention is directed to said methods having a vaccine efficacy, preferably a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline, wherein a reconstituted unit dose or tetravalent dengue virus composition as described herein or placebo is administered at least once, until 15 to 21 months (e.g. 15 or 21 months) after the first administration of the administration schedule. In certain such embodiments, the lower bound is more than 30%, more than 40%, more than 50%, more than 55%, more than 60%, more than 65%, more than 70% or more than 72%. Preferably said reconstituted unit dose or placebo is administered subcutaneously within about 3 months, such as on days 0 and 90.

Therefore, in certain embodiments, the invention is directed to said methods having a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects (or at least 10,000, or at least 15,000 healthy subjects) irrespective of serostatus at baseline and 4 to 16 years of age, wherein a reconstituted unit dose/ tetravalent dengue virus composition as described herein or placebo is administered e.g. at least twice within less than 6 months, such as within 3 months, after the first administration until 18 months after the last administration. In these embodiments, the lower bound is e.g. more than 62%, more than 64%, more than 66%, more than 68%, or more than 69%.

In certain embodiments, the invention is directed to said methods having a vaccine efficacy, preferably a combined vaccine efficacy against all four serotypes, in preventing virologically confirmable dengue disease of more than 30%, when measured against placebo in a subject population of at least 5,000 healthy subjects (or at least 10,000, or at least 15,000 healthy subjects) irrespective of serostatus at baseline and e.g. 14 to 16 years of age, wherein a reconstituted unit dose or tetravalent dengue virus composition as described herein or placebo is administered at least twice within less than 6 months, such as within 3 months, after first administration or 30 days after the second administration/last administration until at least 12 months or until 12 to 18 months (e.g. at 12 or at 18 months) after the second administration/last administration. In certain embodiments, the invention is directed to said methods having a vaccine efficacy, preferably a combined vaccine efficacy against all four serotypes, in preventing virologically confirmable dengue disease of more than 30%, when measured against placebo in a subject population of at least 5,000 healthy subjects (or at least 10,000, or at least 15,000 healthy subjects) irrespective of serostatus at baseline, wherein a reconstituted unit dose or tetravalent dengue virus composition as described herein or placebo is administered at least once, until 15 months after the first administration of the administration schedule. In certain such embodiments, the vaccine efficacy is more than 40%, more than 50%, more than 55%, more than 60%, more than 65%, more than 70%, more than 75%, more than 78%, more than 79% or about 80%. Preferably said reconstituted unit dose or placebo is administered subcutaneously within about 3 month, such as on days 0 and 90.

Therefore, in certain embodiments, the invention is directed to said methods having a combined vaccine efficacy against all four serotypes, in preventing virologically confirmable dengue disease of more than 66%, when measured against placebo in a subject population of at least 5,000 healthy subjects (or at least 10,000, or at least 15,000 healthy subjects) irrespective of serostatus at baseline and 14 to 16 years of age, wherein a reconstituted unit dose/tetravalent dengue virus composition as described herein or placebo is administered e.g. at least twice within less than 6 months, such as within 3 months, after the first administration until 18 months after the last administration. In these embodiments, the vaccine efficacy is e.g. more than 68%, more than 70%, more than 72%, or more than 74%.

In certain embodiments, the invention is directed to said methods having a vaccine efficacy, preferably a combined vaccine efficacy against all four serotypes, in preventing virologically confirmable dengue disease with hospitalization with a 2-sided 95% confidence interval, wherein the lower bound is more than 0%, when measured against placebo in a subject population of at least 5,000 healthy subjects (or at least 10,000, or at least 15,000 healthy subjects) irrespective of serostatus at baseline, wherein a reconstituted unit dose or tetravalent dengue virus composition as described herein or placebo is administered at least twice within less than 6 months, such as within 3 months, 30 days after the second administration until at least 18 months after the second administration. In certain such embodiments, the lower bound is more than 10%, is more than 20%, is more than 30%, is more than 40%, is more than 50%, is more than 55%, is more than 60%, is more than 65%, is more than 70% or is more than 80%, or more than 90%.

In certain embodiments, the invention is directed to said methods having a combined vaccine efficacy against all four dengue serotypes in seronegative subjects with a 2-sided 95% confidence interval, wherein the lower bound is more than 25%, when measured against placebo in a subject population of at least 1,500 or at least 2,000 healthy subjects being seronegative against all serotypes at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, or is more than 55%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 1,500 or at least 2,000 or at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 30%, is more than 35%, is more than 40%, or is more than 45%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 40%, is more than 45%, is more than 50%, is more than 60%, or is more than 65%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the lower bound provided by the seropositive subjects at baseline and the subjects seronegative against all serotypes at baseline is no more than 15%-points.

In certain embodiments, the invention is directed to said methods having a combined vaccine efficacy against all four dengue serotypes in seronegative subjects of more than 30%, when measured against placebo in a subject population of at least 1,500 or at least 2,000 healthy subjects being seronegative against all serotypes at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes in seronegative subjects is more than 40%, is more than 50%, is more than 60%, is more than 65%, or is more than 70%.

In certain embodiments, the invention is directed to said methods having a combined vaccine efficacy against all four serotypes, in preventing virologically confirmable dengue disease, when measured against placebo in a subject population of at least 1,500 or at least 2,000 or at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments the said vaccine efficacy is more than 30%, is more than 40%, is more than 50%, is more than 55%, is more than 60%, or is more than 65%.

In certain embodiments, the invention is directed to said methods having a combined vaccine efficacy against all four serotypes, in preventing virologically confirmable dengue disease, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments the said vaccine efficacy is more than 40%, is more than 50%, is more than 60%, is more than 65%, is more than 70%, or is more than 75%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the lower bound provided by the seropositive subjects at baseline and the subjects seronegative against all serotypes at baseline is no more than 15%-points, or is no more than 10%-points.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 4 to 5 years of age at the time of randomization and irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 45%.

In certain embodiments, the invention is directed to said methods having a combined vaccine efficacy against all four dengue serotypes of more than 30%, when measured against placebo in a subject population of at least 1,000 healthy subjects 4 to 5 years of age at the time of randomization and irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes is more than 40%, is more than 50%, is more than 60%, is more than 65%, or is more than 70%.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 6 to 11 years of age at the time of randomization and irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, or is more than 70%.

In certain embodiments, the invention is directed to said methods having a combined vaccine efficacy against all four dengue serotypes of more than 30%, when measured against placebo in a subject population of at least 1,000 healthy subjects 6 to 11 years of age at the time of randomization and irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes is more than 40%, is more than 50%, is more than 60%, is more than 70%, is more than 75%, or is more than 80%.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 12 to 16 years of age at the time of randomization and irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, is more than 65%, or is more than 68%.

In certain embodiments, the invention is directed to said methods having a combined vaccine efficacy against all four dengue serotypes of more than 30%, when measured against placebo in a subject population of at least 1,000 healthy subjects 12 to 16 years of age at the time of randomization and irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes is more than 40%, is more than 50%, is more than 60%, is more than 70%, is more than 75%, or is more than 80%.

In certain embodiments, the invention is directed to said methods having a vaccine efficacy against dengue serotype 1 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, or is more than 50%.

In certain embodiments, the invention is directed to said methods having a vaccine efficacy against serotype 1, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the lower bound is more than 30%, is more than 35% is more than 40%, is more than 45%, is more than 50%, or is more than 54%. In certain such embodiments the subject population of at least 1,500 is seronegative against all serotypes at base line and the lower bound is more than 35%. In certain such embodiments the seronegative and seropositive population each provide a vaccine efficacy against serotype 1 with a 2-sided 95% confidence interval, wherein the lower bounds are within 10%-points.

In certain embodiments, the invention is directed to said methods having a vaccine efficacy against dengue serotype 1 of more than 30%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the vaccine efficacy against dengue serotype 1 is more than 40%, is more than 50%, is more than 60%, is more than 65%, or is more than 70%.

In certain embodiments, the invention is directed to said methods having a vaccine efficacy against serotype 1, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the vaccine efficacy is more than 40%, is more than 50%, is more than 60%, or is more than 65%. In certain such embodiments the subject population of at least 1,500 is seronegative against all serotypes at base line. In certain such embodiments the seronegative and seropositive population each provide a vaccine efficacy against serotype 1 which are within 5%-points.

In certain embodiments, the invention is directed to said methods having a vaccine efficacy against dengue serotype 2 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50, is more than 60, is more than 70, is more than 80, or is more than 90%.

In certain embodiments, the invention is directed to said methods having a vaccine efficacy against serotype 2, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the lower bound is more than 50%, is more than 60%, is more than 70%, is more than 80%, or is more than 85%. In certain such embodiments the subject population of at least 1,500, is seronegative against all serotypes. In certain such embodiments the seronegative and seropositive population each provide a vaccine efficacy against serotype 2 with a 2-sided 95% confidence interval, wherein the lower bounds are within 5%-points.

In certain embodiments, the invention is directed to said methods having a vaccine efficacy against dengue serotype 2 of more than 30%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the vaccine efficacy against dengue serotype 2 is more than 40%, is more than 50%, is more than 60%, is more than 70%, is more than 80, or is more than 90%.

In certain embodiments, the invention is directed to said methods having a vaccine efficacy against serotype 2, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the vaccine efficacy is more than 60%, is more than 70%, is more than 80%, or is more than 90%. In certain such embodiments the subject population of at least 1,500 is seronegative against all serotypes at base line. In certain such embodiments the seronegative and seropositive population each provide a vaccine efficacy against serotype 2 which are within 5%-points.

In certain embodiments, the invention is directed to said methods having a vaccine efficacy against dengue serotype 3 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, about 30 days after the second administration of the administration schedule until at least 12 months after the second administration of the administration schedule. In certain such embodiments, the lower bound is more than 30%, is more than 40%.

In certain embodiments, the invention is directed to said methods having a vaccine efficacy against dengue serotype 3 of more than 30%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, 30 days after the second administration until at least 12 months after the second administration. In certain such embodiments, the vaccine efficacy against dengue serotype 3 is more than 40%, is more than 50%, is more than 55%, or is more than 60%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from first administration until 12 to 18 months (e.g. at 12 months or at 18 months) after the last administration, or from 30 days post last administration until 12 to 18 months (e.g. at 12 or at 18 months) after the last administration. In certain such embodiments, the lower bound is more than 10%, is more than 20%, is more than 30%, is more than 40%, is more than 50%, is more than 55%, is more than 60%, is more than 65%, is more than 66%, is more than 67%, is more than 70%, is more than 75%, is more than 77%, or is more than 80%.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from first administration until 12 to 18 months (e.g. at 12 months or at 18 months) after the last administration, or from 30 days post last administration until 12 to 18 months (e.g. at 12 or at 18 months) after the last administration. In certain such embodiments, the vaccine efficacy is more than is more than 70%, is more than 75%, is more than 80%, or is more than 82%, or is more than 85%, more than 88%.

In certain embodiments, the invention is directed to said methods having a combined vaccine efficacy against virologically-confirmed dengue with hospitalization against all four serotypes with a 2-sided 95% confidence interval, wherein the lower bound is more than 25%, when measured against placebo in a subject population of at least 1,500 or at least 2,000 healthy subjects being seronegative against all serotypes at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, is more than 70%, or is more than 75%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 60%, is more than 65%, is more than 66%, is more than 67%, is more than 70%, is more than 75%, is more than 77% or is more than 80%.

In certain embodiments, the invention is directed to said methods having a combined vaccine efficacy against virologically-confirmed dengue with hospitalization against all four serotypes of more than 30%, when measured against placebo in a subject population of at least 1,500 or at least 2,000 healthy subjects, healthy subjects being seronegative against all serotypes at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against virologically-confirmed dengue with hospitalization against all four serotypes is more than 40%, is more than 50%, is more than 60%, is more than 70%, is more than 80%, or is more than 90%.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the said vaccine efficacy is more than 60%, is more than 65%, is more than 66%, is more than 67%, is more than 70%, is more than 75%, is more than 77%, is more than 80, or is more than 85%.

In certain embodiments, the invention is directed to said methods having a combined vaccine efficacy against virologically-confirmed dengue with hospitalization against all four serotypes with a 2-sided 95% confidence interval, wherein the lower bound is more than 25%, when measured against placebo in a subject population of at least 1,500 or at least 2,000 healthy subjects being seropositive at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, is more than 70%, or is more than 80%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 60%, is more than 65%, is more than 70%, is more than 75%, or is more than 80%.

In certain embodiments, the invention is directed to said methods having a combined vaccine efficacy against virologically-confirmed dengue with hospitalization against all four serotypes of more than 30%, when measured against placebo in a subject population at least 1,500 or of at least 2,000 healthy subjects, healthy subjects being seropositive at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against virologically-confirmed dengue with hospitalization against all four serotypes is more than 40%, is more than 50%, is more than 60%, is more than 70%, is more than 80%, or is more than 90%.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the vaccine efficacy is more than 75%, is more than 70%, is more than 80%, is more than 85%, or is more than 90%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the lower bound provided by the seropositive subjects at baseline and the subjects seronegative against all serotypes at baseline is no more than 15%-points.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the vaccine efficacy provided by the seropositive subjects at baseline and the subjects seronegative against all serotypes at baseline is no more than 10%-points or no more than 5%-points.

In certain embodiments, the invention is directed to said methods having a relative risk, preferably a combined relative risk against all four serotypes, with a 2-sided 95% confidence interval, wherein the upper bound is less than 0.75, when measured against placebo in a subject population of at least 5,000 healthy subjects (or at least 10,000, or at least 15,000 healthy subjects) irrespective of serostatus at baseline, wherein a reconstituted unit dose/tetravalent dengue virus composition as described herein or placebo is administered at least twice within less than 6 months, such as within 3 months, 30 days after the second administration until at least 12 months after the second administration. In certain such embodiments, the upper bound is less than 0.70, less than 0.65, less than 0.60, less than 0.55, less than 0.50, less than 0.45, less than 0.40, less than 0.35, less than 0.30 or less than 0.28. Preferably said reconstituted unit dose or placebo is administered subcutaneously within about 3 month, such as on days 0 and 90.

In certain embodiments, the invention is directed to said methods having a relative risk, preferably a combined relative risk against all four serotypes, of less than 0.70, when measured against placebo in a subject population of at least 5,000 healthy subjects (or at least 10,000, or at least 15,000 healthy subjects) irrespective of serostatus at baseline, wherein a reconstituted unit dose/tetravalent dengue virus composition as described herein or placebo is administered at least twice within less than 6 months, such as within 3 months, 30 days after the second administration until at least 12 months after the second administration. In certain such embodiments, the relative risk is less than 0.65, less than 0.60, less than 0.55, less than 0.50, less than 0.45, less than 0.40, less than 0.35, less than 0.30, less than 0.25 or less than 0.23. Preferably said reconstituted unit dose or placebo is administered subcutaneously within about 3 month, such as on days 0 and 90.

In certain embodiments, the invention is directed to said methods, wherein virologically confirmable dengue disease occurs in less than 2.5% of the subjects, when measured against placebo in a subject population of at least 5,000 healthy subjects (or at least 10,000, or at least 15,000 healthy subjects) irrespective of serostatus at baseline, wherein a reconstituted unit dose/tetravalent dengue virus composition as described herein or placebo is administered at least twice within less than 6 months, such as within 3 months, 30 days after the second administration until at least 12 months or at least 18 months after the second administration. In certain such embodiments, virologically confirmable dengue disease occurs in less than 2.0% of the subjects, less than 1.5% of the subjects, less than 1.0% of the subjects, less than 0.8% of the subjects, or less than 0.6% of the subjects. Preferably said reconstituted unit dose or placebo is administered subcutaneously within about 3 month, such as on days 0 and 90.

In certain embodiments, the invention is directed to said methods having a combined vaccine efficacy against all four serotypes with a 2-sided 95% confidence interval, wherein the lower bound is more than 61.0%, or more than 65.0 or more than 70.0% or more than 72.0% when measured against placebo in a subject population of at least 5,000 healthy subjects (or at least 10,000, or at least 15,000 healthy subjects) from endemic irrespective of serostatus at baseline and being selected from the group consisting of 4 to 16 year old subjects at the time of randomization, wherein said unit dose/tetravalent dengue virus composition or said placebo is administered at least twice within 6 months or less, about 30 days after the last administration of the administration schedule until at least 12 or 13 months after the last administration of the administration schedule.

In certain embodiments, the invention is directed to said methods having a combined vaccine efficacy against all four serotypes of more than 66%, or of more than 70%, or of more than 75%, or of more than 77%, or of more than 80.0%, when measured against placebo in a subject population of at least 5,000 healthy subjects (or at least 10,000, or at least 15,000 healthy subjects) from endemic areas irrespective of serostatus at baseline and being selected from the group consisting of 4 to 16 year old subjects at the time of randomization, wherein said unit dose/tetravalent dengue virus composition or said placebo is administered at least twice within 6 months or less, about 30 days after the last administration of the administration schedule until at least 12 months or 13 month after the last administration of the administration schedule.

In certain embodiments, the invention is directed to said methods, wherein the combined vaccine efficacy against all four serotypes is measured about 30 days after the last administration of the administration schedule until 12 or 13 months after the last administration of the administration schedule.

In certain embodiments, the invention is directed to said methods, wherein said unit dose or said placebo is administered at least twice within three months, in particular at about day 1 and about day 90, and wherein the combined vaccine efficacy against all four serotypes is measured 30 days after the second administration until 12 or 13 months after the second administration of the administration schedule.

In certain embodiments, the invention is directed to said methods, wherein said methods are effective and safe. In some of these embodiments, the subject or subject population is under 9 years of age, under 4 years of age, or under 2 years of age or from 2 to 9 years of age, or from 2 to 5 years of age, or from 4 to 9 years of age or from 6 to 9 years of age. Optionally the subject is seronegative with respect to all dengue serotypes.

In certain embodiments, the invention is directed to said methods, wherein said methods having a relative risk for virologically confirmed dengue with hospitalization of 1 or less, or 0.8 or less, or 0.6 or less, when measured against placebo in a subject population of at least 5,000 healthy subjects (or at least 10,000, or at least 15,000 healthy subjects). In some of these embodiments, the subject or subject population is under 9 years of age, under 4 years of age, or under 2 years of age or from 2 to 9 years of age, or from 2 to 5 years of age, or from 4 to 9 years of age or from 6 to 9 years of age. Optionally the subject is seronegative with respect to all dengue serotypes.

In certain embodiments, the invention is directed to said methods, wherein the healthy subjects of the subject population are 4 to 16 years of age. In some of such embodiments, the healthy subjects of the subject population are 4 to 5 years of age, 6 to 11 years of age, or 12 to 16 years of age.

In certain embodiments, the invention is directed to said methods, wherein the healthy subjects of the subject population are defined as being healthy in view of the exclusion criteria specified in Example 6.

In certain embodiments, the invention is directed to said methods, wherein the healthy subjects of the subject population are from Asia Pacific or Latin America.

In certain embodiments, the invention is directed to said methods, wherein the healthy subjects of the subject population are seropositive with respect to at least one serotype. In other embodiments, the healthy subjects of the subject population are seronegative with respect to all serotypes.

In certain embodiments, the invention is directed to said methods, wherein the healthy subjects of the subject population are 4-5 years of age and from Asia Pacific, 6-11 years of age and from Asia Pacific, or 12-16 years of age and from Asia Pacific. In other embodiments, the healthy subjects of the subject population are 4-5 years of age and from Latin America, 6-11 years of age and from Latin America, or 12-16 years of age and from Latin America.

In certain embodiments, the invention is directed to said methods, wherein the healthy subjects of the subject population are 4-5 years of age and seropositive for at least 1 dengue serotype, 6-11 years of age and seropositive for at least 1 dengue serotype, or 12-16 years of age and seropositive for at least 1 dengue serotype. In other embodiments, the healthy subjects of the subject population are 4-5 years of age and seronegative for all dengue serotypes, 6-11 years of age and seronegative for all dengue serotypes, or 12-16 years of age and seronegative for all dengue serotypes.

In certain embodiments, the invention is directed to said methods, wherein the healthy subjects of the subject population are from Asia Pacific or Latin America and seropositive for at least one dengue serotype at baseline. In other embodiments, the healthy subjects of the subject population are from Asia Pacific or Latin America and seronegative for at all dengue serotype at baseline.

In certain embodiments, the invention is directed to said methods, wherein the healthy subjects of the subject population are from Asia Pacific, seropositive for at least one dengue serotype at baseline and 4-5 years of age, 6-11 years of age, or 12-16 years of age. In other embodiments, the healthy subjects of the subject population are from Asia Pacific, seronegative for all dengue serotypes at baseline and 4-5 years of age, 6-11 years of age, or 12-16 years of age. In yet other embodiments, the healthy subjects of the subject population are from Latin America, seropositive for at least one dengue serotype at baseline and 4-5 years of age, 6-11 years of age, or 12-16 years of age. In other embodiments, the healthy subjects of the subject population are from America, seronegative for all dengue serotypes at baseline and 4-5 years of age, 6-11 years of age, or 12-16 years of age.

In certain embodiments, the invention is directed to said methods, wherein the healthy subjects of the subject population had prior vaccination against Yellow Fever. In other embodiments, the healthy subjects of the subject population had no prior vaccination against Yellow Fever. Prior vaccination indicates a vaccination prior to the first vaccination with the reconstituted unit dose as described herein. For example for vaccine efficacy (VE) as determined in Example 6 from 30 days post-second vaccination, a prior vaccination of Yellow Fever is defined as a Yellow Fever vaccination occurring before 30 days post-second vaccination.

In certain embodiments, the invention is directed to said methods, wherein the healthy subjects of the subject population had prior vaccination against Japanese Encephalitis. In other embodiments, the healthy subjects of the subject population had no prior vaccination against Japanese Encephalitis.

In certain embodiments, the invention is directed to said methods, wherein the healthy subjects of the subject population received Dengvaxia® within the administration regimen as described herein or within 4.5 years after administration of the first dose. In certain embodiments, the invention is directed to said methods, wherein the occurrence of vaccine related serious adverse events is less than 0.1%.

In certain embodiments, the invention is directed to said methods, wherein the occurrence of vaccine related unsolicited adverse events occurring within 4 weeks of administration is less than 2%.

In certain embodiments, the invention is directed to said methods, wherein the occurrence of vaccine related solicited adverse events occurring within 2 weeks of administration is less than 35%.

In certain embodiments, the invention is directed to said methods, wherein the occurrence of vaccine related solicited local reactions occurring within 1 weeks of administration is less than 40%.

In certain embodiments, the invention is directed to said methods, wherein the method does not increase the risk of virologically-confirmed dengue with hospitalization in the individual, such as in a seronegative individual.

The above methods are also to be considered in the context of a unit dose for use in such methods or in the context of a use of such a unit dose for use in the manufacture of a medicament for such methods.

In certain embodiments, a tetravalent dengue vaccine such as Dengvaxia® is used for inoculating against dengue disease. Dengvaxia® is a tetravalent dengue vaccine based on a yellow fever backbone, CYD-TDV (Dengvaxia®, Sanofi Pasteur, Lyon, France), and has been licensed in several countries based on the clinical demonstration of an overall vaccine efficacy (VE) against virologically-confirmed dengue (VCD) of 56-61% in children in Asia and Latin America (Capeding M R et al. Clinical efficacy and safety of a novel tetravalent dengue vaccine in healthy children in Asia: a phase 3, randomised, observer-masked, placebo-controlled trial. Lancet 2014, 384:1358-65; Villar L A et al. Safety and immunogenicity of a recombinant tetravalent dengue vaccine in 9-16 year olds: a randomized, controlled, phase II trial in Latin America. Pediatr Infect Dis J 2013, 32:1102-9). The preparation of these particular strains CYD1, CYD2, CYD3 and CYD4 has been described in detail in international patent applications WO 98/37911, WO 03/101397, WO07/021672, WO 08/007021, WO 08/047023 and WO 08/065315, to which reference may be made for a precise description of the processes for their preparation. The corresponding nucleotide sequences of the prM-E regions of CYD1, CYD2, CYD3 and CYD4 are provided in WO2016034629 and SEQ ID NOs are set out in Table 16 of this reference.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, and Dengvaxia® disclosed herein are administered simultaneously on the same day to the subject or to the subject population.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, is administered to the subject or to the subject population on day 0/1 as a first administration and Dengvaxia® disclosed herein is subsequently administered to the subject or to the subject population within three months from the first administration, such as on day 90 from the first administration, as a second administration. Alternatively, Dengvaxia® disclosed herein is administered to the subject or to the subject population on day 0/1 as a first administration and the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, is administered subsequently to the subject or the subject population within three months from the first administration, such as on day 90 from the first administration, as a second administration.

In certain embodiments, the invention is directed to said method, wherein the dengue vaccine composition comprises other dengue vaccines such as TV003 or TV005. TV003, developed by the U.S. National Institute of Allergy and Infectious Diseases, comprises vaccine components rDEN1Δ30, rDEN2/4Δ30, rDEN3Δ30/31 and rDEN4Δ30, wherein each of these components is present at a concentration of 3 $\log_{10}$ PFU. TV005 is similar to TV003 with the difference that the concentration of rDEN2/4Δ30 in TV005 is 4 $\log_{10}$ PFU. The vaccines TV003 and TV005 and their vaccine components as well as their production are described in more detail in WO 2008/022196 A2 and S. S. Whitehead, Expert Rev Vaccines, 2016, 15(4): 509 to 517. Using recombinant DNA technology, two attenuation strategies were utilized for the vaccine components of TV003 or TV005: deletions in the 3' untranslated region and structural gene chimerization. For example, the component rDEN4Δ30 contains all the structural and non-structural proteins of a wild type DENV-4, but is attenuated by a 30-nucleotide deletion in the 3' untranslated region (denoted "Δ30"). The other vaccine components are also attenuated due to the 30-nucleotide deletion in the 3' untranslated region. In addition, rDEN3Δ30/31 includes a 31 nucleotide deletion in the 3' untranslated region (shown in detail in FIG. 1c and FIG. 13 of WO 2008/022196 A2). The rDEN2/4Δ30 component was created by substituting the prM and E genes of DENV-2 into the rDEN4Δ30 genome. The complete genomic sequences of dengue strains which can be used to produce TV003 or TV005 are available under the Genbank accession numbers in Table A of WO 2008/022196 A1.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, and TV003 or TV005 disclosed herein are administered simultaneously on the same day to the subject or to the subject population.

In certain embodiments, the invention is directed to said methods, wherein the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, is administered to the subject or the subject population on day 0/1 as a first administration and wherein TV003 or TV005 disclosed herein is subsequently administered to the subject or to the subject population within three months from the first administration, such as on day 90 from the first administration, as a second administration. Alternatively, TV003 or TV005 disclosed herein is administered to the subject or to subject population on day 0/1 as a first administration and the unit dose disclosed herein, which in particular comprises a chimeric dengue serotype 2/1 strain, a live attenuated dengue serotype 2 strain, a chimeric dengue serotype 2/3 strain and a chimeric dengue serotype 2/4 strain, is administered subsequently to the subject or to the subject population within three months from the first administration, such as on day 90 from the first administration, as a second administration.

EXAMPLES

The following Examples are included to demonstrate certain aspects and embodiments of the invention as described in the claims. It should be appreciated by those of skill in the art, however, that the following description is illustrative only and should not be taken in any way as a restriction of the invention.

Example 1: Preparation of the Dengue Virus Strains

The methods used to generate the chimeric dengue strains TDV-1, -3 and -4 were standard molecular cloning and DNA engineering methods and are describe et al. (2003) J. Virology 77(21): 11436-11447. The following well-known methods were used to construct and introduce the prM-E genes of dengue serotypes 1, 3 and 4 into the TDV-2 backbone: Reverse-transcriptase PCR (RT-PCR), PCR, restriction enzyme digestion, DNA fragment ligation, bacterial transformations by electroporation, plasmid DNA preparations, in vitro transcription by T7 RNA polymerase, and transfection of Vero cells by electroporation.

After growing and purifying the different dengue serotypes separately as described in Huang et al. (2013) PLOS Neglected Dis, 7(5):e2243, they are mixed in certain concentrations provided in Example 4. The mixture of dengue serotypes is present in a dengue vaccine composition and combined with a composition of pharmaceutically acceptable excipients resulting in a dengue vaccine composition comprising 15% w/v α,α trehalose dihydrate, 1% w/v poloxamer 407, 0.1% w/v human serum albumin and 100 mM sodium chloride. The dengue vaccine composition is lyophilized and represents a lyophilized unit dose of TDV. The lyophilized unit dose is reconstituted with 37 mM aqueous sodium chloride solution and the reconstituted unit dose comprises 15% w/v α,α trehalose dihydrate, 1% w/v poloxamer 407, 0.1% w/v human serum albumin and 137 mM sodium chloride.

Example 2: Microneutralization Test

Immunogenicity was measured by a microneutralization assay to each one of the four dengue serotypes with titers defined as the dilution resulting in a 50% reduction in plaque values (MNT50). Briefly, on day 1 Vero cells were seeded on 96-well assay plates in DMEM and 10% FBS at a density of $2.5 \times 10^5$ cells/ml and incubated at 37° C. for 24 hours. On day 2 serial dilutions of the heat-inactivated antibody-containing test and control sera samples (dilutions range 1:10 to 1:20480) were prepared and mixed with a constant concentration of dengue viruses, in particular DENV-1 strain 16007, DENV-2 strain 16681, DENV-3 strain 16562 and DENV-4 strain 1036, (target 60-80 pfu/well) in a 96 well microtiter plate and incubated overnight at 2-8° C. to enable the neutralization of the virus by the antibodies present in the sera. After the incubation the mixture of virus and antibodies was transferred onto the 96 well plates with Vero cells and the plates were incubated at 37° C. for 90-120 minutes to infect the Vero cells. A 1% methylcellulose overlay in DMEM was applied to the plate to restrict spread of progeny virus and the plate was incubated for 46-70 hours at 34° C. depending on the Dengue serotype:

DENV1—66±2 hours
DENV2—70±2 hours
DENV3—66+2 hours
DENV4—46±2 hours

After the incubation the cells were washed twice with PBS and fixed by adding cold methanol and incubating for 60 minutes at a temperature of ≤−20° C. After fixing the plates were dried and washed three times with washing buffer (1×PBS, pH 7.4 with 0.5% Tween), before 50 µl of serotype-specific anti-dengue monoclonal antibodies in blocking solution (2.5% nonfat dry milk in PBST) per well were added and incubated with the cells for 18±4 hours at 2-8° C.

The monoclonal antibodies were made as described in Gentry et al. (1982) Am. J. Trop. Med. Hyg. 31, 548-555; Henchal et al. (1985) Am. J. Trop. Med. Hyg. 34, 162-169; and Henchal et al. (1982) Am. J. Trop. Med. Hyg. 31(4): 830-6). Briefly, the anti-DENV-1 HBD was made against dengue 1 strain Hawaii, Envelope, the anti-DENV-2 was made against dengue 2 strain New Guinea C, Envelope, isotype 1, the anti-DENV-3 HBD was made against dengue 3 strain H87, Envelope, isotype 2A, and the anti-DENV-4 HBD was made against dengue 4 strain H241, Envelope, isotype 2A.

After incubation, the plates were washed three times with washing buffer and 50 µl of a secondary peroxidase labelled goat anti-mouse IgG (H+L) (KPL Cat #074-1806) in blocking solution was added and incubated for 90 to 120 minutes at 37° C. Then the plates were washed three times with washing buffer and 50 µl of precipitant substrate (2-amino-9-ethyl carbazole (AEC) tablet in 2.5 ml DMSO, 47.5 ml 50 mM acetate buffer and 250 µl hydrogen peroxide) were added and the mixture was incubated for 20 minutes at room temperature. Finally, the substrate was removed, the plates were rinsed with dH$_2$O and dried.

Sample titers are calculated using the linear regression method and reported as MNT50 titers for each sample. Clinical data are reported as a geometric mean titer for all the individual MNT50 titers in each treatment group. Briefly, the number of infectious foci in each well was counted and the titer of neutralizing antibodies was determined by comparing the percent reduction of infectious foci centers in wells containing antibody (test samples) in comparison to wells containing virus alone. The MNT50 was calculated using the following linear regression equation:

$$\text{MNT50}=10^{\wedge}[(50-c)/m]) \text{ where } c=y \text{ intercept of regression line and } m=\text{slope of regression line}$$

Each test sample was tested in triplicates and the titer was calculated from the average of the triplicates. A schematic drawing of the steps performed in this test is provided in FIG. 2.

Example 3: Phase III Clinical Trial in Children

A Phase III, double-blind, randomized, and placebo-controlled trial in 20100 subjects aged 4 to 16 years living in Thailand, Sri Lanka, Philippines, Panama, Nicaragua, Dominican Republic, Colombia or Brazil was performed evaluating the efficacy, safety and immunogenicity of a tetravalent dengue vaccine referred to hereinafter as TDV (TDV-1, TDV-2, TDV-3 and TDV-4 as described herein). The trial includes 3 parts. Part 1 evaluates vaccine efficacy (VE) and lasts until both of the following 2 criteria are fulfilled: (i) 120 cases of dengue fever are confirmed and (ii) minimum duration of subject follow-up of 12 months post-second vaccination. Part 2 is for an additional 6 months to evaluate VE and for secondary efficacy analyses. Part 3 will evaluate long-term safety by following participants for side effects and will last an additional 3 years.

Part 1: Active surveillance for the primary assessment of efficacy in all subjects. During this time subjects were contacted at least weekly to ensure identification of febrile illness that could potentially be due to dengue. This part commenced on the day of vaccination and finished once both of the following 2 criteria were fulfilled: (i) 120 cases of dengue fever are confirmed and (ii) minimum duration of subject follow-up of 12 months post-second vaccination. The end of Part 1 was defined for each subject so that the duration of follow up after the second vaccination was approximately the same for all subjects. Virologically-confirmed cases in Part 1 count towards the primary efficacy objective if occurring at least 30 days post-second vaccination. Part 1 was finished 12 months post-second vaccination Part 2: Active surveillance for an additional 6 months for each subject following the completion of Part 1, I, i.e. 18 month post second vaccination. During this time subjects were contacted at least weekly to ensure identification of febrile illness that could potentially be due to dengue. Virologically-confirmed cases in Parts 1 and 2 contribute towards the secondary efficacy objectives.

Part 3: Modified active surveillance for the assessment of safety in all subjects following the completion of Part 2 and lasting 3 years for each subject. The modified surveillance during Part 3 will maintain at least weekly contacts through Part 3 of the trial, but the intensity of investigation will be modified based on the need for hospitalization. Surveillance will identify febrile illness of any severity that could potentially be due to dengue.

Criteria for Inclusion include:

The subject was aged 4 to 16 years inclusive, at the time of randomization.

Individuals who were in good health at the time of entry into the trial as determined by medical history, physical examination (including vital signs) and clinical judgment of the Investigator.

The subject and/or the subject's parent/guardian signed and dated an assent/written informed consent form where applicable, and any required privacy authorization prior to the initiation of any trial procedures, after the nature of the trial has been explained according to local regulatory requirements.

Individuals who can comply with trial procedures and are available for the duration of follow-up.

Exclusion criteria include:

1. Febrile illness (temperature≥38° C.) or moderate or severe acute illness or infection at the time of randomization.
2. History or any illness that, in the opinion of the Investigator, might interfere with the results of the trial or pose an additional risk to the subject due to participation in the trial, including but not limited to:
   a. Known hypersensitivity or allergy to any of the vaccine components.
   b. Female subjects (post-menarche) who are pregnant or breastfeeding.
   c. Individuals with any serious chronic or progressive disease according to judgment of the Investigator (e.g., neoplasm, insulin-dependent diabetes, cardiac, renal or hepatic disease, neurologic or seizure disorder or Guillain-Barré syndrome).
   d. Known or suspected impairment/alteration of immune function, including:
      i. Chronic use of oral steroids (equivalent to 20 mg/day prednisone≥12 weeks/≥2 mg/kg body weight/day prednisone≥2 weeks) within 60 days prior to Day 1 (Month 0) (use of inhaled, intranasal, or topical corticosteroids is allowed).
  ii. Receipt of parenteral steroids (equivalent to 20 mg/day prednisone≥12 weeks/≥2 mg/kg body weight/day prednisone≥2 weeks) within 60 days prior to Day 1 (Month 0).
  iii. Administration of immunoglobulins and/or any blood products within the 3 months prior to Day 1 (Month 0) or planned administration during the trial.
  iv. Receipt of immunostimulants within 60 days prior to Day 1 (Month 0).
  v. Immunosuppressive therapy such as anti-cancer chemotherapy or radiation therapy within 6 months prior to Day 1 (Month 0).
  vi. Human Immunodeficiency Virus (HIV) infection or HIV-related disease.
  vii. Genetic immunodeficiency.
3. Receipt of any other vaccine within 14 days (for inactivated vaccines) or 28 days (for live vaccines) prior to Day 1 (Month 0) or planning to receive any vaccine within 28 days after Day 1 (Month 0).
4. Participation in any clinical trial with another investigational product 30 days prior to Day 1 (Month 0) or intent to participate in another clinical trial at any time during the conduct of this trial.
5. Previous participation in any clinical trial of a dengue candidate vaccine, or previous receipt of a dengue vaccine.
6. First degree relatives of individuals involved in trial conduct.
7. Females of childbearing potential who are sexually active, and who have not used any of the acceptable contraceptive method for at least 2 months prior to Day 1 (Month 0).
8. Females of childbearing potential who are sexually active, and who refuse to use an acceptable contraceptive method up to 6 weeks post-second vaccination.
9. Deprived of freedom by administrative or court order, or in an emergency setting, or hospitalized involuntarily.
10. Current alcohol abuse or drug addiction that may interfere with the subject's ability to comply with trial procedures.
11. Identified as an employee of the Investigator or trial center, with direct involvement in the proposed trial or other trials under the direction of that Investigator or trial center.

Eligible subjects were randomized (2:1) into two treatment groups: groups 1 received one subcutaneous (SC) dose of TDV in the upper arm on Day 1 and on Day 90, and group 2 received one subcutaneous dose of placebo in the upper arm on Day 1 and on Day 90. Randomization was stratified by region (Asia Pacific and Latin America) and age range (children aged 4-5 years, 6-11 years, and 12-16 years) to ensure each age range has the appropriate ratio of TDV to placebo in each region. After randomization dropouts were not replaced. Study Day 1 is defined to be the date of the first dose administration of TDV or placebo. The TDV was prepared as described in Example 1. Each subcutaneous dose of TDV was 0.5 mL and the concentration of the four dengue serotypes in the TDV vaccine in each dose was 3.6 $\log_{10}$ PFU/dose, 4.0 $\log_{10}$ PFU/dose, 4.6 $\log_{10}$ PFU/dose and 5.1 $\log_{10}$ PFU/dose of TDV-1, TDV-2, TDV-3 and TDV-4, respectively.

The "total concentration in pfu/0.5 ml" which serves as a base value for the calculation of the percentage concentration for each individual component of a tetravalent dengue vaccine is shown for one exemplary tetravalent vaccine composition comprising dengue serotype 1 in a concentration of 3.60 $\log_{10}$ pfu/0.5 ml, a dengue serotype 2 concentration of 4.00 $\log_{10}$ pfu/0.5 ml, a dengue serotype 3 concentration of 4.60 $\log_{10}$ pfu/0.5 ml and a dengue serotype 4 concentration of 5.11 $\log_{10}$ pfu/0.5 ml.

Primarily, the logarithmic values of the concentrations are converted into numerical values. The results of this conversion are $4 \times 10^3$ pfu/0.5 ml for serotype 1, $1 \times 10^4$ pfu/0.5 ml for serotype 2, $4 \times 10^4$ pfu/0.5 ml for serotype 3 and $1.3 \times 10^5$ pfu/0.5 ml for serotype 4. The total concentration in pfu/0.5 ml is the sum of the preceding numerical values resulting in $1.84 \times 10^5$ pfu/0.5 ml.

The "percentage concentration" for each of the serotypes 1, 2, 3 and 4 is obtained by dividing the numerical concentration value (expressed as pfu/0.5 ml) of an individual serotype by the total concentration (expressed in pfu/0.5 ml) and multiplying the result by 100 i.e.:

Percentage concentration of serotype $1 = (4 \times 10^3$ pfu/0.5 ml $\div 1.84 \times 10^5$ pfu/0.5 ml$) \times 100 = 2\%$ Percentage concentration of serotype $2 = (1 \times 10^4$ pfu/0.5 ml $\div 1.84 \times 10^5$ pfu/0.5 ml$) \times 100 = 5\%$ Percentage concentration of serotype $3 = (4 \times 10^4$ pfu/0.5 ml $\div 1.84 \times 10^5$ pfu/0.5 ml$) \times 100 = 22\%$ Percentage concentration of serotype $4 = (1.3 \times 10^5$ pfu/0.5 ml $\div 1.84 \times 10^5$ pfu/0.5 ml$) \times 100 = 71\%$.

The percentage concentrations are rounded to whole numbers.

Primary Outcome Measures included the vaccine efficacy (VE) of two doses of TDV in preventing virologically-confirmed dengue (VCD) fever induced by any dengue serotype [time frame: 30 days post-second vaccination (Day 120) until the end of Part 1]. VE is defined as $1-(\lambda v/\lambda c)$, wherein λv and λc denote the hazard rates for the TDV and placebo groups, respectively. A virologically-confirmed dengue case is defined as febrile illness (defined as temperature≥38° C. on any 2 of 3 consecutive days) or illness clinically suspected to be dengue by the Investigator with a positive serotype-specific reverse transcriptase polymerase chain reaction (RT-PCR). A febrile illness will require an interval of at least 14 days from a previous febrile illness to avoid overlap of acute and convalescent visits from one episode with those from a second episode.

Secondary Outcome Measures include:
1) VE of two doses of TDV in preventing virologically-confirmed dengue fever induced by each dengue serotype [time frame: from 30 days post-second vaccination (Day 120) until the end of Part 2].
2) VE of two doses of TDV in preventing virologically-confirmed dengue fever induced by any dengue serotype in participants dengue seronegative at baseline [time frame: from 30 days post-second vaccination (Day 120) until the end of Part 2 (up to 21 months)].
3) VE of two doses of TDV in preventing virologically-confirmed dengue fever induced by any dengue serotype in participants dengue seropositive at baseline [time frame: from 30 days post-second vaccination (Day 120) until the end of Part 2].
4) VE of two doses of TDV in preventing hospitalization due to virologically-confirmed dengue fever induced by any dengue serotype [time frame: from 30 days post-second vaccination (Day 120) until the end of Part 2].

5) VE of two doses of TDV in preventing virologically-confirmed severe dengue fever induced by any dengue serotype [time frame: from 30 days post-second vaccination (Day 120) until the end of Part 2].
6) Percentage of participants with solicited local injection site adverse events (AEs) in the safety subset [time frame: Days 1 through 7 after each vaccination] and severity of solicited local injection AEs. Solicited local AEs at injection site are defined as pain, erythema and swelling that occurred within 7 days after each vaccination.
7) Percentage of participants with solicited systemic adverse events (AEs) in the safety subset [time frame: Days 1 through 14 after each vaccination] and severity of solicited systemic AEs. Solicited systemic AEs in children (<6 years) are defined as fever, irritability/fussiness, drowsiness and loss of appetite that occurred within 14 days after each vaccination. Solicited systemic AEs in children (≥6 years) are defined as fever, headache, asthenia, malaise and myalgia that occurred within 14 days after each vaccination.
8) Percentage of participants with any unsolicited adverse events (AEs) in the safety subset [time frame: Days 1 through 28 after each vaccination]. Unsolicited AEs are any AEs that are not solicited local or systemic AEs, as defined above.
9) Percentage of participants with serious adverse events (SAEs) during Parts 1 and 2 [time frame: from Day 1 until the end of Parts 1 and 2]. A serious adverse event (SAE) is any untoward medical occurrence or effect that at any dose results in death, is life-threatening, requires inpatient hospitalization or prolongation of existing hospitalization, results in persistent or significant disability/incapacity, is a congenital anomaly/birth defect or is medically important due to other reasons than the above mentioned criteria.
10) Percentage of participants with fatal SAEs and SAEs related to study drug during the first and second half of Part 3 [time frame: for 3 years (18 month halves) beginning at the end of Part 2 (approximately 21 months after the first vaccination)].
11) Percentage of participants with a seropositive response for each of the four dengue serotypes in the immunogenicity subset [time frame: Day 1 and months 1, 3, 4, 9, 15 and then annually (up to 3 years)]. Seropositive response is defined as a reciprocal neutralizing titer≥10. The four DENV serotypes are DEN-1, DEN-2, DEN-3 and DEN-4.
12) Percentage of participants with a seropositive response for multiple dengue serotypes in the immunogenicity subset [time frame: Day 1 and months 1, 3, 4, 9, 15 and then annually (up to 3 years)].
13) Geometric Mean Titers (GMTs) of neutralizing antibodies for each of the four dengue serotypes in the immunogenicity subset [time frame: Day 1 and months 1, 3, 4, 9, 15 and then annually (up to 3 years)]. GMTs of neutralizing antibodies will be measured via microneutralization test (MNT) as described in Example 2.

a) Study Population

Figure 3:
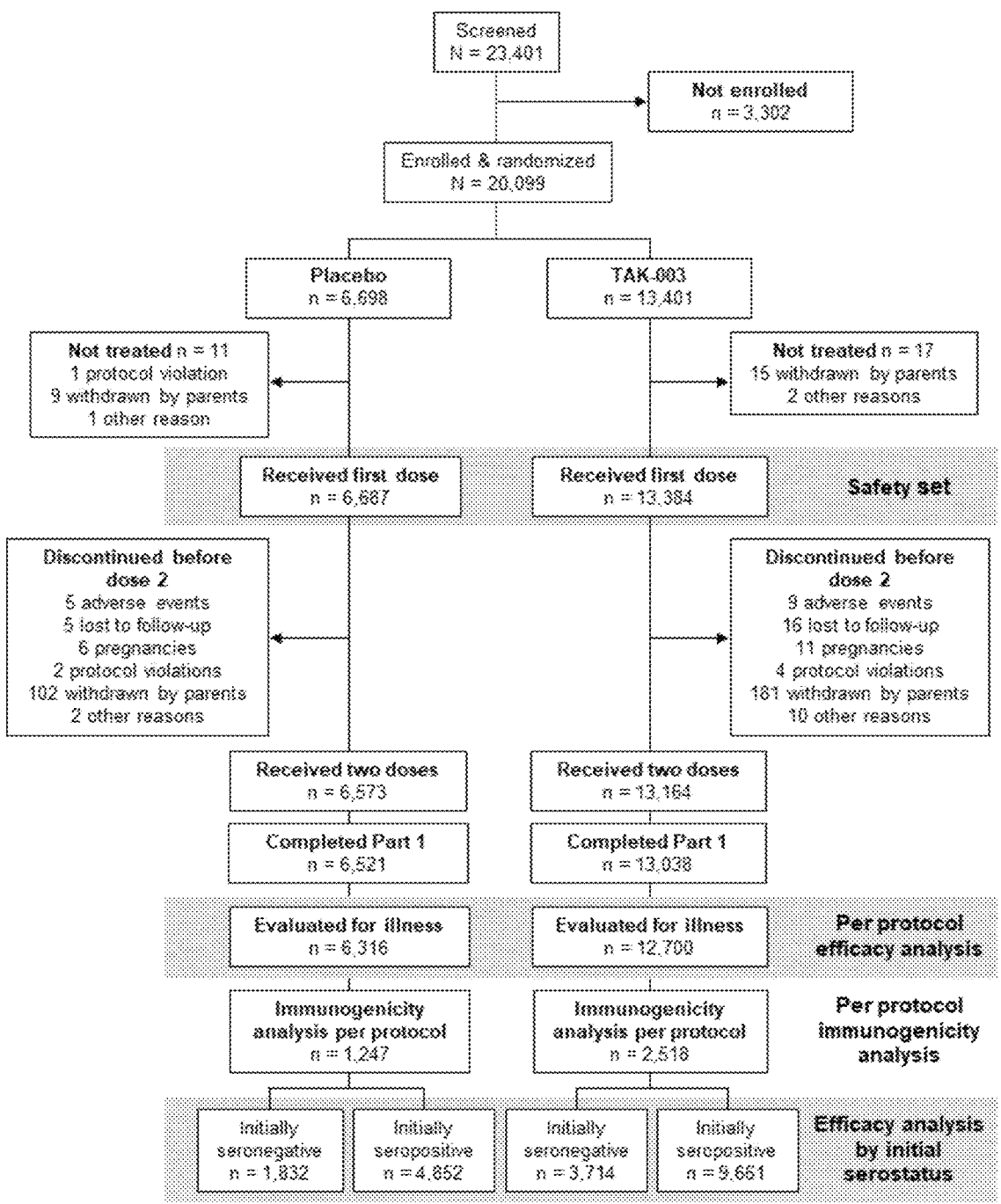
FIG. 3: Flow diagram of the clinical trial of Example 3.
Figure 5:
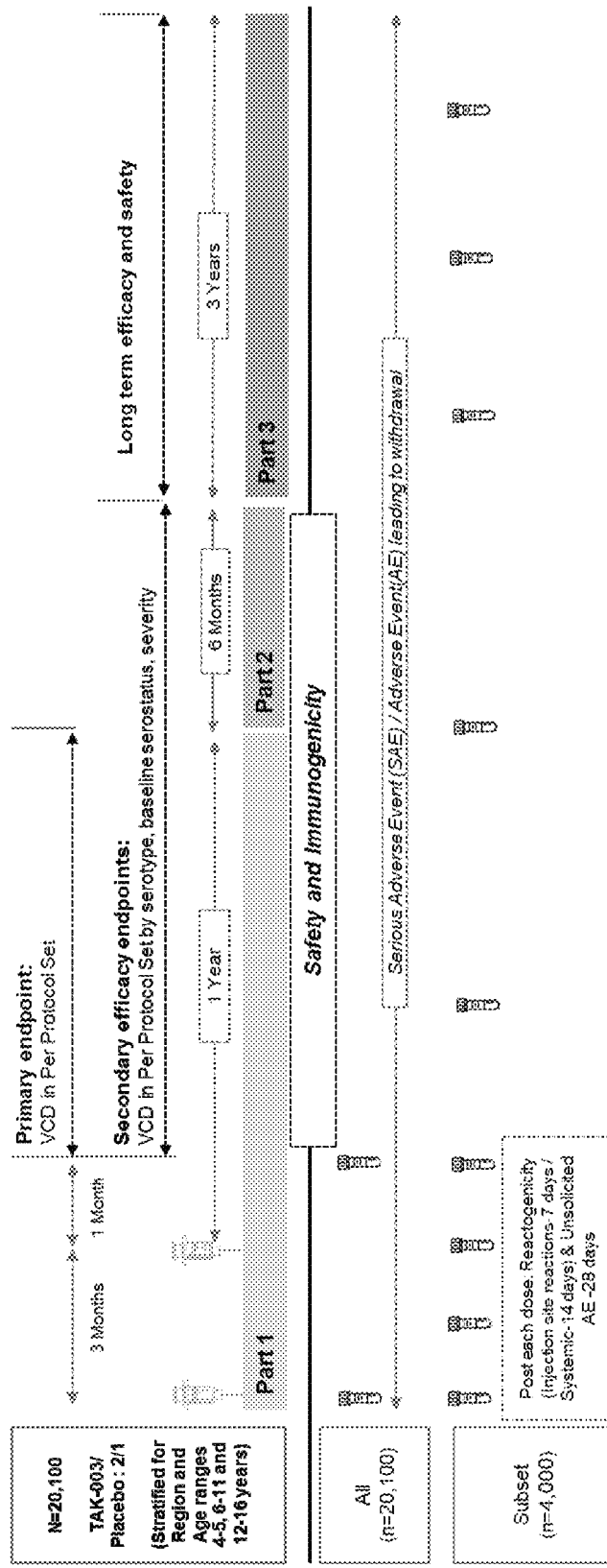
FIG. 5: Study design of phase III study described in example 3.

After screening, 20,099 participants were randomized, and 20,071 received at least one injection. In total, 97.4% of placebo participants (n/N: 6,521/6,698) and 97.3% of vaccinees (n/N: 13,038/13,401) completed Part 1 of the study (FIG. 3). Reasons for study withdrawals included AEs, participants lost to follow-up, pregnancy, protocol violations, and withdrawal by participants (or parents/guardians). Baseline characteristics were similar across both treatment groups (Table 5). Mean age of study participants was 9.6 years, with baseline seronegativity of 27.7%, and enrollment was broadly balanced across regions (46.5% in Asia, 53.5% in Latin America). The highest seronegative rate was in Panama (62.2%), followed by Sri Lanka (38.5%), Thailand (34.4%), Brazil (28.8%), Nicaragua (22.3%), Colombia (15.4%), the Philippines (12.4%), and the Dominican Republic (2.8%).

TABLE 5

Baseline characteristics of study population (number, %)

| | TDV | Placebo | Total |
|---|---|---|---|
| Per Protocol Set | | | |
| Number of Participants | 12,704 | 6,317 | 19,021 |
| Mean Age (Years, SD) | 9.6 (3.35) | 9.6 (3.34) | 9.6 (3.35) |
| Baseline Seronegative[a] | 3,533 (27.8) | 1,726 (27.3) | 5,259 (27.7) |
| Female | 6,314 (49.7) | 3,098 (49.0) | 9,412 (49.5) |
| Male | 6,390 (50.3) | 3,219 (51.0) | 9,609 (50.5) |
| Asia Pacific | 5,896 (46.4) | 2,942 (46.6) | 8,838 (46.5) |
| Baseline Seronegative[a] | 1,503 (25.5) | 773 (26.3) | 2,276 (25.8) |
| Latin America | 6,808 (53.6) | 3,375 (53.4) | 10,183 (53.5) |
| Baseline Seronegative[a] | 2,030 (29.8) | 953 (28.2) | 2,983 (29.3) |
| Safety Set[b] | | | |
| Number of Participants | 13,380 | 6,687 | 20,071 |
| Mean Age (Years, SD) | 9.6 (3.36) | 9.6 (3.34) | 9.6 (3.35) |
| Baseline Seronegative[a] | 3,714 (27.8) | 1,832 (27.4) | 5,547 (27.6) |
| Female | 6,651 (49.7) | 3,276 (49.0) | 9,929 (49.5) |
| Male | 6,729 (50.3) | 3,411 (51.0) | 10,142 (50.5) |
| Safety Set of Subset[b] | | | |
| Number of Participants | 2,663 | 1,329 | 3,993 |
| Baseline Seronegative[a] | 740 (27.8) | 369 (27.8) | 1,109 (27.8) |

[a]Seronegative for all serotypes; seropositive defined as reciprocal neutralizing antibody titer ≥10; SD, standard deviation.
[b]numbers of participants in TVD plus placebo groups are not equal to total numbers shown because misallocated participants (i.e. those who received both TVD and placebo due to an administrative error) are not included in the TDV and placebo group data.

b) Febrile Illnesses and VCD

During Part 1, 5,754 and 4,663 episodes of febrile illness were reported in Asian and Latin American sites, respectively. Acute samples were obtained in 99.5% and 96.6% of these cases, with 98.3% and 85.1% of samples taken within five days, in Asia and Latin America, respectively. There were 278 VCD cases (76 hospitalized) in the safety set during the entire Part 1 period, of which 210 (58 hospitalized) were 30 days post-second vaccination in the PPS (Table 6; Table 8) and were included in primary endpoint analysis.

c) Distribution of VCD Included in Primary Endpoint Analysis

DENV-1 was reported in all countries with VCD and included all the 21 cases in Panama. In Sri Lanka, 54 of 60 VCD were DENV-2, and 87 of 109 VCD in the Philippines were DENV-3. All seven DENV-4 VCD were reported in the Philippines. No VCD were reported in Nicaragua or the Dominican Republic. Of the associated 58 hospitalized VCD, 43 were reported in Sri Lanka. A total of two severe dengue (both DENV-3) and five dengue hemorrhagic fever (DHF; three DENV-2; two DENV-3) cases were reported (Table 7). These seven were also the only such cases in the entire part 1 safety set.

d) Vaccine Efficacy

VE against VCD of any serotype was 80.2% (95% CI: 73.3-85.3; P<0.001). A similar efficacy of 81% (95% CI: 64.1-90.0) between the doses and from first dose onwards in the safety set (Table 6) suggests that the vaccine was efficacious after the first dose. Exploratory analysis of the secondary efficacy endpoints showed a trend of differential efficacy by serotype, with the highest efficacy against DENV-2 (97.7%), followed by DENV-1 (73.7%), DENV-4 (63.2% with CI containing zero), and DENV-3 (62.6%; Table 7). Overall, efficacy was similar in baseline seronegatives (74.9%) and seropositives (82.2%; FIG. 4 above); however, this varied by serotype. Efficacy against DENV-2 was not impacted by serostatus; efficacy against DENV-1 was slightly higher in baseline seropositives (79.8%; 95% CI: 51.3-91.6) than baseline seronegatives (67.2%; 95% CI: 23.2-86.0). No efficacy was observed against DENV-3 in baseline seronegatives (−38.7%; 95% CI: −335.7-55.8) compared to baseline seropositives (71.3%; 95% CI: 54.2-82.0). Efficacy by serostatus could not be calculated for DENV-4 because no cases were observed in baseline seronegatives. In the primary endpoint timeframe of the PPS, only five VCD requiring hospitalization were reported in the vaccine group compared with 53 cases in the placebo group, with a VE of 95.4% (95% CI: 88.4-98.2; 97.2% for baseline seronegatives and 94.4% for baseline seropositives; Table 7; FIG. 4 below), consistent with a VE of 93.3% (95% CI: 86.7-96.7) in the safety set from first dose onwards.

The primary vaccine efficacy (VE) of two doses of TDV in preventing virologically-confirmed dengue (VCD) fever induced by any dengue serotype is shown in Table 6.

TABLE 6

Vaccine efficacy of TDV in preventing virologically-confirmed dengue (VCD) fever against any serotype from 30 days post-second vaccination until end of part 1 Per Protocol Set (PPS), i.e. 12 months post-second vaccination. Safety set analysis from first dose to end of Part 1 study period, i.e. 12 months post-second vaccination

| | Placebo n = 6317 | TDV (PPS) n = 12,704 |
|---|---|---|
| number of subject evaluated | 6,316 | 12,700 |
| number of subjects with febrile illness | 1,712 | 3,195 |
| number of febrile illness cases | 2,591 | 4,692 |
| virologically confirmed dengue fever (n [%]) | 149 [2.4] | 61 [0.5] |
| Person-years at risk | 5,670.1 | 11,578.7 |
| incident density | 2.6 | 0.5 |
| relative risk | | 0.20 |
| 95% CI of relative risk | | (0.15, 0.27) |
| vaccine efficacy (%) | | 80.2 |
| 95% CI of vaccine efficacy | | (73.3, 85.3) |
| p-value for vaccine efficacy | | <0.001 |

| | Placebo | TDV (Safety Set)* |
|---|---|---|
| number of subject evaluated | 6,687 | 13,380 |
| virologically confirmed dengue fever (n [%]) | 199 [3.0] | 78 [0.6] |
| Person-years at risk | 8,072.0 | 16,351.5 |
| incident density | 2.5 | 0.5 |
| vaccine efficacy (%) | | 80.9 |
| 95% CI of vaccine efficacy | | (75.2, 85.3) |

Note 1:
Percentage of virologically confirmed dengue (VCD) fever are based on number of subjects evaluated.
Note 2:
Person-years at risks is defined as cumulative time in years until start of VCD fever or until end of Part 1 study period or discontinuation date, whichever comes first. Incident density is defined as the number of cases per 100 person-years at risk. Percentages are based on total number (denominator) of analysis set participants evaluated and may not be equal to the total number of participants in the per protocol analysis set.
*One participant had two instances of VCD during Part 1, only the first VCD was included in efficacy calculation
Note 3:
Vaccine efficacy (VE) and 2-sided 95% CIs are estimated from a Cox proportional hazard model with TDV as a factor, adjusted for age and stratified by region.
Note 4:
Statistical significance will be concluded if the lower bound of the 95% CI for VE is above 25%. Since the hypotheses will be tested in a confirmatory manner at a 2-sided significance level of 5%, the calculated p-value should be compared with 0.025.
Note 5:
Relative risk is calculated as the number of events divided by the number of subjects evaluated in the TDV group, over the number of events divided by the number of subjects evaluated in the placebo group.

For the efficacy evaluation shown in Table 6, a case of VCD was defined as febrile illness (defined as fever≥38° C. on any 2 of 3 consecutive days) with a positive serotype-specific RT-PCR (i.e., positive dengue detection RT-PCR) and occurring at any time starting from 30 days post-second vaccination (Day 120 [Month 4]) through the end of Part 1. The analysis was performed on the Per-Protocol Set (PPS) and Safety Set.

As used herein, the "Per-Protocol Set (PPS)" consist of all subjects in the Full Analysis Set (FAS) consisting of all randomized subjects who received at least one dose of TDV or placebo who had no major protocol violations. Major protocol violations are not receiving both doses of TDV or placebo administration, not receiving both doses in the correct interval, not having the correct administration of TDV or placebo, use of prohibited medications/vaccines by the subject, the subject meets any of the exclusion criteria of 2d, 3, 4 or 5 defined above or product preparation error.

The p-value is obtained by solving the critical value Z in the following equation:

Upper bound of 1-sided (1−$p$%) CI of HR=0.75,
wherein HR is the hazard ratio and defined as
HR=$\lambda V/\lambda C$.

$e^{\hat{}}[\hat{\beta}+Z*S\hat{}E]=0.75$, wherein $\hat{\beta}$ defines the treatment and $S\hat{}E$ the related standard error.

The 1-sided p-value is 1-(area to the left of the critical value Z from a standard normal distribution). Since the hypotheses will be tested in a confirmatory manner 2-sided at a significance level of 5%, the calculated 1-sided p-value should be compared with 0.025.

In summary in Part 1 of this study, a high vaccine efficacy of 80.2% against virologically-confirmed dengue of any serotype in children 4-16 years of age was found. It included an efficacy of 74.9% in baseline seronegatives and a robust 95.4% reduction in hospitalizations. Onset of protection could be seen after the first dose with 81% efficacy between doses. Overall, these results suggest a potential benefit for each vaccine recipient regardless of prior dengue exposure or age. This finding is significant because vaccine development against dengue has been challenging, especially for dengue naïve individuals, and dengue remains one of the WHO's top ten threats to global health in 2019.19 Furthermore, the onset of protection after the first dose has potential utility in the context of outbreak control or travel vaccination, offering a reduction in the risk of dengue after only one dose.

Severe forms of dengue were assessed as follows: Dengue Hemorrhagic Fever (DHF) as defined by the 1997 WHO definition. Severe Dengue through the Dengue Case Adjudication Committee. The Dengue Case Adjudication Committee (DCAC) consisted of four members: a voting chairperson, two voting members, and an independent non-voting statistician. The three DCAC voting members are all physicians and clinical dengue experts. DCAC members are not study investigators and do not have any conflict of interest that would bias their review of the trial data. All non-hospitalized cases were considered non-severe. The DCAC severe dengue case criteria applied in a blinded manner to virologically-confirmed hospitalized dengue cases are as follows: 1) bleeding abnormality, for a case to be considered severe there needs to be a significant intervention required in response to the bleeding episode such as blood transfusion, nasal packing, hormonal therapy, or, bleeding occurred into critical organs such as the brain; 2) plasma leakage, for a case to be considered severe there needs to be evidence of both plasma leakage and functional impairment (plasma leakage includes clinical evidence, radiological evidence, or hematocrit elevated >20% above normal levels or baseline; functional impairment defined as shock or respiratory distress); 3) liver, for a case to be considered severe there needs to be evidence of both hepatitis and functional impairment (hepatitis defined as an aspartate aminotransferase [AST] or alanine aminotransferase [ALT]>10 upper limit of normal range [ULN]; functional impairment defined as prothrombin [PT]>1.5 ULN or hypoalbuminemia); 4) renal, serum creatinine>2.5 times ULN or requiring dialysis; 5) cardiac, abnormalities intrinsic to the heart (i.e. not resulting from intravascular volume depletion) and with evidence of functional impairment (examples of intrinsic abnormality: myocarditis, pericarditis, and myopericarditis; example of functional impairment: new conduction abnormality resulting in irregular heart rhythm [i.e. not transient first-degree heart block]); 6) central nervous system, any abnormality with the exception of a simple febrile convulsion or a brief delirium; 7) shock, all shock cases considered severe. At least 1 functional impairment (of criterion 3, 4, 5, 6), needs to be present but the totality of data were considered by the members in their assessment.

Further results of part 1 and part 2 are presented in Tables 7a to c.

TABLE 7a

Distribution of cases contributing to primary endpoint by per protocol set subgroup (30 days after second vaccination until end of Part 1, i.e. 12 months after second vaccination)

| | TDV Dengue Cases | TDV Incidence Density | Placebo Dengue Cases | Placebo Incidence Density | Vaccine Efficacy (95% CI) |
|---|---|---|---|---|---|
| VCD cases | | | | | |
| Baseline Seropositive[a] | 41/9,165 (0.4%) | 0.5 | 110/4,587 (2.4%) | 2.7 | 82.2% (74.5%-87.6%) |
| Baseline Seronegative[a] | 20/3,531 (0.6%) | 0.6 | 39/1,726 (2.3%) | 2.5 | 74.9% (57.0%-85.4%) |
| DENV-1 | 16/12,700 (0.1%) | 0.1 | 30/6,316 (0.5%) | 0.5 | 73.7% (51.7%-85.7%) |
| DENV-2 | 3/12,700 (<0.1%) | <0.1 | 64/6,316 (1.0%) | 1.1 | 97.7% (92.7%-99.3%) |
| DENV-3 | 39/12,700 (0.3%) | 0.3 | 51/6,316 (0.8%) | 0.9 | 62.6% (43.3%-75.4%) |
| DENV-4[d] | 3/12,700 (<0.1%) | <0.1 | 4/6,316 (<0.1%) | <0.1 | 63.2% (−64.6%-91.8%) |
| 4-5 Years Old | 13/1,619 (0.8%) | 0.9 | 23/801 (2.9%) | 3.2 | 72.8% (46.2%-86.2%) |
| 6-11 Years Old | 34/7,009 (0.5%) | 0.5 | 85/3,491 (2.4%) | 2.7 | 80.7% (71.3%-87.0%) |
| 12-16 Years Old | 14/4,072 (0.3%) | 0.4 | 41/2,024 (2.0%) | 2.2 | 83.3% (69.3%-90.9%) |
| Asia | 54/5,894 (0.9%) | 1.0 | 127/2,942 (4.3%) | 4.9 | 79.5% (71.8%-85.1%) |
| Latin America | 7/6,806 (0.1%) | 0.1 | 22/3,374 (0.7%) | 0.7 | 84.3% (63.1%-93.3%) |
| Hospitalized VCD cases | | | | | |
| Baseline Seropositive[a] | 4/9,165 (<0.1%) | <0.1 | 35/4,587 (0.8%) | 0.8 | 94.4% (84.3%-98.0%) |
| Baseline Seronegative[a] | 1/3,531 (<0.1%) | <0.1 | 18/1,726 (1.0%) | 1.2 | 97.2% (79.1%-99.6%) |
| Cases of DHF[b] | | | | | |
| All participants | 1/12,700 (<0.1%) | <0.1 | 4/6,316 (<0.1%) | <0.1 | 87.3% (−13.5%-98.6%) |
| Severe VCD Cases[c] | | | | | |
| All participants | 1/12,700 (<0.1%) | <0.1 | 1/6,316 (<0.1%) | <0.1 | 50.8% (−686.9%-96.9%) |

VCD, virologically-confirmed dengue;
DHF, dengue hemorrhagic fever
[a]Seronegative for all serotypes; baseline seropositive defined as reciprocal neutralizing antibody titer ≥10 to one or more serotypes.
[b]VCD cases meeting WHO 1997 DHF criteria; incidence density defined as the number of cases per 100 person-years at risk; percentages are based on total number (denominator) of per protocol set participants evaluated.
[c]two severe VCD were not classified as DHF.
[d]The number of cases identified was sufficient to provide reasonably precise estimates of vaccine efficacy against all individual serotypes, except DENV-4.

TABLE 7b

Distribution of cases contributing to secondary endpoint by per protocol set subgroup (30 days after second vaccination until end of Part 2, i.e. 18 months after second vaccination)

| | TDV Dengue Cases | TDV Incidence Density | Placebo Dengue Cases | Placebo Incidence Density | Vaccine Efficacy (95% CI) |
|---|---|---|---|---|---|
| VCD cases | | | | | |
| Overall | | | | | 73.3% (66.5%-78.8%) |
| Baseline Seropositive[a] | 75 | 0.6 | 150 | 2.4 | 76.1% (68.5%-81.9%) |
| Baseline Seronegative[a] | 39 | 0.8 | 56 | 2.4 | 66.2% (49.1%-77.5%) |
| DENV-1 | 38 | 0.2 | 62 | 0.7 | 69.8% (54.8%-79.9%) |
| Baseline Seropositive[a] | 21 | 0.2 | 37 | 0.6 | 72.0 (52.2%-83.6%) |
| Baseline Seronegative[a] | 17 | 0.3 | 25 | 1 | 67.8 (40.3%-82.6%) |
| DENV-2 | 8 | <0.1 | 80 | 0.9 | 95.1% (89.9%-97.6%) |
| Baseline Seropositive[a] | 7 | <0.1 | 54 | 0.9 | 93.7 (86.1%-97.1%) |
| Baseline Seronegative[a] | 1 | <0.1 | 26 | 1.1 | 98.1 (85.8%-99.7%) |
| Hospitalized VCD cases | | | | | |
| Overall | 13 | <0.1 | 66 | 0.8 | 90.4% (82.6%-94.7%) |
| Baseline Seropositive[a] | 8 | <0.1 | 45 | 0.7 | 91.4% (81.7%-95.9%) |
| Baseline Seronegative[a] | 5 | 0.1 | 21 | 0.9 | 88.1% (68.5%-95.5%) |

VCD, virologically-confirmed dengue;
[a]Seronegative for all serotypes; baseline seropositive defined as reciprocal neutralizing antibody titer ≥10 to one or more serotypes.

TABLE 7c

Distribution of cases contributing to secondary endpoint by safety set (first vaccination until end of Part 2, i.e. 21 months after first vaccination)

| | TDV Dengue Cases | TDV Incidence Density | Placebo Dengue Cases | Placebo Incidence Density | Vaccine Efficacy (95% CI) |
|---|---|---|---|---|---|
| VCD cases | | | | | |
| Overall | | | | | 75.3% (69.5%-80.0%) |
| Overall in between[a] | | | | | 81.0% (64.1%-90.0%) |
| Baseline Seropositive[b] | 89 | 0.5 | 187 | 2.3 | 77.2% (70.6%-82.3%) |
| Baseline Seronegative[b] | 42 | 0.7 | 70 | 2.3 | 70.6% (56.9%-79.9%) |
| DENV-1 | 41 | 0.2 | 78 | 0.7 | 73.9% (61.9%-82.1%) |
| DENV-2 | 14 | <0.1 | 109 | 1.0 | 93.7% (89.0%-96.4%) |
| Hospitalized VCD cases | | | | | |
| Overall | 17 | <0.1 | 81 | 0.7 | 89.7% (82.6%-93.9%) |

VCD, virologically-confirmed dengue;
[a]In between: VCD after first vaccination and before second vaccination.
[b]Seronegative for all serotypes; baseline seropositive defined as reciprocal neutralizing antibody titer ≥10 to one or more serotypes.

TABLE 7d

Dengvaxia ® VCD (first vaccination until 25 months after first vaccination (i.e.13 month after third vaccination), ITT from CYD15, 9 to 16 years of age)[a]

| | Vaccine Efficacy (95% CI) |
|---|---|
| Overall VCD | 64.7% (58.7%-69.8%) |
| Baseline Seropositive[b] | 83.7% (62.2%-93.7%) |
| Baseline Seronegative[b] | 43.2% (−61.5%-80.0%) |
| DENV-1 | 58.8% (40.2%-65.9%) |
| DENV-2 | 50.2% (31.8%-63.6%) |
| Overall Hospitalized VCD | 80.3% (64.7%-89.5%) |

[a]Luis Villar et al. Efficacy of a tetravalent dengue vaccine in Children in Latin America: N Engl J of Med 2015 Vol. 372 No2, 113-123

Clinical signs and symptoms of virologically-confirmed dengue cases during Part 1 study period in safety set data are shown in Table 8.

TABLE 8

Clinical signs and symptoms of virologically-confirmed dengue cases during Part 1 study period (safety set data)

| | TDV (N = 13,380) | Placebo (N = 6,687) | Relative Risk |
|---|---|---|---|
| Number of VCD Cases | 78 | 200 | — |
| Median Duration of Febrile Illness (days; 95% CI)[a] | 6.0 (5.7-7.4) | 6.0 (5.9-6.8) | — |
| Median Duration of Fever (days; 95% CI) | 4.0 (3.9-4.6) | 5.0 (4.5-5.0) | — |
| Number of Hospitalized VCD Cases | 9 | 67 | — |
| Median Duration of Hospitalization (days; 95% CI) | 5.0 (2.8-5.4) | 5.0 (4.6-5.4) | — |
| Evidence of Bleeding (%, n/N) | 3.8% (3/78) | 3.5% (7/200) | 1.10 |
| Plasma Leakage (%, n/N) | 2.6% (2/78) | 6.5% (13/200) | 0.39 |
| Plasma Leakage - Pleural Effusion (%, n/N) | 1.3% (1/78) | 1.5% (3/200) | — |
| Plasma Leakage - Ascites (%, n/N) | 1.3% (1/78) | 3.0% (6/200) | — |
| Plasma Leakage - Radiological Signs (%, n/N) | 40.0% (2/5) | 19.6% (10/51) | — |
| Plasma Leakage - Hematocrit Increase ≥20% (%, n/N)[b] | 3.8% (2/53) | 9.5% (13/137) | — |
| Platelet Count ≤100 × $10^9$ (%, n/N)[c] | 6.4% (5/78) | 22.0% (44/200) | 0.29 |
| Platelet Count ≤50 × $10^9$ (%, n/N)[c] | 3.8% (3/78) | 11.0% (22/200) | 0.35 |
| ALT or AST ≥1000 U/L (%, n/N)[c] | 0% (0/78) | 0% (0/200) | — |

VCD, virologically-confirmed dengue;
ALT, alanine aminotransferase;
AST, aspartate aminotransferase
[a]Duration of febrile illness defined as start date of earliest symptom to end date of latest symptom plus one day (symptoms considered include fever and any general symptoms).
[b]Hematocrit increase defined as maximum hematocrit between Day 3 and Day 7 inclusive, from onset of fever ≥20% increase over minimum hematocrit before Day 3 or after Day 7 from onset of fever.
[c]For platelet, ALT, and AST data, assessments within 14 days of onset of febrile illness have been considered.
N refers to number of VCD cases with available data for the specific parameter e) Immunogenicity The highest geometric mean titers (GMTs) were observed against DENV-2 regardless of baseline serostatus (Table 10). A very high tetravalent seropositivity rate (99.5%) in baseline seronegatives one month after the second dose (Tables 9 and 10) was observed.

Seropositivity rate (% of seropositive subjects) for each of the four dengue serotypes is determined at prevaccination on Day 1 (Month 0), post-first vaccination on Day 30 (Month 1), prevaccination on Day 90 (Month 3), post-second vaccination on Day 120 (Month 4), Day 270 (Month 9), Day 450 (Month 15), and then annually. Seropositivity rates (% participants, 95% CI) by dengue serotype per protocol set for immunogenicity data for Day 0, Day 30, Day 90, Day 120, and Day 270 are shown in Table 9.

Seropositivity rates (% participants, 95% CI) by dengue serotype against three or more serotypes (trivalent) and against all four serotypes (tetravalent) per protocol set for immunogenicity data for Day 0, Day 30, Day 90, Day 120, and Day 270 are shown in Table 9. The tetravalent seropositivity rates were high (>91%) in baseline seronegatives six months after second dose.

TABLE 9

Seropositivity rates (% participants, 95% CI) by dengue serotype (per protocol set for immunogenicity data)

| BASELINE SEROPOSITIVE | | BASELINE SERONEGATIVE | |
|---|---|---|---|
| TDV N = 1,816 | Placebo N = 902 | TDV N = 702 | Placebo N = 345 |
| DENV-1 | | | |
| 89.1 (87.6-90.5) | 90.6 (88.5-92.4) | 0 (0-0.5) | 0 (0-1.1) |
| 99.5 (99.1-99.8) | 88.6 (86.3-90.7) | 94.1 (92.0-95.8) | 4.9 (2.8-7.8) |
| 99.3 (98.8-99.6) | 90.2 (88.1-92.1) | 91.6 (89.3-93.5) | 6.1 (3.8-9.2) |
| >99.9 (99.7-100) | 90.3 (88.1-92.3) | 99.5 (98.6-99.9) | 8.3 (5.5-11.9) |
| 99.6 (99.1-99.8) | 89.8 (87.5-91.8) | 95.1 (93.0-96.6) | 9.0 (6.0-12.8) |
| DENV-2 | | | |
| 96.5 (95.6-97.3) | 97.2 (95.9-98.2) | 0 (0-0.5) | 0 (0-1.1) |
| 99.9 (99.6-100) | 93.3 (91.4-94.9) | 98.6 (97.4-99.4) | 10.7 (7.5-14.5) |
| >99.9 (99.7-100) | 94.0 (92.2-95.5) | 99.0 (98.0-99.6) | 12.2 (8.9-16.1) |
| 99.9 (99.6-100) | 93.6 (91.7-95.2) | 100 (99.4-100) | 14.7 (11.0-19.1) |
| 100 (99.8-100) | 94.6 (92.8-96.1) | 100 (99.4-100) | 18.3 (14.1-23.2) |
| DENV-3 | | | |
| 88.1 (86.5-89.6) | 88.0 (85.7-90.1) | 0 (0-0.5) | 0 (0-1.1) |
| 99.8 (99.4-99.9) | 87.6 (85.1-89.7) | 96.1 (94.3-97.4) | 4.0 (2.1-6.7) |
| 99.5 (99.1-99.8) | 87.3 (84.9-89.4) | 94.4 (92.5-96.0) | 2.0 (0.8-4.1) |
| 99.8 (99.5-100) | 87.9 (85.5-90.1) | 100 (99.4-100) | 5.1 (2.9-8.2) |
| 99.7 (99.4-99.9) | 87.1 (84.6-89.4) | 96.4 (94.6-97.7) | 7.7 (4.9-11.3) |
| DENV-4 | | | |
| 88.1 (86.5-89.6) | 87.4 (85.0-89.5) | 0 (0-0.5) | 0 (0-1.1) |
| 99.6 (99.2-99.9) | 86.6 (84.1-88.8) | 90.5 (88.0-92.6) | 1.8 (0.7-3.9) |
| 99.3 (98.8-99.7) | 86.9 (84.5-89.0) | 92.0 (89.8-93.9) | 2.9 (1.4-5.3) |
| >99.9 (99.7-100) | 88.3 (85.9-90.4) | 99.8 (99.1-100) | 4.8 (2.7-7.8) |
| 99.7 (99.3-99.9) | 87.6 (85.1-89.9) | 97.0 (95.4-98.2) | 6.3 (3.9-9.7) |
| Three or More Serotypes | | | |
| 87.5 (85.9-89.0) | 87.3 (84.9-89.4) | 0 (0-0.5) | 0 (0-1.1) |
| 99.8 (99.5-100) | 87.2 (84.7-89.4) | 96.5 (94.8-97.8) | 1.2 (0.3-3.1) |
| 99.7 (99.3-99.9) | 87.7 (85.3-89.7) | 94.9 (93.0-96.4) | 1.7 (0.6-3.7) |
| 99.9 (99.6-100) | 88.4 (86.0-90.5) | 99.8 (99.1-100) | 4.2 (2.2-7.0) |
| 99.7 (99.4-99.9) | 87.3 (84.7-89.5) | 97.5 (96.0-98.6) | 5.7 (3.3-8.9) |
| All Four Serotypes | | | |
| 83.5 (81.7-85.2) | 83.5 (80.9-85.8) | 0 (0-0.5) | 0 (0-1.1) |
| 99.1 (98.5-99.5) | 82.9 (80.2-85.4) | 85.3 (82.4-87.9) | 0.9 (0.2-2.6) |
| 98.6 (97.9-99.1) | 83.6 (81.0-86.0) | 84.3 (81.4-86.9) | 1.4 (0.5-3.3) |
| 99.8 (99.5-100) | 85.2 (82.6-87.6) | 99.5 (98.6-99.9) | 3.5 (1.8-6.2) |
| 99.2 (98.7-99.6) | 84.6 (81.9-87.0) | 91.3 (88.7-93.4) | 5.3 (3.1-8.5) |

Seropositivity rates (% participants, 95% CI) by dengue serotype (per protocol set for immunogenicity data; seropositive defined as a reciprocal neutralizing antibody titer ≥10; baseline seronegative defined as seronegative to all serotype; baseline seropositive defined as seropositive to one or more serotypes;

N refers to number of participants in the analysis set; number of participants evaluated at each time point may vary)

Geometric mean titers (GMTs) of neutralizing antibodies (microneutralization test [MNT]) for each dengue serotype are determined at pre-vaccination on Day 1 (Month 0), post-first vaccination on Day 30 (Month 1), pre-vaccination on Day 90 (Month 3), post-second vaccination on Day 120 (Month 4), Day 270 (Month 9), Day 450 (Month 15), and then annually. Geometric mean titers (95% CI) by dengue serotype per protocol set for immunogenicity data for Day 0, Day 30, Day 90, Day 120, and Day 270 are shown in Table 10.

TABLE 10

Geometric mean titers (95% CI) by dengue serotype (per protocol set for immunogenicity data)

| | BASELINE SEROPOSITIVE | | BASELINE SERONEGATIVE | |
| --- | --- | --- | --- | --- |
| | TDV N = 1,816 | Placebo N-902 | TDV N = 702 | Placebo N = 345 |
| DENV-1 | | | | |
| Day 1 | 410 (365-461) | 445 (377-524) | 5.0 (5.0-5.0) | 5.0 (5.0-5.0) |
| Day 30 | 2,404 (2,204-2,622) | 430 (361-512) | 118 (106-131) | 5.8 (5.3-6.3) |
| Day 90 | 1,945 (1,791-2,112) | 410 (349-481) | 91 (82-102) | 5.9 (5.4-6.3) |
| Day 120 | 2,115 (1,957-2,286) | 451 (381-534) | 184 (169-201) | 6.3 (5.7-7.0) |
| Day 270 | 1,447 (1,329-1,574) | 415 (350-492) | 87 (79-97) | 6.3 (5.7-6.9) |
| DENV-2 | | | | |
| Day 1 | 745 (674-825) | 802 (697-924) | 5.0 (5.0-5.0) | 5.0 (5.0-5.0) |
| Day 30 | 6,697 (6,301-7,117) | 744 (635-870) | 6,277 (5,648-6,977) | 6.6 (6.0-7.3) |
| Day 90 | 4,826 (4,571-5,096) | 729 (629-845) | 1,682 (1,544-1,834) | 7.0 (6.3-7.9) |
| Day 120 | 4,897 (4,646-5,163) | 766 (655-896) | 1,730 (1,614-1,855) | 7.7 (6.7-8.8) |
| Day 270 | 3,692 (3,496-3,898) | 776 (665-906) | 929 (856-1,010) | 8.7 (7.4-10.2) |
| DENV-3 | | | | |
| Day 1 | 357 (321-398) | 356 (305-415) | 5.0 (5.0-5.0) | 5.0 (5.0-5.0) |
| Day 30 | 2,255 (2,094-2,428) | 349 (298-409) | 194 (173-218) | 5.5 (5.2-5.9) |
| Day 90 | 1,563 (1,453-1,682) | 321 (277-374) | 94 (85-104) | 5.5 (5.1-5.9) |
| Day 120 | 1,761 (1,646-1,885) | 353 (301-414) | 228 (212-246) | 6.0 (5.4-6.6) |
| Day 270 | 1,089 (1,009-1,175) | 307 (261-360) | 72 (66-78) | 6.3 (5.7-7.0) |
| DENV-4 | | | | |
| Day 1 | 218 (198-241) | 234 (203-270) | 5.0 (5.0-5.0) | 5.0 (5.0-5.0) |
| Day 30 | 1,303 (1,221-1,391) | 222 (191-258) | 111 (98-125) | 5.4 (5.0-5.7) |
| Day 90 | 1,002 (940-1,069) | 215 (187-248) | 63 (57-70) | 5.5 (5.1-5.9) |
| Day 120 | 1,129 (1,066-1,196) | 241 (208-280) | 144 (134-155) | 5.8 (5.3-6.4) |
| Day 270 | 778 (730-830) | 229 (197-266) | 64 (59-70) | 6.2 (5.6-6.9) |

Vaccine viremia is assessed by three PCRs: dengue detection RT-PCR, vaccine screening PCR and TDV sequencing in subjects with febrile illness within 30 days after each vaccination.

f) Safety

Rates of serious adverse events (SAEs) were similar in the vaccine and placebo groups (3.1% and 3.8% of participants, respectively; Table 11). One vaccinee and four placebo recipients experienced SAEs considered to be related to receiving blinded investigational product by the investigator (two experienced hypersensitivity, two were diagnosed with dengue, and one with DHF). There were five deaths during Part 1, and all were considered unrelated to the investigational product or study procedures. Total rates of unsolicited AEs were similar between the vaccine and placebo groups. The most commonly (≥1% of vaccine-recipients) reported unsolicited AEs within four weeks of any dose by preferred term were pyrexia (vaccine group 1.5%; placebo 1.4%), nasopharyngitis (vaccine 2.7%; placebo 3.0%), upper respiratory tract infection (vaccine 2.6%; placebo 2.9%), and viral infection (vaccine 1.1%; placebo 0.9%). Solicited local reactions were reported more frequently in the vaccine group.

TABLE 11a

Overview of safety data. Subjects with at least one adverse event after any vaccine dose. Data presented as number of events (percentage of subjects; number [n] of subjects/total [N] subjects) unless otherwise stated (safety set data)

| | TDV | Placebo |
| --- | --- | --- |
| Safety Set | N = 13,380 | N = 6,687 |
| SAEs | 3.1% (409/13,380) | 3.8% (255/6,687) |
| Non-IP-Related[a] SAEs | 3.0% (408/13,380) | 3.8% (251/6,687) |
| IP-Related[a] SAEs | <0.1% (1/13,380) | <0.1% (4/6,687) |

TABLE 11a-continued

Overview of safety data. Subjects with at least one adverse event after any vaccine dose. Data presented as number of events (percentage of subjects; number [n] of subjects/total [N] subjects) unless otherwise stated (safety set data)

|  | TDV | Placebo |
|---|---|---|
| SAEs Leading to IP Withdrawal and/or Trial Discontinuation | 0.1% (18/13,380) | 0.1% (8/6,687) |
| Deaths | <0.1% (4/13,380) | <0.1% (1/6,687) |
| IP-Related Deaths | 0% (0/13,380) | 0% (0/6,687) |
| Safety Subset | N = 2,663 | N = 1,329 |
| Unsolicited AEs Occurring Within 4 Weeks of Any Dose | 18.4% (490/2,663) | 18.8% (250/1,329) |
| IP-Related[a] Unsolicited AEs Occurring Within 4 Weeks of Any Dose | 1.0% (27/2,663) | 1.6% (21/1,329) |
| Solicited Systemic AEs Occurring Within 2 Weeks of Any Dose[b] | 42.0% (1,107/2,635) | 38.0% (501/1,317) |
| IP-Related[a] Solicited Systemic AEs Occurring Within 2 Weeks of Any Dose | 31.2% (821/2,635) | 28.2% (371/1,317) |
| Solicited Local Reactions Occurring Within 1 Week of Any Dose[c] | 36.7% (967/2,633) | 25.7% (338/1,317) |

AE, adverse event;
SAE, serious adverse event;
IP, investigational product/TDV
[a]IP-related, defined as related to the investigational product as assessed by investigator
[b]only participants with diary data available were evaluated
[c]all injection site (solicited local) reactions considered to be IP-related TABLE 11b Number of participants (%) with serious adverse events after any vaccination during Part 1 by MedDRA (Medical Dictionary for Regulatory Activities) System Organ Class in the order of decreasing frequency (safety set data presented by TDV and placebo group for events that occurred in >3 participants due to risk of unblinding).

| MedDRA System Organ Class | TDV N = 13,380 | Placebo N = 6,687 | Total* N = 20,071 |
|---|---|---|---|
| Any Serious Adverse Events | 409 (3.1) | 255 (3.8) | 664 (3.3) |
| Infections and infestations | 235 (1.8) | 179 (2.7) | 414 (2.1) |
| Injury, poisoning and procedural complications | 87 (0.7) | 37 (0.6) | 124 (0.6) |
| Gastrointestinal disorders | 23 (0.2) | 9 (0.1) | 32 (0.2) |
| Nervous system disorders | 14 (0.1) | 6 (<0.1) | 20 (<0.1) |
| Respiratory, thoracic and mediastinal disorders | 14 (0.1) | 6 (<0.1) | 20 (<0.1) |
| Renal and urinary disorders | 15 (0.1) | 3 (<0.1) | 18 (<0.1) |
| Blood and lymphatic system disorders | 8 (<0.1) | 2 (<0.1) | 10 (<0.1) |
| Pregnancy, puerperium and perinatal conditions | 8 (<0.1) | 2 (<0.1) | 10 (<0.1) |
| Skin and subcutaneous tissue disorders | 7 (<0.1) | 3 (<0.1) | 10 (<0.1) |
| Psychiatric disorders | 7 (<0.1) | 2 (<0.1) | 9 (<0.1) |
| General disorders and administration site conditions | 5 (<0.1) | 3 (<0.1) | 8 (<0.1) |
| Immune system disorders | 3 (<0.1) | 4 (<0.1) | 7 (<0.1) |
| Metabolism and nutrition disorders | 6 (<0.1) | 1 (<0.1) | 7 (<0.1) |
| Musculoskeletal and connective tissue | 1 (<0.1) | 5 (<0.1) | 6 (<0.1) |
| Social circumstances | 2 (<0.1) | 4 (<0.1) | 6 (<0.1) |
| Congenital, familial and genetic disorders | 3 (<0.1) | 2 (<0.1) | 5 (<0.1) |
| Neoplasms benign, malignant and unspecified (including cysts and polyps) | 3 (<0.1) | 1 (<0.1) | 4 (<0.1) |
| Endocrine disorders | — | — | 3 (<0.1) |
| Hepatobiliary disorders | — | — | 3 (<0.1) |
| Reproductive system and breast disorders | — | — | 3 (<0.1) |
| Vascular disorders | — | — | 3 (<0.1) |
| Cardiac disorders | — | — | 2 (<0.1) |
| Eye disorders | — | — | 2 (<0.1) |
| Investigations | — | — | 1 (<0.1) |
| Product issues | — | — | 1 (<0.1) |
| Surgical and medical procedures | — | — | 1 (<0.1) |

*Total column includes participants who received both TAK-003 and placebo due to administration error and are excluded from the TAK-003 and placebo groups.
N in column header refers to number of participants in the safety set

TABLE 11c

Number of participants (%) with unsolicited adverse events of any severity up to 28-days after any vaccination by MedDRA System Organ Class in the order of decreasing frequency (Subset of safety set data presented by TDV and placebo group for events that occurred in >6 participants due to risk of unblinding).

| MedDRA System Organ Class | TDV<br>N = 2,663 | Placebo<br>N = 1,329 | Total<br>N = 3,993 |
|---|---|---|---|
| Any Unsolicited Adverse Events | 487 (18.3) | 249 (18.7) | 736 (18.4) |
| Infections and infestations | 368 (13.8) | 190 (14.3) | 558 (14.0) |
| Injury, poisoning and procedural complications | 21 (0.8) | 22 (1.7) | 43 (1.1) |
| Gastrointestinal disorders | 33 (1.2) | 9 (0.7) | 42 (1.1) |
| General disorders and administration site conditions | 30 (1.1) | 11 (0.8) | 41 (1.0) |
| Skin and subcutaneous tissue disorders | 27 (1.0) | 7 (0.5) | 34 (0.9) |
| Nervous system disorders | 18 (0.7) | 13 (1.0) | 31 (0.8) |
| Respiratory, thoracic and mediastinal disorders | 18 (0.7) | 10 (0.8) | 28 (0.7) |
| Blood and lymphatic system disorders | 6 (0.2) | 5 (0.4) | 11 (0.3) |
| Musculoskeletal and connective tissue disorders | 6 (0.2) | 5 (0.4) | 11 (0.3) |
| Immune system disorders | — | — | 6 (0.2) |
| Psychiatric disorders | — | — | 3 (<0.1) |
| Reproductive system and breast disorders | — | — | 3 (<0.1) |
| Ear and labyrinth disorders | — | — | 2 (<0.1) |
| Cardiac disorders | — | — | 1 (<0.1) |
| Congenital, familial and genetic disorders | — | — | 1 (<0.1) |
| Eye disorders | — | — | 1 (<0.1) |
| Renal and urinary disorders | — | — | 1 (<0.1) |
| Social circumstances | — | — | 1 (<0.1) |

*Total column includes participants who received both TAK-003 and placebo due to administration error and are excluded from the TAK-003 and placebo groups. N in column header refers to number of participants in the subset of safety set.

TABLE 11d

Summary of diary reported injection site reactions up to 7 days and systemic adverse events up to 14 days after any vaccination (Subset of safety set data). Data presented as number of participants with events/number of evaluated participants in the analysis set (% of evaluated participants with events).

| Solicited Events | TDV | Placebo |
|---|---|---|
| Injection site reactions (Age <6 years) | | |
| Any | 106/331 (32.0) | 43/169 (25.4) |
| Pain | 104/331 (31.4) | 43/169 (25.4) |
| Erythema | 5/331 (1.5) | 1/169 (0.6) |
| Swelling | 11/331 (3.3) | 2/169 (1.2) |
| Injection site reactions (Age ≥6 years) | | |
| Any | 861/2302 (37.4) | 295/1148 (25.7) |
| Pain | 853/2302 (37.1) | 293/1148 (25.5) |
| Erythema | 33/2301 (1.4) | 1/1147 (<0.1) |
| Swelling | 33/2300 (1.4) | 6/1147 (0.5) |
| Systemic adverse events (Age <6 years) | | |
| Any | 88/331 (26.6) | 35/169 (20.7) |
| Irritability/Fussiness | 41/331 (12.4) | 16/169 (9.5) |
| Drowsiness | 45/331 (13.6) | 21/169 (12.4) |
| Loss of Appetite | 57/331 (17.2) | 22/169 (13.0) |
| Fever (Body temperature >= 38° C. or 100.4° F.) | 45/327 (13.8) | 23/169 (13.6) |
| Systemic adverse events (Age ≥6 years) | | |
| Any | 941/2302 (40.9) | 422/1147 (36.8) |
| Headache | 715/2302 (31.1) | 326/1147 (28.4) |
| Asthenia | 404/2302 (17.5) | 187/1147 (16.3) |
| Malaise | 510/2301 (22.2) | 226/1147 (19.7) |
| Myalgia | 554/2302 (24.1) | 216/1147 (18.8) |
| Fever (Body temperature >= 38° C. or 100.4° F.) | 221/2279 (9.7) | 124/1134 (10.9) |

Additionally, a study to assess the efficacy of a booster dose as a follow-on study of the above-described phase III study, such that booster will be given at 4 to 4.5 years post the second dose in a large enough subset of the above-described phase III study, wherein said subset e.g. includes at least 20 subjects or at least 200 subjects, is possible.

Example 4: Concomitant Administration of a Hepatitis A Vaccine and a Dengue Vaccine

4.1 Introduction, Purpose and Objectives of the Study

A randomized, observer blind, phase 3 trial was conducted in 900 healthy adult subjects aged 18 to 60 years (distributed across the entire age range) in non-endemic countries for dengue disease and hepatitis A virus (HAV) to investigate the immunogenicity and safety of two doses of tetravalent dengue vaccine TDV (subcutaneous (SC) injection), and of the simultaneous on the same day administration of a single dose of HAV vaccine (containing an inactivated HAV; intramuscular (IM) injection) and TDV (SC injection).

A purpose of the study was to assess whether HAV vaccine can be safely administered simultaneously on the same day with TDV as travel vaccines before an international travel of a subject to HAV and dengue (DENV)-endemic countries.

The primary objective of this study was demonstrate non-inferiority (NI) of the immune response to one dose of HAV vaccine simultaneously administered on the same day with one dose TDV on the same day, compared to one dose HAV vaccine simultaneously on the same day administered with placebo on the same day, in DENV/HAV-naïve subjects one month after vaccination.

The secondary objectives of this study were to describe TDV-induced immunogenicity after a single dose of TDV in DENV/HAV-naïve subjects; to describe TDV-induced immunogenicity after two doses of TDV administered 90 days apart in DENV/HAV-naïve subjects; to describe HAV vaccine-induced immunogenicity in DENV/HAV-naïve subjects; and to assess the safety profile after each vaccine injection in all trial groups.

4.2 Eligibility Criteria

Criteria for inclusion include:
1. The participant is aged 18 to 60 years, inclusive.
2. Participants who are in good health at the time of entry into the trial as determined by medical history, physical examination (including vital signs) and the clinical judgment of the Investigator.
3. The participant signs and dates a written informed consent form and any required privacy authorization prior to the initiation of any trial procedures, after the nature of the trial has been explained according to local regulatory requirements.
4. Participants who can comply with trial procedures and are available for the duration of follow-up.

Exclusion criteria include:
1. Participants with an elevated oral temperature (?38° C. or 100.4° F.) within 3 days of the intended date of vaccination.
2. Known hypersensitivity or allergy to any of the vaccine components (including excipients of the investigational vaccines or placebo).
3. Participants with behavioral or cognitive impairment or psychiatric disease that, in the opinion of the Investigator, may interfere with the participant's ability to participate in the trial.
4. Participants with any history of progressive or severe neurologic disorder, seizure disorder or neuro-inflammatory disease (e.g., Guillain-Barré syndrome).
5. Participants with history or any illness that, in the opinion of the Investigator, might interfere with the results of the trial or pose additional risk to the participant due to participation in the trial.
6. Known or suspected impairment/alteration of immune function, including:
   1. Chronic use of oral steroids (equivalent to 20 mg/day prednisone≥12 weeks/≥2 mg/kg body weight/day prednisone≥2 weeks) within 60 days prior to Day 1 (M0) (use of inhaled, intranasal, or topical corticosteroids is allowed).
   2. Receipt of parenteral steroids (equivalent to 20 mg/day prednisone≥12 weeks/≥2 mg/kg body weight/day prednisone≥2 weeks) within 60 days prior to Day 1 (M0).
   3. Administration of immunoglobulins and/or any blood products within the 3 months prior to Day 1 (M0) or planned administration during the trial.
   4. Receipt of immunostimulants within 60 days prior to Day 1 (M0).
   5. Immunosuppressive therapy such as anti-cancer chemotherapy or radiation therapy within 6 months prior to Day 1 (M0).
   6. Human immunodeficiency virus (HIV) infection or HIV-related disease.
   7. Hepatitis A virus (HAV) infection.
   8. Hepatitis C virus infection.
   9. Genetic immunodeficiency.
7. Abnormalities of splenic or thymic function.
8. Participants with a known bleeding diathesis, or any condition that may be associated with a prolonged bleeding time.
9. Participants with any serious chronic or progressive disease according to judgment of the Investigator (e.g., neoplasm, insulin dependent diabetes, cardiac, renal or hepatic disease).
10. Participants with body mass index (BMI) greater than or equal to 35 kg/m^2(=weight in kg/[height in meters$^2$]).
11. Participants participating in any clinical trial with another investigational product 30 days prior to Day 1 (M0) or intent to participate in another clinical trial at any time during the conduct of this trial.
12. Participants who received any other vaccine within 14 days (for inactivated vaccines) or 28 days (for live vaccines) prior to enrollment in this trial or who are planning to receive any vaccine within 28 days of trial vaccine administration.
13. Previous HAV vaccination (in a clinical trial or with an approved product).
14. Participants involved in the trial conduct or their first degree relatives.
15. Participants with history of substance or alcohol abuse within the past 2 years.
16. Female participants who are pregnant or breastfeeding.
17. Females of childbearing potential who are sexually active, and who have not used any of the acceptable contraceptive methods for at least 2 months prior to Day 1 (M0).
    1. Of childbearing potential is defined as status post onset of menarche and not meeting any of the following conditions: bilateral tubal ligation (at least 1 year previously), bilateral oophorectomy (at least 1 year previously) or hysterectomy
    2. Acceptable birth control methods are defined as one or more of the following:
    i. Hormonal contraceptive (such as oral, injection, transdermal patch, implant, cervical ring).
    ii. Barrier method (condom with spermicide or diaphragm with spermicide) each and every time during intercourse.
    iii. Intrauterine device (IUD). iv. Monogamous relationship with vasectomized partner (partner must have been vasectomized for at least 6 months prior to Day 1 [M0]).
    Other contraceptive methods may be considered in agreement with the Sponsor and implemented only after approval of a substantial amendment by the regulatory authorities and by the appropriate ethics committee.
18. Females of childbearing potential who are sexually active, and who refuse to use an acceptable contraceptive method up to 6 weeks after the last dose of trial vaccine (Day 90 [M3]). In addition, they must be advised not to donate ova during this period.
19. Any positive or indeterminate pregnancy test.
20. Previous and planned vaccination (during the trial conduct) against any flaviviruses including dengue, yellow fever (YF), Japanese Encephalitis (JE) viruses or tick-borne encephalitis.
21. Previous participation in any clinical trial of a dengue or other flavivirus (e.g., West Nile [WN] virus) candidate vaccine, except for participants who received placebo in those trials.
22. Participants with a current or previous infection with a flavivirus such as dengue, Zika, YF, JE, WN fever, tick-borne encephalitis or Murray Valley encephalitis and participants with a history of prolonged (≥1 year) habitation in a dengue endemic area.
23. Participants with contraindications, warnings and/or precautions to vaccination with the HAV vaccine as specified within the product information.

4.3 Study Design & Vaccinations

Eligible subjects were randomized equally (1:1:1 ratio) to one of the following 3 trial groups (300 subjects per group):

Group 1: HAV vaccine (IM) and placebo (SC), simultaneously on the same day administered on day 1 (month 0); placebo (SC) administered at day 90 (month 3).

Group 2: TDV (SC) and placebo (IM), simultaneously on the same day administered on day 1 (month 0); TDV (SC) administered at day 90 (month 3).

Group 3: TDV (SC) and HAV vaccine (IM), simultaneously on the same day administered on day 1 (month 0); TDV (SC) administered at day 90 (month 3).

Figure 6:
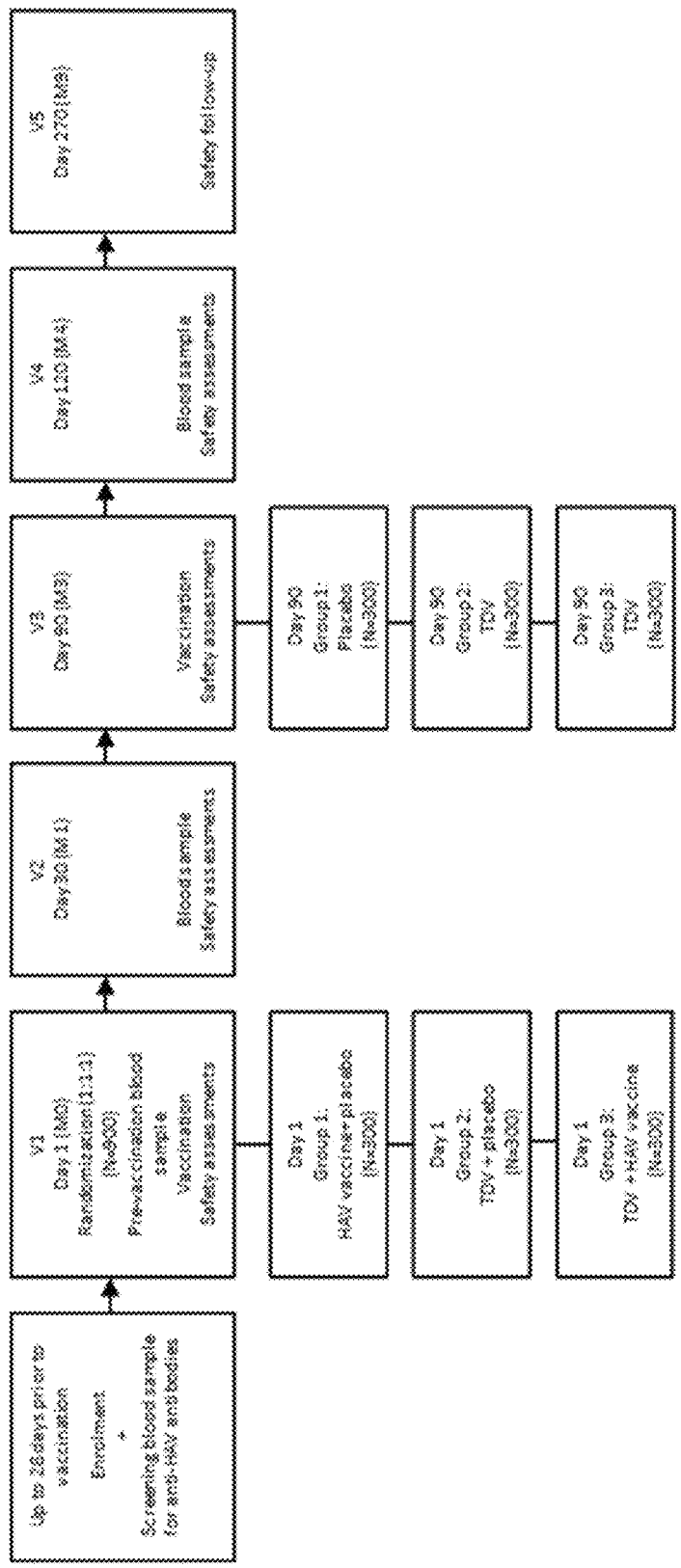
FIG. 6: Scheme of the trial design of the simultaneous HAV and TDV administration study described in Example 4.

A more detailed scheme of the study design is shown in FIG. 6. Up to 28 days prior to the first vaccination, enrolment was carried out and blood samples were taken for screening anti-HAV antibodies. On day 1, pre-vaccination blood samples were taken. On day 30 (after the first vaccination on day 1) post-vaccination blood samples were taken. On day 120 (after the first vaccination on day 1) another blood sample was taken. Safety follow-up took place on day 270 (after the first vaccination on day 1).

The TDV was prepared as described in Example 1. Each subcutaneous dose of the TDV had a volume of 0.5 ml and the concentration of the four dengue serotypes in the TDV in each dose was 5.1 $\log_{10}$ pfu/0.5 ml, 4.5 $\log_{10}$ pfu/0.5 ml, 5.4 $\log_{10}$ pfu/0.5 ml and 5.9 $\log_{10}$ pfu/0.5 ml of TDV-1, TDV-2, TDV-3 and TDV-4, respectively. Each subcutaneous dose comprises the TDV dispersed in 0.5 ml of an aqueous solution containing Pluronic F127 (10.6 mg/ml), trehalose dihydrate (170 mg/ml) and human serum albumin (1.08 mg/ml).

The HAV vaccine includes an inactivated hepatitis A virus, derived from a hepatitis A virus strain HM-175 (see definitions above), and is commercially available under the tradename HAVRIX® as described above. The intramuscular dose of the HAV vaccine administered to groups 1) and 3) was 1 ml and each 1 ml dose has a viral antigen activity of about 1440 EL.U., wherein the viral antigen is adsorbed on 0.5 mg of aluminum in the form of aluminum hydroxide. The hepatitis A vaccine contains excipients in the form of an amino acid supplement (about 0.3% w/v) and in the form of polysorbate (about 0.05 mg/ml) dissolved in a phosphate-buffered saline solution.

Simultaneously on the same day administered trial vaccines were injected to opposite arms. Normal saline solution for injection (0.9% NaCl) was used as placebo. A blood sample for an anti-HAV antibody test were collected at screening from all subjects to exclude subjects who are positive for anti-HAV antibodies up to 28 days prior to vaccination (see FIG. 6). All subjects were followed-up for 6 months after the second vaccination at day 90 (month 3), so the trial duration was 270 days or 9 months for each subject (not including the screening period). Outside the context of this trial, subjects in Groups 1 and 3 will be offered a HAV vaccine booster dose after the completion of trial procedures at day 270 (month 9).

Dengue neutralizing antibodies (microneutralization test (MNT50)) were measured using blood samples collected at pre-first trial vaccination (day 1 (month 0)), 1 month post first trial vaccination (day 30 (month 1)), and 1 month post second trial vaccination (day 120 (month 4)). Blood samples for the measurement of anti-HAV antibodies (enzyme-linked immunosorbent assay (ELISA)) were collected at pre-first trial vaccination (day 1 (month 0)) and 1 month post first trial vaccination (day 30 (month 1)).

4.4 Primary Endpoint

The primary endpoint included the proportion of HAV/DENV-naive subjects at baseline who are seroprotected against HAV at day 30 (month 1) as measured by enzyme-linked immunosorbent assay (ELISA)). In other words, the primary endpoint includes the seroprotection rates (SPRs). Seroprotection is defined as serum anti-HAV antibody levels≥10 mIU/mL. Immunological naivety to HAV/DENV is defined as anti-HAV antibody levels<10 mIU/mL and reciprocal neutralizing titers for all 4 dengue serotypes<10.

4.5 Secondary Endpoints a) Secondary Immunogenicity Endpoints

The secondary endpoints included the geometric mean titers of neutralizing antibodies (GMTs) (microneutralization test (MNT50)) for each of the 4 dengue serotypes at day 30 (month 1) and day 120 (month 4) which were determined in HAV/DENV-naive subjects at baseline; the proportion of HAV/DENV-naive subjects at baseline who are seropositive for each of the 4 dengue serotypes at day 30 (month 1) and day 120 (month 4) (seroprotection rate); and geometric mean concentrations (GMC) of anti-HAV antibodies at day 30 (month 1) in subjects HAV/DENV-naive at baseline.

Seropositivity for dengue virus is defined as a reciprocal neutralizing titer 10 for any of the four dengue serotypes within the secondary immunogenicity endpoints.

b) Secondary Safety Endpoints

Secondary safety endpoints included the frequency and severity of solicited local adverse events (AE) for 7 days after each trial vaccination; the frequency and severity of solicited systemic AEs for 14 days after each trial vaccination; the percentage of subjects with any unsolicited AEs for 28 days after each trial vaccination; the percentage of subjects with serious adverse events (SAE) throughout the trial; and the percentage of subjects with medically attended adverse events (MAAE) throughout the trial.

4.6 Analysis Sets of the Study

Table 12 below displays each analysis set of the present study. In total, 1199 subjects belonging to the group "all screened" included all subjects who signed the informed consent, regardless of whether the subjects were screen failures. After initial screening, 900 subjects were included into the "randomized set" which includes all randomized subjects, regardless of whether any dose of the IPs was received. The safety set, consisting of 897 subjects, includes all randomized subjects who received ≥1 dose of the IPs. The immunogenicity subjects included a total of 359 subjects and is subdivided into the following four subsets. The HAV-full analysis set (HAV-FAS) includes all randomized subjects in the immunogenicity subset who received ≥1 dose of the trial vaccine with available day 1 and day 30 anti-HAV antibody measurements. The HAV-per-protocol set (HAV-PPS) includes all HAV- and DENV-naïve subjects from the HAV-FAS who have no major protocol violations. The TDV-full analysis set (TDV-FAS) includes all randomized subjects in the immunogenicity subset who received ≥1 dose of trial vaccine and with available day 1 and ≥1 post-dose measurements. The TDV-per-protocol set (TDV-PPS), consisting of 197 subjects, includes all HAV- and DENV-naïve subjects from the TDV-FAS who have no major protocol violations.

TABLE 12

| Analysis sets of the study. | | | | |
|---|---|---|---|---|
| | HAV/Pbo | TDV/Pbo | HAV/TDV | Total |
| All Screened[1] | NA | NA | NA | 1199 |
| Randomized Set[2] | 300 | 300 | 300 | 900 |
| Safety Set (SS)[3] | 299 | 300 | 298 | 897 |
| Immunogenicity Subset | 119 | 120 | 120 | 359 |
| HAV Full Analysis Set (HAV-FAS)[4] | 115 | 117 | 114 | 346 |
| HAV Per-Protocol Set (HAV-PPS)[5] | 75 | 71 | 81 | 227 |
| TDV-FAS[6] | 116 | 117 | 115 | 348 |
| TDV-PPS[7] | 67 | 63 | 67 | 197 |
| Subjects analyzed for primary non-inferiority objective[8] | 69/115 | NA | 79/114 | 148/227 |

[1] All Screened: All subjects who signed the informed consent, regardless of whether subjects were screen failures
[2] Randomized Set: All randomized subjects, regardless of whether any dose of the trial vaccines was received.
[3] Safety Set: All randomized subjects who received ≥1 dose of trial vaccines.
[4] HAV-FAS: All randomized subjects in the immunogenicity subset who received ≥1 dose of trial vaccine, with available Day 1 and Day 30 HAV measurements.
[5] HAV-PPS: All HAV & DENV-naïve subjects from the HAV-FAS who have no major protocol violations.
[6] TDV-FAS: All randomized subjects in the immunogenicity subset who received ≥1 dose of trial vaccine and available Day 1 and ≥1 post-dose measurement.
[7] TDV-PPS: All HAV & DENV-naïve subjects from the TDV-FAS who have no major protocol violations.
[8] Subject excluded from TDV-PPS but included into analysis for primary non-inferiority objective had their Day 30 measurement outside the protocol defined visit window.

From a total number of 359 subjects in the immunogenicity subset (including all subjects which received≥1 vaccination), 13 subjects have been excluded from HAV-FAS because of not providing a valid baseline and post-dosing measurement (on day 30) for HAV. Furthermore, HAV-PPS includes all HAV- and DENV-naïve subjects of HAV-FAS who had no major protocol violations. The subjects analyzed for primary non-inferiority objective are based on the HAV-PPS subjects of the HAV/Pbo and HAV/TDV group, wherein based on HAV-PPS of these two groups (HAV/Pbo and HAV//TDV), some subjects were not included in the 30 days analysis (6 subjects of the HAV/Pbo group and 2 Subjects of the HAV/TDV group), since these subjects had their day 30 measurement outside the visit window defined in the protocol. Therefore, a total of 69 subjects was included into the TDV/Pbo group and a total of 79 subjects was included in the HAV/TDV group for analyzing the primary non-inferiority objective.

From a total number of 359 subjects in the immunogenicity subset (including all subjects which received ≥1 vaccination), a total of 11 subjects have been excluded from TDV-FAS, because they did not provide a valid baseline and at least one post-dosing measurement (day 30 and/or day 120) for TDV. Furthermore, a total number of 151 subjects had been excluded from the TDV-PPS for not being HAV & DENV-naïve at baseline or for not receiving both vaccinations 1 and 2 or if vaccination 2 (usually on day 90) is outside the window −15/+25 days or if major protocol violations occur.

4.7 HAV Baseline Serostatus and Demographic & Baseline Characteristics

The safety set evaluated for baseline HAV antibody levels included a total of 362 subjects of which 27.3% were HAV seropositive at baseline (see Table 13).

HAS-FAS included a total of 346 subjects evaluated for baseline HAV antibody levels (see Table 13). HAV-naivety was defined as anti-HAV antibody (ab) level of <10 mIU/ml. However, the ELISA used for serological analysis could not be validated below levels of 12.5 mIU/ml. The qualitative screening test had a specification that effectively amounted to a lower limit of quantification of 70 mIU/ml. In view of these criteria, 72.5% of the subjects of said HAS-FAS evaluated for baseline HAV antibody levels were HAV naive at baseline (see Table 13).

TABLE 13

| HAV baseline serostatus in the safety set and in the HAV-FAS | | | | |
|---|---|---|---|---|
| | HAV/Pbo | TDV/Pbo | HAV/TDV | Total |
| Safety set evaluated for baseline HAV antibody levels | 119 | 121 | 122 | 362 |
| HAV seropositive at baseline | 31 (26.1%) | 38 (31.4%) | 30 (24.6%) | 99 (27.3%) |
| HAV-FAS Evaluated For Baseline HAV antibody levels | 115 (100%) | 117 (100%) | 114 (100%) | 346 (100%) |
| HAV seronegative at baseline <12.5 mIU/ml (a) | 86 (74.8%) | 79 (67.5%) | 86 (74.4%) | 251 (72.5%) |
| HAV seropositive at baseline (b) | 29 (25.2%) | 38 (32.5%) | 28 (24.6%) | 95 (27.5%) |
| baseline 12.5-70 mIU/ml | 18 | 23 | 13 | 54 |
| baseline 70-1000 mIU/ml | 11 | 14 | 14 | 39 |
| baseline >1000 | 0 | 1 | 1 | 2 |

(a) HAV-naivety was defined as anti-HAV ab level of <10 mIU/ml; The ELISA used for serological analysis could not be validated below levels of 12.5 mIU/ml.
(b) The qualitative screening test had a specification that effectively amounted to a lower limit of quantification of 70 mIU/ml The HAV-PPS includes a total number of 227 subjects (see Table 14). The mean age of the total number of subjects of the HAV-PPS, which are DENV- and HAV-naïve was 34.8. 31.3% of the total number of subjects of the HAV-PPS were female (see Table 14). In total, 97.8% of the total subjects of the HAV-PPS were of an ethnicity which is NOT Hispanic or Latino, and, in particular, 89.9% of the HAV-PPS participants were of race "white European", especially in order to reflect the situation of travelers of HAV- and dengue non-endemic countries (see Table 14).

The safety set includes a total number of 897 subjects (see Table 14). The mean age of the total number of subjects of the safety set was 35.4 years of which 31.3% were female. In total, 97.7% of the total subjects of the HAV-PPS were of an ethnicity which is NOT Hispanic or Latino, and, in particular, 87.1% of the HAV-PPS participants were of race "white European", especially in order to reflect the situation of travelers of HAV- and dengue non-endemic countries (see Table 14).

bound of a two-sided 95% confidence interval, calculated using the Newcombe score method, which is lower than the 10% non-inferiority margin. This criterion is fulfilled for each of the groups in Table 15. In the primary endpoint group, the upper bound of the 95% CI of the SPR difference is 4.31% which is less than the non-inferiority margin of 10% (see second line from above in Table 15).

As mentioned above, sensitivity analyses 1 to 3 were used to evaluate populations that included subjects who were seropositive for dengue and/or for hepatitis A at baseline, in particular reflecting "real life" travel clinic settings in non-endemic countries in which subjects, i.e. travelers who plan to go to dengue and HAV endemic countries, are not always aware of their HAV and/or dengue serostatus before requesting pre-travel vaccinations.

TABLE 14

Demographic and baseline characteristics (HAV-PPS and Safety Set)

|  |  | HAV/Pbo | TDV/Pbo | HAV/TDV | Total |
| --- | --- | --- | --- | --- | --- |
| HAV-PPS (DENV/HAV-naïve) | N | 75 | 71 | 81 | 227 |
| Age Years | Mean (SD) | 34.3 (11.68) | 35.5 (11.24) | 34.8 (11.70) | 34.8 (11.51) |
| Gender | Female n (%) | 24 (32.0%) | 30 (42.3%) | 17 (21.0%) | 71 (31.3%) |
| Ethnicity NOT Hispanic or Latino | n (%) | 72 (96.0%) | 71 (100.0%) | 79 (97.5%) | 222 (97.8%) |
| Race White European | n (%) | 64 (85.3%) | 64 (90.1%) | 76 (93.8%) | 204 (89.9%) |
| Safety set | N | 299 | 300 | 298 | 897 |
| Age Years | Mean (SD) | 34.7 (12.04) | 36.0 (11.88) | 35.5 (11.96%) | 35.4 (11.96) |
| Gender | Female n (%) | 107 (35.8%) | 120 (40.0%) | 90 (30.2%) | 317 (35.3%) |
| Ethnicity NOT Hispanic or Latino | n (%) | 289 (96.7%) | 293 (97.7%) | 294 (98.7%) | 876 (97.7%) |
| Race White European | n (%) | 255 (85.3%) | 265 (88.3%) | 261 (87.6%) | 781 (87.1%) |

4.8 Study Results a) Primary Endpoint and Sensitivity Analyses

The present study was successful in meeting the primary objective of non-inferiority for the simultaneous on the same day administration of HAV and TDV. Table 15 displays the seroprotection rates (SPRs) of groups 1 (received HAV/Pbo) and 3 (received HAV/TDV) on day 30 after the first vaccination (on day 1), the SPR differences between the HAV/Pbo group and the HAV/TDV group on day 30, and the confidence intervals (CIs) of these SPR differences for HAV and DENV-baseline naïve subjects. These values (SPRs, SPR differences; CIs) were used for the primary endpoint evaluation of the study. Table 15 further shows these values for the results of three sensitivity analyses (also used for non-inferiority assessments), wherein the subjects had different, i.e. mixed, HAV/TDV serostatuses at baseline. Non-inferiority between the hepatitis A vaccine and the tetravalent dengue vaccine, when simultaneously on the same day administered, in the present study is concluded, if the seroprotection rate (SPR) difference between group 1 (received HAV and placebo on the same day 1) and group 3 (received HAV and TDV on the same day 1) has an upper The object of non-inferiority of the simultaneous on the same day administration was also met in sensitivity analyses 1 to 3 (upper bounds of the 95% CI of the SPR differences: 3.21%; 20.93%; and 2.55% which are each less than the non-inferiority margin of 10%). Furthermore, the SPRs of the HAV/TDV groups (98.8%; 99.0%; 99.1%, respectively, see Table 15) were respectively higher than the SPRs of the HAV/Pbo group (96.2%; 96.9%; 97.2%, respectively, see Table 15).

Therefore, due to the non-inferiority of the simultaneous on the same day administration of the HAV vaccine and TDV to subjects with mixed baseline serostatus (and baseline naivety) with respect to HAV and all dengue serotypes, there is no need for determining or knowing the subject's baseline serostatus with respect to each of the two diseases, prior to simultaneously on the same day administering the HAV vaccine and TDV.

TABLE 15

Primary endpoint: Non-inferiority (NI) assessments & sensitivity analysis

| Analysis | Analysis Set | HAV/Pbo (Group 1) SPR % (n/n) | HAV/TDV (Group3) SPR % (n/n) | SPR difference | 95% CI[1] (of SPR difference) |
|---|---|---|---|---|---|
| Primary endpoint | HAV PPS - includes baseline HAV- and DENV- subjects | 97.1% (67/69) | 98.7% (78/79) | −1.63 | (−8.78, 4.31) |
| Sensitivity Analysis 1 | HAV PPS - includes baseline HAV-, DENV-, and DENV+ subjects | 96.2% (76/79) | 98.8% (83/84) | −2.61 | (−9.46, 3.21) |
| Sensitivity Analysis 2 | HAV PPS - includes baseline HAV-; HAV+ (12.5-70 mIU/ml); DENV-; DENV+ | 96.9% (93/96) | 99.0% (96/97) | −2.09 | (−7.82, 2.93) |
| Sensitivity Analysis 3 | HAV PPS - includes baseline HAV-; HAV+; DENV-; DENV+ | 97.2% (103/106) | 99.1% (109/110) | −1.92 | (−7.14, 2.55) |

[1]CI = Confidence Interval
Non-inferiority Assessment: Seroprotection Rates (SPRs) for HAV Group 1 (HAV + placebo simultaneous on the same day administration ) vs Group 3 (HAV + TDV simultaneous on the same day administration)
Rates difference for primary comparison (Group 1-Group 3) are presented together with 95% CI calculated using Newcombe score method
NI of simultaneous on the same day administration of HAV and TDV to HAV alone will be concluded if the upper bound of the 95% CI is less than NI margin of 10%.

b) Secondary Immunogenicity Endpoints

Table 16 shows GMTs (with respect to each of the four dengue virus serotypes DENV-1 to DENV-4) when measured on day 1 pre-first vaccination, on day 30 after the first vaccination (on day 1), and on day 120 after the first vaccination of the subjects (on day 1) of the DENV-PPS including the groups receiving HAV/TDV, TDV and placebo, as well as HAV and placebo (Pbo), respectively. Table 16 shows positive trends in favor of the simultaneous on the same day administration group (received HAV/TDV) with respect to all dengue GMTs.

Said positive trend in favor of the simultaneous on the same day administration and the day 30 synergism of the simultaneously on the same day administered vaccines is also confirmed in Table 17.

TABLE 16

Immunogenicity of DENV-PPS: GMTs of DENV MNT50. In particular, DENV GMTs against each serotype with respect to mean titers of neutralizing antibodies measured by MNT50 for each dengue serotype by trial visit are shown.

| | | | DENV-1 | | | DENV-2 | | |
|---|---|---|---|---|---|---|---|---|
| | | | HAV/p | TDV/p | HAV/TDV | HAV/p | TDV/p | HAV/TDV |
| Day 1 | n | | 67 | 63 | 67 | 67 | 63 | 67 |
| | GMT | | 5.0 | 5.0 | 5.0 | 5.0 | 5.0 | 5.0 |
| | (SD[1]) | | (1.00) | (1.00) | (1.00) | (1.00) | (1.00) | (1.00) |
| Day 30 | n | | 62 | 60 | 65 | 62 | 60 | 65 |
| | GMT | | 5.0 | 108.2 | 152.5 | 6.0 | 2897.9 | 3960.0 |
| | (SD) | | (1.00) | (5.64) | (4.62) | (1.87) | (13.86) | (8.79) |
| Day 120 | n | | 50 | 55 | 62 | 50 | 55 | 62 |
| | GMT | | 5.0 | 171.3 | 173.7 | 5.7 | 2064.1 | 1764.3 |
| | (SD) | | (1.00) | (6.23) | (4.28) | (1.72) | (3.60) | (4.03) |

| | | | DENV-3 | | | DENV-4 | | |
|---|---|---|---|---|---|---|---|---|
| | | | HAV/p | TDV/p | HAV/TDV | HAV/p | TDV/p | HAV/TDV |
| Day 1 | n | | 67 | 63 | 67 | 67 | 63 | 67 |
| | GMT | | 5.0 | 5.0 | 5.0 | 5.0 | 5.0 | 5.0 |
| | (SD[1]) | | (1.00) | (1.00) | (1.00) | (1.00) | (1.00) | (1.00) |
| Day 30 | n | | 62 | 60 | 65 | 62 | 60 | 65 |
| | GMT | | 5.3 | 95.4 | 140.5 | 5.0 | 74.3 | 142.1 |
| | (SD) | | (1.49) | (6.24) | (4.50) | (1.00) | (5.03) | (6.19) |
| Day 120 | n | | 50 | 55 | 62 | 50 | 55 | 62 |
| | GMT | | 5.0 | 83.8 | 92.6 | 5.0 | 56.1 | 81.4 |
| | (SD) | | (1.00) | (3.66) | (2.80) | (1.00) | (3.19) | (3.49) |

[1]SD = standard deviation.

TABLE 17

Secondary endpoint: HAV Geometric Mean Concentrations (GMCs)

|  | HAV/Pbo | TDV/Pbo | HAV/TDV | Total |
|---|---|---|---|---|
| Baseline |  |  |  |  |
| n | 75 | 71 | 81 | 227 |
| Geometric Mean (SD[1]) | 6.3 (1.00) | 6.3 (1.00) | 6.3 (1.00) | 6.3 (1.00) |
| 95% CI[2] | (NE, NE) | (NE, NE) | (NE, NE) | (NE, NE) |
| Median | 6.3 | 6.3 | 6.3 | 6.3 |
| Min-max | 6, 6 | 6, 6 | 6, 6 | 6, 6 |
| Day 30 |  |  |  |  |
| n | 69 | 66 | 79 | 214 |
| Geometric Mean (SD) | 80.5 (3.01) | 6.7 (1.27) | 93.0 (2.44) | 39.5 (4.27) |
| 95% CI | (61.8, 105.0) | (6.4, 7.2) | (76.1, 113.6) | (32.5, 48.0) |
| Median | 81.5 | 6.3 | 94.5 | 52.4 |
| Min-max | 6, 1044 | 6, 16 | 6, 1859 | 6, 1859 |

[1]SD = standard deviation.
[2]CI = confidence interval.

c) Secondary Safety Endpoints

The safety set was investigated for solicited adverse events, solicited systemic adverse events, unsolicited adverse events and serious adverse events throughout the study. Tables 18a to 21c show the study results of the safety set with respect to each secondary safety endpoint.

TABLE 18a

Frequency of Solicited Local AEs and Solicited Systemic AEs after first vaccination - Safety Set

|  | HAV/Pbo (N = 270) | TDV/Pbo (N = 271) | HAV/TDV (N = 257) |
|---|---|---|---|
| Solicited Local (within 7 days) | 141/289 (48.8) | 152/292 (52.1) | 196/285 (68.8) |
| Solicited Systemic (within 14 days) | 139/289 (48.1) | 132/292 (45.2) | 141/285 (49.5) |
| Related to IP | 98/289 (33.9) | 106/292 (36.3) | 117/285 (41.1) |
| Not related to IP | 41/289 (14.2) | 26/292 (8.9) | 24/285 (8.4) |

Note:
For solicited AEs, excluding prolonged solicited AEs, percentages are calculated based on number of subjects with non-missing data (n) evaluated in each trial group. Subjects with 1 or more AEs for a particular category of AEs are counted only once using the most related event.

TABLE 18b

Frequency of Solicited Local AEs and Solicited Systemic AEs after second vaccination - Saftey Set

|  | Pbo (N = 270) | TDV (N = 271) | TDV (N = 257) |
|---|---|---|---|
| Solicited Local (within 7 days) | 28/255 (11.0) | 100/264 (37.9) | 103/251 (41.0) |
| Solicited Systemic (within 14 days) | 73/254 (28.7) | 82/263 (31.2) | 85/251 (33.9) |
| Related to IP | 49/254 (19.3) | 60/263 (22.8) | 61/251 (24.3) |
| Not related to IP | 24/254 (9.4) | 22/263 (8.4) | 24/251 (9.6) |

Note:
For solicited AEs, excluding prolonged solicited AEs, percentages are calculated based on number of subjects with non-missing data (n) evaluated in each trial group. Subjects with 1 or more AEs for a particular category of AEs are counted only once using the most related event.

TABLE 18c

Frequency of Solicited Local AEs and Solicited Systemic AEs after any vaccination - Safety Set

|  | HAV/Pbo (n = 299) | TDV/Pbo (n = 300) | HAV/TDV (n = 298) |
|---|---|---|---|
| Solicited Local (within 7 days) | 151/289 (52.2) | 175/292 (59.9) | 216/285 (75.8) |
| Solicited Systemic (within 14 days) | 161/289 (55.7) | 167/292 (57.2) | 167/285 (58.6) |
| Related to IP | 121/289 (41.9) | 133/292 (45.5) | 141/285 (49.5) |
| Not related to IP | 40/289 (13.8) | 34/292 (11.6) | 26/285 (9.1) |

Note:
For solicited AEs, excluding prolonged solicited AEs, percentages are calculated based on number of subjects with non-missing data (n) evaluated in each trial group. Subjects with 1 or more AEs for a particular category of AEs are counted only once using the most related event.

TABLE 19a

Overview of Unsolicited AE up to 28 Days Post-vaccination (after first vaccination) - Safety Set

|  | HAV/Pbo N = 299 | TDV/Pbo N = 300 | HAV/TDV N = 298 |
|---|---|---|---|
| [Any AE], n (%) | 43 (14.4%) | 51 (17.0%) | 56 (18.8%) |
| Mild | 32 (10.7%) | 32 (10.7%) | 43 (14.4%) |
| Moderate | 11 (3.7%) | 18 (6.0%) | 12 (4.0%) |
| Severe | 0 | 1 (0.3%) | 1 (0.3%) |

Notes:
This summary includes all unsolicited AEs with a date of onset within 28 days after each trial vaccination.
N is the number of subjects who received the specific vaccination. Percentages are calculated based on N for corresponding column.
Table shows the number of subjects that reported unsolicited AE
Subjects with 1 or more AEs for a particular category of adverse event are counted only once using the most related/most severe/most serious event.

TABLE 19b

Overview of Unsolicited AE up to 28 Days Post-vaccination (after second vaccination) - Safety Set

|  | Pbo N = 270 | TDV N = 271 | TDV N = 257 |
|---|---|---|---|
| Any AE, n (%) | 39 (14.4%) | 27 (10.0%) | 30 (11.7%) |
| Mild | 17 (6.3%) | 14 (5.2%) | 15 (5.8%) |
| Moderate | 22 (8.1%) | 13 (4.8%) | 13 (5.1%) |
| Severe | 0 | 0 | 2 (0.8%) |

Notes:
This summary includes all unsolicited AEs with a date of onset within 28 days after each trial vaccination.
N is the number of subjects who received the specific vaccination. Percentages are calculated based on N for corresponding column.
Table shows the totals of AE that were experienced by the number of subjects that reported unsolicited AE
Subjects with 1 or more AEs for a particular category of adverse event are counted only once using the most related/most severe/most serious event.

TABLE 20

Most Common Unsolicited AEs Up to 28 Days Post-Vaccination (after Any Vaccination)* - Safety Set

| AE, n (%) | HAV/Pbo N = 299 | TDV/Pbo N = 300 | HAV/TDV N = 298 |
|---|---|---|---|
| Nasopharyngitis | 9 (3.0%) | 8 (2.7%) | 11 (3.7%) |

* Reported by >2.0% of subjects

TABLE 21a

Safety: Overview of Serious Adverse Events (SAEs) After any dose - Safety Set

| | Number of events, number (%) subjects with SAE | | | | | | | |
|---|---|---|---|---|---|---|---|---|
| | HAV/Pbo (n = 299) | | TDV/Pbo (n = 300) | | HAV/TDV (n = 298) | | Total (N = 597) | |
| | Events | Subjects | Events | Subjects | Events | Subjects | Events | Subjects |
| SAEs - any | 3 | 2 (0.7%) | 10 | 8 (2.7%) | 10 | 7 (2.3%) | 23 | 17 (2.8%) |
| After 1$^{st}$ dose up to 2$^{nd}$ dose | 0 | 0 | 3 | 3 (1.0%) | 3 | 2 (0.7%) | 6 | 5 (0.8%) |
| After 2$^{nd}$ dose up to trial end | 3 | 2 (0.7%) | 7 | 5 (1.8%) | 7 | 5 (1.9%) | 17 | 12 (2.0%) |
| SAEs - related | 0 | 0 | 0 | 0 | 0 | 0 | 0 | 0 |
| SAE - premature vaccine and/or trial discontinuation | 0 | 0 | 1 | 1 (0.3%) | 0 | 0 | 1 | 1 (0.2%) |
| Deaths | 0 | 0 | 0 | 0 | 0 | 0 | 0 | 0 | p = Placebo

TABLE 21b

Safety: Serious Adverse Events by System Organ Class and Preferred Term after first and after second dose - Safety Set

| Number (%) subjects with SAE | | HAV/Pbo | TDV/Pbo | HAV/TDV |
|---|---|---|---|---|
| SOC | PT | (N = 299) | (N = 300) | (N = 298) |
| After 1$^{st}$ dose up to 2$^{nd}$ dose - any SAE | | 0 | 3 (1.0) | 2 (0.7) |
| Gastrointestinal disorders | Crohn's disease* | 0 | 1 (0.3) | 0 |
| Injury, poisoning and procedural complications | Intentional overdose | 0 | 0 | 1 (0.3) |
| Neoplasms benign, malignant and unspecified | Bladder cancer stage II | 0 | 1 (0.3) | 0 |
| Nervous system disorders | Loss of consciousness** | 0 | 1 (0.3) | 0 |
| Psychiatric disorders | Intentional self-injury | 0 | 0 | 1 (0.3) |
| | | Pbo (N = 270) | TDV (N = 271) | TDV (N = 257) |
| After 2$^{nd}$ dose up to end of trial - any SAE | | 2 (0.7) | 5 (1.8) | 5 (7.9) |
| Cardiac disorders | Supraventricular tachycardia | 0 | 0 | 1 (0.4) |
| Gastrointestinal disorders | Abdominal pain | 0 | 1 (0.4) | 0 |
| | Abdominal strangulated hernia | 1 (0.4) | 0 | 0 |
| | Intestinal ischaemia | 0 | 0 | 1 (0.4) |
| | Mesenteric vein thrombosis | 0 | 0 | 1 (0.4) |
| | Oesophagitis | 0 | 1 (0.4) | 0 |

*Subject had a history of irritable bowel syndrome
**Occurred >2 months after vaccination TABLE 21c Safety: Serious Adverse Events by System Organ Class and Preferred Term After first and after second dose - Safety Set - Continued

| Number (%) subjects with SAE | | Pbo | TDV | TDV |
|---|---|---|---|---|
| SOC | PT | (N = 270) | (N = 271) | (N = 257) |
| Infections and infestations | Appendicitis | 0 | 1 (0.4) | 0 |
| | Wound infection | 1 (0.4) | 0 | 0 |

TABLE 21c-continued

Safety: Serious Adverse Events by System Organ Class and Preferred Term After first and after second dose - Safety Set - Continued

| Number (%) subjects with SAE | | Pbo | TDV | TDV |
|---|---|---|---|---|
| SOC | PT | (N = 270) | (N = 271) | (N = 257) |
| Injury, poisoning and procedural complications | Abdominal injury | 0 | 1 (0.4) | 0 |
| | Cervical vertebral fracture | 0 | 0 | 1 (0.4) |
| | Fractured coccyx | 1 (0.4) | 0 | 0 |
| | Joint dislocation | 0 | 1 (0.4) | 0 |
| | Lower limb fracture | 0 | 0 | 1 (0.4) |
| | Thermal burn | 0 | 1 (0.4) | 0 |
| Neoplasms benign, malignant and unspecified | Invasive ductal breast carcinoma | 0 | 1 (0.4) | 0 |
| | Prostate cancer | 0 | 0 | 1 (0.4) |
| Respiratory, thoracic and mediastinal disorders | Acute respiratory distress syndrome | 0 | 0 | 1 (0.4) |

The invention claimed is:

1. A method of effective vaccination against hepatitis A and dengue disease in a subject or subject population, the method comprising simultaneously on the same day administering a hepatitis A vaccine and a unit dose of a dengue vaccine composition, wherein said unit dose comprises a tetravalent dengue virus composition including four live, attenuated dengue virus strains.

2. The method according to claim 1, wherein the hepatitis A vaccine is an inactivated virus vaccine.

3. The method according to claim 1, wherein the dengue vaccine composition upon reconstitution with 0.5 mL of a pharmaceutically acceptable diluent comprises (i) a chimeric dengue serotype 2/1 strain in a concentration of at least 3.3 log 10 pfu/0.5 mL,
(ii) a dengue serotype 2 strain in a concentration of at least 2.7 log 10 pfu/0.5 mL,
(iii) a chimeric dengue serotype 2/3 strain in a concentration of at least 4.0 log 10 pfu/0.5 mL, and
(iv) a chimeric dengue serotype 2/4 strain in a concentration of at least 4.5 log 10 pfu/0.5 mL.

4. The method according to claim 1, wherein the subject population or subject is seronegative to all dengue serotypes.

5. The method according to claim 1, wherein said unit dose of the dengue vaccine composition is administered by subcutaneous injection and said hepatitis A vaccine is administered by intramuscular injection.

6. The method according to claim 5, wherein said unit dose of the dengue vaccine composition and said hepatitis A vaccine are administered to different anatomical sites.

7. The method according to claim 1, wherein two of said unit doses of the dengue vaccine composition are administered within 12 months or more, or within six months, or within three months.

8. The method according to claim 7 comprising the administration of said first and second unit doses of the dengue vaccine composition and one dose of said hepatitis A vaccine, according to the following schedule:
simultaneous administration of the first unit dose of the dengue vaccine composition and said hepatitis A vaccine on day 0, and
administration of the second unit dose of the dengue vaccine composition after said first simultaneous administration, about 3 months after.

9. The method according to claim 1, wherein the subject population or subject is of 2 to 60 years of age.

10. The method according to claim 1, wherein the subject population or subject is from a dengue endemic region.

11. The method according to claim 1, wherein the subject population or subject is from a dengue non-endemic region.

12. The method according to claim 1, wherein the hepatitis A vaccine comprises a hepatitis A virus derived from a hepatitis A virus strain HM-175.

13. The method according to claim 1, wherein the hepatitis A vaccine comprises an inactivated hepatitis A virus.

14. The method according to claim 1, wherein the hepatitis A vaccine comprises an inactivated hepatitis A virus and wherein the inactivated hepatitis A virus is adsorbed on aluminum.

15. The method according to claim 14, wherein the aluminum is aluminum hydroxide or aluminum hydroxyphosphate sulfate.

16. The method according to claim 1, wherein the hepatitis A vaccine comprises an inactivated hepatitis A virus and wherein the hepatitis A vaccine comprises a phosphate-buffered saline solution and excipients dissolved therein in the form of an amino acid and in and in the form of polysorbate.

17. The method according to claim 1, wherein the hepatitis A vaccine includes a hepatitis A virus expressing a viral antigen in a concentration ranging from 500 ELISA Units (EL.U.) to 2000 ELISA Units (EL.U.).

18. The method according to claim 1, wherein the method does not include a step of determination whether there was a previous dengue infection and/or a previous hepatitis A infection in the subject population or in the subject before the administration of the hepatitis A vaccine and before the administration of the unit dose of the dengue vaccine composition or wherein the hepatitis A serostatus and/or the dengue serostatus of the subject population or of the subject is unknown before the administration of the hepatitis A vaccine and before the administration of the unit dose of the dengue vaccine composition.

19. The method according to claim 18, wherein the method does not include a step of determination whether there was a previous dengue infection and/or a previous hepatitis A infection in the subject population or in the subject at any time before, during and after the steps of administration of the hepatitis A vaccine and of the unit dose of the dengue vaccine composition or wherein the hepatitis A serostatus and/or the dengue serostatus of the subject population or of the subject is unknown at any time before, during or after the steps of administration of the hepatitis A vaccine and of the unit dose of the dengue vaccine composition.

20. The method according to claim 1, wherein the method comprises a primary vaccination consisting of the steps of:
(A) selecting a subject for administration of the unit doses of the tetravalent dengue virus composition and the hepatitis A vaccine in need for protection against dengue infection and hepatitis A infection without determination whether there was a previous dengue infection and/or a previous hepatitis A infection, and
(B) administering a first unit dose of the tetravalent dengue virus composition and a hepatitis A vaccine to the subject, and optionally
(C) administering at least one further unit dose of the tetravalent dengue virus composition to the subject within 3 to 12 months of administration of the first unit dose, and optionally
(D) administering at least one further dose of the hepatitis A vaccine to the subject within 6 to 18 months of administration of the first unit dose.

21. The method according to claim 1, wherein the method comprises a primary vaccination consisting of the steps of:
(A) selecting a subject for administration of the unit doses of the tetravalent dengue virus composition and the hepatitis A vaccine in need for protection against dengue infection and hepatitis A infection, and
(B) administering a first unit dose of the tetravalent dengue virus composition and a hepatitis A vaccine to the subject, and
(C) administering two further unit doses of the tetravalent dengue virus composition to the subject at about 6 and about 12 months of administration of the first unit dose and administering a hepatitis A vaccine to the subject at either about 6 or about 12 months of administration of the first unit dose.

22. The method according to claim 21, wherein step (A) is carried out without determination whether there was a previous hepatitis A infection.

23. The method according to claim 3, wherein upon reconstitution of the dengue vaccine composition with a pharmaceutically acceptable diluent (i), (ii), (iii), and (iv) provide a total concentration of pfu/0.5 mL and based on said total concentration of pfu/0.5 ml the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 6%, at least 8%, or at least 10%, or at least 12%, or at least 14%, or at least 16%, or at least 18%.

24. The method according to claim 1, wherein the method provides compatibility between the dengue vaccine composition and the hepatitis A vaccine.

25. The method according to claim 1, wherein the method provides synergy between the dengue vaccine composition and the hepatitis A vaccine.

26. The method according to claim 1, wherein the method provides non-inferiority in a non-inferiority clinical study including at least 60 or at least 120 healthy subjects divided into one subject population and into one control subject population, wherein the subject population receives simultaneously on the same day the hepatitis A vaccine and the unit dose of the dengue vaccine composition and the control subject population receives simultaneously on the same day a hepatitis A vaccine and a placebo administration.

27. The method according to claim 1, wherein the hepatitis A vaccine provides a hepatitis A seroprotection rate of at least 95% or of at least 98% on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline and being seronegative with respect to all dengue virus serotypes at baseline.

28. The method according to claim 1, wherein the method provides a hepatitis A seroprotection rate difference with respect to a hepatitis A mono-administration, the difference being determined in a non-inferiority clinical study including at least 60 or at least 120 healthy subjects being seronegative with respect to hepatitis A at baseline and seronegative with respect to all dengue virus serotypes at baseline, the healthy subjects being divided into
a) a subject population of at least 30 or at least 50 healthy subjects receiving simultaneously on the same day an administration (on day 0/1) of the hepatitis A vaccine and the unit dose of the dengue vaccine composition, and
b) a control subject population of at least 30 or at least 50 healthy subjects receiving simultaneously on the same day an administration (on day 0/1) of a hepatitis A vaccine and a placebo,
wherein the difference is determined between the hepatitis A seroprotection rate of the control subject population on day 30 after the administration (on day 0/1) and the hepatitis A seroprotection rate of the subject population on day 30 after the administration (on day 0/1), and
wherein the difference has an upper bound within a two-sided 95% confidence interval which is lower than 10%.

29. The method according to claim 1, wherein the hepatitis A vaccine provides a hepatitis A seroprotection rate of at least 95% or of at least 98% or of at least 99% on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline, wherein the healthy subjects include healthy subject(s) which are seropositive with respect to at least one dengue virus serotype at baseline and healthy subject(s) which are seronegative with respect to all dengue virus serotypes at baseline.

30. The method according to claim 1, wherein the method provides a hepatitis A seroprotection rate difference with respect to a hepatitis A mono-administration, the difference being determined in a non-inferiority clinical study including at least 60 or at least 120 healthy subjects being seronegative with respect to hepatitis A at baseline, wherein the healthy subjects include healthy subject(s) which are seropositive with respect to at least one dengue virus serotype at baseline and healthy subject(s) which are seronegative with respect to all dengue virus serotypes at baseline, the healthy subjects being divided into
a subject population of at least 30 or at least 50 healthy subjects receiving simultaneously on the same day an administration (on day 0/1) of the hepatitis A vaccine and the unit dose of the dengue vaccine composition, wherein the subject population includes healthy subject(s) which are seropositive with respect to at least one dengue virus serotype at baseline and healthy subject(s) which are seronegative with respect to all dengue virus serotypes at baseline, and
a control subject population of at least 30 or at least 50 healthy subjects receiving simultaneously on the same day an administration (on day 0/1) of a hepatitis A vaccine and a placebo, wherein the control subject population includes healthy subject(s) which are seropositive with respect to at least one dengue virus serotype at baseline and healthy subject(s) which are seronegative with respect to all dengue virus serotypes at baseline,
wherein the difference is determined between the hepatitis A seroprotection rate of the control subject population on day 30 after the administration (on day 0/1) and the hepatitis A seroprotection rate of the subject population on day 30 after the administration (on day 0/1), and
wherein the difference has an upper bound within a two-sided 95% confidence interval which is lower than 10%.

31. The method according to claim 1, wherein the subject or subject population is exposed to at least one of a hepatitis A virus outbreak and a dengue virus outbreak.

32. The method according to claim 1, wherein the method provides an anti-hepatitis A virus antibody Geometric Mean Concentration (GMC) of at least 70 mIU/ml or at least 80 mIU/ml or at least 90 mIU/ml on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline and being seronegative with respect to all dengue virus serotypes at baseline.

33. The method according to claim 1, wherein the simultaneous on the same day administration of the hepatitis A vaccine and the unit dose of the dengue vaccine composition to the subject or the subject population is safe.

34. The method according to claim 33, wherein there are no serious adverse events related to the simultaneous on the same day administration of the hepatitis A vaccine and the unit dose of the dengue vaccine composition.

35. The method according to claim 1, wherein the method provides the Geometric Mean Titer (GMT) of neutralizing antibodies measured by MNT50 of
at least 110 or at least 140 or at least 150 for dengue serotype 1,
at least 3000 or at least 3500 or at least 3900 for dengue serotype 2,
at least 100 or at least 120 or at least 140 for dengue serotype 3, and/or
at least 80 or at least 110 or at least 140 for dengue serotype 4, on day 30 after an administration (on day 0/1) to a subject population of at least 30 or at least 50 healthy subjects receiving simultaneously on the same day the hepatitis A vaccine and the unit dose of the dengue vaccine composition and being seronegative with respect to hepatitis A at baseline and being seronegative with respect to all dengue virus serotypes at baseline.

36. The method according to claim 1, wherein the subject or subject population is 18 to 60 years of age.

37. The method according to claim 11, wherein the subject population or subject is from a dengue non-endemic region and a hepatitis A non-endemic region.

38. The method according to claim 13, wherein the inactivated hepatitis A virus is derived from a hepatitis A virus strain HM-175.

39. The method according to claim 5, wherein said unit dose of the dengue vaccine composition and said hepatitis A vaccine are both administered to the arm.

40. The method according to claim 39, wherein said unit dose of the dengue vaccine composition and said hepatitis A vaccine are both administered to the deltoid region of the arm.

* * * * *

SEQUENCE LISTING

<160> NUMBER OF SEQ ID NOS: 16

<210> SEQ ID NO 1
<211> LENGTH: 10723
<212> TYPE: DNA
<213> ORGANISM: Artificial Sequence
<220> FEATURE:
<223> OTHER INFORMATION: Chimeric Dengue Serotype 2/1 (MVS)

<400> SEQUENCE: 1
agttgttagt ctacgtggac cgacaaagac agattctttg agggagctaa gctcaatgta 60
gttctaacag ttttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagatctg caggcatgat cattatgctg 420
attccaacag tgatggcgtt ccatttaacc acgcgtgggg gagagccgca tatgatagtt 480
agcaagcagg aaagaggaaa gtcacttttg ttcaagacct ctgcaggtgt caacatgtgc 540
accctcattg cgatggattt gggagagttg tgtgaggaca cgatgaccta caaatgcccc 600
cggatcactg aggcggaacc agatgacgtt gactgttggt gcaatgccac ggacacatgg 660
gtgacctatg gaacgtgctc tcaaactggc gaacaccgac gagacaaacg ttccgtcgca 720
ttggccccac acgtggggct tggcctagaa acaagagccg aaacgtggat gtcctctgaa 780
ggtgcttgga aacagataca aaaagtagag acttgggctc tgagacatcc aggattcacg 840
gtgatagccc tttttctagc acatgccata ggaacatcca tcacccagaa agggatcatt 900
ttcattttgc tgatgctggt aacaccatct atggccatgc gatgcgtggg aataggcaac 960
agagacttcg tggaaggact gtcaggagca acatgggtgg atgtggtact ggagcatgga 1020
agttgcgtca ccaccatggc aaaaaacaaa ccaacactgg acattgaact cttgaagacg 1080
gaggtcacaa accctgcagt tctgcgtaaa ttgtgcattg aagctaaaat atcaaacacc 1140
accaccgatt cgagatgtcc aacacaagga gaagccacac tggtggaaga acaagacgcg 1200
aactttgtgt gccgacgaac gttcgtggac agaggctggg gcaatggctg tgggctattc 1260

```
ggaaaaggta gtctaataac gtgtgccaag tttaagtgtg tgacaaaact agaaggaaag    1320
atagttcaat atgaaaacct aaaatattca gtgatagtca ccgtccacac tggagatcag    1380
caccaggtgg gaaatgagac tacagaacat ggaacaactg caaccataac acctcaagct    1440
cctacgtcgg aaatacagct gaccgactac ggaacccta cattagattg ttcacctagg     1500
acagggctag attttaacga gatggtgttg ctgacaatga agaaagatc atggcttgtc     1560 cacaaacaat ggttcctaga cttaccactg ccttggacct ctggggcttc aacatcccaa    1620
gagacttgga acagacaaga tttactggtc acatttaaga cagctcatgc aaagaagcag    1680
gaagtagtcg tactaggatc acaagaagga gcaatgcaca ctgcgctgac tggagcgaca    1740
gaaatccaaa cgtcaggaac gacaacaatt ttcgcaggac acctaaaatg cagactaaaa    1800
atggacaaac taactttaaa agggatgtca tatgtgatgt gcacaggctc attcaagtta    1860
gagaaagaag tggctgagac ccagcatgga actgttctgg tgcaggttaa atatgaagga    1920
acagacgcac catgcaagat tccctttcg acccaagatg agaaggagc aacccagaat     1980 gggagattaa taacagccaa ccccatagtc actgacaaag aaaaaccagt caatattgag    2040
gcagaaccac cctttggtga gagctacatc gtggtaggag caggtgaaaa agcttttgaaa   2100 ctaagctggt tcaagaaagg aagcagcata gggaaaatgt tgaagcaac tgcccgagga    2160 gcacgaagga tggccattct gggagacacc gcatgggact tcggttctat aggaggagtg    2220
ttcacgtcta tgggaaaact ggtacaccag gttttttggaa ctgcatatgg agttttgttt    2280
agcggagttt cttggaccat gaaaatagga ataggattc tgctgacatg ctaggattg      2340 aattcaagga acacgtccct ttcgatgatg tgcatcgcag ccggcattgt gacactgtat    2400
ttgggagtca tggtgcaggc cgatagtggt tgcgttgtga gctggaaaaa caaagaactg    2460
aaatgtggca gtgggatttt catcacagac aacgtgcaca catggacaga acaatacaag    2520
ttccaaccag aatcccttc aaaactagct tcagctatcc agaaagccca tgaagaggac     2580
atttgtggaa tccgctcagt aacaagactg gagaatctga tgtggaaaca aataacacca    2640
gaattgaatc acattctatc agaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagacctt    2820 ctcattgatg gccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagataag     3060 aaagcctctt tcattgaagt taaaaactgc cactggccaa aatcacacac cctctgagc     3120 aatggagtgc tagaaagtga gatgataatt ccaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct ctttgagaac aaccactgcc tctggaaaaac tcataacaga atggtgctgc    3360
cgatcttgca cattaccacc gctaagtaca agaggtgagg atgggtgctg gtacgggatg    3420
gaaatcagac cattgaagga gaaagaagag aatttggtca actccttggt cacagctgga    3480
catgggcagg tcgacaactt ttcactagga gtcttgggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
```

```
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccctaccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctattttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagatcaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag atcgaagaa tgacattttc cgaaagagaa gactgaccat catggaccct   5100
cacccaggag cggaaagac gaagagatac cttccggcca tagtcagaga gctataaaa   5160 cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggatttt   5460 atgacagcca ctcccccggg aagcagagac ccatttcctc agagcaatgc accaatcata   5520
gatgaagaaa gagaaatccc tgaacgctcg tggaattccg acatgaatg ggtcacggat   5580 tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa aagagggag aataggaaga aatccaaaaa atgagaatga ccagtacata   5940
tacatggggg aacctctgga aaatgatgaa gactgtgcac actggaaaga agctaaaatg   6000
```

-continued

```
ctcctagata acatcaacac gccagaagga atcattccta gcatgttcga accagagcgt    6060
gaaaaggtgg atgccattga tggcgaatac cgcttgagag gagaagcaag gaaaaccttt    6120
gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga atctggaca aaagaagggg aaaggaagaa attgaaaccc     6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg gagggatct ttttattctt gatgagcgca     6600
aggggcatag ggagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga tgggtttc     6840 ctagaaaaaa cgaagaaaga tctcggattg gaagcattg caacccagca acccgagagc     6900
aacatcctgg acatagatct acgtcctgca tcagcatgga cgctgtatgc cgtggccaca    6960
acatttgtta caccaatgtt gagacatagc attgaaaatt cctcagtgaa tgtgtccta     7020 acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctctttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc gaagtttgaa    7320
aagcagttgg acaagtaat gctcctagtc ctctgcgtga ctcaagtatt gatgatgagg     7380
actacatggg ctctgtgtga ggctttaacc ttagctaccg ggcccatctc cacattgtgg    7440
gaaggaaatc cagggaggtt ttggaacact accattgcgg tgtcaatggc taacattttt    7500
agagggagtt acttggccgg agctggactt ctcttttcta ttatgaagaa cacaaccaac    7560
acaagaaggg gaactggcaa cataggagag acgcttggag agaaatggaa agccgattg    7620 aacgcattgg gaaaaagtga attccagatc tacaagaaaa gtggaatcca ggaagtggat    7680
agaaccttag caaagaagg cattaaaaga ggagaaacgg accatcacgc tgtgtcgcga    7740
ggctcagcaa aactgagatg gttcgttgag agaaacatgg tcacaccaga agggaaagta    7800
gtggacctcg gttgtggcag aggaggctgg tcatactatt gtggaggact aaagaatgta    7860
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
```

```
gggaaaagaa tagaaaaaat aaagcaagag catgaaacat catgggcacta tgaccaagac    8460 cacccataca aaacgtgggc ataccatggt agctatgaaa caaaacagac tggatcagca    8520
tcatccatgg tcaacggagt ggtcaggctg ctgacaaaac cttgggacgt cgtccccatg    8580
gtgacacaga tggcaatgac agacacgact ccatttggac aacagcgcgt ttttaaagag    8640
aaagtggaca cgagaaccca agaaccgaaa gaaggcacga agaaactaat gaaaataaca    8700
gcagagtggc tttggaaaga attagggaag aaaaagacac ccaggatgtg caccagagaa    8760
gaattcacaa gaaaggtgag aagcaatgca gccttggggg ccatattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctagggga attcggcaag gcaaaaggca gcagagccat atggtacatg    9000
tggcttggag cacgcttctt agagtttgaa gccctaggat tcttaaatga agatcactgg    9060
ttctccagag agaactccct gagtggagtg gaaggagaag ggctgcacaa gctaggttac    9120
attctaagag acgtgagcaa gaaagaggga ggagcaatgt atgccgatga caccgcagga    9180
tgggatacaa gaatcacact agaagaccta aaaaatgaag aaatggtaac aaaccacatg    9240
gaaggagaac acaagaaact agccgaggcc attttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata ctttccacca tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtgagatga ttgtgttgtg aaacctttag atgacaggtt cgcaagcgct    9600
ttaacagctc taatgacat gggaaagatt aggaaagaca tacaacaatg gaaccttca     9660 agaggatgga atgattggac acaagtgccc ttctgttcac accatttcca tgagttaatc    9720
atgaaagacg gtcgcgtact cgttgttcca tgtagaaacc aagatgaact gattggcaga    9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacggaa gacatgctga cagtctggaa cagggtgtgg   10020
attcaagaaa acccatggat ggaagacaaa actccagtgg aatcatggga ggaaatccca   10080
tacttgggga aaagagaaga ccaatggtgc ggctcattga ttgggttaac aagcagggcc   10140
acctgggcaa agaacatcca agcagcaata aatcaagtta gatcccttat aggcaatgaa   10200
gaatacacag attacatgcc atccatgaaa agattcagaa gagaagagga agaagcagga   10260
gttctgtggt agaaagcaaa actaacatga acaaggcta gaagtcaggt cggattaagc    10320
catagtacgg aaaaaactat gctacctgtg agccccgtcc aaggacgtta aaagaagtca   10380
ggccatcata aatgccatag cttgagtaaa ctatgcagcc tgtagctcca cctgagaagg   10440
tgtaaaaaat ccggggaggcc acaaaccatg gaagctgtac gcatggcgta gtggactagc   10500
ggttagagga gacccctccc ttacaaatcg cagcaacaat ggggggccaa ggcgagatga   10560
agctgtagtc tcgctggaag gactagaggt tagaggagac ccccccgaaa caaaaaacag   10620
catattgacg ctgggaaaga ccagagatcc tgctgtctcc tcagcatcat tccaggcaca   10680
gaacgccaga aaatggaatg gtgctgttga atcaacaggt tct                     10723
```

<210> SEQ ID NO 2
<211> LENGTH: 3391
<212> TYPE: PRT
<213> ORGANISM: Artificial Sequence
<220> FEATURE:
<223> OTHER INFORMATION: Chimeric Dengue Serotype 2/1 (MVS)

<400> SEQUENCE: 2

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Gly Gly Glu Pro His Met Ile Val
        115                 120                 125

Ser Lys Gln Glu Arg Gly Lys Ser Leu Leu Phe Lys Thr Ser Ala Gly
    130                 135                 140

Val Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Ala Glu Pro Asp
                165                 170                 175

Asp Val Asp Cys Trp Cys Asn Ala Thr Asp Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Ala Glu Thr Trp
    210                 215                 220

Met Ser Ser Glu Gly Ala Trp Lys Gln Ile Gln Lys Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asn Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Asp Ser
            340                 345                 350

Arg Cys Pro Thr Gln Gly Glu Ala Thr Leu Val Glu Glu Gln Asp Ala
        355                 360                 365
```

```
Asn Phe Val Cys Arg Arg Thr Phe Val Asp Arg Gly Trp Gly Asn Gly
    370                 375                 380

Cys Gly Leu Phe Gly Lys Gly Ser Leu Ile Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
                420                 425                 430

Asn Glu Thr Thr Glu His Gly Thr Ala Thr Ile Thr Pro Gln Ala
            435                 440                 445

Pro Thr Ser Glu Ile Gln Leu Thr Asp Tyr Gly Thr Leu Thr Leu Asp
450                 455                 460

Cys Ser Pro Arg Thr Gly Leu Asp Phe Asn Glu Met Val Leu Leu Thr
465                 470                 475                 480

Met Lys Glu Arg Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
                500                 505                 510

Arg Gln Asp Leu Leu Val Thr Phe Lys Thr Ala His Ala Lys Lys Gln
                515                 520                 525

Glu Val Val Val Leu Gly Ser Gln Glu Gly Ala Met His Thr Ala Leu
                530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575

Met Ser Tyr Val Met Cys Thr Gly Ser Phe Lys Leu Glu Lys Glu Val
                580                 585                 590

Ala Glu Thr Gln His Gly Thr Val Leu Val Gln Val Lys Tyr Glu Gly
                595                 600                 605

Thr Asp Ala Pro Cys Lys Ile Pro Phe Ser Thr Gln Asp Glu Lys Gly
        610                 615                 620

Ala Thr Gln Asn Gly Arg Leu Ile Thr Ala Asn Pro Ile Val Thr Asp
625                 630                 635                 640

Lys Glu Lys Pro Val Asn Ile Glu Ala Glu Pro Pro Phe Gly Glu Ser
                645                 650                 655

Tyr Ile Val Val Gly Ala Gly Glu Lys Ala Leu Lys Leu Ser Trp Phe
                660                 665                 670

Lys Lys Gly Ser Ser Ile Gly Lys Met Phe Glu Ala Thr Ala Arg Gly
            675                 680                 685

Ala Arg Arg Met Ala Ile Leu Gly Asp Thr Ala Trp Asp Phe Gly Ser
690                 695                 700

Ile Gly Gly Val Phe Thr Ser Met Gly Lys Leu Val His Gln Val Phe
705                 710                 715                 720

Gly Thr Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Asn
                740                 745                 750

Thr Ser Leu Ser Met Met Cys Ile Ala Ala Gly Ile Val Thr Leu Tyr
            755                 760                 765

Leu Gly Val Met Val Gln Ala Asp Ser Gly Cys Val Val Ser Trp Lys
770                 775                 780

Asn Lys Glu Leu Lys Cys Gly Ser Gly Ile Phe Ile Thr Asp Asn Val
```

```
            785                 790                 795                 800
His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
                820                 825                 830

Arg Ser Val Thr Arg Leu Glu Asn Leu Met Trp Lys Gln Ile Thr Pro
                835                 840                 845

Glu Leu Asn His Ile Leu Ser Glu Asn Glu Val Lys Leu Thr Ile Met
        850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
                900                 905                 910

Pro Glu Thr Ala Glu Cys Pro Asn Thr Asn Arg Ala Trp Asn Ser Leu
                915                 920                 925

Glu Val Glu Asp Tyr Gly Phe Gly Val Phe Thr Thr Asn Ile Trp Leu
        930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
                980                 985                 990

Ile Glu Val Lys Asn Cys His Trp Pro Lys Ser His Thr Leu Trp Ser
        995                 1000                1005

Asn Gly Val Leu Glu Ser Glu Met Ile Ile Pro Lys Asn Leu Ala
            1010                1015                1020

Gly Pro Val Ser Gln His Asn Tyr Arg Pro Gly Tyr His Thr Gln
            1025                1030                1035

Ile Thr Gly Pro Trp His Leu Gly Lys Leu Glu Met Asp Phe Asp
            1040                1045                1050

Phe Cys Asp Gly Thr Thr Val Val Val Thr Glu Asp Cys Gly Asn
            1055                1060                1065

Arg Gly Pro Ser Leu Arg Thr Thr Thr Ala Ser Gly Lys Leu Ile
            1070                1075                1080

Thr Glu Trp Cys Cys Arg Ser Cys Thr Leu Pro Pro Leu Arg Tyr
            1085                1090                1095

Arg Gly Glu Asp Gly Cys Trp Tyr Gly Met Glu Ile Arg Pro Leu
            1100                1105                1110

Lys Glu Lys Glu Glu Asn Leu Val Asn Ser Leu Val Thr Ala Gly
            1115                1120                1125

His Gly Gln Val Asp Asn Phe Ser Leu Gly Val Leu Gly Met Ala
            1130                1135                1140

Leu Phe Leu Glu Glu Met Leu Arg Thr Arg Val Gly Thr Lys His
            1145                1150                1155

Ala Ile Leu Leu Val Ala Val Ser Phe Val Thr Leu Ile Thr Gly
            1160                1165                1170

Asn Met Ser Phe Arg Asp Leu Gly Arg Val Met Val Met Val Gly
            1175                1180                1185

Ala Thr Met Thr Asp Asp Ile Gly Met Gly Val Thr Tyr Leu Ala
            1190                1195                1200
```

| | | | | | | | | | | |
|---|---|---|---|---|---|---|---|---|---|---|
| Leu | Leu | Ala | Ala | Phe | Lys | Val | Arg | Pro | Thr | Phe | Ala | Ala | Gly | Leu |
| | 1205 | | | | 1210 | | | | 1215 | |
| Leu | Leu | Arg | Lys | Leu | Thr | Ser | Lys | Glu | Leu | Met | Met | Thr | Thr | Ile |
| | 1220 | | | | 1225 | | | | 1230 | |
| Gly | Ile | Val | Leu | Leu | Ser | Gln | Ser | Thr | Leu | Pro | Glu | Thr | Ile | Leu |
| | 1235 | | | | 1240 | | | | 1245 | |
| Glu | Leu | Thr | Asp | Ala | Leu | Ala | Leu | Gly | Met | Met | Val | Leu | Lys | Met |
| | 1250 | | | | 1255 | | | | 1260 | |
| Val | Arg | Asn | Met | Glu | Lys | Tyr | Gln | Leu | Ala | Val | Thr | Ile | Met | Ala |
| | 1265 | | | | 1270 | | | | 1275 | |
| Ile | Leu | Cys | Val | Pro | Asn | Ala | Val | Ile | Leu | Gln | Asn | Ala | Trp | Lys |
| | 1280 | | | | 1285 | | | | 1290 | |
| Val | Ser | Cys | Thr | Ile | Leu | Ala | Val | Val | Ser | Val | Ser | Pro | Leu | Phe |
| | 1295 | | | | 1300 | | | | 1305 | |
| Leu | Thr | Ser | Ser | Gln | Gln | Lys | Thr | Asp | Trp | Ile | Pro | Leu | Ala | Leu |
| | 1310 | | | | 1315 | | | | 1320 | |
| Thr | Ile | Lys | Gly | Leu | Asn | Pro | Thr | Ala | Ile | Phe | Leu | Thr | Thr | Leu |
| | 1325 | | | | 1330 | | | | 1335 | |
| Ser | Arg | Thr | Ser | Lys | Lys | Arg | Ser | Trp | Pro | Leu | Asn | Glu | Ala | Ile |
| | 1340 | | | | 1345 | | | | 1350 | |
| Met | Ala | Val | Gly | Met | Val | Ser | Ile | Leu | Ala | Ser | Ser | Leu | Leu | Lys |
| | 1355 | | | | 1360 | | | | 1365 | |
| Asn | Asp | Ile | Pro | Met | Thr | Gly | Pro | Leu | Val | Ala | Gly | Gly | Leu | Leu |
| | 1370 | | | | 1375 | | | | 1380 | |
| Thr | Val | Cys | Tyr | Val | Leu | Thr | Gly | Arg | Ser | Ala | Asp | Leu | Glu | Leu |
| | 1385 | | | | 1390 | | | | 1395 | |
| Glu | Arg | Ala | Ala | Asp | Val | Lys | Trp | Glu | Asp | Gln | Ala | Glu | Ile | Ser |
| | 1400 | | | | 1405 | | | | 1410 | |
| Gly | Ser | Ser | Pro | Ile | Leu | Ser | Ile | Thr | Ile | Ser | Glu | Asp | Gly | Ser |
| | 1415 | | | | 1420 | | | | 1425 | |
| Met | Ser | Ile | Lys | Asn | Glu | Glu | Glu | Asp | Gln | Thr | Leu | Thr | Ile | Leu |
| | 1430 | | | | 1435 | | | | 1440 | |
| Ile | Arg | Thr | Gly | Leu | Leu | Val | Ile | Ser | Gly | Leu | Phe | Pro | Val | Ser |
| | 1445 | | | | 1450 | | | | 1455 | |
| Ile | Pro | Ile | Thr | Ala | Ala | Ala | Trp | Tyr | Leu | Trp | Glu | Val | Lys | Lys |
| | 1460 | | | | 1465 | | | | 1470 | |
| Gln | Arg | Ala | Gly | Val | Leu | Trp | Asp | Val | Pro | Ser | Pro | Pro | Pro | Met |
| | 1475 | | | | 1480 | | | | 1485 | |
| Gly | Lys | Ala | Glu | Leu | Glu | Asp | Gly | Ala | Tyr | Arg | Ile | Lys | Gln | Lys |
| | 1490 | | | | 1495 | | | | 1500 | |
| Gly | Ile | Leu | Gly | Tyr | Ser | Gln | Ile | Gly | Ala | Gly | Val | Tyr | Lys | Glu |
| | 1505 | | | | 1510 | | | | 1515 | |
| Gly | Thr | Phe | His | Thr | Met | Trp | His | Val | Thr | Arg | Gly | Ala | Val | Leu |
| | 1520 | | | | 1525 | | | | 1530 | |
| Met | His | Lys | Gly | Lys | Arg | Ile | Glu | Pro | Ser | Trp | Ala | Asp | Val | Lys |
| | 1535 | | | | 1540 | | | | 1545 | |
| Lys | Asp | Leu | Ile | Ser | Tyr | Gly | Gly | Gly | Trp | Lys | Leu | Glu | Gly | Glu |
| | 1550 | | | | 1555 | | | | 1560 | |
| Trp | Lys | Glu | Gly | Glu | Glu | Val | Gln | Val | Leu | Ala | Leu | Glu | Pro | Gly |
| | 1565 | | | | 1570 | | | | 1575 | |
| Lys | Asn | Pro | Arg | Ala | Val | Gln | Thr | Lys | Pro | Gly | Leu | Phe | Lys | Thr |
| | 1580 | | | | 1585 | | | | 1590 | |

-continued

Asn Ala Gly Thr Ile Gly Ala Val Ser Leu Asp Phe Ser Pro Gly
1595                1600                1605

Thr Ser Gly Ser Pro Ile Ile Asp Lys Lys Gly Lys Val Val Gly
1610                1615                1620

Leu Tyr Gly Asn Gly Val Val Thr Arg Ser Gly Ala Tyr Val Ser
1625                1630                1635

Ala Ile Ala Gln Thr Glu Lys Ser Ile Glu Asp Asn Pro Glu Ile
1640                1645                1650

Glu Asp Asp Ile Phe Arg Lys Arg Arg Leu Thr Ile Met Asp Leu
1655                1660                1665

His Pro Gly Ala Gly Lys Thr Lys Arg Tyr Leu Pro Ala Ile Val
1670                1675                1680

Arg Glu Ala Ile Lys Arg Gly Leu Arg Thr Leu Ile Leu Ala Pro
1685                1690                1695

Thr Arg Val Val Ala Ala Glu Met Glu Glu Ala Leu Arg Gly Leu
1700                1705                1710

Pro Ile Arg Tyr Gln Thr Pro Ala Ile Arg Ala Val His Thr Gly
1715                1720                1725

Arg Glu Ile Val Asp Leu Met Cys His Ala Thr Phe Thr Met Arg
1730                1735                1740

Leu Leu Ser Pro Val Arg Val Pro Asn Tyr Asn Leu Ile Ile Met
1745                1750                1755

Asp Glu Ala His Phe Thr Asp Pro Ala Ser Ile Ala Ala Arg Gly
1760                1765                1770

Tyr Ile Ser Thr Arg Val Glu Met Gly Glu Ala Ala Gly Ile Phe
1775                1780                1785

Met Thr Ala Thr Pro Pro Gly Ser Arg Asp Pro Phe Pro Gln Ser
1790                1795                1800

Asn Ala Pro Ile Ile Asp Glu Glu Arg Glu Ile Pro Glu Arg Ser
1805                1810                1815

Trp Asn Ser Gly His Glu Trp Val Thr Asp Phe Lys Gly Lys Thr
1820                1825                1830

Val Trp Phe Val Pro Ser Ile Lys Ala Gly Asn Asp Ile Ala Ala
1835                1840                1845

Cys Leu Arg Lys Asn Gly Lys Lys Val Ile Gln Leu Ser Arg Lys
1850                1855                1860

Thr Phe Asp Ser Glu Tyr Val Lys Thr Arg Thr Asn Asp Trp Asp
1865                1870                1875

Phe Val Val Thr Thr Asp Ile Ser Glu Met Gly Ala Asn Phe Lys
1880                1885                1890

Ala Glu Arg Val Ile Asp Pro Arg Arg Cys Met Lys Pro Val Ile
1895                1900                1905

Leu Thr Asp Gly Glu Glu Arg Val Ile Leu Ala Gly Pro Met Pro
1910                1915                1920

Val Thr His Ser Ser Ala Ala Gln Arg Arg Gly Arg Ile Gly Arg
1925                1930                1935

Asn Pro Lys Asn Glu Asn Asp Gln Tyr Ile Tyr Met Gly Glu Pro
1940                1945                1950

Leu Glu Asn Asp Glu Asp Cys Ala His Trp Lys Glu Ala Lys Met
1955                1960                1965

Leu Leu Asp Asn Ile Asn Thr Pro Glu Gly Ile Ile Pro Ser Met
1970                1975                1980

Phe Glu Pro Glu Arg Glu Lys Val Asp Ala Ile Asp Gly Glu Tyr

```
            1985                1990                1995
Arg Leu Arg Gly Glu Ala Arg Lys Thr Phe Val Asp Leu Met Arg
    2000                2005                2010

Arg Gly Asp Leu Pro Val Trp Leu Ala Tyr Arg Val Ala Ala Glu
    2015                2020                2025

Gly Ile Asn Tyr Ala Asp Arg Arg Trp Cys Phe Asp Gly Val Lys
    2030                2035                2040

Asn Asn Gln Ile Leu Glu Glu Asn Val Glu Val Glu Ile Trp Thr
    2045                2050                2055

Lys Glu Gly Glu Arg Lys Lys Leu Lys Pro Arg Trp Leu Asp Ala
    2060                2065                2070

Arg Ile Tyr Ser Asp Pro Leu Ala Leu Lys Glu Phe Lys Glu Phe
    2075                2080                2085

Ala Ala Gly Arg Lys Ser Leu Thr Leu Asn Leu Ile Thr Glu Met
    2090                2095                2100

Gly Arg Leu Pro Thr Phe Met Thr Gln Lys Ala Arg Asp Ala Leu
    2105                2110                2115

Asp Asn Leu Ala Val Leu His Thr Ala Glu Ala Gly Gly Arg Ala
    2120                2125                2130

Tyr Asn His Ala Leu Ser Glu Leu Pro Glu Thr Leu Glu Thr Leu
    2135                2140                2145

Leu Leu Leu Thr Leu Leu Ala Thr Val Thr Gly Gly Ile Phe Leu
    2150                2155                2160

Phe Leu Met Ser Ala Arg Gly Ile Gly Lys Met Thr Leu Gly Met
    2165                2170                2175

Cys Cys Ile Ile Thr Ala Ser Ile Leu Leu Trp Tyr Ala Gln Ile
    2180                2185                2190

Gln Pro His Trp Ile Ala Ala Ser Ile Ile Leu Glu Phe Phe Leu
    2195                2200                2205

Ile Val Leu Leu Ile Pro Glu Pro Glu Lys Gln Arg Thr Pro Gln
    2210                2215                2220

Asp Asn Gln Leu Thr Tyr Val Val Ile Ala Ile Leu Thr Val Val
    2225                2230                2235

Ala Ala Thr Met Ala Asn Glu Met Gly Phe Leu Glu Lys Thr Lys
    2240                2245                2250

Lys Asp Leu Gly Leu Gly Ser Ile Ala Thr Gln Gln Pro Glu Ser
    2255                2260                2265

Asn Ile Leu Asp Ile Asp Leu Arg Pro Ala Ser Ala Trp Thr Leu
    2270                2275                2280

Tyr Ala Val Ala Thr Thr Phe Val Thr Pro Met Leu Arg His Ser
    2285                2290                2295

Ile Glu Asn Ser Ser Val Asn Val Ser Leu Thr Ala Ile Ala Asn
    2300                2305                2310

Gln Ala Thr Val Leu Met Gly Leu Gly Lys Gly Trp Pro Leu Ser
    2315                2320                2325

Lys Met Asp Ile Gly Val Pro Leu Leu Ala Ile Gly Cys Tyr Ser
    2330                2335                2340

Gln Val Asn Pro Ile Thr Leu Thr Ala Ala Leu Phe Leu Leu Val
    2345                2350                2355

Ala His Tyr Ala Ile Ile Gly Pro Gly Leu Gln Ala Lys Ala Thr
    2360                2365                2370

Arg Glu Ala Gln Lys Arg Ala Ala Ala Gly Ile Met Lys Asn Pro
    2375                2380                2385
```

```
Thr Val Asp Gly Ile Thr Val Ile Asp Leu Asp Pro Ile Pro Tyr
    2390            2395                2400
Asp Pro Lys Phe Glu Lys Gln Leu Gly Gln Val Met Leu Leu Val
    2405            2410                2415
Leu Cys Val Thr Gln Val Leu Met Met Arg Thr Thr Trp Ala Leu
    2420            2425                2430
Cys Glu Ala Leu Thr Leu Ala Thr Gly Pro Ile Ser Thr Leu Trp
    2435            2440                2445
Glu Gly Asn Pro Gly Arg Phe Trp Asn Thr Thr Ile Ala Val Ser
    2450            2455                2460
Met Ala Asn Ile Phe Arg Gly Ser Tyr Leu Ala Gly Ala Gly Leu
    2465            2470                2475
Leu Phe Ser Ile Met Lys Asn Thr Thr Asn Thr Arg Arg Gly Thr
    2480            2485                2490
Gly Asn Ile Gly Glu Thr Leu Gly Glu Lys Trp Lys Ser Arg Leu
    2495            2500                2505
Asn Ala Leu Gly Lys Ser Glu Phe Gln Ile Tyr Lys Lys Ser Gly
    2510            2515                2520
Ile Gln Glu Val Asp Arg Thr Leu Ala Lys Glu Gly Ile Lys Arg
    2525            2530                2535
Gly Glu Thr Asp His His Ala Val Ser Arg Gly Ser Ala Lys Leu
    2540            2545                2550
Arg Trp Phe Val Glu Arg Asn Met Val Thr Pro Glu Gly Lys Val
    2555            2560                2565
Val Asp Leu Gly Cys Gly Arg Gly Gly Trp Ser Tyr Tyr Cys Gly
    2570            2575                2580
Gly Leu Lys Asn Val Arg Glu Val Lys Gly Leu Thr Lys Gly Gly
    2585            2590                2595
Pro Gly His Glu Glu Pro Ile Pro Met Ser Thr Tyr Gly Trp Asn
    2600            2605                2610
Leu Val Arg Leu Gln Ser Gly Val Asp Val Phe Phe Ile Pro Pro
    2615            2620                2625
Glu Lys Cys Asp Thr Leu Leu Cys Asp Ile Gly Glu Ser Ser Pro
    2630            2635                2640
Asn Pro Thr Val Glu Ala Gly Arg Thr Leu Arg Val Leu Asn Leu
    2645            2650                2655
Val Glu Asn Trp Leu Asn Asn Asn Thr Gln Phe Cys Ile Lys Val
    2660            2665                2670
Leu Asn Pro Tyr Met Pro Ser Val Ile Glu Lys Met Glu Ala Leu
    2675            2680                2685
Gln Arg Lys Tyr Gly Gly Ala Leu Val Arg Asn Pro Leu Ser Arg
    2690            2695                2700
Asn Ser Thr His Glu Met Tyr Trp Val Ser Asn Ala Ser Gly Asn
    2705            2710                2715
Ile Val Ser Ser Val Asn Met Ile Ser Arg Met Leu Ile Asn Arg
    2720            2725                2730
Phe Thr Met Arg Tyr Lys Lys Ala Thr Tyr Glu Pro Asp Val Asp
    2735            2740                2745
Leu Gly Ser Gly Thr Arg Asn Ile Gly Ile Glu Ser Glu Ile Pro
    2750            2755                2760
Asn Leu Asp Ile Ile Gly Lys Arg Ile Glu Lys Ile Lys Gln Glu
    2765            2770                2775
```

-continued

His Glu Thr Ser Trp His Tyr Asp Gln Asp His Pro Tyr Lys Thr
2780                2785                2790

Trp Ala Tyr His Gly Ser Tyr Glu Thr Lys Gln Thr Gly Ser Ala
2795                2800                2805

Ser Ser Met Val Asn Gly Val Val Arg Leu Leu Thr Lys Pro Trp
2810                2815                2820

Asp Val Val Pro Met Val Thr Gln Met Ala Met Thr Asp Thr Thr
2825                2830                2835

Pro Phe Gly Gln Gln Arg Val Phe Lys Glu Lys Val Asp Thr Arg
2840                2845                2850

Thr Gln Glu Pro Lys Glu Gly Thr Lys Lys Leu Met Lys Ile Thr
2855                2860                2865

Ala Glu Trp Leu Trp Lys Glu Leu Gly Lys Lys Lys Thr Pro Arg
2870                2875                2880

Met Cys Thr Arg Glu Glu Phe Thr Arg Lys Val Arg Ser Asn Ala
2885                2890                2895

Ala Leu Gly Ala Ile Phe Thr Asp Glu Asn Lys Trp Lys Ser Ala
2900                2905                2910

Arg Glu Ala Val Glu Asp Ser Arg Phe Trp Glu Leu Val Asp Lys
2915                2920                2925

Glu Arg Asn Leu His Leu Glu Gly Lys Cys Glu Thr Cys Val Tyr
2930                2935                2940

Asn Met Met Gly Lys Arg Glu Lys Lys Leu Gly Glu Phe Gly Lys
2945                2950                2955

Ala Lys Gly Ser Arg Ala Ile Trp Tyr Met Trp Leu Gly Ala Arg
2960                2965                2970

Phe Leu Glu Phe Glu Ala Leu Gly Phe Leu Asn Glu Asp His Trp
2975                2980                2985

Phe Ser Arg Glu Asn Ser Leu Ser Gly Val Glu Gly Glu Gly Leu
2990                2995                3000

His Lys Leu Gly Tyr Ile Leu Arg Asp Val Ser Lys Lys Glu Gly
3005                3010                3015

Gly Ala Met Tyr Ala Asp Asp Thr Ala Gly Trp Asp Thr Arg Ile
3020                3025                3030

Thr Leu Glu Asp Leu Lys Asn Glu Glu Met Val Thr Asn His Met
3035                3040                3045

Glu Gly Glu His Lys Lys Leu Ala Glu Ala Ile Phe Lys Leu Thr
3050                3055                3060

Tyr Gln Asn Lys Val Val Arg Val Gln Arg Pro Thr Pro Arg Gly
3065                3070                3075

Thr Val Met Asp Ile Ile Ser Arg Arg Asp Gln Arg Gly Ser Gly
3080                3085                3090

Gln Val Gly Thr Tyr Gly Leu Asn Thr Phe Thr Asn Met Glu Ala
3095                3100                3105

Gln Leu Ile Arg Gln Met Glu Gly Glu Gly Val Phe Lys Ser Ile
3110                3115                3120

Gln His Leu Thr Ile Thr Glu Glu Ile Ala Val Gln Asn Trp Leu
3125                3130                3135

Ala Arg Val Gly Arg Glu Arg Leu Ser Arg Met Ala Ile Ser Gly
3140                3145                3150

Asp Asp Cys Val Val Lys Pro Leu Asp Asp Arg Phe Ala Ser Ala
3155                3160                3165

Leu Thr Ala Leu Asn Asp Met Gly Lys Ile Arg Lys Asp Ile Gln 3170                3175                3180
Gln Trp Glu Pro Ser Arg Gly Trp Asn Asp Trp Thr Gln Val Pro
        3185                3190                3195

Phe Cys Ser His His Phe His Glu Leu Ile Met Lys Asp Gly Arg
        3200                3205                3210

Val Leu Val Val Pro Cys Arg Asn Gln Asp Glu Leu Ile Gly Arg
        3215                3220                3225

Ala Arg Ile Ser Gln Gly Ala Gly Trp Ser Leu Arg Glu Thr Ala
        3230                3235                3240

Cys Leu Gly Lys Ser Tyr Ala Gln Met Trp Ser Leu Met Tyr Phe
        3245                3250                3255

His Arg Arg Asp Leu Arg Leu Ala Ala Asn Ala Ile Cys Ser Ala
        3260                3265                3270

Val Pro Ser His Trp Val Pro Thr Ser Arg Thr Thr Trp Ser Ile
        3275                3280                3285

His Ala Lys His Glu Trp Met Thr Thr Glu Asp Met Leu Thr Val
        3290                3295                3300

Trp Asn Arg Val Trp Ile Gln Glu Asn Pro Trp Met Glu Asp Lys
        3305                3310                3315

Thr Pro Val Glu Ser Trp Glu Glu Ile Pro Tyr Leu Gly Lys Arg
        3320                3325                3330

Glu Asp Gln Trp Cys Gly Ser Leu Ile Gly Leu Thr Ser Arg Ala
        3335                3340                3345

Thr Trp Ala Lys Asn Ile Gln Ala Ala Ile Asn Gln Val Arg Ser
        3350                3355                3360

Leu Ile Gly Asn Glu Glu Tyr Thr Asp Tyr Met Pro Ser Met Lys
        3365                3370                3375

Arg Phe Arg Arg Glu Glu Glu Ala Gly Val Leu Trp
        3380                3385                3390

<210> SEQ ID NO 3
<211> LENGTH: 10723
<212> TYPE: DNA
<213> ORGANISM: Dengue virus type 2

<400> SEQUENCE: 3
agttgttagt ctacgtggac cgacaaagac agattctttg agggagctaa gctcaatgta      60
gttctaacag ttttttaatt agagagcaga tctctgatga ataaccaacg gaaaaaggcg     120
aaaaacacgc ctttcaatat gctgaaacgc gagagaaacc gcgtgtcgac tgtgcaacag     180
ctgacaaaga gattctcact tggaatgctg cagggacgag gaccattaaa actgttcatg     240
gccctggtgg cgttccttcg tttcctaaca atcccaccaa cagcagggat attgaagaga     300
tggggaacaa ttaaaaaatc aaaagctatt aatgttttga gagggttcag aaagagaatt     360
ggaaggatgc tgaacatctt gaataggaga cgcagatctg caggcatgat cattatgctg     420
attccaacag tgatggcgtt ccatttaacc acacgtaacg agaaccacat gatcgtc       480 agcagacaag agaaagggaa agtcttctg tttaaaacag aggttggcgt gaacatgtgt     540
accctcatgg ccatggacct tggtgaattg tgtgaagaca caatcactgta cgagtgtccc     600 cttctcaggc agaatgagcc agaagacata gactgttggt gcaactctac gtccacgtgg     660
gtaacttatg gacgtgtac caccatggga gaacatagaa gagaaaaag atcagtggca     720 ctcgttccac atgtgggaat gggactggag acacgaactg aaacatggat gtcatcagaa     780
ggggcctgga aacatgtcca gagaattgaa acttggatct tgagacatcc aggcttcacc     840

```
atgatggcag caatcctggc atacaccata ggaacgacac atttccaaag agccctgatc    900
ttcatcttac tgacagctgt cactccttca atgacaatgc gttgcatagg aatgtcaaat    960
agagactttg tggaaggggt ttcaggagga agctgggttg acatagtctt agaacatgga   1020
agctgtgtga cgacgatggc aaaaaacaaa ccaacattgg attttgaact gataaaaaca   1080
gaagccaaac agcctgccac cctaaggaag tactgtatag aggcaaagct aaccaacaca   1140
acaacagaat ctcgctgccc aacacaaggg gaacccagcc taaatgaaga gcaggacaaa   1200
aggttcgtct gcaaacactc catggtagac agaggatggg gaaatggatg tggactattt   1260
ggaaagggag gcattgtgac ctgtgctatg ttcagatgca aaaagaacat ggaaggaaaa   1320
gttgtgcaac cagaaaactt ggaatacacc attgtgataa cacctcactc aggggaagag   1380
catgcagtcg gaaatgacac aggaaaacat ggcaaggaaa tcaaaataac accacagagt   1440
tccatcacag aagcagaatt gacaggttat ggcactgtca caatggagtg ctctccaaga   1500
acgggcctcg acttcaatga gatggtgttg ctgcagatgg aaaataaagc ttggctggtg   1560
cacaggcaat ggttcctaga cctgccgtta ccatggttgc ccggagcgga cacacaaggg   1620
tcaaattgga tacagaaaga gacattggtc actttcaaaa atccccatgc gaagaaacag   1680
gatgttgttg ttttaggatc ccaagaaggg gccatgcaca cagcacttac aggggccaca   1740
gaaatccaaa tgtcatcagg aaacttactc ttcacaggac atctcaagtg caggctgaga   1800
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat ccccttttgag ataatggatt tggaaaaaag acatgtctta   1980
ggtcgcctga ttacagtcaa cccaattgtg acagaaaaag atagcccagt caacatagaa   2040
gcagaacctc catttggaga cagctacatc atcataggag tagagccggg acaactgaag   2100
ctcaactggt ttaagaaagg aagttctatc ggccaaatgt tgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga ctggaaaaa caagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca ataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catgggcaa agcaaaaatg ctctctacag agtctcataa ccagaccttt   2820
ctcattgatg cccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa atcacacac cctctggagc   3120
aatggagtgc tagaaagtga gatgataatt ccaaagaatc tcgctggacc agtgtctcaa   3180
```

```
cacaactata gaccaggcta ccatacacaa ataacaggac catggcatct aggtaagctt    3240
gagatggact tgatttctg tgatggaaca acagtggtag tgactgagga ctgcggaaat    3300
agaggaccct ctttgagaac aaccactgcc tctggaaaac tcataacaga atggtgctgc    3360
cgatcttgca cattaccacc gctaagatac agaggtgagg atgggtgctg gtacgggatg    3420
gaaatcagac cattgaagga gaaagaagag aatttggtca actccttggt cacagctgga    3480
catgggcagg tcgacaactt ttcactagga gtcttgggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcagac aacttttgc agctggacta ctcttgagaa agctgacctc caaggaattg    3780
atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctattttct aacaaccctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttggaactg gagagagcag ccgatgtcaa atgggaagac    4320
caggcagaga tatcaggaag cagtccaatc ctgtcaataa caatatcaga agatggtagc    4380
atgtcgataa aaaatgaaga ggaagaacaa acactgacca tactcattag aacaggattg    4440
ctggtgatct caggactttt tcctgtatca ataccaatca cggcagcagc atggtacctg    4500
tgggaagtga gaaaacaacg ggccggagta ttgtgggatg ttccttcacc cccacccatg    4560
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaggaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860
ggtcttttca aaaccaacgc cggaacaata ggtgctgtat ctctggactt ttctcctgga    4920
acgtcaggat ctccaattat cgacaaaaaa ggaaaagttg tgggtcttta tggtaatggt    4980
gttgttacaa ggagtggagc atatgtgagt gctatagccc agactgaaaa aagcattgaa    5040
gacaacccag agatcgaaga tgacattttc cgaaagagaa gactgaccat catggaccte    5100 cacccaggag cgggaaagac gaagagatac cttccggcca tagtcagaga agctataaaa    5160
cggggtttga gaacattaat cttggccccc actagagttg tggcagctga atggaggaa    5220 gcccttagag gacttccaat aagataccag accccagcca tcagagctgt gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggattttt    5460
atgacagcca ctccccgggg aagcagagac ccatttcctc agagcaatgc accaatcata    5520
gatgaagaaa gagaaatccc tgaacgctcg tggaattccg gacatgaatg ggtcacggat    5580
```

```
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa aagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct ttttattctt gatgagcgca   6600
aggggcatag gaagatgac cctgggaatg tgctgcataa tcacggctag catcctccta   6660
tggtacgcac aaatacagcc acactggata gcagcttcaa taatactgga gttttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg acaagtaat gctcctagtc ctctgcgtga ctcaagtatt gatgatgagg   7380
actacatggg ctctgtgtga ggctttaacc ttagctaccg gcccatctc acattgtgg   7440 gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
```

```
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atggaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460
cacccataca aaacgtgggc ataccatggt agctatgaaa caaaacagac tggatcagca    8520
tcatccatgg tcaacggagt ggtcaggctg ctgacaaaac cttgggacgt cgtccccatg    8580
gtgacacaga tggcaatgac agacacgact ccatttggac aacagcgcgt ttttaaagag    8640
aaagtggaca cgagaaccca agaaccgaaa gaaggcacga gaaactaat gaaataaca    8700
gcagagtggc tttggaaaga attagggaag aaaagacac ccaggatgtg caccagagaa    8760
gaattcacaa gaaggtgag aagcaatgca gccttgggggg ccgtattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctagggga attcggcaag gcaaaaggca gcagagccat atggtacatg    9000
tggcttggag cacgcttctt agagtttgaa gccctaggat tcttaaatga agatcactgg    9060
ttctccagag agaactccct gagtggagtg aaggagaag ggctgcacaa gctaggttac    9120
attctaagag acgtgagcaa gaaagaggga ggagcaatgt atgccgatga caccgcagga    9180
tgggatacaa gaatcacact agaagaccta aaaaatgaag aaatggtaac aaaccacatg    9240
gaaggagaac acaagaaact agccgaggcc atttttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata cttttcaccaa tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtggagatga ttgtgttgtg aaacctttag atgacaggtt cgcaagcgct    9600
ttaacagctc taaatgacat gggaaagatt aggaaagaca tacaacaatg gaaccttca    9660
agaggatgga atgattggac acaagtgccc ttctgttcac accatttcca tgagttaatc    9720
atgaaagacg gtcgcgtact cgttgttcca tgtagaaacc aagatgaact gattggcaga    9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacggaa gacatgctga cagtctggaa cagggtgtgg   10020
attcaagaaa acccatggat ggaagacaaa actccagtgg aatcatggga ggaaatccca   10080
tacttgggga aagagaaga ccaatggtgc ggctcattga ttgggttaac aagcagggcc   10140
acctgggcaa agaacatcca agcagcaata aatcaagtta gatcccttat aggcaatgaa   10200
gaatacacag attacatgcc atccatgaaa agattcagaa gagaagagga agaagcagga   10260
gttctgtggt agaaagcaaa actaacatga acaaggcta gaagtcaggt cggattaagc   10320
```

```
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                    10723
```

```
<210> SEQ ID NO 4
<211> LENGTH: 3391
<212> TYPE: PRT
<213> ORGANISM: Dengue virus type 2

<400> SEQUENCE: 4

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Val Gly
    130                 135                 140

Val Asn Met Cys Thr Leu Met Ala Met Asp Leu Gly Glu Leu Cys Glu
145                 150                 155                 160

Asp Thr Ile Thr Tyr Glu Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300
```

```
Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
            325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
            355                 360                 365

Arg Phe Val Cys Lys His Ser Met Val Asp Arg Gly Trp Gly Asn Gly
            370                 375                 380

Cys Gly Leu Phe Gly Lys Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
                420                 425                 430

Asn Asp Thr Gly Lys His Gly Lys Glu Ile Lys Ile Thr Pro Gln Ser
            435                 440                 445

Ser Ile Thr Glu Ala Glu Leu Thr Gly Tyr Gly Thr Val Thr Met Glu
450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
                500                 505                 510

Gln Lys Glu Thr Leu Val Thr Phe Lys Asn Pro His Ala Lys Lys Gln
            515                 520                 525

Asp Val Val Leu Gly Ser Gln Glu Gly Ala Met His Thr Ala Leu
            530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
                580                 585                 590

Ala Glu Thr Gln His Gly Thr Ile Val Ile Arg Val Gln Tyr Glu Gly
            595                 600                 605

Asp Gly Ser Pro Cys Lys Ile Pro Phe Glu Ile Met Asp Leu Glu Lys
            610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
                660                 665                 670

Lys Lys Gly Ser Ser Ile Gly Gln Met Phe Glu Thr Thr Met Arg Gly
            675                 680                 685

Ala Lys Arg Met Ala Ile Leu Gly Asp Thr Ala Trp Asp Phe Gly Ser
            690                 695                 700

Leu Gly Gly Val Phe Thr Ser Ile Gly Lys Ala Leu His Gln Val Phe
705                 710                 715                 720
```

-continued

```
Gly Ala Ile Tyr Gly Ala Ala Phe Ser Gly Val Ser Trp Thr Met Lys
            725                 730                 735

Ile Leu Ile Gly Val Ile Ile Thr Trp Ile Gly Met Asn Ser Arg Ser
        740                 745                 750

Thr Ser Leu Ser Val Thr Leu Val Leu Val Gly Ile Val Thr Leu Tyr
    755                 760                 765

Leu Gly Val Met Val Gln Ala Asp Ser Gly Cys Val Val Ser Trp Lys
770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp Pro Lys Ser His Thr Leu Trp Ser
        995                1000                1005

Asn Gly Val Leu Glu Ser Glu Met Ile Ile Pro Lys Asn Leu Ala
    1010                1015                1020

Gly Pro Val Ser Gln His Asn Tyr Arg Pro Gly Tyr His Thr Gln
    1025                1030                1035

Ile Thr Gly Pro Trp His Leu Gly Lys Leu Glu Met Asp Phe Asp
    1040                1045                1050

Phe Cys Asp Gly Thr Thr Val Val Val Thr Glu Asp Cys Gly Asn
    1055                1060                1065

Arg Gly Pro Ser Leu Arg Thr Thr Ala Ser Gly Lys Leu Ile
    1070                1075                1080

Thr Glu Trp Cys Cys Arg Ser Cys Thr Leu Pro Pro Leu Arg Tyr
    1085                1090                1095

Arg Gly Glu Asp Gly Cys Trp Tyr Gly Met Glu Ile Arg Pro Leu
    1100                1105                1110

Lys Glu Lys Glu Glu Asn Leu Val Asn Ser Leu Val Thr Ala Gly
    1115                1120                1125

His Gly Gln Val Asp Asn Phe Ser Leu Gly Val Leu Gly Met Ala
```

```
            1130                1135                1140
Leu Phe Leu Glu Glu Met Leu Arg Thr Arg Val Gly Thr Lys His
        1145                1150                1155
Ala Ile Leu Leu Val Ala Val Ser Phe Val Thr Leu Ile Thr Gly
        1160                1165                1170
Asn Met Ser Phe Arg Asp Leu Gly Arg Val Met Val Met Val Gly
        1175                1180                1185
Ala Thr Met Thr Asp Asp Ile Gly Met Gly Val Thr Tyr Leu Ala
        1190                1195                1200
Leu Leu Ala Ala Phe Lys Val Arg Pro Thr Phe Ala Ala Gly Leu
        1205                1210                1215
Leu Leu Arg Lys Leu Thr Ser Lys Glu Leu Met Met Thr Thr Ile
        1220                1225                1230
Gly Ile Val Leu Leu Ser Gln Ser Thr Ile Pro Glu Thr Ile Leu
        1235                1240                1245
Glu Leu Thr Asp Ala Leu Ala Leu Gly Met Met Val Leu Lys Met
        1250                1255                1260
Val Arg Asn Met Glu Lys Tyr Gln Leu Ala Val Thr Ile Met Ala
        1265                1270                1275
Ile Leu Cys Val Pro Asn Ala Val Ile Leu Gln Asn Ala Trp Lys
        1280                1285                1290
Val Ser Cys Thr Ile Leu Ala Val Val Ser Val Ser Pro Leu Phe
        1295                1300                1305
Leu Thr Ser Ser Gln Gln Lys Thr Asp Trp Ile Pro Leu Ala Leu
        1310                1315                1320
Thr Ile Lys Gly Leu Asn Pro Thr Ala Ile Phe Leu Thr Thr Leu
        1325                1330                1335
Ser Arg Thr Ser Lys Lys Arg Ser Trp Pro Leu Asn Glu Ala Ile
        1340                1345                1350
Met Ala Val Gly Met Val Ser Ile Leu Ala Ser Ser Leu Leu Lys
        1355                1360                1365
Asn Asp Ile Pro Met Thr Gly Pro Leu Val Ala Gly Gly Leu Leu
        1370                1375                1380
Thr Val Cys Tyr Val Leu Thr Gly Arg Ser Ala Asp Leu Glu Leu
        1385                1390                1395
Glu Arg Ala Ala Asp Val Lys Trp Glu Asp Gln Ala Glu Ile Ser
        1400                1405                1410
Gly Ser Ser Pro Ile Leu Ser Ile Thr Ile Ser Glu Asp Gly Ser
        1415                1420                1425
Met Ser Ile Lys Asn Glu Glu Glu Gln Thr Leu Thr Ile Leu
        1430                1435                1440
Ile Arg Thr Gly Leu Leu Val Ile Ser Gly Leu Phe Pro Val Ser
        1445                1450                1455
Ile Pro Ile Thr Ala Ala Ala Trp Tyr Leu Trp Glu Val Lys Lys
        1460                1465                1470
Gln Arg Ala Gly Val Leu Trp Asp Val Pro Ser Pro Pro Pro Met
        1475                1480                1485
Gly Lys Ala Glu Leu Glu Asp Gly Ala Tyr Arg Ile Lys Gln Lys
        1490                1495                1500
Gly Ile Leu Gly Tyr Ser Gln Ile Gly Ala Gly Val Tyr Lys Glu
        1505                1510                1515
Gly Thr Phe His Thr Met Trp His Val Thr Arg Gly Ala Val Leu
        1520                1525                1530
```

```
Met His Lys Gly Lys Arg Ile Glu Pro Ser Trp Ala Asp Val Lys
1535                1540                1545

Lys Asp Leu Ile Ser Tyr Gly Gly Trp Lys Leu Glu Gly Glu
1550                1555                1560

Trp Lys Glu Gly Glu Glu Val Gln Val Leu Ala Leu Glu Pro Gly
1565                1570                1575

Lys Asn Pro Arg Ala Val Gln Thr Lys Pro Gly Leu Phe Lys Thr
1580                1585                1590

Asn Ala Gly Thr Ile Gly Ala Val Ser Leu Asp Phe Ser Pro Gly
1595                1600                1605

Thr Ser Gly Ser Pro Ile Ile Asp Lys Lys Gly Lys Val Val Gly
1610                1615                1620

Leu Tyr Gly Asn Gly Val Val Thr Arg Ser Gly Ala Tyr Val Ser
1625                1630                1635

Ala Ile Ala Gln Thr Glu Lys Ser Ile Glu Asp Asn Pro Glu Ile
1640                1645                1650

Glu Asp Asp Ile Phe Arg Lys Arg Arg Leu Thr Ile Met Asp Leu
1655                1660                1665

His Pro Gly Ala Gly Lys Thr Lys Arg Tyr Leu Pro Ala Ile Val
1670                1675                1680

Arg Glu Ala Ile Lys Arg Gly Leu Arg Thr Leu Ile Leu Ala Pro
1685                1690                1695

Thr Arg Val Val Ala Ala Glu Met Glu Glu Ala Leu Arg Gly Leu
1700                1705                1710

Pro Ile Arg Tyr Gln Thr Pro Ala Ile Arg Ala Val His Thr Gly
1715                1720                1725

Arg Glu Ile Val Asp Leu Met Cys His Ala Thr Phe Thr Met Arg
1730                1735                1740

Leu Leu Ser Pro Val Arg Val Pro Asn Tyr Asn Leu Ile Ile Met
1745                1750                1755

Asp Glu Ala His Phe Thr Asp Pro Ala Ser Ile Ala Ala Arg Gly
1760                1765                1770

Tyr Ile Ser Thr Arg Val Glu Met Gly Glu Ala Ala Gly Ile Phe
1775                1780                1785

Met Thr Ala Thr Pro Pro Gly Ser Arg Asp Pro Phe Pro Gln Ser
1790                1795                1800

Asn Ala Pro Ile Ile Asp Glu Glu Arg Glu Ile Pro Glu Arg Ser
1805                1810                1815

Trp Asn Ser Gly His Glu Trp Val Thr Asp Phe Lys Gly Lys Thr
1820                1825                1830

Val Trp Phe Val Pro Ser Ile Lys Ala Gly Asn Asp Ile Ala Ala
1835                1840                1845

Cys Leu Arg Lys Asn Gly Lys Lys Val Ile Gln Leu Ser Arg Lys
1850                1855                1860

Thr Phe Asp Ser Glu Tyr Val Lys Thr Arg Thr Asn Asp Trp Asp
1865                1870                1875

Phe Val Val Thr Thr Asp Ile Ser Glu Met Gly Ala Asn Phe Lys
1880                1885                1890

Ala Glu Arg Val Ile Asp Pro Arg Arg Cys Met Lys Pro Val Ile
1895                1900                1905

Leu Thr Asp Gly Glu Glu Arg Val Ile Leu Ala Gly Pro Met Pro
1910                1915                1920
```

-continued

Val Thr His Ser Ser Ala Ala Gln Arg Arg Gly Arg Ile Gly Arg
1925                 1930                1935

Asn Pro Lys Asn Glu Asn Asp Gln Tyr Ile Tyr Met Gly Glu Pro
1940                 1945                1950

Leu Glu Asn Asp Glu Asp Cys Ala His Trp Lys Glu Ala Lys Met
1955                 1960                1965

Leu Leu Asp Asn Ile Asn Thr Pro Glu Gly Ile Ile Pro Ser Met
1970                 1975                1980

Phe Glu Pro Glu Arg Glu Lys Val Asp Ala Ile Asp Gly Glu Tyr
1985                 1990                1995

Arg Leu Arg Gly Glu Ala Arg Lys Thr Phe Val Asp Leu Met Arg
2000                 2005                2010

Arg Gly Asp Leu Pro Val Trp Leu Ala Tyr Arg Val Ala Ala Glu
2015                 2020                2025

Gly Ile Asn Tyr Ala Asp Arg Arg Trp Cys Phe Asp Gly Val Lys
2030                 2035                2040

Asn Asn Gln Ile Leu Glu Glu Asn Val Glu Val Glu Ile Trp Thr
2045                 2050                2055

Lys Glu Gly Glu Arg Lys Lys Leu Lys Pro Arg Trp Leu Asp Ala
2060                 2065                2070

Arg Ile Tyr Ser Asp Pro Leu Ala Leu Lys Glu Phe Lys Glu Phe
2075                 2080                2085

Ala Ala Gly Arg Lys Ser Leu Thr Leu Asn Leu Ile Thr Glu Met
2090                 2095                2100

Gly Arg Leu Pro Thr Phe Met Thr Gln Lys Ala Arg Asp Ala Leu
2105                 2110                2115

Asp Asn Leu Ala Val Leu His Thr Ala Glu Ala Gly Gly Arg Ala
2120                 2125                2130

Tyr Asn His Ala Leu Ser Glu Leu Pro Glu Thr Leu Glu Thr Leu
2135                 2140                2145

Leu Leu Leu Thr Leu Leu Ala Thr Val Thr Gly Gly Ile Phe Leu
2150                 2155                2160

Phe Leu Met Ser Ala Arg Gly Ile Gly Lys Met Thr Leu Gly Met
2165                 2170                2175

Cys Cys Ile Ile Thr Ala Ser Ile Leu Leu Trp Tyr Ala Gln Ile
2180                 2185                2190

Gln Pro His Trp Ile Ala Ala Ser Ile Ile Leu Glu Phe Phe Leu
2195                 2200                2205

Ile Val Leu Leu Ile Pro Glu Pro Glu Lys Gln Arg Thr Pro Gln
2210                 2215                2220

Asp Asn Gln Leu Thr Tyr Val Val Ile Ala Ile Leu Thr Val Val
2225                 2230                2235

Ala Ala Thr Met Ala Asn Glu Met Gly Phe Leu Glu Lys Thr Lys
2240                 2245                2250

Lys Asp Leu Gly Leu Gly Ser Ile Ala Thr Gln Gln Pro Glu Ser
2255                 2260                2265

Asn Ile Leu Asp Ile Asp Leu Arg Pro Ala Ser Ala Trp Thr Leu
2270                 2275                2280

Tyr Ala Val Ala Thr Thr Phe Val Thr Pro Met Leu Arg His Ser
2285                 2290                2295

Ile Glu Asn Ser Ser Val Asn Val Ser Leu Thr Ala Ile Ala Asn
2300                 2305                2310

Gln Ala Thr Val Leu Met Gly Leu Gly Lys Gly Trp Pro Leu Ser

-continued

```
              2315                2320                2325
Lys Met Asp Ile Gly Val Pro Leu Leu Ala Ile Gly Cys Tyr Ser
        2330                2335                2340
Gln Val Asn Pro Ile Thr Leu Thr Ala Ala Leu Phe Leu Leu Val
        2345                2350                2355
Ala His Tyr Ala Ile Ile Gly Pro Gly Leu Gln Ala Lys Ala Thr
        2360                2365                2370
Arg Glu Ala Gln Lys Arg Ala Ala Ala Gly Ile Met Lys Asn Pro
        2375                2380                2385
Thr Val Asp Gly Ile Thr Val Ile Asp Leu Asp Pro Ile Pro Tyr
        2390                2395                2400
Asp Pro Lys Phe Glu Lys Gln Leu Gly Gln Val Met Leu Leu Val
        2405                2410                2415
Leu Cys Val Thr Gln Val Leu Met Met Arg Thr Thr Trp Ala Leu
        2420                2425                2430
Cys Glu Ala Leu Thr Leu Ala Thr Gly Pro Ile Ser Thr Leu Trp
        2435                2440                2445
Glu Gly Asn Pro Gly Arg Phe Trp Asn Thr Thr Ile Ala Val Ser
        2450                2455                2460
Met Ala Asn Ile Phe Arg Gly Ser Tyr Leu Ala Gly Ala Gly Leu
        2465                2470                2475
Leu Phe Ser Ile Met Lys Asn Thr Thr Asn Thr Arg Arg Gly Thr
        2480                2485                2490
Gly Asn Ile Gly Glu Thr Leu Gly Glu Lys Trp Lys Ser Arg Leu
        2495                2500                2505
Asn Ala Leu Gly Lys Ser Glu Phe Gln Ile Tyr Lys Lys Ser Gly
        2510                2515                2520
Ile Gln Glu Val Asp Arg Thr Leu Ala Lys Glu Gly Ile Lys Arg
        2525                2530                2535
Gly Glu Thr Asp His His Ala Val Ser Arg Gly Ser Ala Lys Leu
        2540                2545                2550
Arg Trp Phe Val Glu Arg Asn Met Val Thr Pro Glu Gly Lys Val
        2555                2560                2565
Val Asp Leu Gly Cys Gly Arg Gly Gly Trp Ser Tyr Tyr Cys Gly
        2570                2575                2580
Gly Leu Lys Asn Val Arg Glu Val Lys Gly Leu Thr Lys Gly Gly
        2585                2590                2595
Pro Gly His Glu Glu Pro Ile Pro Met Ser Thr Tyr Gly Trp Asn
        2600                2605                2610
Leu Val Arg Leu Gln Ser Gly Val Asp Val Phe Phe Ile Pro Pro
        2615                2620                2625
Glu Lys Cys Asp Thr Leu Leu Cys Asp Ile Gly Glu Ser Ser Pro
        2630                2635                2640
Asn Pro Thr Val Glu Ala Gly Arg Thr Leu Arg Val Leu Asn Leu
        2645                2650                2655
Val Glu Asn Trp Leu Asn Asn Asn Thr Gln Phe Cys Ile Lys Val
        2660                2665                2670
Leu Asn Pro Tyr Met Pro Ser Val Ile Glu Lys Met Glu Ala Leu
        2675                2680                2685
Gln Arg Lys Tyr Gly Gly Ala Leu Val Arg Asn Pro Leu Ser Arg
        2690                2695                2700
Asn Ser Thr His Glu Met Tyr Trp Val Ser Asn Ala Ser Gly Asn
        2705                2710                2715
```

-continued

```
Ile Val Ser Ser Val Asn Met Ile Ser Arg Met Leu Ile Asn Arg
    2720                2725                2730

Phe Thr Met Arg Tyr Lys Lys Ala Thr Tyr Glu Pro Asp Val Asp
    2735                2740                2745

Leu Gly Ser Gly Thr Arg Asn Ile Gly Ile Glu Ser Glu Ile Pro
    2750                2755                2760

Asn Leu Asp Ile Ile Gly Lys Arg Ile Glu Lys Ile Lys Gln Glu
    2765                2770                2775

His Glu Thr Ser Trp His Tyr Asp Gln Asp His Pro Tyr Lys Thr
    2780                2785                2790

Trp Ala Tyr His Gly Ser Tyr Glu Thr Lys Gln Thr Gly Ser Ala
    2795                2800                2805

Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
    2870                2875                2880

Met Cys Thr Arg Glu Glu Phe Thr Arg Lys Val Arg Ser Asn Ala
    2885                2890                2895

Ala Leu Gly Ala Val Phe Thr Asp Glu Asn Lys Trp Lys Ser Ala
    2900                2905                2910

Arg Glu Ala Val Glu Asp Ser Arg Phe Trp Glu Leu Val Asp Lys
    2915                2920                2925

Glu Arg Asn Leu His Leu Glu Gly Lys Cys Glu Thr Cys Val Tyr
    2930                2935                2940

Asn Met Met Gly Lys Arg Glu Lys Lys Leu Gly Glu Phe Gly Lys
    2945                2950                2955

Ala Lys Gly Ser Arg Ala Ile Trp Tyr Met Trp Leu Gly Ala Arg
    2960                2965                2970

Phe Leu Glu Phe Glu Ala Leu Gly Phe Leu Asn Glu Asp His Trp
    2975                2980                2985

Phe Ser Arg Glu Asn Ser Leu Ser Gly Val Glu Gly Glu Gly Leu
    2990                2995                3000

His Lys Leu Gly Tyr Ile Leu Arg Asp Val Ser Lys Lys Glu Gly
    3005                3010                3015

Gly Ala Met Tyr Ala Asp Asp Thr Ala Gly Trp Asp Thr Arg Ile
    3020                3025                3030

Thr Leu Glu Asp Leu Lys Asn Glu Glu Met Val Thr Asn His Met
    3035                3040                3045

Glu Gly Glu His Lys Lys Leu Ala Glu Ala Ile Phe Lys Leu Thr
    3050                3055                3060

Tyr Gln Asn Lys Val Val Arg Val Gln Arg Pro Thr Pro Arg Gly
    3065                3070                3075

Thr Val Met Asp Ile Ile Ser Arg Arg Asp Gln Arg Gly Ser Gly
    3080                3085                3090

Gln Val Gly Thr Tyr Gly Leu Asn Thr Phe Thr Asn Met Glu Ala
    3095                3100                3105
```

| | | | | | | | | | | | |
|---|---|---|---|---|---|---|---|---|---|---|---|
| Gln | Leu | Ile | Arg | Gln | Met | Glu | Gly | Glu | Gly | Val | Phe | Lys | Ser | Ile |
| | 3110 | | | | 3115 | | | | 3120 | | |

Gln Leu Ile Arg Gln Met Glu Gly Glu Gly Val Phe Lys Ser Ile
    3110                3115                3120

Gln His Leu Thr Ile Thr Glu Glu Ile Ala Val Gln Asn Trp Leu
    3125                3130                3135

Ala Arg Val Gly Arg Glu Arg Leu Ser Arg Met Ala Ile Ser Gly
    3140                3145                3150

Asp Asp Cys Val Val Lys Pro Leu Asp Asp Arg Phe Ala Ser Ala
    3155                3160                3165

Leu Thr Ala Leu Asn Asp Met Gly Lys Ile Arg Lys Asp Ile Gln
    3170                3175                3180

Gln Trp Glu Pro Ser Arg Gly Trp Asn Asp Trp Thr Gln Val Pro
    3185                3190                3195

Phe Cys Ser His His Phe His Glu Leu Ile Met Lys Asp Gly Arg
    3200                3205                3210

Val Leu Val Val Pro Cys Arg Asn Gln Asp Glu Leu Ile Gly Arg
    3215                3220                3225

Ala Arg Ile Ser Gln Gly Ala Gly Trp Ser Leu Arg Glu Thr Ala
    3230                3235                3240

Cys Leu Gly Lys Ser Tyr Ala Gln Met Trp Ser Leu Met Tyr Phe
    3245                3250                3255

His Arg Arg Asp Leu Arg Leu Ala Ala Asn Ala Ile Cys Ser Ala
    3260                3265                3270

Val Pro Ser His Trp Val Pro Thr Ser Arg Thr Thr Trp Ser Ile
    3275                3280                3285

His Ala Lys His Glu Trp Met Thr Thr Glu Asp Met Leu Thr Val
    3290                3295                3300

Trp Asn Arg Val Trp Ile Gln Glu Asn Pro Trp Met Glu Asp Lys
    3305                3310                3315

Thr Pro Val Glu Ser Trp Glu Glu Ile Pro Tyr Leu Gly Lys Arg
    3320                3325                3330

Glu Asp Gln Trp Cys Gly Ser Leu Ile Gly Leu Thr Ser Arg Ala
    3335                3340                3345

Thr Trp Ala Lys Asn Ile Gln Ala Ala Ile Asn Gln Val Arg Ser
    3350                3355                3360

Leu Ile Gly Asn Glu Glu Tyr Thr Asp Tyr Met Pro Ser Met Lys
    3365                3370                3375

Arg Phe Arg Arg Glu Glu Glu Ala Gly Val Leu Trp
    3380                3385                3390

<210> SEQ ID NO 5
<211> LENGTH: 10717
<212> TYPE: DNA
<213> ORGANISM: Artificial Sequence
<220> FEATURE:
<223> OTHER INFORMATION: Chimeric Dengue Serotype 2/3 (MVS)

<400> SEQUENCE: 5
agttgttagt ctacgtggac cgacaaagac agattctttg agggagctaa gctcaatgta     60
gttctaacag tttttttaatt agagagcaga tctctgatga ataaccaacg gaaaaaggcg    120
aaaaacacgc ctttcaatat gctgaaacgc gagagaaacc gcgtgtcgac tgtgcaacag   180
ctgacaaaga gattctcact tggaatgctg caggacgag gaccattaaa actgttcatg    240 gcccctggtgg cgttccttcg tttcctaaca atcccaccaa cagcagggat attgaagaga   300 tgggggaacaa ttaaaaaatc aaaagctatt aatgtttgta gagggttcag gaaagagatt   360

```
ggaaggatgc tgaacatctt gaataggaga cgcagatctg caggcatgat cattatgctg    420
attccaacag tgatggcgtt ccatttaacc acgcgtgatg gagagccgcg catgattgtg    480
gggaagaatg aaagaggaaa atccctactt ttcaagacag cctctggaat caacatgtgc    540
acactcatag ctatggatct gggagagatg tgtgatgaca cggtcactta caaatgcccc    600
cacattaccg aagtggagcc tgaagacatt gactgctggt gcaaccttac atcgacatgg    660
gtgacttatg aacatgcaa tcaagctgga gagcatagac gcgataagag atcagtggcg    720
ttagctcccc atgttggcat gggactggac acacgcactc aaacctggat gtcggctgaa    780
ggagcttgga gacaagtcga gaaggtagag acatgggccc ttaggcaccc agggtttacc    840
atactagccc tatttcttgc ccattacata ggcacttcct tgacccagaa agtggttatt    900
tttatactat taatgctggt taccccatcc atgacaatga gatgtgtagg agtaggaaac    960
agagattttg tggaaggcct atcgggagct acgtgggttg acgtggtgct cgagcacggt   1020
gggtgtgtga ctaccatggc taagaacaag cccacgctgg acatagagct tcagaagacc   1080
gaggccaccc aactggcgac cctaaggaag ctatgcatta gggaaaaat taccaacata   1140 acaaccgact caagatgtcc cacccaaggg gaagcgattt tacctgagga gcaggaccag   1200
aactacgtgt gtaagcatac atacgtggac agaggctggg gaaacggttg tggtttgttt   1260
ggcaagggaa gcttggtgac atgcgcgaaa tttcaatgtt tagaatcaat agagggaaaa   1320
gtggtgcaac atgagaacct caaatacacc gtcatcatca cagtgcacac aggagaccaa   1380
caccaggtgg gaaatgaaac gcagggagtc acggctgaga taacaccccca ggcatcaacc   1440 gctgaagcca ttttacctga atatggaacc ctcgggctag aatgctcacc acggacaggt   1500
ttggatttca atgaaatgat ctcattgaca atgaagaaca agcatggat ggtacataga   1560 caatggttct ttgacttacc cctaccatgg acatcaggag cttcagcaga acaccaact   1620 tggaacagga aagagcttct tgtgacattt aaaaatgcac atgcaaaaaa gcaagaagta   1680
gttgttcttg gatcacaaga gggagcaatg catacagcac tgacaggagc tacagagatc   1740
caaacctcag gaggcacaag tatctttgcg gggcacttaa aatgtagact caagatggac   1800
aaattggaac tcaaggggat gagctatgca atgtgcttga gtagctttgt gttgaagaaa   1860
gaagtctccg aaacgcagca tgggacaata ctcattaagg ttgagtacaa aggggaagat   1920
gcaccctgca agattccttt ctccacggag gatggacaag gaaaagctct caatggcaga   1980
ctgatcacag ccaatccagt ggtgaccaag aaggaggagc ctgtcaacat tgaggctgaa   2040 cctcctttg gagaaagtaa catagtaatt ggaattggag acaaagccct gaaaatcaac   2100
tggtacaaga agggaagctc gattgggaag atgttcgagg ccactgccag aggtgcaagg   2160
cgcatggcca tcttgggaga cacagcctgg gactttggat cagtgggtgg tgtttttgaat   2220 tcattaggga aaatggtcca ccaaatattt gggagtgctt acacagccct atttggtgga   2280
gtctcctgga tgatgaaaat tggaataggt gtcctcttaa cctggatagg gttgaactca   2340
aaaaatactt ctatgtcatt ttcatgcatc gcggccggca ttgtgacact gtatttggga   2400
gtcatggtgc aggccgatag tggttgcgtt gtgagctgga aaaacaaaga actgaaatgt   2460
ggcagtggga ttttcatcac agacaacgtg cacacatgga cagaacaata caagttccaa   2520
ccagaatccc cttcaaaact agcttcagct atccagaaag cccatgaaga ggacatttgt   2580
ggaatccgct cagtaacaag actggagaat ctgatgtgga acaaataac accagaattg   2640 aatcacattc tatcagaaaa tgaggtgaag ttaactatta tgacaggaga catcaaagga   2700
atcatgcagg caggaaaacg atctctgcgg cctcagccca ctgagctgaa gtattcatgg   2760
```

```
aaaacatggg gcaaagcaaa aatgctctct acagagtctc ataaccagac ctttctcatt   2820
gatggcccg aaacagcaga atgccccaac acaaatagag cttggaattc gttggaagtt   2880
gaagactatg gctttggagt attcaccacc aatatatggc taaaattgaa agaaaaacag   2940
gatgtattct gcgactcaaa actcatgtca gcggccataa aagacaacag agccgtccat   3000
gccgatatgg gttattggat agaaagtgca ctcaatgaca catggaagat agagaaagcc   3060
tctttcattg aagttaaaaa ctgccactgg ccaaaatcac acaccctctg agcaatgga   3120
gtgctagaaa gtgagatgat aattccaaag aatctcgctg gaccagtgtc tcaacacaac   3180
tatagaccag gctaccatac acaaataaca ggaccatggc atctaggtaa gcttgagatg   3240
gactttgatt tctgtgatgg aacaacagtg gtagtgactg aggactgcgg aaatagagga   3300
ccctctttga gaacaaccac tgcctctgga aaactcataa cagaatggtg ctgccgatct   3360
tgcacattac caccgctaag atacagaggt gaggatgggt gctggtacgg gatggaaatc   3420
agaccattga aggagaaaga agagaatttg gtcaactcct tggtcacagc tggacatggg   3480
caggtcgaca acttttcact aggagtcttg ggaatggcat tgttcctgga ggaaatgctt   3540
aggacccgag taggaacgaa acatgcaata ctactagttg cagtttcttt tgtgacattg   3600
atcacaggga acatgtcctt tagagacctg ggaagagtga tggttatggt aggcgccact   3660
atgacggatg acataggtat gggcgtgact tatcttgccc tactagcagc cttcaaagtc   3720
agaccaactt ttgcagctgg actactcttg agaaagctga cctccaagga attgatgatg   3780
actactatag gaattgtact cctctcccag agcaccatac agagaccat tcttgagttg   3840
actgatgcgt tagccttagg catgatggtc ctcaaaatgg tgagaaatat ggaaaagtat   3900
caattggcag tgactatcat ggctatcttg tgcgtcccaa acgcagtgat attacaaaac   3960
gcatggaaag tgagttgcac aatattggca gtggtgtccg tttccccact gttcttaaca   4020
tcctcacagc aaaaaacaga ttggatacca ttagcattga cgatcaaagg tctcaatcca   4080
acagctattt ttctaacaac cctctcaaga accagcaaga aaaggagctg gccattaaat   4140
gaggctatca tggcagtcgg gatggtgagc attttagcca gttctctcct aaaaaatgat   4200
attcccatga caggaccatt agtggctgga gggctcctca ctgtgtgcta cgtgctcact   4260
ggacgatcgg ccgatttgga actggagaga gcagccgatg tcaaatggga agaccaggca   4320
gagatatcag gaagcagtcc aatcctgtca ataacaatat cagaagatgg tagcatgtcg   4380
ataaaaaatg aagaggaaga acaaacactg accatactca ttagaacagg attgctggtg   4440
atctcaggac ttttttcctgt atcaataccaa atcacgcag cagcatggta cctgtgggaa   4500
gtgaagaaac aacgggccgg agtattgtgg gatgttcctt caccccacc catgggaaag   4560
gctgaactgg aagatggagc ctatagaatt aagcaaaaag ggattcttgg atattcccag   4620
atcggagccg gagtttacaa agaaggaaca ttccatacaa tgtggcatgt cacacgtggc   4680
gctgttctaa tgcataaagg aaagaggatt gaaccatcat gggcggacgt caagaaagac   4740
ctaatatcat atggaggagg ctggaagtta gaaggagaat ggaaggaagg agaagaagtc   4800
caggtattgg cactggagcc tggaaaaaat ccaagagccg tccaaacgaa acctggtctt   4860
ttcaaaacca cgccggaac aataggtgct gtatctctgg acttttctcc tggaacgtca   4920
ggatctccaa ttatcgacaa aaaaggaaaa gttgtgggtc tttatggtaa tggtgttgtt   4980
acaaggagtg gagcatatgt gagtgctata gcccagacta aaaaaagcat tgaagacaac   5040
ccagagatcg aagatgacat tttccgaaag agaagactga ccatcatgga cctccaccca   5100
```

```
ggagcgggaa agacgaagag ataccttccg gccatagtca gagaagctat aaaacggggt   5160
ttgagaacat taatcttggc ccccactaga gttgtggcag ctgaaatgga ggaagccctt   5220
agaggacttc caataagata ccagacccca gccatcagag ctgtgcacac cgggcgggag   5280
attgtggacc taatgtgtca tgccacattt accatgaggc tgctatcacc agttagagtg   5340
ccaaactaca acctgattat catggacgaa gcccatttca cagacccagc aagtatagca   5400
gctagaggat acatctcaac tcgagtggag atgggtgagg cagctgggat ttttatgaca   5460
gccactcccc cgggaagcag agacccattt cctcagagca atgcaccaat catagatgaa   5520
gaaagagaaa tccctgaacg ctcgtggaat tccggacatg aatgggtcac ggattttaaa   5580
gggaagactg tttggttcgt tccaagtata aaagcaggaa atgatatagc agcttgcctg   5640
aggaaaaatg gaaagaaagt gatacaactc agtaggaaga cctttgattc tgagtatgtc   5700
aagactagaa ccaatgattg ggacttcgtg gttacaactg acatttcaga aatgggtgcc   5760
aatttcaagg ctgagagggt tatagacccc agacgctgca tgaaaccagt catactaaca   5820
gatggtgaag agcgggtgat tctggcagga cctatgccag tgacccactc tagtgcagca   5880
caaagaagag ggagaatagg aagaaatcca aaaatgaga atgaccagta catatacatg   5940
ggggaacctc tggaaaatga tgaagactgt gcacactgga agaagctaa aatgctccta   6000 gataacatca acacgccaga aggaatcatt cctagcatgt tcgaaccaga gcgtgaaaag   6060
gtggatgcca ttgatggcga ataccgcttg agaggagaag caaggaaaac ctttgtagac   6120
ttaatgagaa gaggagacct accagtctgg ttggcctaca gagtggcagc tgaaggcatc   6180
aactacgcag acagaaggtg gtgttttgat ggagtcaaga caaccaaat cctagaagaa   6240 aacgtggaag ttgaaatctg acaaaagaa ggggaaagga agaaattgaa acccagatgg   6300
ttggatgcta ggatctattc tgacccactg gcgctaaaag aatttaagga atttgcagcc   6360
ggaagaaagt ctctgacccc gaacctaatc acagaaatgg gtaggctccc aaccttcatg   6420
actcagaagg caagagacgc actggacaac ttagcagtgc tgcacacggc tgaggcaggt   6480
ggaagggcgt acaaccatgc tctcagtgaa ctgccggaga ccctggagac attgcttta   6540 ctgacacttc tggctacagt cacgggaggg atcttttat tcttgatgag cgcaaggggc   6600
atagggaaga tgaccctggg aatgtgctgc ataatcacgg ctagcatcct cctatggtac   6660
gcacaaatac agccacactg gatagcagct caataatac tggagttttt tctcatagtt   6720
ttgcttattc cagaacctga aaaacagaga acaccccaag caaccaact gacctacgtt   6780 gtcatagcca tcctcacagt ggtggccgca accatggcaa acgagatggg tttcctagaa   6840
aaaacgaaga aagatctcgg attgggaagc attgcaaccc agcaacccga gagcaacatc   6900
ctggacatag atctacgtcc tgcatcagca tggacgctgt atgccgtggc cacaacattt   6960
gttacaccaa tgttgagaca tagcattgaa aattcctcag tgaatgtgtc cctaacagct   7020
atagccaacc aagccacagt gttaatgggt ctcgggaaag gatggccatt gtcaaagatg   7080
gacatcggag ttccccttct cgccattgga tgctactcac aagtcaaccc cataactctc   7140
acagcagctc ttttcttatt ggtagcacat tatgccatca tagggccagg actccaagca   7200
aaagcaacca gagaagctca gaaaagagca gcggcgggca tcatgaaaaa cccaactgtc   7260
gatggaataa cagtgattga cctagatcca ataccttatg atccaaagtt tgaaaagcag   7320
ttgggacaag taatgctcct agtcctctgc gtgactcaag tattgatgat gaggactaca   7380
tgggctctgt gtgaggcttt aaccttagct accgggccca tctccacatt gtgggaagga   7440
aatccaggga ggttttggaa cactaccatt gcggtgtcaa tggctaacat ttttagaggg   7500
```

```
agttacttgg ccggagctgg acttctcttt tctattatga agaacacaac caacacaaga    7560
aggggaactg gcaacatagg agagacgctt ggagagaaat ggaaaagccg attgaacgcg    7620
ttgggaaaaa gtgaattcca gatctacaag aaaagtggaa tccaggaagt ggatagaacc    7680
ttagcaaaag aaggcattaa aagaggagaa acgaccatc acgctgtgtc gcgaggctca     7740
gcaaaactga gatggttcgt tgagagaaac atggtcacac cagaagggaa agtagtggac    7800
ctcggttgtg gcagaggagg ctggtcatac tattgtggag gactaaagaa tgtaagagaa    7860
gtcaaaggcc taacaaaagg aggaccagga cacgaagaac ccatccccat gtcaacatat    7920
gggtggaatc tagtgcgtct tcaaagtgga gttgacgttt tcttcatccc gccagaaaag    7980
tgtgacacat tattgtgtga cataggggag tcatcaccaa atcccacagt ggaagcagga    8040
cgaacactca gagtccttaa cttagtagaa aattggttga caacaacac tcaattttgc     8100 ataaaggttc tcaacccata tatgccctca gtcatagaaa aaatggaagc actacaaagg    8160
aaatatggag gagccttagt gaggaatcca ctctcacgaa actccacaca tgagatgtac    8220
tgggtatcca atgcttccgg gaacatagtg tcatcagtga acatgatttc aaggatgttg    8280
atcaacagat ttacaatgag atacaagaaa gccacttacg agccggatgt tgacctcgga    8340
agcggaaccc gtaacatcgg gattgaaagt gagataccaa acctagatat aattgggaaa    8400
agaatagaaa aaataaagca agagcatgaa acatcatggc actatgacca agaccaccca    8460
tacaaaacgt gggcatacca tggtagctat gaaacaaaac agactggatc agcatcatcc    8520
atggtcaacg gagtggtcag gctgctgaca aaaccttggg acgtcgtccc catggtgaca    8580
cagatggcaa tgacagacac gactccattt ggacaacagc gcgtttttaa agagaaagtg    8640
gacacgagaa cccaagaacc gaaagaaggc acgaagaaac taatgaaaat aacagcagag    8700
tggctttgga aagaattagg gaagaaaaag acacccagga tgtgcaccag agaagaattc    8760
acaagaaagg tgagaagcaa tgcagccttg ggggccatat tcactgatga gaacaagtgg    8820
aagtcggcac gtgaggctgt tgaagatagt aggttttggg agctggttga caaggaaagg    8880
aatctccatc ttgaaggaaa gtgtgaaaca tgtgtgtaca acatgatggg aaaaagagag    8940
aagaagctag gggaattcgg caaggcaaaa ggcagcagag ccatatggta catgtggctt    9000
ggagcacgct tcttagagtt tgaagcccta ggattcttaa atgaagatca ctggttctcc    9060
agagagaact ccctgagtgg agtggaagga gaagggctgc acaagctagg ttacattcta    9120
agagacgtga gcaagaaaga gggaggagca atgtatgccg atgacaccgc aggatgggat    9180
acaagaatca cactagaaga cctaaaaaat gaagaaatgg taacaaacca catggaagga    9240
gaacacaaga actagccga ggccattttc aaactaacgt accaaaacaa ggtggtgcgt     9300
gtgcaaagac caacaccaag aggcacagta atggacatca tatcgagaag agaccaaaga    9360
ggtagtggac aagttggcac ctatggactc aatacttca ccaatatgga agcccaacta     9420
atcagacaga tggagggaga aggagtcttt aaaagcattc agcacctaac aatcacagaa    9480
gaaatcgctg tgcaaaactg gttagcaaga gtggggcgcg aaaggttatc aagaatggcc    9540
atcagtggag atgattgtgt tgtgaaacct ttagatgaca ggttcgcaag cgctttaaca    9600
gctctaaatg acatgggaaa gattaggaaa gacatacaac aatgggaacc ttcaagagga    9660
tggaatgatt ggacacaagt gcccttctgt tcacaccatt tccatgagtt aatcatgaaa    9720
gacggtcgcg tactcgttgt tccatgtaga aaccaagatg aactgattgg cagagcccga    9780
atctcccaag gagcagggtg gtctttgcgg gagacggcct gtttggggaa gtcttacgcc    9840
```

-continued

```
caaatgtgga gcttgatgta cttccacaga cgcgacctca ggctggcggc aaatgctatt    9900
tgctcggcag taccatcaca ttgggttcca acaagtcgaa caacctggtc catacatgct    9960
aaacatgaat ggatgacaac ggaagacatg ctgacagtct ggaacagggt gtggattcaa   10020
gaaaacccat ggatggaaga caaaactcca gtggaatcat gggaggaaat cccatacttg   10080
gggaaaagag aagaccaatg gtgcggctca ttgattgggt taacaagcag ggccacctgg   10140
gcaaagaaca tccaagcagc aataaatcaa gttagatccc ttataggcaa tgaagaatac   10200
acagattaca tgccatccat gaaaagattc agaagagaag aggaagaagc aggagttctg   10260
tggtagaaag caaaactaac atgaaacaag gctagaagtc aggtcggatt aagccatagt   10320
acggaaaaaa ctatgctacc tgtgagcccc gtccaaggac gttaaaagaa gtcaggccat   10380
cataaatgcc atagcttgag taaactatgc agcctgtagc tccacctgag aaggtgtaaa   10440
aaatccggga ggccacaaac catggaagct gtacgcatgg cgtagtggac tagcggttag   10500
aggagacccc tcccttacaa atcgcagcaa caatgggggc ccaaggcgag atgaagctgt   10560
agtctcgctg gaaggactag aggttagagg agacccccccc gaaacaaaaa acagcatatt   10620
gacgctggga aagaccagag atcctgctgt ctcctcagca tcattccagg cacagaacgc   10680
cagaaaatgg aatggtgctg ttgaatcaac aggttct                            10717
```

<210> SEQ ID NO 6
<211> LENGTH: 3389
<212> TYPE: PRT
<213> ORGANISM: Artificial Sequence
<220> FEATURE:
<223> OTHER INFORMATION: Chimeric Dengue Serotype 2/3 (MVS)

<400> SEQUENCE: 6

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro His Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205
```

-continued

| | | | | | | | | | | | | |
|---|---|---|---|---|---|---|---|---|---|---|---|---|
|Leu|Ala|Pro|His|Val|Gly|Met|Gly|Leu|Asp|Thr|Arg|Thr Gln Thr Trp|
| |210| | | |215| | | |220| | | |
|Met|Ser|Ala|Glu|Gly|Ala|Trp|Arg|Gln|Val|Glu|Lys|Val Glu Thr Trp|
|225| | | |230| | | |235| | | |240|
|Ala|Leu|Arg|His|Pro|Gly|Phe|Thr|Ile|Leu|Ala|Leu|Phe Leu Ala His|
| | | |245| | | |250| | | |255| |
|Tyr|Ile|Gly|Thr|Ser|Leu|Thr|Gln|Lys|Val|Val|Ile|Phe Ile Leu Leu|
| | |260| | | |265| | | |270| | |
|Met|Leu|Val|Thr|Pro|Ser|Met|Thr|Met|Arg|Cys|Val|Gly Val Gly Asn|
| |275| | | |280| | | |285| | | |
|Arg|Asp|Phe|Val|Glu|Gly|Leu|Ser|Gly|Ala|Thr|Trp|Val Asp Val Val|
|290| | | |295| | | |300| | | | |
|Leu|Glu|His|Gly|Gly|Cys|Val|Thr|Thr|Met|Ala|Lys|Asn Lys Pro Thr|
|305| | | |310| | | |315| | | |320|
|Leu|Asp|Ile|Glu|Leu|Gln|Lys|Thr|Glu|Ala|Thr|Gln|Leu Ala Thr Leu|
| | | |325| | | |330| | | |335| |
|Arg|Lys|Leu|Cys|Ile|Glu|Gly|Lys|Ile|Thr|Asn|Ile|Thr Thr Asp Ser|
| | |340| | | |345| | | |350| | |
|Arg|Cys|Pro|Thr|Gln|Gly|Glu|Ala|Ile|Leu|Pro|Glu|Glu Gln Asp Gln|
| |355| | | |360| | | |365| | | |
|Asn|Tyr|Val|Cys|Lys|His|Thr|Tyr|Val|Asp|Arg|Gly|Trp Gly Asn Gly|
|370| | | |375| | | |380| | | | |
|Cys|Gly|Leu|Phe|Gly|Lys|Gly|Ser|Leu|Val|Thr|Cys|Ala Lys Phe Gln|
|385| | | |390| | | |395| | | |400|
|Cys|Leu|Glu|Ser|Ile|Glu|Gly|Lys|Val|Val|Gln|His|Glu Asn Leu Lys|
| | | |405| | | |410| | | |415| |
|Tyr|Thr|Val|Ile|Ile|Thr|Val|His|Thr|Gly|Asp|Gln|His Gln Val Gly|
| | |420| | | |425| | | |430| | |
|Asn|Glu|Thr|Gln|Gly|Val|Thr|Ala|Glu|Ile|Thr|Pro|Gln Ala Ser Thr|
| |435| | | |440| | | |445| | | |
|Ala|Glu|Ala|Ile|Leu|Pro|Glu|Tyr|Gly|Thr|Leu|Gly|Leu Glu Cys Ser|
|450| | | |455| | | |460| | | | |
|Pro|Arg|Thr|Gly|Leu|Asp|Phe|Asn|Glu|Met|Ile|Ser|Leu Thr Met Lys|
|465| | | |470| | | |475| | | |480|
|Asn|Lys|Ala|Trp|Met|Val|His|Arg|Gln|Trp|Phe|Phe|Asp Leu Pro Leu|
| | | |485| | | |490| | | |495| |
|Pro|Trp|Thr|Ser|Gly|Ala|Ser|Ala|Glu|Thr|Pro|Thr|Trp Asn Arg Lys|
| | |500| | | |505| | | |510| | |
|Glu|Leu|Leu|Val|Thr|Phe|Lys|Asn|Ala|His|Ala|Lys|Lys Gln Glu Val|
| |515| | | |520| | | |525| | | |
|Val|Val|Leu|Gly|Ser|Gln|Glu|Gly|Ala|Met|His|Thr|Ala Leu Thr Gly|
|530| | | |535| | | |540| | | | |
|Ala|Thr|Glu|Ile|Gln|Thr|Ser|Gly|Gly|Thr|Ser|Ile|Phe Ala Gly His|
|545| | | |550| | | |555| | | |560|
|Leu|Lys|Cys|Arg|Leu|Lys|Met|Asp|Lys|Leu|Glu|Leu|Lys Gly Met Ser|
| | | |565| | | |570| | | |575| |
|Tyr|Ala|Met|Cys|Leu|Ser|Ser|Phe|Val|Leu|Lys|Lys|Glu Val Ser Glu|
| | |580| | | |585| | | |590| | |
|Thr|Gln|His|Gly|Thr|Ile|Leu|Ile|Lys|Val|Glu|Tyr|Lys Gly Glu Asp|
| |595| | | |600| | | |605| | | |
|Ala|Pro|Cys|Lys|Ile|Pro|Phe|Ser|Thr|Glu|Asp|Gly|Gln Gly Lys Ala|
|610| | | |615| | | |620| | | | |
|Leu|Asn|Gly|Arg|Leu|Ile|Thr|Ala|Asn|Pro|Val|Val|Thr Lys Lys Glu|

```
                625                 630                 635                 640
        Glu Pro Val Asn Ile Glu Ala Glu Pro Pro Phe Gly Glu Ser Asn Ile
                        645                 650                 655

Val Ile Gly Ile Gly Asp Lys Ala Leu Lys Ile Asn Trp Tyr Lys Lys
                        660                 665                 670

Gly Ser Ser Ile Gly Lys Met Phe Glu Ala Thr Ala Arg Gly Ala Arg
                        675                 680                 685

Arg Met Ala Ile Leu Gly Asp Thr Ala Trp Asp Phe Gly Ser Val Gly
        690                 695                 700

Gly Val Leu Asn Ser Leu Gly Lys Met Val His Gln Ile Phe Gly Ser
        705                 710                 715                 720

Ala Tyr Thr Ala Leu Phe Gly Gly Val Ser Trp Met Met Lys Ile Gly
                        725                 730                 735

Ile Gly Val Leu Leu Thr Trp Ile Gly Leu Asn Ser Lys Asn Thr Ser
                        740                 745                 750

Met Ser Phe Ser Cys Ile Ala Ala Gly Ile Val Thr Leu Tyr Leu Gly
                        755                 760                 765

Val Met Val Gln Ala Asp Ser Gly Cys Val Val Ser Trp Lys Asn Lys
        770                 775                 780

Glu Leu Lys Cys Gly Ser Gly Ile Phe Ile Thr Asp Asn Val His Thr
        785                 790                 795                 800

Trp Thr Glu Gln Tyr Lys Phe Gln Pro Glu Ser Pro Ser Lys Leu Ala
                        805                 810                 815

Ser Ala Ile Gln Lys Ala His Glu Glu Asp Ile Cys Gly Ile Arg Ser
                        820                 825                 830

Val Thr Arg Leu Glu Asn Leu Met Trp Lys Gln Ile Thr Pro Glu Leu
                        835                 840                 845

Asn His Ile Leu Ser Glu Asn Glu Val Lys Leu Thr Ile Met Thr Gly
        850                 855                 860

Asp Ile Lys Gly Ile Met Gln Ala Gly Lys Arg Ser Leu Arg Pro Gln
        865                 870                 875                 880

Pro Thr Glu Leu Lys Tyr Ser Trp Lys Thr Trp Gly Lys Ala Lys Met
                        885                 890                 895

Leu Ser Thr Glu Ser His Asn Gln Thr Phe Leu Ile Asp Gly Pro Glu
                        900                 905                 910

Thr Ala Glu Cys Pro Asn Thr Asn Arg Ala Trp Asn Ser Leu Glu Val
                        915                 920                 925

Glu Asp Tyr Gly Phe Gly Val Phe Thr Thr Asn Ile Trp Leu Lys Leu
        930                 935                 940

Lys Glu Lys Gln Asp Val Phe Cys Asp Ser Lys Leu Met Ser Ala Ala
        945                 950                 955                 960

Ile Lys Asp Asn Arg Ala Val His Ala Asp Met Gly Tyr Trp Ile Glu
                        965                 970                 975

Ser Ala Leu Asn Asp Thr Trp Lys Ile Glu Lys Ala Ser Phe Ile Glu
                        980                 985                 990

Val Lys Asn Cys His Trp Pro Lys Ser His Thr Leu Trp Ser Asn Gly
                        995                1000                1005

Val Leu Glu Ser Glu Met Ile Ile Pro Lys Asn Leu Ala Gly Pro
                       1010                1015                1020

Val Ser Gln His Asn Tyr Arg Pro Gly Tyr His Thr Gln Ile Thr
                       1025                1030                1035

Gly Pro Trp His Leu Gly Lys Leu Glu Met Asp Phe Asp Phe Cys
                       1040                1045                1050
```

-continued

Asp Gly Thr Thr Val Val Thr Glu Asp Cys Gly Asn Arg Gly
    1055            1060             1065

Pro Ser Leu Arg Thr Thr Ala Ser Gly Lys Leu Ile Thr Glu
    1070            1075             1080

Trp Cys Cys Arg Ser Cys Thr Leu Pro Pro Leu Arg Tyr Arg Gly
    1085            1090             1095

Glu Asp Gly Cys Trp Tyr Gly Met Glu Ile Arg Pro Leu Lys Glu
    1100            1105             1110

Lys Glu Glu Asn Leu Val Asn Ser Leu Val Thr Ala Gly His Gly
    1115            1120             1125

Gln Val Asp Asn Phe Ser Leu Gly Val Leu Gly Met Ala Leu Phe
    1130            1135             1140

Leu Glu Glu Met Leu Arg Thr Arg Val Gly Thr Lys His Ala Ile
    1145            1150             1155

Leu Leu Val Ala Val Ser Phe Val Thr Leu Ile Thr Gly Asn Met
    1160            1165             1170

Ser Phe Arg Asp Leu Gly Arg Val Met Val Met Val Gly Ala Thr
    1175            1180             1185

Met Thr Asp Asp Ile Gly Met Gly Val Thr Tyr Leu Ala Leu Leu
    1190            1195             1200

Ala Ala Phe Lys Val Arg Pro Thr Phe Ala Ala Gly Leu Leu Leu
    1205            1210             1215

Arg Lys Leu Thr Ser Lys Glu Leu Met Met Thr Thr Ile Gly Ile
    1220            1225             1230

Val Leu Leu Ser Gln Ser Thr Ile Pro Glu Thr Ile Leu Glu Leu
    1235            1240             1245

Thr Asp Ala Leu Ala Leu Gly Met Met Val Leu Lys Met Val Arg
    1250            1255             1260

Asn Met Glu Lys Tyr Gln Leu Ala Val Thr Ile Met Ala Ile Leu
    1265            1270             1275

Cys Val Pro Asn Ala Val Ile Leu Gln Asn Ala Trp Lys Val Ser
    1280            1285             1290

Cys Thr Ile Leu Ala Val Val Ser Val Ser Pro Leu Phe Leu Thr
    1295            1300             1305

Ser Ser Gln Gln Lys Thr Asp Trp Ile Pro Leu Ala Leu Thr Ile
    1310            1315             1320

Lys Gly Leu Asn Pro Thr Ala Ile Phe Leu Thr Thr Leu Ser Arg
    1325            1330             1335

Thr Ser Lys Lys Arg Ser Trp Pro Leu Asn Glu Ala Ile Met Ala
    1340            1345             1350

Val Gly Met Val Ser Ile Leu Ala Ser Ser Leu Leu Lys Asn Asp
    1355            1360             1365

Ile Pro Met Thr Gly Pro Leu Val Ala Gly Gly Leu Leu Thr Val
    1370            1375             1380

Cys Tyr Val Leu Thr Gly Arg Ser Ala Asp Leu Glu Leu Glu Arg
    1385            1390             1395

Ala Ala Asp Val Lys Trp Glu Asp Gln Ala Glu Ile Ser Gly Ser
    1400            1405             1410

Ser Pro Ile Leu Ser Ile Thr Ile Ser Glu Asp Gly Ser Met Ser
    1415            1420             1425

Ile Lys Asn Glu Glu Glu Glu Gln Thr Leu Thr Ile Leu Ile Arg
    1430            1435             1440

```
Thr Gly Leu Leu Val Ile Ser Gly Leu Phe Pro Val Ser Ile Pro
    1445                1450                1455

Ile Thr Ala Ala Ala Trp Tyr Leu Trp Glu Val Lys Lys Gln Arg
    1460                1465                1470

Ala Gly Val Leu Trp Asp Val Pro Ser Pro Pro Met Gly Lys
    1475                1480                1485

Ala Glu Leu Glu Asp Gly Ala Tyr Arg Ile Lys Gln Lys Gly Ile
    1490                1495                1500

Leu Gly Tyr Ser Gln Ile Gly Ala Gly Val Tyr Lys Glu Gly Thr
    1505                1510                1515

Phe His Thr Met Trp His Val Thr Arg Gly Ala Val Leu Met His
    1520                1525                1530

Lys Gly Lys Arg Ile Glu Pro Ser Trp Ala Asp Val Lys Lys Asp
    1535                1540                1545

Leu Ile Ser Tyr Gly Gly Gly Trp Lys Leu Glu Gly Glu Trp Lys
    1550                1555                1560

Glu Gly Glu Glu Val Gln Val Leu Ala Leu Glu Pro Gly Lys Asn
    1565                1570                1575

Pro Arg Ala Val Gln Thr Lys Pro Gly Leu Phe Lys Thr Asn Ala
    1580                1585                1590

Gly Thr Ile Gly Ala Val Ser Leu Asp Phe Ser Pro Gly Thr Ser
    1595                1600                1605

Gly Ser Pro Ile Ile Asp Lys Lys Gly Lys Val Val Gly Leu Tyr
    1610                1615                1620

Gly Asn Gly Val Val Thr Arg Ser Gly Ala Tyr Val Ser Ala Ile
    1625                1630                1635

Ala Gln Thr Glu Lys Ser Ile Glu Asp Asn Pro Glu Ile Glu Asp
    1640                1645                1650

Asp Ile Phe Arg Lys Arg Arg Leu Thr Ile Met Asp Leu His Pro
    1655                1660                1665

Gly Ala Gly Lys Thr Lys Arg Tyr Leu Pro Ala Ile Val Arg Glu
    1670                1675                1680

Ala Ile Lys Arg Gly Leu Arg Thr Leu Ile Leu Ala Pro Thr Arg
    1685                1690                1695

Val Val Ala Ala Glu Met Glu Glu Ala Leu Arg Gly Leu Pro Ile
    1700                1705                1710

Arg Tyr Gln Thr Pro Ala Ile Arg Ala Val His Thr Gly Arg Glu
    1715                1720                1725

Ile Val Asp Leu Met Cys His Ala Thr Phe Thr Met Arg Leu Leu
    1730                1735                1740

Ser Pro Val Arg Val Pro Asn Tyr Asn Leu Ile Ile Met Asp Glu
    1745                1750                1755

Ala His Phe Thr Asp Pro Ala Ser Ile Ala Ala Arg Gly Tyr Ile
    1760                1765                1770

Ser Thr Arg Val Glu Met Gly Glu Ala Ala Gly Ile Phe Met Thr
    1775                1780                1785

Ala Thr Pro Pro Gly Ser Arg Asp Pro Phe Pro Gln Ser Asn Ala
    1790                1795                1800

Pro Ile Ile Asp Glu Glu Arg Glu Ile Pro Glu Arg Ser Trp Asn
    1805                1810                1815

Ser Gly His Glu Trp Val Thr Asp Phe Lys Gly Lys Thr Val Trp
    1820                1825                1830

Phe Val Pro Ser Ile Lys Ala Gly Asn Asp Ile Ala Ala Cys Leu
```

```
            1835                1840                1845

Arg Lys Asn Gly Lys Lys Val Ile Gln Leu Ser Arg Lys Thr Phe
            1850                1855                1860

Asp Ser Glu Tyr Val Lys Thr Arg Thr Asn Asp Trp Asp Phe Val
            1865                1870                1875

Val Thr Thr Asp Ile Ser Glu Met Gly Ala Asn Phe Lys Ala Glu
            1880                1885                1890

Arg Val Ile Asp Pro Arg Arg Cys Met Lys Pro Val Ile Leu Thr
            1895                1900                1905

Asp Gly Glu Glu Arg Val Ile Leu Ala Gly Pro Met Pro Val Thr
            1910                1915                1920

His Ser Ser Ala Ala Gln Arg Arg Gly Arg Ile Gly Arg Asn Pro
            1925                1930                1935

Lys Asn Glu Asn Asp Gln Tyr Ile Tyr Met Gly Glu Pro Leu Glu
            1940                1945                1950

Asn Asp Glu Asp Cys Ala His Trp Lys Glu Ala Lys Met Leu Leu
            1955                1960                1965

Asp Asn Ile Asn Thr Pro Glu Gly Ile Ile Pro Ser Met Phe Glu
            1970                1975                1980

Pro Glu Arg Glu Lys Val Asp Ala Ile Asp Gly Glu Tyr Arg Leu
            1985                1990                1995

Arg Gly Glu Ala Arg Lys Thr Phe Val Asp Leu Met Arg Arg Gly
            2000                2005                2010

Asp Leu Pro Val Trp Leu Ala Tyr Arg Val Ala Ala Glu Gly Ile
            2015                2020                2025

Asn Tyr Ala Asp Arg Arg Trp Cys Phe Asp Gly Val Lys Asn Asn
            2030                2035                2040

Gln Ile Leu Glu Glu Asn Val Glu Val Glu Ile Trp Thr Lys Glu
            2045                2050                2055

Gly Glu Arg Lys Lys Leu Lys Pro Arg Trp Leu Asp Ala Arg Ile
            2060                2065                2070

Tyr Ser Asp Pro Leu Ala Leu Lys Glu Phe Lys Glu Phe Ala Ala
            2075                2080                2085

Gly Arg Lys Ser Leu Thr Leu Asn Leu Ile Thr Glu Met Gly Arg
            2090                2095                2100

Leu Pro Thr Phe Met Thr Gln Lys Ala Arg Asp Ala Leu Asp Asn
            2105                2110                2115

Leu Ala Val Leu His Thr Ala Glu Ala Gly Gly Arg Ala Tyr Asn
            2120                2125                2130

His Ala Leu Ser Glu Leu Pro Glu Thr Leu Glu Thr Leu Leu Leu
            2135                2140                2145

Leu Thr Leu Leu Ala Thr Val Thr Gly Gly Ile Phe Leu Phe Leu
            2150                2155                2160

Met Ser Ala Arg Gly Ile Gly Lys Met Thr Leu Gly Met Cys Cys
            2165                2170                2175

Ile Ile Thr Ala Ser Ile Leu Leu Trp Tyr Ala Gln Ile Gln Pro
            2180                2185                2190

His Trp Ile Ala Ala Ser Ile Ile Leu Glu Phe Phe Leu Ile Val
            2195                2200                2205

Leu Leu Ile Pro Glu Pro Glu Lys Gln Arg Thr Pro Gln Asp Asn
            2210                2215                2220

Gln Leu Thr Tyr Val Val Ile Ala Ile Leu Thr Val Val Ala Ala
            2225                2230                2235
```

-continued

Thr Met Ala Asn Glu Met Gly Phe Leu Glu Lys Thr Lys Lys Asp
2240                2245                2250

Leu Gly Leu Gly Ser Ile Ala Thr Gln Gln Pro Glu Ser Asn Ile
2255                2260                2265

Leu Asp Ile Asp Leu Arg Pro Ala Ser Ala Trp Thr Leu Tyr Ala
2270                2275                2280

Val Ala Thr Thr Phe Val Thr Pro Met Leu Arg His Ser Ile Glu
2285                2290                2295

Asn Ser Ser Val Asn Val Ser Leu Thr Ala Ile Ala Asn Gln Ala
2300                2305                2310

Thr Val Leu Met Gly Leu Gly Lys Gly Trp Pro Leu Ser Lys Met
2315                2320                2325

Asp Ile Gly Val Pro Leu Leu Ala Ile Gly Cys Tyr Ser Gln Val
2330                2335                2340

Asn Pro Ile Thr Leu Thr Ala Ala Leu Phe Leu Leu Val Ala His
2345                2350                2355

Tyr Ala Ile Ile Gly Pro Gly Leu Gln Ala Lys Ala Thr Arg Glu
2360                2365                2370

Ala Gln Lys Arg Ala Ala Ala Gly Ile Met Lys Asn Pro Thr Val
2375                2380                2385

Asp Gly Ile Thr Val Ile Asp Leu Asp Pro Ile Pro Tyr Asp Pro
2390                2395                2400

Lys Phe Glu Lys Gln Leu Gly Gln Val Met Leu Leu Val Leu Cys
2405                2410                2415

Val Thr Gln Val Leu Met Met Arg Thr Thr Trp Ala Leu Cys Glu
2420                2425                2430

Ala Leu Thr Leu Ala Thr Gly Pro Ile Ser Thr Leu Trp Glu Gly
2435                2440                2445

Asn Pro Gly Arg Phe Trp Asn Thr Thr Ile Ala Val Ser Met Ala
2450                2455                2460

Asn Ile Phe Arg Gly Ser Tyr Leu Ala Gly Ala Gly Leu Leu Phe
2465                2470                2475

Ser Ile Met Lys Asn Thr Thr Asn Thr Arg Arg Gly Thr Gly Asn
2480                2485                2490

Ile Gly Glu Thr Leu Gly Glu Lys Trp Lys Ser Arg Leu Asn Ala
2495                2500                2505

Leu Gly Lys Ser Glu Phe Gln Ile Tyr Lys Lys Ser Gly Ile Gln
2510                2515                2520

Glu Val Asp Arg Thr Leu Ala Lys Glu Gly Ile Lys Arg Gly Glu
2525                2530                2535

Thr Asp His His Ala Val Ser Arg Gly Ser Ala Lys Leu Arg Trp
2540                2545                2550

Phe Val Glu Arg Asn Met Val Thr Pro Glu Gly Lys Val Val Asp
2555                2560                2565

Leu Gly Cys Gly Arg Gly Gly Trp Ser Tyr Tyr Cys Gly Gly Leu
2570                2575                2580

Lys Asn Val Arg Glu Val Lys Gly Leu Thr Lys Gly Gly Pro Gly
2585                2590                2595

His Glu Glu Pro Ile Pro Met Ser Thr Tyr Gly Trp Asn Leu Val
2600                2605                2610

Arg Leu Gln Ser Gly Val Asp Val Phe Phe Ile Pro Pro Glu Lys
2615                2620                2625

```
Cys Asp Thr Leu Leu Cys Asp Ile Gly Glu Ser Ser Pro Asn Pro
2630                2635                2640

Thr Val Glu Ala Gly Arg Thr Leu Arg Val Leu Asn Leu Val Glu
2645                2650                2655

Asn Trp Leu Asn Asn Thr Gln Phe Cys Ile Lys Val Leu Asn
2660                2665                2670

Pro Tyr Met Pro Ser Val Ile Glu Lys Met Glu Ala Leu Gln Arg
2675                2680                2685

Lys Tyr Gly Gly Ala Leu Val Arg Asn Pro Leu Ser Arg Asn Ser
2690                2695                2700

Thr His Glu Met Tyr Trp Val Ser Asn Ala Ser Gly Asn Ile Val
2705                2710                2715

Ser Ser Val Asn Met Ile Ser Arg Met Leu Ile Asn Arg Phe Thr
2720                2725                2730

Met Arg Tyr Lys Lys Ala Thr Tyr Glu Pro Asp Val Asp Leu Gly
2735                2740                2745

Ser Gly Thr Arg Asn Ile Gly Ile Glu Ser Glu Ile Pro Asn Leu
2750                2755                2760

Asp Ile Ile Gly Lys Arg Ile Glu Lys Ile Lys Gln Glu His Glu
2765                2770                2775

Thr Ser Trp His Tyr Asp Gln Asp His Pro Tyr Lys Thr Trp Ala
2780                2785                2790

Tyr His Gly Ser Tyr Glu Thr Lys Gln Thr Gly Ser Ala Ser Ser
2795                2800                2805

Met Val Asn Gly Val Val Arg Leu Leu Thr Lys Pro Trp Asp Val
2810                2815                2820

Val Pro Met Val Thr Gln Met Ala Met Thr Asp Thr Thr Pro Phe
2825                2830                2835

Gly Gln Gln Arg Val Phe Lys Glu Lys Val Asp Thr Arg Thr Gln
2840                2845                2850

Glu Pro Lys Glu Gly Thr Lys Lys Leu Met Lys Ile Thr Ala Glu
2855                2860                2865

Trp Leu Trp Lys Glu Leu Gly Lys Lys Lys Thr Pro Arg Met Cys
2870                2875                2880

Thr Arg Glu Glu Phe Thr Arg Lys Val Arg Ser Asn Ala Ala Leu
2885                2890                2895

Gly Ala Ile Phe Thr Asp Glu Asn Lys Trp Lys Ser Ala Arg Glu
2900                2905                2910

Ala Val Glu Asp Ser Arg Phe Trp Glu Leu Val Asp Lys Glu Arg
2915                2920                2925

Asn Leu His Leu Glu Gly Lys Cys Glu Thr Cys Val Tyr Asn Met
2930                2935                2940

Met Gly Lys Arg Glu Lys Lys Leu Gly Glu Phe Gly Lys Ala Lys
2945                2950                2955

Gly Ser Arg Ala Ile Trp Tyr Met Trp Leu Gly Ala Arg Phe Leu
2960                2965                2970

Glu Phe Glu Ala Leu Gly Phe Leu Asn Glu Asp His Trp Phe Ser
2975                2980                2985

Arg Glu Asn Ser Leu Ser Gly Val Glu Gly Glu Gly Leu His Lys
2990                2995                3000

Leu Gly Tyr Ile Leu Arg Asp Val Ser Lys Lys Glu Gly Gly Ala
3005                3010                3015

Met Tyr Ala Asp Asp Thr Ala Gly Trp Asp Thr Arg Ile Thr Leu
```

```
            3020                    3025                    3030
Glu Asp Leu Lys Asn Glu Glu Met Val Thr Asn His Met Glu Gly
            3035                    3040                    3045
Glu His Lys Lys Leu Ala Glu Ala Ile Phe Lys Leu Thr Tyr Gln
            3050                    3055                    3060
Asn Lys Val Val Arg Val Gln Arg Pro Thr Pro Arg Gly Thr Val
            3065                    3070                    3075
Met Asp Ile Ile Ser Arg Arg Asp Gln Arg Gly Ser Gly Gln Val
            3080                    3085                    3090
Gly Thr Tyr Gly Leu Asn Thr Phe Thr Asn Met Glu Ala Gln Leu
            3095                    3100                    3105
Ile Arg Gln Met Glu Gly Glu Gly Val Phe Lys Ser Ile Gln His
            3110                    3115                    3120
Leu Thr Ile Thr Glu Glu Ile Ala Val Gln Asn Trp Leu Ala Arg
            3125                    3130                    3135
Val Gly Arg Glu Arg Leu Ser Arg Met Ala Ile Ser Gly Asp Asp
            3140                    3145                    3150
Cys Val Val Lys Pro Leu Asp Asp Arg Phe Ala Ser Ala Leu Thr
            3155                    3160                    3165
Ala Leu Asn Asp Met Gly Lys Ile Arg Lys Asp Ile Gln Gln Trp
            3170                    3175                    3180
Glu Pro Ser Arg Gly Trp Asn Asp Trp Thr Gln Val Pro Phe Cys
            3185                    3190                    3195
Ser His His Phe His Glu Leu Ile Met Lys Asp Gly Arg Val Leu
            3200                    3205                    3210
Val Val Pro Cys Arg Asn Gln Asp Glu Leu Ile Gly Arg Ala Arg
            3215                    3220                    3225
Ile Ser Gln Gly Ala Gly Trp Ser Leu Arg Glu Thr Ala Cys Leu
            3230                    3235                    3240
Gly Lys Ser Tyr Ala Gln Met Trp Ser Leu Met Tyr Phe His Arg
            3245                    3250                    3255
Arg Asp Leu Arg Leu Ala Ala Asn Ala Ile Cys Ser Ala Val Pro
            3260                    3265                    3270
Ser His Trp Val Pro Thr Ser Arg Thr Thr Trp Ser Ile His Ala
            3275                    3280                    3285
Lys His Glu Trp Met Thr Thr Glu Asp Met Leu Thr Val Trp Asn
            3290                    3295                    3300
Arg Val Trp Ile Gln Glu Asn Pro Trp Met Glu Asp Lys Thr Pro
            3305                    3310                    3315
Val Glu Ser Trp Glu Glu Ile Pro Tyr Leu Gly Lys Arg Glu Asp
            3320                    3325                    3330
Gln Trp Cys Gly Ser Leu Ile Gly Leu Thr Ser Arg Ala Thr Trp
            3335                    3340                    3345
Ala Lys Asn Ile Gln Ala Ala Ile Asn Gln Val Arg Ser Leu Ile
            3350                    3355                    3360
Gly Asn Glu Glu Tyr Thr Asp Tyr Met Pro Ser Met Lys Arg Phe
            3365                    3370                    3375
Arg Arg Glu Glu Glu Glu Ala Gly Val Leu Trp
            3380                    3385

<210> SEQ ID NO 7
<211> LENGTH: 10723
<212> TYPE: DNA
<213> ORGANISM: Artificial Sequence
```

<220> FEATURE:
<223> OTHER INFORMATION: Chimeric Dengue Serotype 2/4 (MVS)
<220> FEATURE:
<221> NAME/KEY: r
<222> LOCATION: (3773)..(3773)
<223> OTHER INFORMATION: a or g

<400> SEQUENCE: 7

| | | |
|---|---|---|
| agttgttagt ctacgtggac cgacaaagac agattctttg agggagctaa gctcaatgta | 60 |
| gttctaacag ttttttaatt agagagcaga tctctgatga ataaccaacg gaaaaaggcg | 120 |
| aaaaacacgc ctttcaatat gctgaaacgc gagagaaacc gcgtgtcgac tgtgcaacag | 180 |
| ctgacaaaga gattctcact tggaatgctg cagggacgag gaccttttaaa actgttcatg | 240 |
| gccctggtgg cgttccttcg tttcctaaca atcccaccaa cagcagggat attgaagaga | 300 |
| tggggaacaa ttaaaaaatc aaaagctatt aatgttttga gagggttcag gaagagatt | 360 |
| ggaaggatgc tgaacatctt gaataggaga cgcagctctg caggcatgat cattatgctg | 420 |
| attccaacag tgatggcgtt ccatttaacc acgcgtgatg gcgaaccct catgatagtg | 480 |
| gcaaaacatg aaaggggag acctctcttg tttaagacaa cagagggat caacaaatgc | 540 |
| actctcattg ccatggactt gggtgaaatg tgtgaggaca ctgtcacgta taatgcccc | 600 |
| ttactggtca ataccgaacc tgaagacatt gattgctggt gcaatctcac gtctacctgg | 660 |
| gtcatgtatg gacatgcac ccagagcgga gaacggagac gagagaagcg ctcagtagct | 720 |
| ttaacaccac attcaggaat gggattggaa caagagctg agacatggat gtcatcggaa | 780 |
| ggggcttgga agcatgctca gagagtagag agctggatac tcagaaaccc aggattcgcg | 840 |
| ctcttggcag gatttatggc ttatatgatt gggcaaacag gaatccagcg aactgtcttc | 900 |
| tttgtcctaa tgatgctggt cgccccatcc tacggaatgc gatgcgtagg agtaggaaac | 960 |
| agagactttg tggaaggagt ctcaggtgga gcatgggtcg atctggtgct agaacatgga | 1020 |
| ggatgcgtca caaccatggc ccagggaaaa ccaaccttgg atttgaact gactaagaca | 1080 |
| acagccaagg aagtggctct gttaagaacc tattgcattg aagcctcaat atcaaacata | 1140 |
| accacggcaa caagatgtcc aacgcaagga gagccttatc taaaagagga caagaccaa | 1200 |
| cagtacattt gccggagaga tgtggtagac agaggtgggg gcaatggctg tggcttgttt | 1260 |
| ggaaaaggag gagttgtgac atgtgcgaag ttttcatgtt cggggaagat aacaggcaat | 1320 |
| ttggtccaaa ttgagaacct tgaatacaca gtggttgtaa cagtcacaa tggagacacc | 1380 |
| catgcagtag gaaatgacac gtccaatcat ggagttacag ccacgataac tcccaggtca | 1440 |
| ccatcggtgg aagtcaaatt gccggactat ggagaactaa cactcgattg tgaacccagg | 1500 |
| tctggaattg actttaatga gatgattctg atgaaaatga aaagaaaac atggcttgtg | 1560 |
| cataagcaat ggttttttgga tctacctcta ccatggacag caggagcaga cacatcagag | 1620 |
| gttcactgga attacaaaga gagaatggtg acatttaagg ttcctcatgc caagagacag | 1680 |
| gatgtgacag tgctgggatc tcaggaagga gccatgcatt ctgccctcgc tggagccaca | 1740 |
| gaagtggact ccggtgatgg aaatcacatg tttgcaggac atctcaagtg caaagtccgt | 1800 |
| atggagaaat tgagaatcaa gggaatgtca tacacgatgt gttcaggaaa gttctcaatt | 1860 |
| gacaaagaga tggcagaaac acagcatggg acaacagtg tgaaagtcaa gtatgaaggt | 1920 |
| gctggagctc cgtgtaaagt ccccatagag ataagagatg tgaacaagga aaaagtggtt | 1980 |
| gggcgtatca tctcatccac ccctttggct gagaatacca acagtgtaac caacatagag | 2040 |
| ttagaaccccc cctttgggga cagctacata gtgataggtg ttggaaacag tgcattaaca | 2100 |

```
ctccattggt tcaggaaagg gagttccatt ggcaagatgt ttgagtccac atacagaggt    2160
gcaaaacgaa tggccattct aggtgaaaca gcttgggatt ttggttccgt tggtggactg    2220
ttcacatcat tgggaaaggc tgtgcaccag ttttttggaa gtgtgtatac aaccctgttt    2280
ggaggagtct catggatgat tagaatccta attgggttcc tagtgttgtg gattggcacg    2340
aactcaagga acacttcaat ggctatgacg tgcatagctg ccggcattgt gacactgtat    2400 ttggggtca tggtgcaggc cgatagtggt tgcgttgtga gctggaaaaa caaagaactg    2460
aaatgtggca gtgggatttt catcacagac aacgtgcaca catggacaga acaatacaag    2520
ttccaaccag aatccccttc aaaactagct tcagctatcc agaaagccca tgaagaggac    2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg gccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa aatcacacac cctctggagc    3120
aatggagtgc tagaaagtga gatgataatt ccaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct ctttgagaac aaccactgcc tctggaaaac tcataacaga atggtgctgc    3360
cgatcttgca cattaccacc gctaagatac agaggtgagg atgggtgctg gtacgggatg    3420
gaaatcagac cattgaagga aagaagag aatttggtca actccttggt cacagctgga    3480
catgggcagg tcgacaactt ttcactagga gtcttgggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggtgacat aggtatgggc gtgacttatc ttgccctact agcagccttc    3720
aaagtcagac caacttttgc agctggacta ctcttgagaa agctgacctc carggaattg    3780
atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atccttgtgc tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctattttct aacaaccctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctgagggc tcctcactgt gtgctacgtg    4260
ctcactggac gatcggccga tttggaactg gagagagcag ccgatgtcaa atgggaagac    4320
caggcagaga tatcaggaag cagtccaatc ctgtcaataa caatatcaga agatggtagc    4380
atgtcgataa aaaatgaaga ggaagaacaa acactgacca tactcattag aacaggattg    4440
ctggtgatct caggactttt tcctgtatca ataccaatca cggcagcagc atggtacctg    4500
```

```
tgggaagtga agaaacaacg ggccggagta ttgtgggatg ttccttcacc cccacccatg    4560
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaaggaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca acgaaacct    4860 ggtcttttca aaccaacgc cggaacaata ggtgctgtat ctctggactt ttctcctgga    4920
acgtcaggat ctccaattat cgacaaaaaa ggaaaagttg tgggtcttta tggtaatggt    4980
gttgttacaa ggagtggagc atatgtgagt gctatagccc agactgaaaa aagcattgaa    5040
gacaacccag atcgaagaa tgacattttc cgaaagagaa gactgaccat catggacctc    5100
cacccaggag cgggaaagac gaagagatac cttccggcca tagtcagaga agctataaaa    5160
cggggtttga gaacattaat cttggccccc actagagttg tggcagctga aatggaggaa    5220
gcccttagag gacttccaat aagataccag accccagcca tcagagctgt gcacaccggg    5280
cgggagattg tggacctaat gtgtcatgcc acatttacca tgaggctgct atcaccagtt    5340
agagtgccaa actcaaacct gattatcatg gacgaagccc atttcacaga tccagcaagt    5400
atagcagcta gaggatacat ctcaactcga gtggagatgg gtgaggcagc tgggattttt    5460
atgacagcca ctcccccggg aagcagagac ccatttcctc agagcaatgc accaatcata    5520
gatgaagaaa gagaaatccc tgaacgctcg tggaattccg gacatgaatg ggtcacggat    5580
tttaaaggga agactgtttg gttcgttcca gtataaaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata gaccccagac gctgcatgaa accagtcata    5820
ctaacagatg gtgaagagcg ggtgattctg gcaggaccta tgccagtgac ccactctagt    5880
gcagcacaaa aagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag gagaagcaag gaaaaccttt    6120
gtagacttaa tgagaagagg agacctacca gtctggttgg cctacagagt ggcagctgaa    6180
ggcatcaact acgcagacag aagtggtgt tttgatggag tcaagaacaa ccaaatccta    6240
gaagaaaacg tggaagttga aatctggaca aaagaagggg aaaggaagaa attgaaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggtaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600 agggcatag gaagatgac cctgggatg tgctgcaata tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
```

```
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagccatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaagtgaa attccagatc tacaagaaaa gtggaatcca ggaagtggat   7680
agaaccttag caaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtcccatg   8580 gtgacacaga tggcaatgac agacacgact ccatttggac aacagcgcgt ttttaaagag   8640
aaagtggaca cgagaaccca agaaccgaaa gaaggcacga gaaactaat gaaaataaca   8700 gcagagtggc tttggaaaga attagggaag aaaagacac ccaggatgtg caccagagaa   8760
gaattcacaa gaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaggca gcagagccat atggtacatg   9000
tggcttggag cacgcttctt agagtttgaa gccctaggat tcttaaatga agatcactgg   9060
ttctccagag agaactcct gagtggagtg aaggagaag gctgcacaa gctaggttac   9120 attctaagag acgtgagcaa gaaagaggga ggagcaatgt atgccgatga caccgcagga   9180
tgggatacaa gaatcacact agaagaccta aaaaatgaag aaatggtaac aaaccacatg   9240
```

-continued

```
gaaggagaac acaagaaact agccgaggcc attttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata ctttcaccaa tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtgagatga ttgtgttgtg aaacctttag atgacaggtt cgcaagcgct    9600
ttaacagctc taaatgacat gggaaagatt aggaaagaca tacaacaatg gaaccttca    9660
agaggatgga atgattggac acaagtgccc ttctgttcac accatttcca tgagttaatc    9720
atgaaagacg tcgcgtact cgttgttccc tgtagaaacc aagatgaact gattggcaga    9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacggaa gacatgctga cagtctggaa cagggtgtgg    10020
attcaagaaa acccatggat ggaagacaaa actccagtgg aatcatggga ggaaatccca    10080
tacttgggga aagagaaga ccaatggtgc ggctcattga ttgggttaac aagcagggcc    10140
acctgggcaa agaacatcca agcagcaata aatcaagtta gatcccttat aggcaatgaa    10200
gaatacacag attacatgcc atccatgaaa agattcagaa gagaagagga agaagcagga    10260
gttctgtggt agaaagcaaa actaacatga acaaggcta gaagtcaggt cggattaagc    10320
catagtacgg aaaaaactat gctacctgtg agccccgtcc aaggacgtta aaagaagtca    10380
ggccatcata aatgccatag cttgagtaaa ctatgcagcc tgtagctcca cctgagaagg    10440
tgtaaaaaat ccgggaggcc acaaaccatg gaagctgtac gcatggcgta gtggactagc    10500
ggttagagga gaccctccc ttacaaatcg cagcaacaat gggggcccaa ggcgagatga    10560
agctgtagtc tcgctggaag gactagaggt tagaggagac cccccgaaa caaaaaacag    10620
catattgacg ctgggaaaga ccagagatcc tgctgtctcc tcagcatcat tccaggcaca    10680
gaacgccaga aaatggaatg gtgctgttga atcaacaggt tct                      10723
```

<210> SEQ ID NO 8
<211> LENGTH: 3391
<212> TYPE: PRT
<213> ORGANISM: Artificial Sequence
<220> FEATURE:
<223> OTHER INFORMATION: Chimeric Dengue Serotype 2/4 (MVS)
<220> FEATURE:
<221> NAME/KEY: Xaa
<222> LOCATION: (1226)..(1226)
<223> OTHER INFORMATION: Arg or Lys

<400> SEQUENCE: 8

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80
```

```
Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Lys Lys Thr Trp Leu Val His Lys Gln Trp Phe Leu Asp Leu
                485                 490                 495
```

-continued

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
515                 520                 525

Asp Val Thr Val Leu Gly Ser Gln Glu Gly Ala Met His Ser Ala Leu
            530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
            565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
            595                 600                 605

Ala Gly Ala Pro Cys Lys Val Pro Ile Glu Ile Arg Asp Val Asn Lys
            610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
            645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
            675                 680                 685

Ala Lys Arg Met Ala Ile Leu Gly Glu Thr Ala Trp Asp Phe Gly Ser
690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
            725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
            755                 760                 765

Leu Gly Val Met Val Gln Ala Asp Ser Gly Cys Val Val Ser Trp Lys
770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
            805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
            835                 840                 845

Glu Leu Asn His Ile Leu Ser Glu Asn Glu Val Lys Leu Thr Ile Met
            850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
            885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu

```
            915                 920                 925
Glu Val Glu Asp Tyr Gly Phe Gly Val Phe Thr Thr Asn Ile Trp Leu
930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
                980                 985                 990

Ile Glu Val Lys Asn Cys His Trp Pro Lys Ser His Thr Leu Trp Ser
                995                 1000                1005

Asn Gly Val Leu Glu Ser Glu Met Ile Ile Pro Lys Asn Leu Ala
    1010                1015                1020

Gly Pro Val Ser Gln His Asn Tyr Arg Pro Gly Tyr His Thr Gln
    1025                1030                1035

Ile Thr Gly Pro Trp His Leu Gly Lys Leu Glu Met Asp Phe Asp
    1040                1045                1050

Phe Cys Asp Gly Thr Thr Val Val Val Thr Glu Asp Cys Gly Asn
    1055                1060                1065

Arg Gly Pro Ser Leu Arg Thr Thr Ala Ser Gly Lys Leu Ile
    1070                1075                1080

Thr Glu Trp Cys Cys Arg Ser Cys Thr Leu Pro Pro Leu Arg Tyr
    1085                1090                1095

Arg Gly Glu Asp Gly Cys Trp Tyr Gly Met Glu Ile Arg Pro Leu
    1100                1105                1110

Lys Glu Lys Glu Glu Asn Leu Val Asn Ser Leu Val Thr Ala Gly
    1115                1120                1125

His Gly Gln Val Asp Asn Phe Ser Leu Gly Val Leu Gly Met Ala
    1130                1135                1140

Leu Phe Leu Glu Glu Met Leu Arg Thr Arg Val Gly Thr Lys His
    1145                1150                1155

Ala Ile Leu Leu Val Ala Val Ser Phe Val Thr Leu Ile Thr Gly
    1160                1165                1170

Asn Met Ser Phe Arg Asp Leu Gly Arg Val Met Val Met Val Gly
    1175                1180                1185

Ala Thr Met Thr Gly Asp Ile Gly Met Gly Val Thr Tyr Leu Ala
    1190                1195                1200

Leu Leu Ala Ala Phe Lys Val Arg Pro Thr Phe Ala Ala Gly Leu
    1205                1210                1215

Leu Leu Arg Lys Leu Thr Ser Xaa Glu Leu Met Met Thr Thr Ile
    1220                1225                1230

Gly Ile Val Leu Leu Ser Gln Ser Thr Ile Pro Glu Thr Ile Leu
    1235                1240                1245

Glu Leu Thr Asp Ala Leu Ala Leu Gly Met Met Val Leu Lys Met
    1250                1255                1260

Val Arg Asn Met Glu Lys Tyr Gln Leu Ala Val Thr Ile Met Ala
    1265                1270                1275

Ile Leu Cys Val Pro Asn Ala Val Ile Leu Gln Asn Ala Trp Lys
    1280                1285                1290

Val Ser Cys Thr Ile Leu Ala Val Val Ser Val Ser Pro Leu Phe
    1295                1300                1305

Leu Thr Ser Ser Gln Gln Lys Thr Asp Trp Ile Pro Leu Ala Leu
    1310                1315                1320
```

```
Thr Ile Lys Gly Leu Asn Pro Thr Ala Ile Phe Leu Thr Thr Leu
1325                1330                1335

Ser Arg Thr Ser Lys Lys Arg Ser Trp Pro Leu Asn Glu Ala Ile
1340                1345                1350

Met Ala Val Gly Met Val Ser Ile Leu Ala Ser Ser Leu Leu Lys
1355                1360                1365

Asn Asp Ile Pro Met Thr Gly Pro Leu Val Ala Gly Gly Leu Leu
1370                1375                1380

Thr Val Cys Tyr Val Leu Thr Gly Arg Ser Ala Asp Leu Glu Leu
1385                1390                1395

Glu Arg Ala Ala Asp Val Lys Trp Glu Asp Gln Ala Glu Ile Ser
1400                1405                1410

Gly Ser Ser Pro Ile Leu Ser Ile Thr Ile Ser Glu Asp Gly Ser
1415                1420                1425

Met Ser Ile Lys Asn Glu Glu Glu Gln Thr Leu Thr Ile Leu
1430                1435                1440

Ile Arg Thr Gly Leu Leu Val Ile Ser Gly Leu Phe Pro Val Ser
1445                1450                1455

Ile Pro Ile Thr Ala Ala Ala Trp Tyr Leu Trp Glu Val Lys Lys
1460                1465                1470

Gln Arg Ala Gly Val Leu Trp Asp Val Pro Ser Pro Pro Pro Met
1475                1480                1485

Gly Lys Ala Glu Leu Glu Asp Gly Ala Tyr Arg Ile Lys Gln Lys
1490                1495                1500

Gly Ile Leu Gly Tyr Ser Gln Ile Gly Ala Gly Val Tyr Lys Glu
1505                1510                1515

Gly Thr Phe His Thr Met Trp His Val Thr Arg Gly Ala Val Leu
1520                1525                1530

Met His Lys Gly Lys Arg Ile Glu Pro Ser Trp Ala Asp Val Lys
1535                1540                1545

Lys Asp Leu Ile Ser Tyr Gly Gly Gly Trp Lys Leu Glu Gly Glu
1550                1555                1560

Trp Lys Glu Gly Glu Glu Val Gln Val Leu Ala Leu Glu Pro Gly
1565                1570                1575

Lys Asn Pro Arg Ala Val Gln Thr Lys Pro Gly Leu Phe Lys Thr
1580                1585                1590

Asn Ala Gly Thr Ile Gly Ala Val Ser Leu Asp Phe Ser Pro Gly
1595                1600                1605

Thr Ser Gly Ser Pro Ile Ile Asp Lys Lys Gly Lys Val Val Gly
1610                1615                1620

Leu Tyr Gly Asn Gly Val Val Thr Arg Ser Gly Ala Tyr Val Ser
1625                1630                1635

Ala Ile Ala Gln Thr Glu Lys Ser Ile Glu Asp Asn Pro Glu Ile
1640                1645                1650

Glu Asp Asp Ile Phe Arg Lys Arg Arg Leu Thr Ile Met Asp Leu
1655                1660                1665

His Pro Gly Ala Gly Lys Thr Lys Arg Tyr Leu Pro Ala Ile Val
1670                1675                1680

Arg Glu Ala Ile Lys Arg Gly Leu Arg Thr Leu Ile Leu Ala Pro
1685                1690                1695

Thr Arg Val Val Ala Ala Glu Met Glu Glu Ala Leu Arg Gly Leu
1700                1705                1710
```

```
Pro Ile Arg Tyr Gln Thr Pro Ala Ile Arg Ala Val His Thr Gly
    1715                1720                1725

Arg Glu Ile Val Asp Leu Met Cys His Ala Thr Phe Thr Met Arg
    1730                1735                1740

Leu Leu Ser Pro Val Arg Val Pro Asn Tyr Asn Leu Ile Ile Met
    1745                1750                1755

Asp Glu Ala His Phe Thr Asp Pro Ala Ser Ile Ala Ala Arg Gly
    1760                1765                1770

Tyr Ile Ser Thr Arg Val Glu Met Gly Glu Ala Ala Gly Ile Phe
    1775                1780                1785

Met Thr Ala Thr Pro Pro Gly Ser Arg Asp Pro Phe Pro Gln Ser
    1790                1795                1800

Asn Ala Pro Ile Ile Asp Glu Glu Arg Glu Ile Pro Glu Arg Ser
    1805                1810                1815

Trp Asn Ser Gly His Glu Trp Val Thr Asp Phe Lys Gly Lys Thr
    1820                1825                1830

Val Trp Phe Val Pro Ser Ile Lys Ala Gly Asn Asp Ile Ala Ala
    1835                1840                1845

Cys Leu Arg Lys Asn Gly Lys Lys Val Ile Gln Leu Ser Arg Lys
    1850                1855                1860

Thr Phe Asp Ser Glu Tyr Val Lys Thr Arg Thr Asn Asp Trp Asp
    1865                1870                1875

Phe Val Val Thr Thr Asp Ile Ser Glu Met Gly Ala Asn Phe Lys
    1880                1885                1890

Ala Glu Arg Val Ile Asp Pro Arg Arg Cys Met Lys Pro Val Ile
    1895                1900                1905

Leu Thr Asp Gly Glu Glu Arg Val Ile Leu Ala Gly Pro Met Pro
    1910                1915                1920

Val Thr His Ser Ser Ala Ala Gln Arg Arg Gly Arg Ile Gly Arg
    1925                1930                1935

Asn Pro Lys Asn Glu Asn Asp Gln Tyr Ile Tyr Met Gly Glu Pro
    1940                1945                1950

Leu Glu Asn Asp Glu Asp Cys Ala His Trp Lys Glu Ala Lys Met
    1955                1960                1965

Leu Leu Asp Asn Ile Asn Thr Pro Glu Gly Ile Ile Pro Ser Met
    1970                1975                1980

Phe Glu Pro Glu Arg Glu Lys Val Asp Ala Ile Asp Gly Glu Tyr
    1985                1990                1995

Arg Leu Arg Gly Glu Ala Arg Lys Thr Phe Val Asp Leu Met Arg
    2000                2005                2010

Arg Gly Asp Leu Pro Val Trp Leu Ala Tyr Arg Val Ala Ala Glu
    2015                2020                2025

Gly Ile Asn Tyr Ala Asp Arg Arg Trp Cys Phe Asp Gly Val Lys
    2030                2035                2040

Asn Asn Gln Ile Leu Glu Glu Asn Val Glu Val Glu Ile Trp Thr
    2045                2050                2055

Lys Glu Gly Glu Arg Lys Lys Leu Lys Pro Arg Trp Leu Asp Ala
    2060                2065                2070

Arg Ile Tyr Ser Asp Pro Leu Ala Leu Lys Glu Phe Lys Glu Phe
    2075                2080                2085

Ala Ala Gly Arg Lys Ser Leu Thr Leu Asn Leu Ile Thr Glu Met
    2090                2095                2100

Gly Arg Leu Pro Thr Phe Met Thr Gln Lys Val Arg Asp Ala Leu
```

```
              2105                2110                2115
Asp Asn Leu Ala Val Leu His Thr Ala Glu Ala Gly Gly Arg Ala
    2120                2125                2130
Tyr Asn His Ala Leu Ser Glu Leu Pro Glu Thr Leu Glu Thr Leu
    2135                2140                2145
Leu Leu Leu Thr Leu Leu Ala Thr Val Thr Gly Gly Ile Phe Leu
    2150                2155                2160
Phe Leu Met Ser Ala Arg Gly Ile Gly Lys Met Thr Leu Gly Met
    2165                2170                2175
Cys Cys Ile Ile Thr Ala Ser Ile Leu Leu Trp Tyr Ala Gln Ile
    2180                2185                2190
Gln Pro His Trp Ile Ala Ala Ser Ile Ile Leu Glu Phe Phe Leu
    2195                2200                2205
Ile Val Leu Leu Ile Pro Glu Pro Glu Lys Gln Arg Thr Pro Gln
    2210                2215                2220
Asp Asn Gln Leu Thr Tyr Val Val Ile Ala Ile Leu Thr Val Val
    2225                2230                2235
Ala Ala Thr Met Ala Asn Glu Met Gly Phe Leu Glu Lys Thr Lys
    2240                2245                2250
Lys Asp Leu Gly Leu Gly Ser Ile Ala Thr Gln Gln Pro Glu Ser
    2255                2260                2265
Asn Ile Leu Asp Ile Asp Leu Arg Pro Ala Ser Ala Trp Thr Leu
    2270                2275                2280
Tyr Ala Val Ala Thr Thr Phe Val Thr Pro Met Leu Arg His Ser
    2285                2290                2295
Ile Glu Asn Ser Ser Val Asn Val Ser Leu Thr Ala Ile Ala Asn
    2300                2305                2310
Gln Ala Thr Val Leu Met Gly Leu Gly Lys Gly Trp Pro Leu Ser
    2315                2320                2325
Lys Met Asp Ile Gly Val Pro Leu Leu Ala Ile Gly Cys Tyr Ser
    2330                2335                2340
Gln Val Asn Pro Ile Thr Leu Thr Ala Ala Leu Phe Leu Leu Val
    2345                2350                2355
Ala His Tyr Ala Ile Ile Gly Pro Gly Leu Gln Ala Lys Ala Thr
    2360                2365                2370
Arg Glu Ala Gln Lys Arg Ala Ala Ala Gly Ile Met Lys Asn Pro
    2375                2380                2385
Thr Val Asp Gly Ile Thr Val Ile Asp Leu Asp Pro Ile Pro Tyr
    2390                2395                2400
Asp Pro Lys Phe Glu Lys Gln Leu Gly Gln Val Met Leu Leu Val
    2405                2410                2415
Leu Cys Val Thr Gln Val Leu Met Met Arg Thr Thr Trp Ala Leu
    2420                2425                2430
Cys Glu Ala Leu Thr Leu Ala Thr Gly Pro Ile Ser Thr Leu Trp
    2435                2440                2445
Glu Gly Asn Pro Gly Arg Phe Trp Asn Thr Thr Ile Ala Val Ser
    2450                2455                2460
Met Ala Asn Ile Phe Arg Gly Ser Tyr Leu Ala Gly Ala Gly Leu
    2465                2470                2475
Leu Phe Ser Ile Met Lys Asn Thr Thr Asn Thr Arg Arg Gly Thr
    2480                2485                2490
Gly Asn Ile Gly Glu Thr Leu Gly Glu Lys Trp Lys Ser Arg Leu
    2495                2500                2505
```

```
Asn Ala Leu Gly Lys Ser Glu Phe Gln Ile Tyr Lys Lys Ser Gly
        2510                2515                2520

Ile Gln Glu Val Asp Arg Thr Leu Ala Lys Glu Gly Ile Lys Arg
        2525                2530                2535

Gly Glu Thr Asp His His Ala Val Ser Arg Gly Ser Ala Lys Leu
        2540                2545                2550

Arg Trp Phe Val Glu Arg Asn Met Val Thr Pro Glu Gly Lys Val
        2555                2560                2565

Val Asp Leu Gly Cys Gly Arg Gly Gly Trp Ser Tyr Tyr Cys Gly
        2570                2575                2580

Gly Leu Lys Asn Val Arg Glu Val Lys Gly Leu Thr Lys Gly Gly
        2585                2590                2595

Pro Gly His Glu Glu Pro Ile Pro Met Ser Thr Tyr Gly Trp Asn
        2600                2605                2610

Leu Val Arg Leu Gln Ser Gly Val Asp Val Phe Phe Ile Pro Pro
        2615                2620                2625

Glu Lys Cys Asp Thr Leu Leu Cys Asp Ile Gly Glu Ser Ser Pro
        2630                2635                2640

Asn Pro Thr Val Glu Ala Gly Arg Thr Leu Arg Val Leu Asn Leu
        2645                2650                2655

Val Glu Asn Trp Leu Asn Asn Asn Thr Gln Phe Cys Ile Lys Val
        2660                2665                2670

Leu Asn Pro Tyr Met Pro Ser Val Ile Glu Lys Met Glu Ala Leu
        2675                2680                2685

Gln Arg Lys Tyr Gly Gly Ala Leu Val Arg Asn Pro Leu Ser Arg
        2690                2695                2700

Asn Ser Thr His Glu Met Tyr Trp Val Ser Asn Ala Ser Gly Asn
        2705                2710                2715

Ile Val Ser Ser Val Asn Met Ile Ser Arg Met Leu Ile Asn Arg
        2720                2725                2730

Phe Thr Met Arg Tyr Lys Lys Ala Thr Tyr Glu Pro Asp Val Asp
        2735                2740                2745

Leu Gly Ser Gly Thr Arg Asn Ile Gly Ile Glu Ser Glu Ile Pro
        2750                2755                2760

Asn Leu Asp Ile Ile Gly Lys Arg Ile Glu Lys Ile Lys Gln Glu
        2765                2770                2775

His Glu Thr Ser Trp His Tyr Asp Gln Asp His Pro Tyr Lys Thr
        2780                2785                2790

Trp Ala Tyr His Gly Ser Tyr Glu Thr Lys Gln Thr Gly Ser Ala
        2795                2800                2805

Ser Ser Met Val Asn Gly Val Val Arg Leu Leu Thr Lys Pro Trp
        2810                2815                2820

Asp Val Val Pro Met Val Thr Gln Met Ala Met Thr Asp Thr Thr
        2825                2830                2835

Pro Phe Gly Gln Gln Arg Val Phe Lys Glu Lys Val Asp Thr Arg
        2840                2845                2850

Thr Gln Glu Pro Lys Glu Gly Thr Lys Lys Leu Met Lys Ile Thr
        2855                2860                2865

Ala Glu Trp Leu Trp Lys Glu Leu Gly Lys Lys Lys Thr Pro Arg
        2870                2875                2880

Met Cys Thr Arg Glu Glu Phe Thr Arg Lys Val Arg Ser Asn Ala
        2885                2890                2895
```

```
Ala Leu Gly Ala Ile Phe Thr Asp Glu Asn Lys Trp Lys Ser Ala
    2900                2905                2910
Arg Glu Ala Val Glu Asp Ser Arg Phe Trp Glu Leu Val Asp Lys
    2915                2920                2925
Glu Arg Asn Leu His Leu Glu Gly Lys Cys Glu Thr Cys Val Tyr
    2930                2935                2940
Asn Met Met Gly Lys Arg Glu Lys Lys Leu Gly Glu Phe Gly Lys
    2945                2950                2955
Ala Lys Gly Ser Arg Ala Ile Trp Tyr Met Trp Leu Gly Ala Arg
    2960                2965                2970
Phe Leu Glu Phe Glu Ala Leu Gly Phe Leu Asn Glu Asp His Trp
    2975                2980                2985
Phe Ser Arg Glu Asn Ser Leu Ser Gly Val Glu Gly Glu Gly Leu
    2990                2995                3000
His Lys Leu Gly Tyr Ile Leu Arg Asp Val Ser Lys Lys Glu Gly
    3005                3010                3015
Gly Ala Met Tyr Ala Asp Asp Thr Ala Gly Trp Asp Thr Arg Ile
    3020                3025                3030
Thr Leu Glu Asp Leu Lys Asn Glu Glu Met Val Thr Asn His Met
    3035                3040                3045
Glu Gly Glu His Lys Lys Leu Ala Glu Ala Ile Phe Lys Leu Thr
    3050                3055                3060
Tyr Gln Asn Lys Val Val Arg Val Gln Arg Pro Thr Pro Arg Gly
    3065                3070                3075
Thr Val Met Asp Ile Ile Ser Arg Arg Asp Gln Arg Gly Ser Gly
    3080                3085                3090
Gln Val Gly Thr Tyr Gly Leu Asn Thr Phe Thr Asn Met Glu Ala
    3095                3100                3105
Gln Leu Ile Arg Gln Met Glu Gly Glu Gly Val Phe Lys Ser Ile
    3110                3115                3120
Gln His Leu Thr Ile Thr Glu Glu Ile Ala Val Gln Asn Trp Leu
    3125                3130                3135
Ala Arg Val Gly Arg Glu Arg Leu Ser Arg Met Ala Ile Ser Gly
    3140                3145                3150
Asp Asp Cys Val Val Lys Pro Leu Asp Asp Arg Phe Ala Ser Ala
    3155                3160                3165
Leu Thr Ala Leu Asn Asp Met Gly Lys Ile Arg Lys Asp Ile Gln
    3170                3175                3180
Gln Trp Glu Pro Ser Arg Gly Trp Asn Asp Trp Thr Gln Val Pro
    3185                3190                3195
Phe Cys Ser His His Phe His Glu Leu Ile Met Lys Asp Gly Arg
    3200                3205                3210
Val Leu Val Val Pro Cys Arg Asn Gln Asp Glu Leu Ile Gly Arg
    3215                3220                3225
Ala Arg Ile Ser Gln Gly Ala Gly Trp Ser Leu Arg Glu Thr Ala
    3230                3235                3240
Cys Leu Gly Lys Ser Tyr Ala Gln Met Trp Ser Leu Met Tyr Phe
    3245                3250                3255
His Arg Arg Asp Leu Arg Leu Ala Ala Asn Ala Ile Cys Ser Ala
    3260                3265                3270
Val Pro Ser His Trp Val Pro Thr Ser Arg Thr Thr Trp Ser Ile
    3275                3280                3285
His Ala Lys His Glu Trp Met Thr Thr Glu Asp Met Leu Thr Val
```

```
                    3290            3295            3300
Trp Asn Arg Val Trp Ile Gln Glu Asn Pro Trp Met Glu Asp Lys
    3305            3310            3315

Thr Pro Val Glu Ser Trp Glu Glu Ile Pro Tyr Leu Gly Lys Arg
    3320            3325            3330

Glu Asp Gln Trp Cys Gly Ser Leu Ile Gly Leu Thr Ser Arg Ala
    3335            3340            3345

Thr Trp Ala Lys Asn Ile Gln Ala Ala Ile Asn Gln Val Arg Ser
    3350            3355            3360

Leu Ile Gly Asn Glu Glu Tyr Thr Asp Tyr Met Pro Ser Met Lys
    3365            3370            3375

Arg Phe Arg Arg Glu Glu Glu Glu Ala Gly Val Leu Trp
    3380            3385            3390

<210> SEQ ID NO 9
<211> LENGTH: 10735
<212> TYPE: DNA
<213> ORGANISM: Dengue virus

<400> SEQUENCE: 9
```

| | | | | | |
|---|---|---|---|---|---|
| agttgttagt | ctacgtggac | cgacaagaac | agtttcgaat | cggaagcttg | cttaacgtag | 60 |
| ttctaacagt | tttttattag | agagcagatc | tctgatgatc | aaccaacgaa | aaaagacggg | 120 |
| tcgaccgtct | ttcaatatgc | tgaaacgcgc | gagaaaccgc | gtgtcaactg | tttcacagtt | 180 |
| ggcgaagaga | ttctcaaaag | gattgctctc | aggccaagga | cccatgaaat | tggtgatggc | 240 |
| tttcatagca | ttcttaagat | ttctagccat | accccccaaca | gcaggaattt | tggctagatg | 300 |
| gggctcattc | aagaagaatg | gagcgattaa | agtgttacgg | ggtttcaaga | gagaaatctc | 360 |
| aaacatgcta | aacataatga | acaggaggaa | agatccgtg | accatgctcc | ttatgctgct | 420 |
| gcccacagcc | ctggcgttcc | atctgacgac | acgaggggga | gagccgcata | tgatagttag | 480 |
| caagcaggaa | agaggaaagt | cacttttgtt | caagacctct | gcaggtgtca | acatgtgcac | 540 |
| cctcattgcg | atggatttgg | agagttgtg | tgaggacacg | atgacctaca | atgcccccg | 600 |
| gatcactgag | gcggaaccag | atgacgttga | ctgttggtgc | aatgccacgg | acacatgggt | 660 |
| gacctatgga | acgtgctctc | aaactggcga | acaccgacga | gacaaacgtt | ccgtcgcatt | 720 |
| ggcccccacac | gtgggggcttg | gcctagaaac | aagagccgaa | acgtggatgt | cctctgaagg | 780 |
| tgcttggaaa | cagatacaaa | aagtagagac | ttgggctctg | agacatccag | gattcacggt | 840 |
| gatagccctt | tttctagcac | atgccatagg | aacatccatc | acccagaaag | ggatcatttt | 900 |
| cattttgctg | atgctggtaa | caccatctat | ggccatgcga | tgcgtgggaa | taggcaacag | 960 |
| agacttcgtg | gaaggactgt | caggagcaac | atgggtggat | gtggtactgg | agcatggaag | 1020 |
| ttgcgtcacc | accatggcaa | aaacaaacc | aacactggac | attgaactct | tgaagacgga | 1080 |
| ggtcacaaac | cctgcagttc | tgcgtaaatt | gtgcattgaa | gctaaaatat | caaacaccac | 1140 |
| caccgattcg | agatgtccaa | cacaaggaga | agccacactg | gtggaagaac | aagacgcgaa | 1200 |
| ctttgtgtgc | cgacgaacgt | tcgtggacag | aggctggggc | aatggctgtg | ggctattcgg | 1260 |
| aaaaggtagt | ctaataacgt | gtgccaagtt | taagtgtgtg | acaaaactag | aaggaaagat | 1320 |
| agttcaatat | gaaaacctaa | aatattcagt | gatagtcacc | gtccacactg | gagatcagca | 1380 |
| ccaggtggga | aatgagacta | cagaacatgg | aacaactgca | accataacac | ctcaagctcc | 1440 |
| tacgtcggaa | atacagctga | ccgactacgg | aaccctttaca | ttagattgtt | cacctaggac | 1500 |
| agggctagat | tttaacgaga | tggtgttgct | gacaatgaaa | gaaagatcat | ggcttgtcca | 1560 |

```
caaacaatgg tttctagact taccactgcc ttggacctct ggggcttcaa catcccaaga    1620
gacttggaac agacaagatt tactggtcac atttaagaca gctcatgcaa agaagcagga    1680
agtagtcgta ctaggatcac aagaaggagc aatgcacact gcgctgactg gagcgacaga    1740
aatccaaacg tcaggaacga caacaatttt cgcaggacac ctaaaatgca gactaaaaat    1800
ggacaaacta actttaaaag ggatgtcata tgtgatgtgc acaggctcat tcaagttaga    1860
gaaagaagtg gctgagaccc agcatggaac tgttctggtg caggttaaat atgaaggaac    1920
agacgcacca tgcaagattc ccttttcgac ccaagatgag aaaggagcaa cccagaatgg    1980
gagattaata acagccaacc ccatagtcac tgacaaagaa aaaccagtca atattgaggc    2040
agaaccaccc tttggtgaga gctacatcgt ggtaggagca ggtgaaaaag ctttgaaact    2100
aagctggttc aagaaaggaa gcagcatagg gaaaatgttt gaagcaactg cccgaggagc    2160
acgaaggatg gccattctgg agacaccgc atgggacttc ggttctatag gaggagtgtt    2220
cacgtctatg gaaaactgg tacaccaggt ttttggaact gcatatggag ttttgtttag    2280
cggagtttct tggaccatga aataggaat agggattctg ctgacatggc taggattaaa    2340
ttcaaggaac acgtcccttt cgatgatgtg catcgcagtt ggcatggtca cactgtacct    2400
aggagtcatg gttcaggcag attcgggatg tgtaatcaac tggaaaggca gagaacttaa    2460
atgtggaagc ggcattttg tcactaatga agttcacact tggacagagc aatacaaatt    2520
ccaggctgac tcccccaaga gactatcagc agccattggg aaggcatggg aggagggtgt    2580
gtgtggaatc cgatcagcca ctcgtctcga gaacatcatg tggaaacaaa tatcaaatga    2640
attgaaccac atcctacttg aaaatgacat gaaatttaca gtggtcgtgg agatgttag    2700
tggaatcttg gcccaaggga aaaaatgat taggccacaa cccatggaac acaaatactc    2760
gtggaaaagc tggggaaaag ccaaaatcat aggagcggat gtacagaaca ccaccttcat    2820
catcgacggc ccaaacaccc cagaatgccc tgacaatcaa agagcatgga atatttggga    2880
agtagaggac tatggatttg ggattttcac gacaaacata tggttgaaat tgcgtgactc    2940
ctacacccaa gtatgtgacc accggctgat gtcagctgcc attaaggaca gcaaggcagt    3000
ccatgctgac atggggtact ggatagaaag tgaaaagaac gagacatgga gttggcgag    3060
agcctccttt atagaagtta agacatgcat ctggccaaaa tcccacactc tatggagcaa    3120
tggagttctg gaaagtgaaa tgataattcc aaagatatat ggaggaccaa tatctcagca    3180
caactacaga ccaggatatt tcacacaaac agcagggccg tggcacctag caagttgga    3240
actagatttc gatttttgtg aaggtaccac agttgttgtg gatgaacatt gtggaaatcg    3300
aggaccatct ctcagaacca acagtcac aggaaagata atccatgaat ggtgctgcag    3360
atcttgtacg ctaccccccc tacgtttcaa aggggaagac gggtgttggt acggcatgga    3420
aatcagacca gtgaaggaca aggaagagaa cctggtcaag tcaatggtct ctgcagggtc    3480
aggagaagtg gacagctttt cactaggact gctatgcata tcaataatga ttgaagaagt    3540
gatgagatcc agatggagca aaaaaatgct gatgactgga acactggctg tgttcctcct    3600
tcttataatg ggacaattga catggagtga tctgatcagg ttatgtatta tggttgggagc    3660
caacgcttca gacaagatgg ggatgggaac aacgtaccta gctttaatgg ccactttcaa    3720
aatgagacca atgttcgccg tcgggctatt atttcgcaga ctaacatcta gagaagttct    3780
tcttcttaca attggcttga gcctggtggc atccgtggag ctaccaagtt ccctagagga    3840
gctgggggat ggacttgcaa taggcatcat gatgttgaaa ttattgactg attttcagtc    3900
```

```
acaccagcta tgggctactc tgctatcctt gacatttatt aaaacaactt tttcattgca    3960
ctatgcatgg aagacaatgg ctatggtact gtcaattgta tctctcttcc ctttatgcct    4020
gtccacgacc tctcaaaaaa caacatggct tccggtgctg ttgggatctc ttggatgcaa    4080
accactaccc atgtttctta aacagaaaa caaaatctgg ggaaggaaga gttggcccct     4140
caatgaagga attatggctg ttggaatagt tagtattcta ctaagttcac ttttaaaaaa    4200
tgatgtgccg ctagccggcc cattaatagc tggaggcatg ctaatagcat gttatgtcat    4260
atccggaagc tcagctgatt tatcactgga gaaagcggct gaggtctcct gggaggaaga    4320
agcagaacac tcaggcgcct cacacaacat actagtagag gttcaagatg atggaaccat    4380
gaagataaaa gatgaagaga gagatgacac gctcaccatt ctccttaaag caactctgct    4440
ggcagtctca ggggtgtacc caatgtcaat accagcgacc ctttttgtgt ggtattttg     4500
gcagaaaaag aaacagagat caggagtgct atgggacaca cccagccccc cagaagtgga    4560
aagagcagtt cttgatgatg gcatctatag aattttgcaa agaggactgt tgggcaggtc    4620
ccaagtagga gtaggagttt tccaagaagg cgtgttccac acaatgtggc acgtcactag    4680
gggagctgtc ctcatgtatc aaggaaaaag gctggaacca agctgggcca gtgtcaaaaa    4740
agacttgatc tcatatggag gaggttggag gtttcaagga tcctggaaca cgggagaaga    4800
agtacaggtg attgctgttg aaccgggaaa aaaccccaaa aatgtacaaa caacgccggg    4860
tacccttcaag acccctgaag gcgaagttgg agccatagcc ttagacttta aacctggcac    4920
atctggatct cccatcgtaa acagagaggg aaaaatagta ggtctttatg gaaatggagt    4980
ggtgacaaca agcggaactt acgttagtgc catagctcaa gctaaggcat cacaagaagg    5040
gcctctacca gagattgagg acgaggtgtt taggaaaaga aacttaacaa taatggacct    5100
acatccagga tcgggaaaaa caagaagata ccttccagcc atagtccgtg aggccataaa    5160
aaggaagctg cgcacgctaa tcctagctcc cacaagagtt gtcgcttctg aaatggcaga    5220
ggcactcaag ggagtgccaa taaggtatca gacaacagca gtgaagagtg aacacacagg    5280
aaaggagata gttgacctta tgtgccacgc cactttcacc atgcgcctcc tgtctcccgt    5340
gagagttccc aattataaca tgattatcat ggatgaagca cacttcaccg atccagccag    5400
catagcagcc agagggtaca tctcaacccg agtgggtatg ggtgaagcag ctgcgatctt    5460
tatgacagcc actcccccag gatcggtgga ggccttttcca cagagcaatg caattatcca    5520
agatgaggaa agagacattc ctgagagatc atggaactca ggctatgact ggatcactga    5580
ttttccaggt aaaacagtct ggtttgttcc aagcatcaaa tcaggaaatg acattgccaa    5640
ctgtttaaga aaaacgggaa acgggtgat ccaattgagc agaaaaccct ttgacactga    5700
gtaccagaaa acaaaaaaca acgactggga ctatgtcgtc acaacagaca tttccgaaat    5760
gggagcaaat ttccgggccg acagggtaat agacccaagg cggtgtctga accggtaat    5820
actaaaagat ggtccagagc gcgtcattct agccggaccg atgccagtga ctgtggccag    5880
tgccgcccag aggagaggaa gaattggaag gaaccaaaac aaggaaggtg atcagtatat    5940
ttacatggga cagccttta acaatgatga ggaccacgct cattggacag aagcaaagat    6000
gctccttgac aatataaaca caccagaagg gattatccca gccctctatg agccggagag    6060
agaaaagagt gcagctatag acgggaata cagactgcgg ggtgaagcaa ggaaaacgtt    6120
cgtggagctc atgagaagag gggatctacc agtctggcta tcctacaaag ttgcctcaga    6180
aggcttccag tactccgaca aaggtgtgtg cttcgatggg gaaaggaaca accaggtgtt    6240
ggaggagaac atggacgtgg agatctggac aaaagaagga gaaagaaaga aactacgacc    6300
```

```
tcgctggttg dacgccagaa catactctga cccactggct ctgcgcgagt ttaaagagtt     6360
tgcagcagga agaagaagcg tctcaggtga cctaatatta gaaataggga aacttccaca     6420
acatttgacg caaagggccc agaatgcttt ggacaacttg gtcatgttgc acaattccga     6480
acaaggagga aaagcctata gacatgctat ggaagaactg ccagacacaa tagaaacgtt     6540
gatgctccta gccttgatag ctgtgttgac tggtggagtg acgctgttct tcctatcagg     6600
aagaggtcta ggaaaaacat ctatcggctt actctgcgtg atggcctcaa cgcactgtt     6660
atggatggcc agtgtggagc cccattggat agcggcctcc atcatactgg agttctttct     6720
gatggtactg cttattccag agccagacag acagcgcact ccacaggaca accagctagc     6780
atatgtggtg ataggtctgt tattcatgat attgacagtg gcagccaatg agatgggatt     6840
attggaaacc acaaagaaag acctggggat tggccatgta gctgctgaaa accaccacca     6900
tgctacaatg ctggacgtag acctacatcc agcttcagcc tggaccctct atgcagtggc     6960
cacaacaatc atcactccta tgatgagaca cacaattgaa aacacaacgg caaatatttc     7020
cctgacagcc atcgcaaacc aagcagctat attgatggga cttgacaagg gatggccaat     7080
atcgaagatg gacataggag ttccacttct cgccttgggg tgctattccc aagtgaatcc     7140
gctgacactg atagcggcag tattgatgct agtagctcat tacgccataa ttggacctgg     7200
actgcaagca aaagctacta gagaagctca aaaagaaca gcggctggaa taatgaaaaa     7260
tccaactgtc gacgggattg ttgcaataga cttagatccc gtggtttacg atgcaaaatt     7320
tgaaaaacaa ctaggccaaa taatgttgtt gatactttgc acatcacaga ttctttttgat     7380
gcggactaca tgggccttgt gtgaatccat cacattggct actggacctc tgaccactct     7440
ttgggaggga tctccaggaa aattctggaa caccacaata gcggtatcca tgcaaacat     7500
tttcagggg agttatctag caggagcagg tctggccttc tcattaatga aatctctagg     7560
aggaggtagg agaggcacgg gagcccaagg ggaaacactg ggagaaaaat ggaaagaca     7620
actaaaccaa ctgagcaagt cagaattcaa tacttacaag aggagtggga ttatggaggt     7680
ggatagatcc gaagccaaag agggactgaa aagaggagaa acaaccaaac acgcagtatc     7740
gagaggaacg gccaaactga ggtggttcgt ggagaggaac cttgtgaaac cagaagggaa     7800
agtcatagac ctcggttgtg aagaggtgg ctggtcatat tattgcgctg ggctgaagaa     7860
agtcacagaa gtgaaaggat acacaaaagg aggacctgga catgaggaac caatcccaat     7920
ggcgacctat ggatggaacc tagtaaagct gcactccgga aaagatgtat ttttatacc     7980
acctgagaaa tgtgacaccc ttttgtgtga tattggtgag tcctctccga acccaactat     8040
agaggaagga gaacgttac gtgttctgaa aatggtggaa ccatggctca gaggaaacca     8100
attttgcata aaaattctaa atccctatat gccgagcgtg gtagaaactc tggaacaaat     8160
gcaaagaaaa catggaggaa tgctagtgcg aaacccactc tcaagaaatt ccacccatga     8220
aatgtactgg gttttcatgtg aacaggaaa cattgtgtca gcagtaaaca tgacatctag     8280
aatgttgcta aatcggttca caatggctca caggaagcca acatatgaaa gagacgtgga     8340
cttaggcgct ggaacaagac atgtggcagt agaaccagag gtagccaacc tagatatcat     8400
tggccagagg atagagaata taaaaaatga acataagtca acatggcatt atgatgagga     8460
caatccatac aaaacatggg cctatcatgg atcatatgag gttaagccat caggatcggc     8520
ctcatccatg gtcaatggcg tggtgagatt gctcaccaaa ccatgggatg ttatccccat     8580
ggtcacacaa atagccatga ctgataccac accctttgga caacagaggg tgtttaaga     8640
```

| | |
|---|---|
| gaaagttgac acgcgcacac caaaagcaaa acgtggcaca gcacaaatta tggaagtgac | 8700 |
| agccaggtgg ttatggggtt tcctttctag aaacaaaaaa cccagaattt gcacaagaga | 8760 |
| ggagtttaca agaaaagtta ggtcaaacgc agctattgga gcagtgttcg ttgatgaaaa | 8820 |
| tcaatggaac tcggcaaaag aagcagtgga agacgaacgg ttctgggaac ttgtccacag | 8880 |
| agagagggag cttcataaac aggggaaatg tgccacgtgt gtctacaata tgatggggaa | 8940 |
| gagagagaaa aaattaggag agttcggaaa ggcaaaagga agtcgtgcaa tatggtacat | 9000 |
| gtggttggga gcacgcttcc tagagtttga agcccttggt ttcatgaatg aagatcactg | 9060 |
| gttcagtaga gagaattcac tcagtggagt ggaaggagaa ggactccaca aacttggata | 9120 |
| catactcaga gacatatcaa ggattccagg ggggaacatg tatgcagatg acacagccgg | 9180 |
| atgggacaca agaataacag aggatgatct ccagaatgag gctaaaatca ctgacatcat | 9240 |
| ggagcccgaa catgccctgc tggctacgtc aatctttaag ctgacctacc aaaataaggt | 9300 |
| ggtaagggtg cagagaccag caaaaaatgg aaccgtgatg gatgttatat ccagacgtga | 9360 |
| ccagagaggc agtggacagg ttggaactta tggcttaaac actttcacca acatggaggc | 9420 |
| ccaactgata agacaaatgg agtccgaggg aatcttttta cccagcgaat ggaaaccccc | 9480 |
| aaatctagcc ggaagagttc tcgactggtt ggaaaaatat ggtgtcgaaa ggctgaaaag | 9540 |
| aatggcaatc agcggagatg actgtgtggt gaaaccaatt gatgacaggt tcgcaacagc | 9600 |
| cttaacagct ttgaatgaca tgggaaaagt aagaaaagac ataccacaat gggaaccttc | 9660 |
| aaaaggatgg aatgattggc aacaagtgcc tttctgttca caccacttcc accagctaat | 9720 |
| tatgaaggat gggagggaga tagtggtgcc atgccgcaac caagatgaac ttgtggggag | 9780 |
| ggccagagta tcacaaggcg ccggatggag cctgagagaa accgcatgcc taggcaagtc | 9840 |
| atatgcacaa atgtggcagc tgatgtattt ccacaggaga gacctgagac tggcggctaa | 9900 |
| cgctatttgt tcagccgttc cagttgattg ggtcccaacc agccgcacca cctggtcgat | 9960 |
| ccatgcccat caccaatgga tgacaacaga agacatgtta tcagtatgga ataggtctg | 10020 |
| gatagaggaa aacccatgga tggaggataa gactcatgtg tccagttggg aagaagttcc | 10080 |
| ataccttagga aagaggggaag atcagtggtg tggatccctg ataggcttaa cagcaagggc | 10140 |
| cacctgggcc actaatatac aagtggccat aaaccaagtg agaaggctca ttgggaatga | 10200 |
| gaattatcta gattacatga catcaatgaa gagattcaag aatgagagtg atcccgaagg | 10260 |
| ggcactctgg taagtcaaca cattcacaaa ataaggaaaa ataaaaaatc aaatgaggca | 10320 |
| agaagtcagg ccagattaag ccatagtacg gtaagagcta tgctgcctgt gagccccgtc | 10380 |
| caaggacgta aaatgaagtc aggccgaaag ccacggtttg agcaagccgt gctgcctgtg | 10440 |
| gctccatcgt ggggatgtaa aaacccggga ggctgcaacc catggaagct gtacgcatgg | 10500 |
| ggtagcagac tagtggttag aggagacccc tcccaagaca caacgcagca gcggggccca | 10560 |
| acaccggggg aagctgtacc ctggtggtaa ggactagagg ttagaggaga ccccccgcgt | 10620 |
| aacaataaac agcatattga cgctgggaga ccagagat cctgctgtct ctacagcatc | 10680 |
| attccaggca cagaacgcca gaaaatggaa tggtgctgtt gaatcaacag gttct | 10735 |

<210> SEQ ID NO 10
<211> LENGTH: 3392
<212> TYPE: PRT
<213> ORGANISM: Dengue virus

<400> SEQUENCE: 10

Met Ile Asn Gln Arg Lys Lys Thr Gly Arg Pro Ser Phe Asn Met Leu

```
1               5                   10                  15
Lys Arg Ala Arg Asn Arg Val Ser Thr Val Ser Gln Leu Ala Lys Arg
            20                  25                  30
Phe Ser Lys Gly Leu Leu Ser Gly Gln Gly Pro Met Lys Leu Val Met
            35                  40                  45
Ala Phe Ile Ala Phe Leu Arg Phe Leu Ala Ile Pro Pro Thr Ala Gly
 50                  55                  60
Ile Leu Ala Arg Trp Gly Ser Phe Lys Lys Asn Gly Ala Ile Lys Val
 65                  70                  75                  80
Leu Arg Gly Phe Lys Arg Glu Ile Ser Asn Met Leu Asn Ile Met Asn
                85                  90                  95
Arg Arg Lys Arg Ser Val Thr Met Leu Leu Met Leu Leu Pro Thr Ala
               100                 105                 110
Leu Ala Phe His Leu Thr Thr Arg Gly Gly Glu Pro His Met Ile Val
               115                 120                 125
Ser Lys Gln Glu Arg Gly Lys Ser Leu Leu Phe Lys Thr Ser Ala Gly
           130                 135                 140
Val Asn Met Cys Thr Leu Ile Ala Met Asp Leu Gly Glu Leu Cys Glu
145                 150                 155                 160
Asp Thr Met Thr Tyr Lys Cys Pro Arg Ile Thr Glu Ala Glu Pro Asp
                165                 170                 175
Asp Val Asp Cys Trp Cys Asn Ala Thr Asp Thr Trp Val Thr Tyr Gly
                180                 185                 190
Thr Cys Ser Gln Thr Gly Glu His Arg Arg Asp Lys Arg Ser Val Ala
            195                 200                 205
Leu Ala Pro His Val Gly Leu Gly Leu Glu Thr Arg Ala Glu Thr Trp
210                 215                 220
Met Ser Ser Glu Gly Ala Trp Lys Gln Ile Gln Lys Val Glu Thr Trp
225                 230                 235                 240
Ala Leu Arg His Pro Gly Phe Thr Val Ile Ala Leu Phe Leu Ala His
                245                 250                 255
Ala Ile Gly Thr Ser Ile Thr Gln Lys Gly Ile Ile Phe Ile Leu Leu
                260                 265                 270
Met Leu Val Thr Pro Ser Met Ala Met Arg Cys Val Gly Ile Gly Asn
            275                 280                 285
Arg Asp Phe Val Glu Gly Leu Ser Gly Ala Thr Trp Val Asp Val Val
            290                 295                 300
Leu Glu His Gly Ser Cys Val Thr Thr Met Ala Lys Asn Lys Pro Thr
305                 310                 315                 320
Leu Asp Ile Glu Leu Leu Lys Thr Glu Val Thr Asn Pro Ala Val Leu
                325                 330                 335
Arg Lys Leu Cys Ile Glu Ala Lys Ile Ser Asn Thr Thr Thr Asp Ser
            340                 345                 350
Arg Cys Pro Thr Gln Gly Glu Ala Thr Leu Val Glu Glu Gln Asp Ala
            355                 360                 365
Asn Phe Val Cys Arg Arg Thr Phe Val Asp Arg Gly Trp Gly Asn Gly
            370                 375                 380
Cys Gly Leu Phe Gly Lys Gly Ser Leu Ile Thr Cys Ala Lys Phe Lys
385                 390                 395                 400
Cys Val Thr Lys Leu Glu Gly Lys Ile Val Gln Tyr Glu Asn Leu Lys
                405                 410                 415
Tyr Ser Val Ile Val Thr Val His Thr Gly Asp Gln His Gln Val Gly
                420                 425                 430
```

-continued

```
Asn Glu Thr Thr Glu His Gly Thr Thr Ala Thr Ile Thr Pro Gln Ala
        435                 440                 445
Pro Thr Ser Glu Ile Gln Leu Thr Asp Tyr Gly Thr Leu Thr Leu Asp
    450                 455                 460
Cys Ser Pro Arg Thr Gly Leu Asp Phe Asn Glu Met Val Leu Leu Thr
465                 470                 475                 480
Met Lys Glu Arg Ser Trp Leu Val His Lys Gln Trp Phe Leu Asp Leu
                485                 490                 495
Pro Leu Pro Trp Thr Ser Gly Ala Ser Thr Ser Gln Glu Thr Trp Asn
            500                 505                 510
Arg Gln Asp Leu Leu Val Thr Phe Lys Thr Ala His Ala Lys Lys Gln
        515                 520                 525
Glu Val Val Leu Gly Ser Gln Glu Gly Ala Met His Thr Ala Leu
    530                 535                 540
Thr Gly Ala Thr Glu Ile Gln Thr Ser Gly Thr Thr Ile Phe Ala
545                 550                 555                 560
Gly His Leu Lys Cys Arg Leu Lys Met Asp Lys Leu Thr Leu Lys Gly
                565                 570                 575
Met Ser Tyr Val Met Cys Thr Gly Ser Phe Lys Leu Glu Lys Glu Val
            580                 585                 590
Ala Glu Thr Gln His Gly Thr Val Leu Val Gln Val Lys Tyr Glu Gly
        595                 600                 605
Thr Asp Ala Pro Cys Lys Ile Pro Phe Ser Thr Gln Asp Glu Lys Gly
    610                 615                 620
Ala Thr Gln Asn Gly Arg Leu Ile Thr Ala Asn Pro Ile Val Thr Asp
625                 630                 635                 640
Lys Glu Lys Pro Val Asn Ile Glu Ala Glu Pro Pro Phe Gly Glu Ser
                645                 650                 655
Tyr Ile Val Val Gly Ala Gly Glu Lys Ala Leu Lys Leu Ser Trp Phe
            660                 665                 670
Lys Lys Gly Ser Ser Ile Gly Lys Met Phe Glu Ala Thr Ala Arg Gly
        675                 680                 685
Ala Arg Arg Met Ala Ile Leu Gly Asp Thr Ala Trp Asp Phe Gly Ser
    690                 695                 700
Ile Gly Gly Val Phe Thr Ser Met Gly Lys Leu Val His Gln Val Phe
705                 710                 715                 720
Gly Thr Ala Tyr Gly Val Leu Phe Ser Gly Val Ser Trp Thr Met Lys
                725                 730                 735
Ile Gly Ile Gly Ile Leu Leu Thr Trp Leu Gly Leu Asn Ser Arg Asn
            740                 745                 750
Thr Ser Leu Ser Met Met Cys Ile Ala Val Gly Met Val Thr Leu Tyr
        755                 760                 765
Leu Gly Val Met Val Gln Ala Asp Ser Gly Cys Val Ile Asn Trp Lys
    770                 775                 780
Gly Arg Glu Leu Lys Cys Gly Ser Gly Ile Phe Val Thr Asn Glu Val
785                 790                 795                 800
His Thr Trp Thr Glu Gln Tyr Lys Phe Gln Ala Asp Ser Pro Lys Arg
                805                 810                 815
Leu Ser Ala Ala Ile Gly Lys Ala Trp Glu Glu Gly Val Cys Gly Ile
            820                 825                 830
Arg Ser Ala Thr Arg Leu Glu Asn Ile Met Trp Lys Gln Ile Ser Asn
        835                 840                 845
```

-continued

```
Glu Leu Asn His Ile Leu Leu Glu Asn Asp Met Lys Phe Thr Val Val
850                 855                 860
Val Gly Asp Val Ser Gly Ile Leu Ala Gln Gly Lys Lys Met Ile Arg
865                 870                 875                 880
Pro Gln Pro Met Glu His Lys Tyr Ser Trp Lys Ser Trp Gly Lys Ala
                885                 890                 895
Lys Ile Ile Gly Ala Asp Val Gln Asn Thr Thr Phe Ile Ile Asp Gly
                900                 905                 910
Pro Asn Thr Pro Glu Cys Pro Asp Asn Gln Arg Ala Trp Asn Ile Trp
                915                 920                 925
Glu Val Glu Asp Tyr Gly Phe Gly Ile Phe Thr Thr Asn Ile Trp Leu
930                 935                 940
Lys Leu Arg Asp Ser Tyr Thr Gln Val Cys Asp His Arg Leu Met Ser
945                 950                 955                 960
Ala Ala Ile Lys Asp Ser Lys Ala Val His Ala Asp Met Gly Tyr Trp
                965                 970                 975
Ile Glu Ser Glu Lys Asn Glu Thr Trp Lys Leu Ala Arg Ala Ser Phe
                980                 985                 990
Ile Glu Val Lys Thr Cys Ile Trp Pro Lys Ser His Thr Leu Trp Ser
                995                 1000                1005
Asn Gly Val Leu Glu Ser Glu Met Ile Ile Pro Lys Ile Tyr Gly
    1010                1015                1020
Gly Pro Ile Ser Gln His Asn Tyr Arg Pro Gly Tyr Phe Thr Gln
    1025                1030                1035
Thr Ala Gly Pro Trp His Leu Gly Lys Leu Glu Leu Asp Phe Asp
    1040                1045                1050
Phe Cys Glu Gly Thr Thr Val Val Val Asp Glu His Cys Gly Asn
    1055                1060                1065
Arg Gly Pro Ser Leu Arg Thr Thr Val Thr Gly Lys Ile Ile
    1070                1075                1080
His Glu Trp Cys Cys Arg Ser Cys Thr Leu Pro Pro Leu Arg Phe
    1085                1090                1095
Lys Gly Glu Asp Gly Cys Trp Tyr Gly Met Glu Ile Arg Pro Val
    1100                1105                1110
Lys Asp Lys Glu Glu Asn Leu Val Lys Ser Met Val Ser Ala Gly
    1115                1120                1125
Ser Gly Glu Val Asp Ser Phe Ser Leu Gly Leu Leu Cys Ile Ser
    1130                1135                1140
Ile Met Ile Glu Glu Val Met Arg Ser Arg Trp Ser Lys Lys Met
    1145                1150                1155
Leu Met Thr Gly Thr Leu Ala Val Phe Leu Leu Leu Ile Met Gly
    1160                1165                1170
Gln Leu Thr Trp Ser Asp Leu Ile Arg Leu Cys Ile Met Val Gly
    1175                1180                1185
Ala Asn Ala Ser Asp Lys Met Gly Met Gly Thr Thr Tyr Leu Ala
    1190                1195                1200
Leu Met Ala Thr Phe Lys Met Arg Pro Met Phe Ala Val Gly Leu
    1205                1210                1215
Leu Phe Arg Arg Leu Thr Ser Arg Glu Val Leu Leu Leu Thr Ile
    1220                1225                1230
Gly Leu Ser Leu Val Ala Ser Val Glu Leu Pro Ser Ser Leu Glu
    1235                1240                1245
Glu Leu Gly Asp Gly Leu Ala Ile Gly Ile Met Met Leu Lys Leu
```

```
            1250                1255                1260
Leu Thr Asp Phe Gln Ser His Gln Leu Trp Ala Thr Leu Leu Ser
    1265                1270                1275
Leu Thr Phe Ile Lys Thr Thr Phe Ser Leu His Tyr Ala Trp Lys
    1280                1285                1290
Thr Met Ala Met Val Leu Ser Ile Val Ser Leu Phe Pro Leu Cys
    1295                1300                1305
Leu Ser Thr Thr Ser Gln Lys Thr Thr Trp Leu Pro Val Leu Leu
    1310                1315                1320
Gly Ser Leu Gly Cys Lys Pro Leu Pro Met Phe Leu Ile Thr Glu
    1325                1330                1335
Asn Lys Ile Trp Gly Arg Lys Ser Trp Pro Leu Asn Glu Gly Ile
    1340                1345                1350
Met Ala Val Gly Ile Val Ser Ile Leu Leu Ser Ser Leu Leu Lys
    1355                1360                1365
Asn Asp Val Pro Leu Ala Gly Pro Leu Ile Ala Gly Gly Met Leu
    1370                1375                1380
Ile Ala Cys Tyr Val Ile Ser Gly Ser Ser Ala Asp Leu Ser Leu
    1385                1390                1395
Glu Lys Ala Ala Glu Val Ser Trp Glu Glu Glu Ala Glu His Ser
    1400                1405                1410
Gly Ala Ser His Asn Ile Leu Val Glu Val Gln Asp Asp Gly Thr
    1415                1420                1425
Met Lys Ile Lys Asp Glu Glu Arg Asp Asp Thr Leu Thr Ile Leu
    1430                1435                1440
Leu Lys Ala Thr Leu Leu Ala Val Ser Gly Val Tyr Pro Met Ser
    1445                1450                1455
Ile Pro Ala Thr Leu Phe Val Trp Tyr Phe Trp Gln Lys Lys Lys
    1460                1465                1470
Gln Arg Ser Gly Val Leu Trp Asp Thr Pro Ser Pro Pro Glu Val
    1475                1480                1485
Glu Arg Ala Val Leu Asp Asp Gly Ile Tyr Arg Ile Leu Gln Arg
    1490                1495                1500
Gly Leu Leu Gly Arg Ser Gln Val Gly Val Gly Val Phe Gln Glu
    1505                1510                1515
Gly Val Phe His Thr Met Trp His Val Thr Arg Gly Ala Val Leu
    1520                1525                1530
Met Tyr Gln Gly Lys Arg Leu Glu Pro Ser Trp Ala Ser Val Lys
    1535                1540                1545
Lys Asp Leu Ile Ser Tyr Gly Gly Gly Trp Arg Phe Gln Gly Ser
    1550                1555                1560
Trp Asn Thr Gly Glu Glu Val Gln Val Ile Ala Val Glu Pro Gly
    1565                1570                1575
Lys Asn Pro Lys Asn Val Gln Thr Thr Pro Gly Thr Phe Lys Thr
    1580                1585                1590
Pro Glu Gly Glu Val Gly Ala Ile Ala Leu Asp Phe Lys Pro Gly
    1595                1600                1605
Thr Ser Gly Ser Pro Ile Val Asn Arg Glu Gly Lys Ile Val Gly
    1610                1615                1620
Leu Tyr Gly Asn Gly Val Val Thr Thr Ser Gly Thr Tyr Val Ser
    1625                1630                1635
Ala Ile Ala Gln Ala Lys Ala Ser Gln Glu Gly Pro Leu Pro Glu
    1640                1645                1650
```

-continued

Ile Glu Asp Glu Val Phe Arg Lys Arg Asn Leu Thr Ile Met Asp
1655                1660                1665

Leu His Pro Gly Ser Gly Lys Thr Arg Arg Tyr Leu Pro Ala Ile
1670                1675                1680

Val Arg Glu Ala Ile Lys Arg Lys Leu Arg Thr Leu Ile Leu Ala
1685                1690                1695

Pro Thr Arg Val Val Ala Ser Glu Met Ala Glu Ala Leu Lys Gly
1700                1705                1710

Val Pro Ile Arg Tyr Gln Thr Thr Ala Val Lys Ser Glu His Thr
1715                1720                1725

Gly Lys Glu Ile Val Asp Leu Met Cys His Ala Thr Phe Thr Met
1730                1735                1740

Arg Leu Leu Ser Pro Val Arg Val Pro Asn Tyr Asn Met Ile Ile
1745                1750                1755

Met Asp Glu Ala His Phe Thr Asp Pro Ala Ser Ile Ala Ala Arg
1760                1765                1770

Gly Tyr Ile Ser Thr Arg Val Gly Met Gly Glu Ala Ala Ala Ile
1775                1780                1785

Phe Met Thr Ala Thr Pro Pro Gly Ser Val Glu Ala Phe Pro Gln
1790                1795                1800

Ser Asn Ala Ile Ile Gln Asp Glu Glu Arg Asp Ile Pro Glu Arg
1805                1810                1815

Ser Trp Asn Ser Gly Tyr Asp Trp Ile Thr Asp Phe Pro Gly Lys
1820                1825                1830

Thr Val Trp Phe Val Pro Ser Ile Lys Ser Gly Asn Asp Ile Ala
1835                1840                1845

Asn Cys Leu Arg Lys Asn Gly Lys Arg Val Ile Gln Leu Ser Arg
1850                1855                1860

Lys Thr Phe Asp Thr Glu Tyr Gln Lys Thr Lys Asn Asn Asp Trp
1865                1870                1875

Asp Tyr Val Val Thr Thr Asp Ile Ser Glu Met Gly Ala Asn Phe
1880                1885                1890

Arg Ala Asp Arg Val Ile Asp Pro Arg Arg Cys Leu Lys Pro Val
1895                1900                1905

Ile Leu Lys Asp Gly Pro Glu Arg Val Ile Leu Ala Gly Pro Met
1910                1915                1920

Pro Val Thr Val Ala Ser Ala Ala Gln Arg Arg Gly Arg Ile Gly
1925                1930                1935

Arg Asn Gln Asn Lys Glu Gly Asp Gln Tyr Ile Tyr Met Gly Gln
1940                1945                1950

Pro Leu Asn Asn Asp Glu Asp His Ala His Trp Thr Glu Ala Lys
1955                1960                1965

Met Leu Leu Asp Asn Ile Asn Thr Pro Glu Gly Ile Ile Pro Ala
1970                1975                1980

Leu Tyr Glu Pro Glu Arg Glu Lys Ser Ala Ala Ile Asp Gly Glu
1985                1990                1995

Tyr Arg Leu Arg Gly Glu Ala Arg Lys Thr Phe Val Glu Leu Met
2000                2005                2010

Arg Arg Gly Asp Leu Pro Val Trp Leu Ser Tyr Lys Val Ala Ser
2015                2020                2025

Glu Gly Phe Gln Tyr Ser Asp Arg Arg Trp Cys Phe Asp Gly Glu
2030                2035                2040

```
Arg Asn Asn Gln Val Leu Glu Glu Asn Met Asp Val Glu Ile Trp
    2045                2050                2055

Thr Lys Glu Gly Glu Arg Lys Lys Leu Arg Pro Arg Trp Leu Asp
    2060                2065                2070

Ala Arg Thr Tyr Ser Asp Pro Leu Ala Leu Arg Glu Phe Lys Glu
    2075                2080                2085

Phe Ala Ala Gly Arg Arg Ser Val Ser Gly Asp Leu Ile Leu Glu
    2090                2095                2100

Ile Gly Lys Leu Pro Gln His Leu Thr Gln Arg Ala Gln Asn Ala
    2105                2110                2115

Leu Asp Asn Leu Val Met Leu His Asn Ser Glu Gln Gly Gly Lys
    2120                2125                2130

Ala Tyr Arg His Ala Met Glu Glu Leu Pro Asp Thr Ile Glu Thr
    2135                2140                2145

Leu Met Leu Leu Ala Leu Ile Ala Val Leu Thr Gly Gly Val Thr
    2150                2155                2160

Leu Phe Phe Leu Ser Gly Arg Gly Leu Gly Lys Thr Ser Ile Gly
    2165                2170                2175

Leu Leu Cys Val Met Ala Ser Ser Ala Leu Leu Trp Met Ala Ser
    2180                2185                2190

Val Glu Pro His Trp Ile Ala Ala Ser Ile Ile Leu Glu Phe Phe
    2195                2200                2205

Leu Met Val Leu Leu Ile Pro Glu Pro Asp Arg Gln Arg Thr Pro
    2210                2215                2220

Gln Asp Asn Gln Leu Ala Tyr Val Val Ile Gly Leu Leu Phe Met
    2225                2230                2235

Ile Leu Thr Val Ala Ala Asn Glu Met Gly Leu Leu Glu Thr Thr
    2240                2245                2250

Lys Lys Asp Leu Gly Ile Gly His Val Ala Ala Glu Asn His His
    2255                2260                2265

His Ala Thr Met Leu Asp Val Asp Leu His Pro Ala Ser Ala Trp
    2270                2275                2280

Thr Leu Tyr Ala Val Ala Thr Thr Ile Ile Thr Pro Met Met Arg
    2285                2290                2295

His Thr Ile Glu Asn Thr Thr Ala Asn Ile Ser Leu Thr Ala Ile
    2300                2305                2310

Ala Asn Gln Ala Ala Ile Leu Met Gly Leu Asp Lys Gly Trp Pro
    2315                2320                2325

Ile Ser Lys Met Asp Ile Gly Val Pro Leu Leu Ala Leu Gly Cys
    2330                2335                2340

Tyr Ser Gln Val Asn Pro Leu Thr Leu Ile Ala Ala Val Leu Met
    2345                2350                2355

Leu Val Ala His Tyr Ala Ile Ile Gly Pro Gly Leu Gln Ala Lys
    2360                2365                2370

Ala Thr Arg Glu Ala Gln Lys Arg Thr Ala Ala Gly Ile Met Lys
    2375                2380                2385

Asn Pro Thr Val Asp Gly Ile Val Ala Ile Asp Leu Asp Pro Val
    2390                2395                2400

Val Tyr Asp Ala Lys Phe Glu Lys Gln Leu Gly Gln Ile Met Leu
    2405                2410                2415

Leu Ile Leu Cys Thr Ser Gln Ile Leu Leu Met Arg Thr Thr Trp
    2420                2425                2430

Ala Leu Cys Glu Ser Ile Thr Leu Ala Thr Gly Pro Leu Thr Thr
```

-continued

```
                2435                2440                2445
Leu Trp Glu Gly Ser Pro Gly Lys Phe Trp Asn Thr Thr Ile Ala
    2450                2455                2460
Val Ser Met Ala Asn Ile Phe Arg Gly Ser Tyr Leu Ala Gly Ala
    2465                2470                2475
Gly Leu Ala Phe Ser Leu Met Lys Ser Leu Gly Gly Gly Arg Arg
    2480                2485                2490
Gly Thr Gly Ala Gln Gly Glu Thr Leu Gly Glu Lys Trp Lys Arg
    2495                2500                2505
Gln Leu Asn Gln Leu Ser Lys Ser Glu Phe Asn Thr Tyr Lys Arg
    2510                2515                2520
Ser Gly Ile Met Glu Val Asp Arg Ser Glu Ala Lys Glu Gly Leu
    2525                2530                2535
Lys Arg Gly Glu Thr Thr Lys His Ala Val Ser Arg Gly Thr Ala
    2540                2545                2550
Lys Leu Arg Trp Phe Val Glu Arg Asn Leu Val Lys Pro Glu Gly
    2555                2560                2565
Lys Val Ile Asp Leu Gly Cys Gly Arg Gly Gly Trp Ser Tyr Tyr
    2570                2575                2580
Cys Ala Gly Leu Lys Lys Val Thr Glu Val Lys Gly Tyr Thr Lys
    2585                2590                2595
Gly Gly Pro Gly His Glu Glu Pro Ile Pro Met Ala Thr Tyr Gly
    2600                2605                2610
Trp Asn Leu Val Lys Leu His Ser Gly Lys Asp Val Phe Phe Ile
    2615                2620                2625
Pro Pro Glu Lys Cys Asp Thr Leu Leu Cys Asp Ile Gly Glu Ser
    2630                2635                2640
Ser Pro Asn Pro Thr Ile Glu Glu Gly Arg Thr Leu Arg Val Leu
    2645                2650                2655
Lys Met Val Glu Pro Trp Leu Arg Gly Asn Gln Phe Cys Ile Lys
    2660                2665                2670
Ile Leu Asn Pro Tyr Met Pro Ser Val Val Glu Thr Leu Glu Gln
    2675                2680                2685
Met Gln Arg Lys His Gly Gly Met Leu Val Arg Asn Pro Leu Ser
    2690                2695                2700
Arg Asn Ser Thr His Glu Met Tyr Trp Val Ser Cys Gly Thr Gly
    2705                2710                2715
Asn Ile Val Ser Ala Val Asn Met Thr Ser Arg Met Leu Leu Asn
    2720                2725                2730
Arg Phe Thr Met Ala His Arg Lys Pro Thr Tyr Glu Arg Asp Val
    2735                2740                2745
Asp Leu Gly Ala Gly Thr Arg His Val Ala Val Glu Pro Glu Val
    2750                2755                2760
Ala Asn Leu Asp Ile Ile Gly Gln Arg Ile Glu Asn Ile Lys Asn
    2765                2770                2775
Glu His Lys Ser Thr Trp His Tyr Asp Glu Asp Asn Pro Tyr Lys
    2780                2785                2790
Thr Trp Ala Tyr His Gly Ser Tyr Glu Val Lys Pro Ser Gly Ser
    2795                2800                2805
Ala Ser Ser Met Val Asn Gly Val Val Arg Leu Leu Thr Lys Pro
    2810                2815                2820
Trp Asp Val Ile Pro Met Val Thr Gln Ile Ala Met Thr Asp Thr
    2825                2830                2835
```

-continued

```
Thr Pro Phe Gly Gln Gln Arg Val Phe Lys Glu Lys Val Asp Thr
2840                2845                2850

Arg Thr Pro Lys Ala Lys Arg Gly Thr Ala Gln Ile Met Glu Val
2855                2860                2865

Thr Ala Arg Trp Leu Trp Gly Phe Leu Ser Arg Asn Lys Lys Pro
2870                2875                2880

Arg Ile Cys Thr Arg Glu Glu Phe Thr Arg Lys Val Arg Ser Asn
2885                2890                2895

Ala Ala Ile Gly Ala Val Phe Val Asp Glu Asn Gln Trp Asn Ser
2900                2905                2910

Ala Lys Glu Ala Val Glu Asp Glu Arg Phe Trp Glu Leu Val His
2915                2920                2925

Arg Glu Arg Glu Leu His Lys Gln Gly Lys Cys Ala Thr Cys Val
2930                2935                2940

Tyr Asn Met Met Gly Lys Arg Glu Lys Lys Leu Gly Glu Phe Gly
2945                2950                2955

Lys Ala Lys Gly Ser Arg Ala Ile Trp Tyr Met Trp Leu Gly Ala
2960                2965                2970

Arg Phe Leu Glu Phe Glu Ala Leu Gly Phe Met Asn Glu Asp His
2975                2980                2985

Trp Phe Ser Arg Glu Asn Ser Leu Ser Gly Val Glu Gly Glu Gly
2990                2995                3000

Leu His Lys Leu Gly Tyr Ile Leu Arg Asp Ile Ser Arg Ile Pro
3005                3010                3015

Gly Gly Asn Met Tyr Ala Asp Asp Thr Ala Gly Trp Asp Thr Arg
3020                3025                3030

Ile Thr Glu Asp Asp Leu Gln Asn Glu Ala Lys Ile Thr Asp Ile
3035                3040                3045

Met Glu Pro Glu His Ala Leu Leu Ala Thr Ser Ile Phe Lys Leu
3050                3055                3060

Thr Tyr Gln Asn Lys Val Val Arg Val Gln Arg Pro Ala Lys Asn
3065                3070                3075

Gly Thr Val Met Asp Val Ile Ser Arg Arg Asp Gln Arg Gly Ser
3080                3085                3090

Gly Gln Val Gly Thr Tyr Gly Leu Asn Thr Phe Thr Asn Met Glu
3095                3100                3105

Ala Gln Leu Ile Arg Gln Met Glu Ser Glu Gly Ile Phe Leu Pro
3110                3115                3120

Ser Glu Leu Glu Thr Pro Asn Leu Ala Gly Arg Val Leu Asp Trp
3125                3130                3135

Leu Glu Lys Tyr Gly Val Glu Arg Leu Lys Arg Met Ala Ile Ser
3140                3145                3150

Gly Asp Asp Cys Val Val Lys Pro Ile Asp Asp Arg Phe Ala Thr
3155                3160                3165

Ala Leu Thr Ala Leu Asn Asp Met Gly Lys Val Arg Lys Asp Ile
3170                3175                3180

Pro Gln Trp Glu Pro Ser Lys Gly Trp Asn Asp Trp Gln Gln Val
3185                3190                3195

Pro Phe Cys Ser His His Phe His Gln Leu Ile Met Lys Asp Gly
3200                3205                3210

Arg Glu Ile Val Val Pro Cys Arg Asn Gln Asp Glu Leu Val Gly
3215                3220                3225
```

| | | | | | | | | | | | |
|---|---|---|---|---|---|---|---|---|---|---|---|
| Arg | Ala | Arg | Val | Ser | Gln | Gly | Ala | Gly | Trp | Ser | Leu | Arg | Glu | Thr |
| | 3230 | | | | 3235 | | | | 3240 | | |

Arg Ala Arg Val Ser Gln Gly Ala Gly Trp Ser Leu Arg Glu Thr
    3230                3235                3240

Ala Cys Leu Gly Lys Ser Tyr Ala Gln Met Trp Gln Leu Met Tyr
    3245                3250                3255

Phe His Arg Arg Asp Leu Arg Leu Ala Ala Asn Ala Ile Cys Ser
    3260                3265                3270

Ala Val Pro Val Asp Trp Val Pro Thr Ser Arg Thr Thr Trp Ser
    3275                3280                3285

Ile His Ala His His Gln Trp Met Thr Thr Glu Asp Met Leu Ser
    3290                3295                3300

Val Trp Asn Arg Val Trp Ile Glu Glu Asn Pro Trp Met Glu Asp
    3305                3310                3315

Lys Thr His Val Ser Ser Trp Glu Glu Val Pro Tyr Leu Gly Lys
    3320                3325                3330

Arg Glu Asp Gln Trp Cys Gly Ser Leu Ile Gly Leu Thr Ala Arg
    3335                3340                3345

Ala Thr Trp Ala Thr Asn Ile Gln Val Ala Ile Asn Gln Val Arg
    3350                3355                3360

Arg Leu Ile Gly Asn Glu Asn Tyr Leu Asp Tyr Met Thr Ser Met
    3365                3370                3375

Lys Arg Phe Lys Asn Glu Ser Asp Pro Glu Gly Ala Leu Trp
    3380                3385                3390

<210> SEQ ID NO 11
<211> LENGTH: 10723
<212> TYPE: DNA
<213> ORGANISM: Dengue virus

<400> SEQUENCE: 11

```
agttgttagt ctacgtggac cgacaaagac agattctttg agggagctaa gctcaacgta    60
gttctaacag tttttaatt agagagcaga tctctgatga ataaccaacg gaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acacgtaacg agaaccaca catgatcgtc    480
agcagacaag agaagggaa aagtcttctg tttaaaacag aggatggcgt gaacatgtgt    540
accctcatgg ccatggacct tggtgaattg tgtgaagaca caatcacgta caagtgtccc    600
cttctcaggc agaatgagcc agaagacata gactgttggt gcaactctac gtccacgtgg    660
gtaacttatg gacgtgtac caccatggga gaacatagaa gagaaaaag atcagtggca    720
ctcgttccac atgtgggaat gggactggag acacgaactg aaacatggat gtcatcagaa    780
ggggcctgga acatgtcca gagaattgaa acttggatct tgagacatcc aggcttcacc    840
atgatggcag caatcctggc atacaccata gaacgacac atttccaaag agccctgatt    900
ttcatcttac tgcagctgt cactccttca atgacaatgc gttgcatagg aatgtcaat    960
agagactttg tggaagggt ttcaggaga agctggttg acatagtctt agaacatgga    1020
agctgtgtga cgacgatggc aaaaaacaaa ccaacattgg attttgaact gataaaaaca    1080
gaagccaaac agcctgccac cctaaggaag tactgtatag aggcaaagct aaccaacaca    1140
```

```
acaacagaat ctcgctgccc aacacaaggg gaacccagcc taaatgaaga gcaggacaaa    1200
aggttcgtct gcaaacactc catggtagac agaggatggg gaaatggatg tggactattt    1260
ggaaagggag gcattgtgac ctgtgctatg ttcagatgca aaagaacat ggaaggaaaa     1320 gttgtgcaac cagaaaactt ggaatacacc attgtgataa cacctcactc aggggaagag    1380
catgcagtcg gaaatgacac aggaaaacat ggcaaggaaa tcaaaataac accacagagt    1440
tccatcacag aagcagaatt gacaggttat ggcactgtca caatggagtg ctctccaaga    1500
acgggcctcg acttcaatga gatggtgttg ctgcagatgg aaaataaagc ttggctggtg    1560
cacaggcaat ggttcctaga cctgccgtta ccatggttgc ccggagcgga cacacaaggg    1620
tcaaattgga tacagaaaga gacattggtc actttcaaaa atccccatgc gaagaaacag    1680
gatgttgttg ttttaggatc ccaagaaggg gccatgcaca cagcacttac agggccaca    1740 gaaatccaaa tgtcatcagg aaacttactc ttcacaggac atctcaagtg caggctgaga    1800
atggacaagc tacagctcaa aggaatgtca tactctatgt gcacaggaaa gtttaaagtt    1860
gtgaaggaaa tagcagaaac acaacatgga acaaatagtta tcagagtgca atatgaaggg    1920
gacggctctc catgcaagat ccctttgag ataatggatt tggaaaaaag acatgtctta    1980
ggtcgcctga ttacagtcaa cccaattgtg acagaaaaag atagcccagt caacatagaa    2040
gcagaacctc cattcggaga cagctacatc atcataggag tagagccggg acaactgaag    2100
ctcaactggt ttaagaaagg aagttctatc ggccaaatgt tgagacaac aatgagggg     2160 gcgaagagaa tggccatttt aggtgacaca gcctgggatt ttggatcctt gggaggagtg    2220
tttacatcta taggaaaggc tctccaccaa gtctttggag caatctatgg agctgccttc    2280
agtggggttt catggactat gaaaatcctc ataggagtca ttatcacatg gataggaatg    2340
aattcacgca gcacctcact gtctgtgaca ctagtattgg tgggaattgt gacactgtat    2400
ttgggagtca tggtgcaggc cgatagtggt tgcgttgtga gctggaaaaa caaagaactg    2460
aaatgtggca gtgggatttt catcacagac aacgtgcaca catggacaga acaatacaag    2520
ttccaaccag aatccccttc aaaactagct tcagctatcc agaaagccca tgaagagggc    2580
atttgtggaa tccgctcagt aacaagactg gagaatctga tgtggaaaca aataaccacca    2640 gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg gccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca tgacacatg gaagatagag    3060 aaagcctctt tcattgaagt taaaaactgc cactggccaa aatcacacac cctctggagc    3120
aatggagtgc tagaaagtga gatgataatt ccaaagaatc tcgctggacc agtgtctcaa    3180
cacaactata gaccaggcta ccatacacaa ataacaggac catggcatct aggtaagctt    3240
gagatggact tgatttctg tgatggaaca acagtggtag tgactgagga ctgcggaaat    3300
agaggaccct ctttgagaac aaccactgcc tctggaaaac tcataacaga atggtgctgc    3360
cgatcttgca cattaccacc gctaagatac agaggtgagg atgggtgctg gtacgggatg    3420
gaaatcagac cattgaagga gaagaagag aatttggtca actccttggt cacagctgga    3480
catgggcagg tcgacaactt ttcactagga gtcttgggaa tggcattgtt cctggaggaa    3540
```

-continued

```
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgctc   4020
ttaacatcct cacagcaaaa aacagattgg ataccattag cattgacgat caaaggtctc   4080
aatccaacag ctattttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactgaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacatttc cgaaagagaa gactgaccat catggaccte   5100 cacccaggag cgggaaagac gaagagatac cttccggcca tagtcagaga gctataaaa   5160 cggggtttga gaacattaat cttggccccc actagagttg tggcagctga atggaggaa   5220 gcccttagag gacttccaat aagataccag accccagcca tcagagctga gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctccccgggg aagcagagac ccatttcctc agagcaatgc accaatcata   5520
gatgaagaaa gagaaatccc tgaacgttcg tggaattccg acatgaatg ggtcacggat   5580 tttaaaggga gactgttttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
```

```
gcagcacaaa gaagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag agaagcaag gaaaaccttt     6120
gtagacttaa tgagaagagg agacctacca gtctggttgg cctacagagt ggcagctgaa    6180
ggcatcaact acgcagacag aaggtggtgt tttgatggag tcaagaacaa ccaaatccta    6240
gaagaaaacg tggaagttga aatctggaca aaagaagggg aaaggaagaa attgaaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgga    6600
aggggcatag gaagatgac cctgggaatg tgctgcaaa tcacggctag catcctccta     6660
tggtacgcac aaatacagcc acactggata gcagcttcaa taatactgga gttttttctc    6720
atagttttgc ttattccaga acctgaaaaa cagagaaac cccaagacaa ccaactgacc     6780
tacgttgtca tagccatcct cacagtggtg ccgcaaacca tggcaaacga gatgggtttc    6840
ctagaaaaaa cgaagaaaga tctcggattg ggaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctctttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg acaagtaat gctcctagtc ctctgcgtga ctcaagtatt gatgatgagg     7380
actacatggg ctctgtgtga ggcttaacc ttagctaccg ggcccatctc cacattgtgg     7440
gaaggaaatc cagggaggtt ttggaacact accattgcgg tgtcaatggc taacattttt    7500
agagggagtt acttggccgg agctggactt ctcttttcta ttatgaagaa cacaaccaac    7560
acaagaaggg gaactggcaa cataggagag acgcttggag agaaatggaa aagccgattg    7620
aacgcattgg gaaaaagtga attccagatc tacaagaaaa gtggaatcca ggaagtggat    7680
agaaccttag caaagaaggg cattaaaaga ggagaaacgg accatcacgc tgtgtcgcga    7740
ggctcagcaa aactgagatg gttcgttgag agaaacatgg tcacaccaga agggaaagta    7800
gtggacctcg gttgtggcag aggaggctgg tcatactatt gtggaggact aaagaatgta    7860
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattatt gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atgagggagc cttagtgagg aatccactct cacgaaactc cacacatgag    8220
atgtactggg tatccaatgc ttccgggaac atagtgtcat cagtgaacat gatttcaagg    8280
```

```
atgttgatca acagatttac aatgagatac aagaaagcca cttacgagcc ggatgttgac    8340
ctcggaagcg gaacccgtaa catcgggatt gaaagtgaga taccaaacct agatataatt    8400
gggaaaagaa tagaaaaaat aaagcaagag catgaaacat catggcacta tgaccaagac    8460
cacccataca aaacgtgggc ataccatggt agctatgaaa caaaacagac tggatcagca    8520
tcatccatgg tcaacggagt ggtcaggctg ctgacaaaac cttgggacgt cgtccccatg    8580
gtgacacaga tggcaatgac agacacgact ccatttggac aacagcgcgt ttttaaagag    8640
aaagtggaca cgagaaccca gaaccgaaa gaaggcacga agaaactaat gaaaataaca     8700
gcagagtggc tttggaaaga attagggaag aaaaagacac caggatgtg caccagagaa     8760
gaattcacaa gaaaggtgag aagcaatgca gccttggggg ccatattcac tgatgagaac    8820
aagtggaagt cggcacgtga ggctgttgaa gatagtaggt tttgggagct ggttgacaag    8880
gaaaggaatc tccatcttga aggaaagtgt gaaacatgtg tgtacaacat gatgggaaaa    8940
agagagaaga agctagggga attcggcaag gcaaaaggca gcagagccat atggtacatg    9000
tggcttggag cacgcttctt agagtttgaa gccctaggat tcttaaatga agatcactgg    9060
ttctccagag agaactccct gagtggagtg gaaggagaag ggtcacaa gctaggttac      9120
attctaagag acgtgagcaa gaaagaggga ggagcaatgt atgccgatga caccgcagga    9180
tgggatacaa gaatcacact agaagaccta aaaaatgaag aaatggtaac aaaccacatg    9240
gaaggagaac acaagaaact agccgaggcc attttcaaac taacgtacca aaacaaggtg    9300
gtgcgtgtgc aaagaccaac accaagaggc acagtaatgg acatcatatc gagaagagac    9360
caaagaggta gtggacaagt tggcacctat ggactcaata ctttcaccaa tatggaagcc    9420
caactaatca gacagatgga gggagaagga gtctttaaaa gcattcagca cctaacaatc    9480
acagaagaaa tcgctgtgca aaactggtta gcaagagtgg ggcgcgaaag gttatcaaga    9540
atggccatca gtggagatga ttgtgttgtg aaacctttag atgacaggtt cgcaagcgct    9600
ttaacagctc taaatgacat gggaaagatt aggaaagaca tacaacaatg gaaccttca    9660
agaggatgga atgattggac acaagtgccc ttctgttcac accatttcca tgagttaatc    9720
atgaaagacg gtcgcgtact cgttgttcca tgtagaaacc aagatgaact gattggcaga    9780
gcccgaatct cccaaggagc agggtggtct ttgcgggaga cggcctgttt ggggaagtct    9840
tacgcccaaa tgtggagctt gatgtacttc cacagacgcg acctcaggct ggcggcaaat    9900
gctatttgct cggcagtacc atcacattgg gttccaacaa gtcgaacaac ctggtccata    9960
catgctaaac atgaatggat gacaacggaa gacatgctga cagtctggaa cagggtgtgg    10020
attcaagaaa acccatggat ggaagacaaa actccagtgg aatcatggga ggaaatccca   10080
tacttgggga aaagagaaga ccaatggtgc ggctcattga ttgggttaac aagcagggcc   10140
acctgggcaa agaacatcca agcagcaata aatcaagtta gatcccttat aggcaatgaa   10200
gaatacacag attacatgcc atccatgaaa agattcagaa gagaagagga agcagga      10260
gttctgtggt agaaagcaaa actaacatga acaaggcta gaagtcaggt cggattaagc    10320
catagtacgg aaaaactat gctacctgtg agccccgtcc aaggacgtta aagaagtca     10380
ggccatcata aatgccatag ctggagtaaa ctatgcagcc tgtagctcca cctgagaagg   10440
tgtaaaaaat ccgggaggcc acaaaccatg gaagctgtac gcatggcgta gtggactagc   10500
ggttagagga gacccctccc ttacaaatcg cagcaacaat gggggcccaa ggcgagatga   10560
agctgtagtc tcgctggaag gactagaggt tagaggagac cccccgaaa caaaaaacag    10620
```

```
catattgacg ctgggaaaga ccagagatcc tgctgtctcc tcagcatcat tccaggcaca    10680
gaacgccaga aatggaatg gtgctgttga atcaacaggt tct                       10723
```

<210> SEQ ID NO 12
<211> LENGTH: 3391
<212> TYPE: PRT
<213> ORGANISM: Dengue virus

<400> SEQUENCE: 12

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Asp Gly
    130                 135                 140

Val Asn Met Cys Thr Leu Met Ala Met Asp Leu Gly Glu Leu Cys Glu
145                 150                 155                 160

Asp Thr Ile Thr Tyr Lys Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
```

-continued

```
            355                 360                 365
Arg Phe Val Cys Lys His Ser Met Val Asp Arg Gly Trp Gly Asn Gly
370                 375                 380

Cys Gly Leu Phe Gly Lys Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu His Ala Val Gly
                420                 425                 430

Asn Asp Thr Gly Lys His Gly Lys Glu Ile Lys Ile Thr Pro Gln Ser
            435                 440                 445

Ser Ile Thr Glu Ala Glu Leu Thr Gly Tyr Gly Thr Val Thr Met Glu
            450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
                500                 505                 510

Gln Lys Glu Thr Leu Val Thr Phe Lys Asn Pro His Ala Lys Lys Gln
            515                 520                 525

Asp Val Val Leu Gly Ser Gln Glu Gly Ala Met His Thr Ala Leu
530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
                580                 585                 590

Ala Glu Thr Gln His Gly Thr Ile Val Ile Arg Val Gln Tyr Glu Gly
            595                 600                 605

Asp Gly Ser Pro Cys Lys Ile Pro Phe Glu Ile Met Asp Leu Glu Lys
610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
                660                 665                 670

Lys Lys Gly Ser Ser Ile Gly Gln Met Phe Glu Thr Thr Met Arg Gly
            675                 680                 685

Ala Lys Arg Met Ala Ile Leu Gly Asp Thr Ala Trp Asp Phe Gly Ser
            690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
                740                 745                 750

Thr Ser Leu Ser Val Thr Leu Val Leu Val Gly Ile Val Thr Leu Tyr
            755                 760                 765

Leu Gly Val Met Val Gln Ala Asp Ser Gly Cys Val Val Ser Trp Lys
770                 775                 780
```

-continued

Asn Lys Glu Leu Lys Cys Gly Ser Gly Ile Phe Ile Thr Asp Asn Val
785            790                795                800

His Thr Trp Thr Glu Gln Tyr Lys Phe Gln Pro Glu Ser Pro Ser Lys
                805                810                815

Leu Ala Ser Ala Ile Gln Lys Ala His Glu Glu Gly Ile Cys Gly Ile
            820                825                830

Arg Ser Val Thr Arg Leu Glu Asn Leu Met Trp Lys Gln Ile Thr Pro
        835                840                845

Glu Leu Asn His Ile Leu Ser Glu Asn Glu Val Lys Leu Thr Ile Met
850                855                860

Thr Gly Asp Ile Lys Gly Ile Met Gln Ala Gly Lys Arg Ser Leu Arg
865                870                875                880

Pro Gln Pro Thr Glu Leu Lys Tyr Ser Trp Lys Thr Trp Gly Lys Ala
                885                890                895

Lys Met Leu Ser Thr Glu Ser His Asn Gln Thr Phe Leu Ile Asp Gly
            900                905                910

Pro Glu Thr Ala Glu Cys Pro Asn Thr Asn Arg Ala Trp Asn Ser Leu
        915                920                925

Glu Val Glu Asp Tyr Gly Phe Gly Val Phe Thr Thr Asn Ile Trp Leu
930                935                940

Lys Leu Lys Glu Lys Gln Asp Val Phe Cys Asp Ser Lys Leu Met Ser
945                950                955                960

Ala Ala Ile Lys Asp Asn Arg Ala Val His Ala Asp Met Gly Tyr Trp
                965                970                975

Ile Glu Ser Ala Leu Asn Asp Thr Trp Lys Ile Glu Lys Ala Ser Phe
            980                985                990

Ile Glu Val Lys Asn Cys His Trp Pro Lys Ser His Thr Leu Trp Ser
        995                1000               1005

Asn Gly Val Leu Glu Ser Glu Met Ile Ile Pro Lys Asn Leu Ala
    1010               1015               1020

Gly Pro Val Ser Gln His Asn Tyr Arg Pro Gly Tyr His Thr Gln
    1025               1030               1035

Ile Thr Gly Pro Trp His Leu Gly Lys Leu Glu Met Asp Phe Asp
    1040               1045               1050

Phe Cys Asp Gly Thr Thr Val Val Val Thr Glu Asp Cys Gly Asn
    1055               1060               1065

Arg Gly Pro Ser Leu Arg Thr Thr Thr Ala Ser Gly Lys Leu Ile
    1070               1075               1080

Thr Glu Trp Cys Cys Arg Ser Cys Thr Leu Pro Pro Leu Arg Tyr
    1085               1090               1095

Arg Gly Glu Asp Gly Cys Trp Tyr Gly Met Glu Ile Arg Pro Leu
    1100               1105               1110

Lys Glu Lys Glu Glu Asn Leu Val Asn Ser Leu Val Thr Ala Gly
    1115               1120               1125

His Gly Gln Val Asp Asn Phe Ser Leu Gly Val Leu Gly Met Ala
    1130               1135               1140

Leu Phe Leu Glu Glu Met Leu Arg Thr Arg Val Gly Thr Lys His
    1145               1150               1155

Ala Ile Leu Leu Val Ala Val Ser Phe Val Thr Leu Ile Thr Gly
    1160               1165               1170

Asn Met Ser Phe Arg Asp Leu Gly Arg Val Met Val Met Val Gly
    1175               1180               1185

```
Ala Thr Met Thr Asp Asp Ile Gly Met Gly Val Thr Tyr Leu Ala
    1190            1195             1200

Leu Leu Ala Ala Phe Lys Val Arg Pro Thr Phe Ala Ala Gly Leu
    1205            1210             1215

Leu Leu Arg Lys Leu Thr Ser Lys Glu Leu Met Met Thr Thr Ile
    1220            1225             1230

Gly Ile Val Leu Leu Ser Gln Ser Thr Ile Pro Glu Thr Ile Leu
    1235            1240             1245

Glu Leu Thr Asp Ala Leu Ala Leu Gly Met Met Val Leu Lys Met
    1250            1255             1260

Val Arg Asn Met Glu Lys Tyr Gln Leu Ala Val Thr Ile Met Ala
    1265            1270             1275

Ile Leu Cys Val Pro Asn Ala Val Ile Leu Gln Asn Ala Trp Lys
    1280            1285             1290

Val Ser Cys Thr Ile Leu Ala Val Val Ser Val Ser Pro Leu Leu
    1295            1300             1305

Leu Thr Ser Ser Gln Gln Lys Thr Asp Trp Ile Pro Leu Ala Leu
    1310            1315             1320

Thr Ile Lys Gly Leu Asn Pro Thr Ala Ile Phe Leu Thr Thr Leu
    1325            1330             1335

Ser Arg Thr Ser Lys Lys Arg Ser Trp Pro Leu Asn Glu Ala Ile
    1340            1345             1350

Met Ala Val Gly Met Val Ser Ile Leu Ala Ser Ser Leu Leu Lys
    1355            1360             1365

Asn Asp Ile Pro Met Thr Gly Pro Leu Val Ala Gly Gly Leu Leu
    1370            1375             1380

Thr Val Cys Tyr Val Leu Thr Gly Arg Ser Ala Asp Leu Glu Leu
    1385            1390             1395

Glu Arg Ala Ala Asp Val Lys Trp Glu Asp Gln Ala Glu Ile Ser
    1400            1405             1410

Gly Ser Ser Pro Ile Leu Ser Ile Thr Ile Ser Glu Asp Gly Ser
    1415            1420             1425

Met Ser Ile Lys Asn Glu Glu Glu Gln Thr Leu Thr Ile Leu
    1430            1435             1440

Ile Arg Thr Gly Leu Leu Val Ile Ser Gly Leu Phe Pro Val Ser
    1445            1450             1455

Ile Pro Ile Thr Ala Ala Ala Trp Tyr Leu Trp Glu Val Lys Lys
    1460            1465             1470

Gln Arg Ala Gly Val Leu Trp Asp Val Pro Ser Pro Pro Pro Met
    1475            1480             1485

Gly Lys Ala Glu Leu Glu Asp Gly Ala Tyr Arg Ile Lys Gln Lys
    1490            1495             1500

Gly Ile Leu Gly Tyr Ser Gln Ile Gly Ala Gly Val Tyr Lys Glu
    1505            1510             1515

Gly Thr Phe His Thr Met Trp His Val Thr Arg Gly Ala Val Leu
    1520            1525             1530

Met His Lys Gly Lys Arg Ile Glu Pro Ser Trp Ala Asp Val Lys
    1535            1540             1545

Lys Asp Leu Ile Ser Tyr Gly Gly Gly Trp Lys Leu Glu Gly Glu
    1550            1555             1560

Trp Lys Glu Gly Glu Glu Val Gln Val Leu Ala Leu Glu Pro Gly
    1565            1570             1575

Lys Asn Pro Arg Ala Val Gln Thr Lys Pro Gly Leu Phe Lys Thr
```

```
            1580                1585                1590

Asn Ala Gly Thr Ile Gly Ala Val Ser Leu Asp Phe Ser Pro Gly
    1595                1600                1605

Thr Ser Gly Ser Pro Ile Ile Asp Lys Lys Gly Lys Val Val Gly
    1610                1615                1620

Leu Tyr Gly Asn Gly Val Val Thr Arg Ser Gly Ala Tyr Val Ser
    1625                1630                1635

Ala Ile Ala Gln Thr Glu Lys Ser Ile Glu Asp Asn Pro Glu Ile
    1640                1645                1650

Glu Asp Asp Ile Phe Arg Lys Arg Arg Leu Thr Ile Met Asp Leu
    1655                1660                1665

His Pro Gly Ala Gly Lys Thr Lys Arg Tyr Leu Pro Ala Ile Val
    1670                1675                1680

Arg Glu Ala Ile Lys Arg Gly Leu Arg Thr Leu Ile Leu Ala Pro
    1685                1690                1695

Thr Arg Val Val Ala Ala Glu Met Glu Glu Ala Leu Arg Gly Leu
    1700                1705                1710

Pro Ile Arg Tyr Gln Thr Pro Ala Ile Arg Ala Glu His Thr Gly
    1715                1720                1725

Arg Glu Ile Val Asp Leu Met Cys His Ala Thr Phe Thr Met Arg
    1730                1735                1740

Leu Leu Ser Pro Val Arg Val Pro Asn Tyr Asn Leu Ile Ile Met
    1745                1750                1755

Asp Glu Ala His Phe Thr Asp Pro Ala Ser Ile Ala Ala Arg Gly
    1760                1765                1770

Tyr Ile Ser Thr Arg Val Glu Met Gly Glu Ala Ala Gly Ile Phe
    1775                1780                1785

Met Thr Ala Thr Pro Pro Gly Ser Arg Asp Pro Phe Pro Gln Ser
    1790                1795                1800

Asn Ala Pro Ile Ile Asp Glu Glu Arg Glu Ile Pro Glu Arg Ser
    1805                1810                1815

Trp Asn Ser Gly His Glu Trp Val Thr Asp Phe Lys Gly Lys Thr
    1820                1825                1830

Val Trp Phe Val Pro Ser Ile Lys Ala Gly Asn Asp Ile Ala Ala
    1835                1840                1845

Cys Leu Arg Lys Asn Gly Lys Lys Val Ile Gln Leu Ser Arg Lys
    1850                1855                1860

Thr Phe Asp Ser Glu Tyr Val Lys Thr Arg Thr Asn Asp Trp Asp
    1865                1870                1875

Phe Val Val Thr Thr Asp Ile Ser Glu Met Gly Ala Asn Phe Lys
    1880                1885                1890

Ala Glu Arg Val Ile Asp Pro Arg Arg Cys Met Lys Pro Val Ile
    1895                1900                1905

Leu Thr Asp Gly Glu Glu Arg Val Ile Leu Ala Gly Pro Met Pro
    1910                1915                1920

Val Thr His Ser Ser Ala Ala Gln Arg Arg Gly Arg Ile Gly Arg
    1925                1930                1935

Asn Pro Lys Asn Glu Asn Asp Gln Tyr Ile Tyr Met Gly Glu Pro
    1940                1945                1950

Leu Glu Asn Asp Glu Asp Cys Ala His Trp Lys Glu Ala Lys Met
    1955                1960                1965

Leu Leu Asp Asn Ile Asn Thr Pro Glu Gly Ile Ile Pro Ser Met
    1970                1975                1980
```

```
Phe Glu Pro Glu Arg Glu Lys Val Asp Ala Ile Asp Gly Glu Tyr
    1985            1990                1995

Arg Leu Arg Gly Glu Ala Arg Lys Thr Phe Val Asp Leu Met Arg
    2000            2005                2010

Arg Gly Asp Leu Pro Val Trp Leu Ala Tyr Arg Val Ala Ala Glu
    2015            2020                2025

Gly Ile Asn Tyr Ala Asp Arg Arg Trp Cys Phe Asp Gly Val Lys
    2030            2035                2040

Asn Asn Gln Ile Leu Glu Glu Asn Val Glu Val Glu Ile Trp Thr
    2045            2050                2055

Lys Glu Gly Glu Arg Lys Lys Leu Lys Pro Arg Trp Leu Asp Ala
    2060            2065                2070

Arg Ile Tyr Ser Asp Pro Leu Ala Leu Lys Glu Phe Lys Glu Phe
    2075            2080                2085

Ala Ala Gly Arg Lys Ser Leu Thr Leu Asn Leu Ile Thr Glu Met
    2090            2095                2100

Gly Arg Leu Pro Thr Phe Met Thr Gln Lys Ala Arg Asp Ala Leu
    2105            2110                2115

Asp Asn Leu Ala Val Leu His Thr Ala Glu Ala Gly Gly Arg Ala
    2120            2125                2130

Tyr Asn His Ala Leu Ser Glu Leu Pro Glu Thr Leu Glu Thr Leu
    2135            2140                2145

Leu Leu Leu Thr Leu Leu Ala Thr Val Thr Gly Gly Ile Phe Leu
    2150            2155                2160

Phe Leu Met Ser Gly Arg Gly Ile Gly Lys Met Thr Leu Gly Met
    2165            2170                2175

Cys Cys Ile Ile Thr Ala Ser Ile Leu Leu Trp Tyr Ala Gln Ile
    2180            2185                2190

Gln Pro His Trp Ile Ala Ala Ser Ile Ile Leu Glu Phe Phe Leu
    2195            2200                2205

Ile Val Leu Leu Ile Pro Glu Pro Glu Lys Gln Arg Thr Pro Gln
    2210            2215                2220

Asp Asn Gln Leu Thr Tyr Val Val Ile Ala Ile Leu Thr Val Val
    2225            2230                2235

Ala Ala Thr Met Ala Asn Glu Met Gly Phe Leu Glu Lys Thr Lys
    2240            2245                2250

Lys Asp Leu Gly Leu Gly Ser Ile Ala Thr Gln Gln Pro Glu Ser
    2255            2260                2265

Asn Ile Leu Asp Ile Asp Leu Arg Pro Ala Ser Ala Trp Thr Leu
    2270            2275                2280

Tyr Ala Val Ala Thr Thr Phe Val Thr Pro Met Leu Arg His Ser
    2285            2290                2295

Ile Glu Asn Ser Ser Val Asn Val Ser Leu Thr Ala Ile Ala Asn
    2300            2305                2310

Gln Ala Thr Val Leu Met Gly Leu Gly Lys Gly Trp Pro Leu Ser
    2315            2320                2325

Lys Met Asp Ile Gly Val Pro Leu Leu Ala Ile Gly Cys Tyr Ser
    2330            2335                2340

Gln Val Asn Pro Ile Thr Leu Thr Ala Ala Leu Phe Leu Leu Val
    2345            2350                2355

Ala His Tyr Ala Ile Ile Gly Pro Gly Leu Gln Ala Lys Ala Thr
    2360            2365                2370
```

Arg Glu Ala Gln Lys Arg Ala Ala Gly Ile Met Lys Asn Pro
2375                2380                2385

Thr Val Asp Gly Ile Thr Val Ile Asp Leu Asp Pro Ile Pro Tyr
2390                2395                2400

Asp Pro Lys Phe Glu Lys Gln Leu Gly Gln Val Met Leu Leu Val
2405                2410                2415

Leu Cys Val Thr Gln Val Leu Met Met Arg Thr Thr Trp Ala Leu
2420                2425                2430

Cys Glu Ala Leu Thr Leu Ala Thr Gly Pro Ile Ser Thr Leu Trp
2435                2440                2445

Glu Gly Asn Pro Gly Arg Phe Trp Asn Thr Thr Ile Ala Val Ser
2450                2455                2460

Met Ala Asn Ile Phe Arg Gly Ser Tyr Leu Ala Gly Ala Gly Leu
2465                2470                2475

Leu Phe Ser Ile Met Lys Asn Thr Thr Asn Thr Arg Arg Gly Thr
2480                2485                2490

Gly Asn Ile Gly Glu Thr Leu Gly Glu Lys Trp Lys Ser Arg Leu
2495                2500                2505

Asn Ala Leu Gly Lys Ser Glu Phe Gln Ile Tyr Lys Lys Ser Gly
2510                2515                2520

Ile Gln Glu Val Asp Arg Thr Leu Ala Lys Glu Gly Ile Lys Arg
2525                2530                2535

Gly Glu Thr Asp His His Ala Val Ser Arg Gly Ser Ala Lys Leu
2540                2545                2550

Arg Trp Phe Val Glu Arg Asn Met Val Thr Pro Glu Gly Lys Val
2555                2560                2565

Val Asp Leu Gly Cys Gly Arg Gly Gly Trp Ser Tyr Tyr Cys Gly
2570                2575                2580

Gly Leu Lys Asn Val Arg Glu Val Lys Gly Leu Thr Lys Gly Gly
2585                2590                2595

Pro Gly His Glu Glu Pro Ile Pro Met Ser Thr Tyr Gly Trp Asn
2600                2605                2610

Leu Val Arg Leu Gln Ser Gly Val Asp Val Phe Phe Ile Pro Pro
2615                2620                2625

Glu Lys Cys Asp Thr Leu Leu Cys Asp Ile Gly Glu Ser Ser Pro
2630                2635                2640

Asn Pro Thr Val Glu Ala Gly Arg Thr Leu Arg Val Leu Asn Leu
2645                2650                2655

Val Glu Asn Trp Leu Asn Asn Asn Thr Gln Phe Cys Ile Lys Val
2660                2665                2670

Leu Asn Pro Tyr Met Pro Ser Val Ile Glu Lys Met Glu Ala Leu
2675                2680                2685

Gln Arg Lys Tyr Gly Gly Ala Leu Val Arg Asn Pro Leu Ser Arg
2690                2695                2700

Asn Ser Thr His Glu Met Tyr Trp Val Ser Asn Ala Ser Gly Asn
2705                2710                2715

Ile Val Ser Ser Val Asn Met Ile Ser Arg Met Leu Ile Asn Arg
2720                2725                2730

Phe Thr Met Arg Tyr Lys Lys Ala Thr Tyr Glu Pro Asp Val Asp
2735                2740                2745

Leu Gly Ser Gly Thr Arg Asn Ile Gly Ile Glu Ser Glu Ile Pro
2750                2755                2760

Asn Leu Asp Ile Ile Gly Lys Arg Ile Glu Lys Ile Lys Gln Glu

```
            2765                2770                2775
     His Glu Thr Ser Trp His Tyr Asp Gln Asp His Pro Tyr Lys Thr
            2780                2785                2790

Trp Ala Tyr His Gly Ser Tyr Glu Thr Lys Gln Thr Gly Ser Ala
            2795                2800                2805

Ser Ser Met Val Asn Gly Val Val Arg Leu Leu Thr Lys Pro Trp
            2810                2815                2820

Asp Val Val Pro Met Val Thr Gln Met Ala Met Thr Asp Thr Thr
            2825                2830                2835

Pro Phe Gly Gln Gln Arg Val Phe Lys Glu Lys Val Asp Thr Arg
            2840                2845                2850

Thr Gln Glu Pro Lys Glu Gly Thr Lys Lys Leu Met Lys Ile Thr
            2855                2860                2865

Ala Glu Trp Leu Trp Lys Glu Leu Gly Lys Lys Lys Thr Pro Arg
            2870                2875                2880

Met Cys Thr Arg Glu Glu Phe Thr Arg Lys Val Arg Ser Asn Ala
            2885                2890                2895

Ala Leu Gly Ala Ile Phe Thr Asp Glu Asn Lys Trp Lys Ser Ala
            2900                2905                2910

Arg Glu Ala Val Glu Asp Ser Arg Phe Trp Glu Leu Val Asp Lys
            2915                2920                2925

Glu Arg Asn Leu His Leu Glu Gly Lys Cys Glu Thr Cys Val Tyr
            2930                2935                2940

Asn Met Met Gly Lys Arg Glu Lys Lys Leu Gly Glu Phe Gly Lys
            2945                2950                2955

Ala Lys Gly Ser Arg Ala Ile Trp Tyr Met Trp Leu Gly Ala Arg
            2960                2965                2970

Phe Leu Glu Phe Glu Ala Leu Gly Phe Leu Asn Glu Asp His Trp
            2975                2980                2985

Phe Ser Arg Glu Asn Ser Leu Ser Gly Val Glu Gly Glu Gly Leu
            2990                2995                3000

His Lys Leu Gly Tyr Ile Leu Arg Asp Val Ser Lys Lys Glu Gly
            3005                3010                3015

Gly Ala Met Tyr Ala Asp Asp Thr Ala Gly Trp Asp Thr Arg Ile
            3020                3025                3030

Thr Leu Glu Asp Leu Lys Asn Glu Glu Met Val Thr Asn His Met
            3035                3040                3045

Glu Gly Glu His Lys Lys Leu Ala Glu Ala Ile Phe Lys Leu Thr
            3050                3055                3060

Tyr Gln Asn Lys Val Val Arg Val Gln Arg Pro Thr Pro Arg Gly
            3065                3070                3075

Thr Val Met Asp Ile Ile Ser Arg Arg Asp Gln Arg Gly Ser Gly
            3080                3085                3090

Gln Val Gly Thr Tyr Gly Leu Asn Thr Phe Thr Asn Met Glu Ala
            3095                3100                3105

Gln Leu Ile Arg Gln Met Glu Gly Glu Gly Val Phe Lys Ser Ile
            3110                3115                3120

Gln His Leu Thr Ile Thr Glu Glu Ile Ala Val Gln Asn Trp Leu
            3125                3130                3135

Ala Arg Val Gly Arg Glu Arg Leu Ser Arg Met Ala Ile Ser Gly
            3140                3145                3150

Asp Asp Cys Val Val Lys Pro Leu Asp Asp Arg Phe Ala Ser Ala
            3155                3160                3165
```

| Leu | Thr | Ala | Leu | Asn | Asp | Met | Gly | Lys | Ile | Arg | Lys | Asp | Ile | Gln |
|---|---|---|---|---|---|---|---|---|---|---|---|---|---|---|
| | 3170 | | | | 3175 | | | | | 3180 | | | | |

| Gln | Trp | Glu | Pro | Ser | Arg | Gly | Trp | Asn | Asp | Trp | Thr | Gln | Val | Pro |
|---|---|---|---|---|---|---|---|---|---|---|---|---|---|---|
| 3185 | | | | | 3190 | | | | | 3195 | | | | |

| Phe | Cys | Ser | His | His | Phe | His | Glu | Leu | Ile | Met | Lys | Asp | Gly | Arg |
|---|---|---|---|---|---|---|---|---|---|---|---|---|---|---|
| | 3200 | | | | | 3205 | | | | 3210 | | | | |

| Val | Leu | Val | Val | Pro | Cys | Arg | Asn | Gln | Asp | Glu | Leu | Ile | Gly | Arg |
|---|---|---|---|---|---|---|---|---|---|---|---|---|---|---|
| 3215 | | | | | 3220 | | | | | 3225 | | | | |

| Ala | Arg | Ile | Ser | Gln | Gly | Ala | Gly | Trp | Ser | Leu | Arg | Glu | Thr | Ala |
|---|---|---|---|---|---|---|---|---|---|---|---|---|---|---|
| | 3230 | | | | 3235 | | | | | 3240 | | | | |

| Cys | Leu | Gly | Lys | Ser | Tyr | Ala | Gln | Met | Trp | Ser | Leu | Met | Tyr | Phe |
|---|---|---|---|---|---|---|---|---|---|---|---|---|---|---|
| 3245 | | | | | 3250 | | | | | 3255 | | | | |

| His | Arg | Arg | Asp | Leu | Arg | Leu | Ala | Ala | Asn | Ala | Ile | Cys | Ser | Ala |
|---|---|---|---|---|---|---|---|---|---|---|---|---|---|---|
| | 3260 | | | | | 3265 | | | | 3270 | | | | |

| Val | Pro | Ser | His | Trp | Val | Pro | Thr | Ser | Arg | Thr | Thr | Trp | Ser | Ile |
|---|---|---|---|---|---|---|---|---|---|---|---|---|---|---|
| 3275 | | | | | 3280 | | | | | 3285 | | | | |

| His | Ala | Lys | His | Glu | Trp | Met | Thr | Thr | Glu | Asp | Met | Leu | Thr | Val |
|---|---|---|---|---|---|---|---|---|---|---|---|---|---|---|
| | 3290 | | | | 3295 | | | | | 3300 | | | | |

| Trp | Asn | Arg | Val | Trp | Ile | Gln | Glu | Asn | Pro | Trp | Met | Glu | Asp | Lys |
|---|---|---|---|---|---|---|---|---|---|---|---|---|---|---|
| 3305 | | | | | 3310 | | | | | 3315 | | | | |

| Thr | Pro | Val | Glu | Ser | Trp | Glu | Glu | Ile | Pro | Tyr | Leu | Gly | Lys | Arg |
|---|---|---|---|---|---|---|---|---|---|---|---|---|---|---|
| | 3320 | | | | 3325 | | | | | 3330 | | | | |

| Glu | Asp | Gln | Trp | Cys | Gly | Ser | Leu | Ile | Gly | Leu | Thr | Ser | Arg | Ala |
|---|---|---|---|---|---|---|---|---|---|---|---|---|---|---|
| 3335 | | | | | 3340 | | | | | 3345 | | | | |

| Thr | Trp | Ala | Lys | Asn | Ile | Gln | Ala | Ala | Ile | Asn | Gln | Val | Arg | Ser |
|---|---|---|---|---|---|---|---|---|---|---|---|---|---|---|
| | 3350 | | | | 3355 | | | | | 3360 | | | | |

| Leu | Ile | Gly | Asn | Glu | Glu | Tyr | Thr | Asp | Tyr | Met | Pro | Ser | Met | Lys |
|---|---|---|---|---|---|---|---|---|---|---|---|---|---|---|
| 3365 | | | | | 3370 | | | | | 3375 | | | | |

| Arg | Phe | Arg | Arg | Glu | Glu | Glu | Ala | Gly | Val | Leu | Trp |
|---|---|---|---|---|---|---|---|---|---|---|---|
| | 3380 | | | | 3385 | | | | | 3390 | |

<210> SEQ ID NO 13
<211> LENGTH: 10696
<212> TYPE: DNA
<213> ORGANISM: Dengue virus

<400> SEQUENCE: 13

```
agttgttagt ctacgtggac cgacaagaac agtttcgact cggaagcttg cttaacgtag     60
tgctgacagt tttttattag agagcagatc tctgatgaac aaccaacgga aaaagacggg    120
aaaaccgtct atcaatatgc tgaaacgcgt gagaaaccgt gtgtcaactg gatcacagtt    180
ggcgaagaga ttctcaagag gattgctgaa cggccaagga ccaatgaaat tggttatggc    240
atttatagct ttcctcagat ttctagccat tccaccgaca gcaggagtct tggctagatg    300
gggtaccttt aagaagtcgg gggctattaa ggtcttaaaa ggcttcaaga aggagatctc    360
aaacatgctg agcattatca acaaacggaa aaagacatcg ctctgtctca tgatgatgtt    420
accagcaaca cttgctttcc acttaacttc acgagatgga gagccgcgca tgattgtggg    480
gaagaatgaa agaggaaaat ccctactttt caagacagcc tctggaatca acatgtgcac    540
actcatagcc atggatctgg agagatgtgt gatgacacg gtcacttaca atgccccca    600
cattaccgaa gtggagcctg aagacattga ctgctggtgc aaccttacat cgacatgggt    660
gacttatgga acatgcaatc aagctggaga gcatagacgc gataagagat cagtggcgtt    720
agctccccat gttggcatgg gactggacac acgcactcaa acctggatgt cggctgaagg    780
```

```
agcttggaga caagtcgaga aggtagagac atgggccctt aggcacccag ggtttaccat      840
actagcccta tttcttgccc attacatagg cacttccttg acccagaaag tggttatttt      900
tatactatta atgctggtta ccccatccat gacaatgaga tgtgtaggag taggaaacag      960
agattttgtg gaaggcctat cgggagctac gtgggttgac gtggtgctcg agcacggtgg     1020
gtgtgtgact accatggcta agaacaagcc cacgctggac atagagcttc agaagaccga     1080
ggccacccaa ctggcgaccc taaggaagct atgcattgag ggaaaaatta ccaacataac     1140
aaccgactca agatgtccca cccaagggga agcgatttta cctgaggagc aggaccagaa     1200
ctacgtgtgt aagcatacat acgtggacag aggctgggga acggttgtg gtttgtttgg      1260 caagggaagc ttggtgacat gcgcgaaatt tcaatgttta gaatcaatag agggaaaagt     1320
ggtgcaacat gagaacctca aatacaccgt catcatcaca gtgcacacag agaccaaca      1380 ccaggtggga aatgaaacgc agggagtcac ggctgagata cacccccagg catcaaccgc     1440
tgaagtcatt ttacctgaat atggaaccct cgggctagaa tgctcaccac ggacaggttt     1500
ggatttcaat gaaatgatct cattgacaat gaagaacaaa gcatggatgg tacatagaca     1560
atggttcttt gacttacccc taccatggac atcaggagct acagcagaaa caccaacttg     1620
gaacaggaaa gagcttcttg tgacatttaa aaatgcacat gcaaaaaagc aagaagtagt     1680
tgttcttgga tcacaagagg gagcaatgca tacagcactg acaggagcta cagagatcca     1740
aacctcagga ggcacaagta tctttgcggg gcacttaaaa tgtagactca agatggacaa     1800
attggaactc aaggggatga gctatgcaat gtgcttgagt agctttgtgt tgaagaaaga     1860
agtctccgaa acgcagcatg ggacaatact cattaaggtt gagtacaaag gggaagatgc     1920
accctgcaag attcctttct ccacggagga tggacaagga aaagctcaca atggcagact     1980
gatcacagcc aatccagtgg tgaccaagaa ggaggagcct gtcaacattg aggctgaacc     2040
tccttttgga gaaagtaaca tagtaattgg aattggagac aaagccctga aaatcaactg     2100
gtacaagaag ggaagctcga ttgggaagat gttcgaggcc actgccagag gtgcaaggcg     2160
catggccatc ttgggagaca cagcctggga ctttggatca gtgggtggtg ttttgaattc     2220
attagggaaa atggtccacc aaatatttgg gagtgcttac acagcccttt tggtggagt      2280 ctcctggatg atgaaaattg gaataggtgt cctcttaacc tggataggt tgaactcaaa      2340 aaatacttct atgtcatttt catgcatcgc gataggaatc attacactct atctgggagc     2400
cgtggtgcaa gctgacatgg ggtgtgtcat aaactggaaa ggcaaagaac tcaaatgtgg     2460
aagtggaatt ttcgtcacta atgaggtcca cacctggaca gagcaataca aatttcaagc     2520
agactccccc aagagactgg caacagccat tgcaggcgct tgggaaaatg gagtgtgcgg     2580
aattaggtca caaccagaa tggagaacct cttgtggaag caaatagcca atgaactgaa      2640
ttacatatta tgggaaaaca acattaaatt aacggtagtt gtaggcgaca taactggggt     2700
cttagagcaa gggaaaagaa cactaacacc acaacccatg gagctaaaat attcttggaa     2760
aacatgggga aaggcaaaaa tagtgacagc tgaaacacaa aattcctctt tcataataga     2820
tgggccaagc acaccggagt gtccaagtgc ctcaagagca tggaatgtgt gggaggtgga     2880
ggattacggg ttcggagttt tcacaaccaa catatggctg aaactccgag aggtgtacac     2940
ccaactatgt gaccataggc taatgtcggc agccgtcaag gatgagaggg ctgtacatgc     3000
cgacatgggc tattggatag aaagccaaaa gaatgggagt tggaagctag aaaaagcatc     3060
cttcatagag gtgaaaacct gcacatggcc aaaatcacac actctctgga gcaatggtgt     3120
```

```
gctagagagt gacatgatta tcccaaagag tctagctggt cccatttcgc aacacaacca   3180
caggcccggg taccacaccc aaacggcagg accctggcac ttaggaaaat tggagctgga   3240
cttcaactat tgtgaaggaa caacagttgt catctcagaa aactgtggga caagaggccc   3300
atcattgaga acaacaacgg tgtcagggaa gttgatacac gaatggtgct gccgctcgtg   3360
cacacttcct cccctacgat acatgggaga agacggctgc tggtatggca tggaaatcag   3420
acccattaat gagaaagaag agaatatggt aaagtctcta gcctcagcag ggagtggaaa   3480
ggtggacaac ttcacaatgg gtgtcttgtg tttggcaatc ctctttgaag aggtgatgag   3540
aggaaaattt gggaaaaaac acatgattgc aggggttctc ttcacgtttg tgctcctcct   3600
ctcagggcaa ataacatgga gagacatggc gcacacactc ataatgattg gtccaacgc    3660
ctctgacaga atggggatgg gcgtcactta cctagctcta attgcaacat ttaaaattca   3720
gccattcctg gctttgggat tcttcctgag gaaactgaca tctagagaaa atttattgct   3780
gggagttggg ttggccatgg cagcaacgtt acgactgcca gaggacattg aacagatggc   3840
gaatggaatt gctttggggc tcatggctct taaactgata acacaatttg aaacatacca   3900
actatggacg gcattagttt ccctaacgtg ttcaaataca attttcacgt tgactgttgc   3960
ctggagaaca gccactctga ttttagccgg aatttcgctt ttgccagtgt gccagtcttc   4020
gagcatgagg aaaacagatt ggctcccaat gactgtggca gctatgggag ctcaacccct   4080
accactttt attttcagtc tgaaagatac actcaaaagg agaagctggc cactgaatga   4140
gggggtgatg cagttggac ttgtgagcat tctagctagt tctctcctta ggaatgatgt   4200
gcctatggct ggaccattag tggctggggg cttgctgata gcgtgctacg tcataactgg   4260
cacgtcagca gacctcactg tagaaaaagc agcagatgta acatgggagg aagaggccga   4320
gcaaacagga gtgtcccaca atttaatggt cacagttgat gatgatgaa caatgagaat   4380
aaaagatgac gagactgaga acatcttaac agtgcttta aaaacagcac tactaatagt   4440
atcaggcatc tttccatact ccatacccgc aacactgttg gtctggcata cttggcaaaa   4500
gcaaacccaa agatccggcg tcctatggga cgtacccagc cccccagaga cacagaaagc   4560
ggaactggaa gaaggggtct ataggatcaa acagcaagga atttttggga aaacccaagt   4620
ggggggttgga gtacagaaag aaggagtttt ccacaccatg tggcatgtca agagggggc   4680
agtgttgaca cacaatggga aaagactgga accaaactgg gctagcgtga aaaagatct    4740
gatttcatac ggaggaggat ggagattgag tgcacaatgg caaaggggg aggaggtgca   4800
ggttattgcc gtagagcctg gaagaaccc aaagaacttt caaaccatgc caggcatttt   4860
tcagacaaca acaggggaaa taggagcaat tgcactggat ttcaagcctg aacttcagg    4920
atctcccatc ataaacagag agggaaaggt agtgggactg tatggcaatg gagtggttac   4980
aaagaatgga ggctatgtca gtggaatagc gcaaacaaat gcagaaccag atggaccgac   5040
accagagttg gaagaagaga tgttcaaaaa gcgaaatcta accataatgg atctccatcc   5100
tgggtcagga aagacgcgga aatatcttcc agctattgtt agagaggcaa tcaagagacg   5160
cttaaggact ctaattttgg caccaacaag ggtagttgca gctgagatgg aagaagcatt   5220
gaaagggctc ccaataaggt atcaaacaac tgcaacaaaa tctgaacaca caggaagaga   5280
gattgttgat ctaatgtgtc acgcaacgtt cacaatgcgc ttgctgtcac cagtcagggt   5340
tccaaactac aacttgataa taatggatga ggcccatttc acagaccag ccagtatagc    5400
ggctagaggg tacatatcaa ctcgtgtagg aatgggagag gcagccgcaa ttttcatgac   5460
agcaacacc cctgaacag ctgatgcctt tcctcagagc aacgctccaa ttcaagatga    5520
```

```
agagagagac ataccggaac gctcatggaa ttcaggcaat gaatggatta ctgactttgt    5580
tgggaagaca gtgtggtttg tccctagcat caaagccgga aatgacatag caaactgctt    5640
gcggaaaaat ggaaaaaagg ttattcaact cagcaggaag acctttgaca cagaatatca    5700
aaagaccaaa ctgaatgatt gggactttgt ggtgacaaca gacatttcag aaatgggagc    5760
caatttcaaa gcagatagag tgatcgaccc aagaagatgt ctcaagccgg tgattttgac    5820
agatggaccc gagcgggtga tcctggctgg accaatgcca gtcaccgtag cgagcgctgc    5880
gcaaaggaga gggagagttg gcaggaaccc acaaaaagaa aatgaccagt acatattcat    5940
gggccagcct ctcaacaatg atgaagacca tgctcactgg acagaagcaa aaatgctgct    6000
ggacaacatc aacacaccag aagggattat accagctctc tttgaaccag aaagggagaa    6060
gtcagccgcc atagcggcg aataccgcct gaagggtgag tccaggaaga ctttcgtgga    6120
actcatgagg aggggtgacc tcccagtttg gctagcccat aaagtagcat cagaagggat    6180
caaatataca gatagaaaat ggtgctttga tggagaacgt aataatcaaa ttttagagga    6240
gaatatggat gtggaaatct ggacaaagga aggagaaaag aaaaaactga gacctaggtg    6300
gcttgatgcc cgcacttatt cagatccttt agcactcaaa gaattcaagg attttgcagc    6360
tggcagaaag tcaatcgccc ttgatcttgt gacagaaata ggaagagtgc cttcacactt    6420
agcccacaga acgagaaacg ccctggataa tttggtgatg ctgcacacgt cagaacatgg    6480
cggtagggcc tacaggcatg cagtggagga actaccagaa acgatggaaa cactcttact    6540
cctgggactg atgatcttgt taacaggtgg agcaatgctc ttcttgatat caggtaaagg    6600
gattggaaag acttcaatag gactcatttg tgtaattgct tccagcggca tgttatggat    6660
ggctgatgtc ccactccaat ggatcgcatc ggctatagtc ctggagtttt ttatgatggt    6720
gttgctcata ccagaaccag aaaagcagag aactccccaa acaaccaac tcgcatatgt    6780
cgtgataggc atacttacat tggctgcaat agtagcggcc aatgaaatgg gactgttgga    6840
aactacaaag agagatttag gaatgtctaa agaaccaggt gttgtttctc caaccagcta    6900
tttggatgtg gacttgcacc cagcatcagc ctggacattg tacgccgtgg ccacaacagt    6960
aataacacca atgttgagac acaccataga gaattccaca gcaaatgtgt ctctggcagc    7020
catagctaac caggcagtgg tcctgatggg tttagacaaa ggatggccga tatcgaaaat    7080
ggacttgggc gtaccactat ggcactgggt tgctattca caagtgaacc cactaactct    7140
tgcagcggca gtacttttgc tagtcacaca ttatgcaatt ataggtccag gattgcaggc    7200
aaaagccacc cgtgaagctc agaaaaggac agctgctgga ataatgaaga atccaacggt    7260
ggatggaata atgacaatag acctagatcc tgtaatatat gattcaaaat ttgaaaagca    7320
actaggacag gtcatgctcc tggttctgtg tgcagtccaa cttttattga tgagaacatc    7380
atgggcttg tgtgaagttc taacccctagc cacaggacca ataacaacac tctgggaagg    7440
atcacctggg aagttctgga acaccacgat agctgtttcc atggcgaaca tctttagagg    7500
gagctattta gcaggagctg ggcttgcttt ttctatcatg aaatcagttg gaacaggaaa    7560
gagaggaaca gggtcacaag gtgaaacctt aggagaaaag tggaaaagaa aattaaatca    7620
gttatcccgg aaagagtttg accttttacaa gaaatccgga atcaccgaag tggatagaac    7680
agaagccaaa gaagggttaa aaagaggaga ataacacac catgccgtgt ccagaggcag    7740
cgcaaaactt caatggttcg tggagagaaa catggtcatt cctgaaggaa gagtcataga    7800
cctaggctgt ggaagaggag ctggtcata ttactgtgca ggactgaaaa aagttacaga    7860
```

```
agtgcgagga tacacaaaag gcggcccagg acacgaagaa ccagtaccta tgtctacata   7920
cggatggaac atagtcaagt taatgagtgg aaaggatgtt ttttatctgc cacctgaaaa   7980
gtgtgatacc ctattgtgtg acattggaga atcttcacca agcccaacag tggaagaaag   8040
cagaaccata agagttttga agatggttga accatggcta agaacaacc agttttgcat    8100 taaagtattg aacccataca tgccaactgt gattgagcac ttagaaagac tacaaaggaa   8160
acatggagga atgcttgtga gaaatccact ctcacgaaac tccacgcacg aaatgtattg   8220
gatatccaat ggtacaggca atatcgtctc ttcagtcaac atggtatcca gattgctact   8280
gaacagattc acaatgacac acaggagacc caccatagag aaagatgtgg atctaggagc   8340
aggaacccga catgtcaatg cggaaccaga acacccaac atggatgtca ttggggaaag    8400
aataaaaagg atcaaagagg agcatagttc aacatggcac tatgatgatg aaaatcctta   8460
caaaacgtgg gcttaccatg gatcctatga agtaaaagcc acaggctcag cctcctccat   8520
gataaatgga gtcgtgaaac tcctcacaaa accatgggat gtggtgccca tggtgacaca   8580
gatggcaatg acagatacaa ctccattcgg ccagcaaaga gttttttaaag agaaagtgga   8640 caccaggaca cctaggccca tgccaggaac aagaaaggtt atggagatca cagcggagtg   8700
gctttggagg accctgggaa ggaacaaaag acccagatta tgcacaaggg aggaattcac   8760
aaagaaggtc agaaccaacg cagctatggg cgctgtcttc acagaagaga accaatggga   8820
cagtgcgaga gctgctgttg aggacgaaga attttggaaa cttgtggaca gagaacgtga   8880
actccacaaa ctgggcaagt gtggaagctg cgtttacaac atgatgggca agagagagaa   8940
aaaacttgga gagtttggta aagcaaaagg cagtagggct atatggtaca tgtggttggg   9000
agccaggtac cttgagttcg aggcgctcgg attcctcaat gaagaccact ggttctcgcg   9060
tgaaaactct tacagtggag tagaaggaga aggactgcac aagctgggat acatcttgag   9120
agatatttcc aagataccg gaggagccat gtatgctgat gacacagccg gttgggacac   9180
aagaataaca gaagatgacc tgcacaatga ggaaaaaatc acacagcaga tggaccctga   9240
acacaggcag ctagcgaacg ctatattcaa gctcacatac caaaacaaag tggtcaaagt   9300
ccaacgacca actccaaagg gcacggtaat ggacatcata tctaggaaag accaaagagg   9360
cagtggacag gtgggaactt atggtctgaa cacattcacc aacatggaag cccagctaat   9420
cagacaaatg gaaggagaag gcgtgttgtc aaaggcagac ctcgagaacc ccatccgct    9480 agagaagaaa attacacaat ggttggaaac taaaggagtg gaaaggttaa aaagaatggc   9540
catcagcggg gatgattgcg ttgtgaaacc aatcgacgac agattcgcca tgcctgct    9600 tgccctgaac gatatgggaa aggttagaaa ggacatacct caatggcagc catcaaaggg   9660
atggcatgat tggcaacagg tcccttctg ctcccaccac tttcatgaat tgatcatgaa     9720
agatggaaga aagttggtag ttccctgcag accccaggac gaactaatag gaagagcgag   9780
aatctcccaa ggagcaggat ggagccttag agaaactgca tgtctaggga agcctacgc    9840 tcaaatgtgg gctctcatgt attttcacag aagagatctt agactagcat ccaacgccat   9900
atgttcagca gtaccagtcc actgggtccc cacgagcaga acgacatggt ctattcatgc   9960
tcaccatcag tggatgacta cagaagacat gcttactgtc tggaacaggg tgtgatagaga  10020 ggacaatcca tggatggaag acaaaactcc agtcacaacg tgggaagatg ttccatatct  10080
agggaagaga gaagaccaat ggtgcggatc actcataggt ctcacttcca gagcaacctg  10140
ggcccagaac atactcacag caatccaaca ggtgagaagc ctcataggca atgaagagtt  10200
tctggactac atgccttcga tgaagagatt caggaaggag gaggagtcag agggagccat  10260
```

```
ttggtaaaag caggaggtaa actgtcaggc acattaagc cacagtacgg aagaagctgt    10320
gcagcctgtg agccccgtcc aaggacgtta aagaagaag tcaggcccaa aagccacggt    10380
ttgagcaaac cgtgctgcct gtagctccgt cgtggggacg taaagcctgg gaggctgcaa    10440
accgtggaag ctgtacgcac ggtgtagcag actagtggtt agaggagacc cctcccatga    10500
cacaacgcag cagcggggcc cgagcactga gggaagctgt acctccttgc aaaggactag    10560
aggttagagg agaccccccg caaacaaaaa cagcatattg acgctgggag agaccagaga    10620
tcctgctgtc tcctcagcat cattccaggc acagaacgcc agaaaatgga atggtgctgt    10680
tgaatcaaca ggttct                                                   10696

<210> SEQ ID NO 14
<211> LENGTH: 3390
<212> TYPE: PRT
<213> ORGANISM: Dengue virus

<400> SEQUENCE: 14

Met Asn Asn Gln Arg Lys Lys Thr Gly Lys Pro Ser Ile Asn Met Leu
1               5                   10                  15

Lys Arg Val Arg Asn Arg Val Ser Thr Gly Ser Gln Leu Ala Lys Arg
            20                  25                  30

Phe Ser Arg Gly Leu Leu Asn Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

Val Leu Ala Arg Trp Gly Thr Phe Lys Lys Ser Gly Ala Ile Lys Val
65                  70                  75                  80

Leu Lys Gly Phe Lys Lys Glu Ile Ser Asn Met Leu Ser Ile Ile Asn
                85                  90                  95

Lys Arg Lys Lys Thr Ser Leu Cys Leu Met Met Met Leu Pro Ala Thr
            100                 105                 110

Leu Ala Phe His Leu Thr Ser Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro His Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Leu Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
        275                 280                 285
```

-continued

```
Arg Asp Phe Val Glu Gly Leu Ser Gly Ala Thr Trp Val Asp Val Val
290                 295                 300
Leu Glu His Gly Gly Cys Val Thr Thr Met Ala Lys Asn Lys Pro Thr
305                 310                 315                 320
Leu Asp Ile Glu Leu Gln Lys Thr Glu Ala Thr Gln Leu Ala Thr Leu
                    325                 330                 335
Arg Lys Leu Cys Ile Glu Gly Lys Ile Thr Asn Ile Thr Thr Asp Ser
                340                 345                 350
Arg Cys Pro Thr Gln Gly Glu Ala Ile Leu Pro Glu Gln Asp Gln
                355                 360                 365
Asn Tyr Val Cys Lys His Thr Tyr Val Asp Arg Gly Trp Gly Asn Gly
370                 375                 380
Cys Gly Leu Phe Gly Lys Gly Ser Leu Val Thr Cys Ala Lys Phe Gln
385                 390                 395                 400
Cys Leu Glu Ser Ile Glu Gly Lys Val Val Gln His Glu Asn Leu Lys
                405                 410                 415
Tyr Thr Val Ile Ile Thr Val His Thr Gly Asp Gln His Gln Val Gly
                420                 425                 430
Asn Glu Thr Gln Gly Val Thr Ala Glu Ile Thr Pro Gln Ala Ser Thr
                435                 440                 445
Ala Glu Val Ile Leu Pro Glu Tyr Gly Thr Leu Gly Leu Glu Cys Ser
450                 455                 460
Pro Arg Thr Gly Leu Asp Phe Asn Glu Met Ile Ser Leu Thr Met Lys
465                 470                 475                 480
Asn Lys Ala Trp Met Val His Arg Gln Trp Phe Phe Asp Leu Pro Leu
                485                 490                 495
Pro Trp Thr Ser Gly Ala Thr Ala Glu Thr Pro Thr Trp Asn Arg Lys
                500                 505                 510
Glu Leu Leu Val Thr Phe Lys Asn Ala His Ala Lys Lys Gln Glu Val
                515                 520                 525
Val Val Leu Gly Ser Gln Glu Gly Ala Met His Thr Ala Leu Thr Gly
530                 535                 540
Ala Thr Glu Ile Gln Thr Ser Gly Gly Thr Ser Ile Phe Ala Gly His
545                 550                 555                 560
Leu Lys Cys Arg Leu Lys Met Asp Lys Leu Glu Leu Lys Gly Met Ser
                565                 570                 575
Tyr Ala Met Cys Leu Ser Ser Phe Val Leu Lys Lys Glu Val Ser Glu
                580                 585                 590
Thr Gln His Gly Thr Ile Leu Ile Lys Val Glu Tyr Lys Gly Glu Asp
                595                 600                 605
Ala Pro Cys Lys Ile Pro Phe Ser Thr Glu Asp Gly Gln Gly Lys Ala
610                 615                 620
His Asn Gly Arg Leu Ile Thr Ala Asn Pro Val Val Thr Lys Lys Glu
625                 630                 635                 640
Glu Pro Val Asn Ile Glu Ala Glu Pro Pro Phe Gly Glu Ser Asn Ile
                645                 650                 655
Val Ile Gly Ile Gly Asp Lys Ala Leu Lys Ile Asn Trp Tyr Lys Lys
                660                 665                 670
Gly Ser Ser Ile Gly Lys Met Phe Glu Ala Thr Ala Arg Gly Ala Arg
                675                 680                 685
Arg Met Ala Ile Leu Gly Asp Thr Ala Trp Asp Phe Gly Ser Val Gly
690                 695                 700
Gly Val Leu Asn Ser Leu Gly Lys Met Val His Gln Ile Phe Gly Ser
```

```
        705                 710                 715                 720
Ala Tyr Thr Ala Leu Phe Gly Gly Val Ser Trp Met Met Lys Ile Gly
                725                 730                 735

Ile Gly Val Leu Leu Thr Trp Ile Gly Leu Asn Ser Lys Asn Thr Ser
                740                 745                 750

Met Ser Phe Ser Cys Ile Ala Ile Gly Ile Ile Thr Leu Tyr Leu Gly
                755                 760                 765

Ala Val Val Gln Ala Asp Met Gly Cys Val Ile Asn Trp Lys Gly Lys
                770                 775                 780

Glu Leu Lys Cys Gly Ser Gly Ile Phe Val Thr Asn Glu Val His Thr
785                 790                 795                 800

Trp Thr Glu Gln Tyr Lys Phe Gln Ala Asp Ser Pro Lys Arg Leu Ala
                805                 810                 815

Thr Ala Ile Ala Gly Ala Trp Glu Asn Gly Val Cys Gly Ile Arg Ser
                820                 825                 830

Thr Thr Arg Met Glu Asn Leu Leu Trp Lys Gln Ile Ala Asn Glu Leu
                835                 840                 845

Asn Tyr Ile Leu Trp Glu Asn Ile Lys Leu Thr Val Val Val Gly
850                 855                 860

Asp Ile Thr Gly Val Leu Glu Gln Gly Lys Arg Thr Leu Thr Pro Gln
865                 870                 875                 880

Pro Met Glu Leu Lys Tyr Ser Trp Lys Thr Trp Gly Lys Ala Lys Ile
                885                 890                 895

Val Thr Ala Glu Thr Gln Asn Ser Ser Phe Ile Ile Asp Gly Pro Ser
                900                 905                 910

Thr Pro Glu Cys Pro Ser Ala Ser Arg Ala Trp Asn Val Trp Glu Val
                915                 920                 925

Glu Asp Tyr Gly Phe Gly Val Phe Thr Thr Asn Ile Trp Leu Lys Leu
                930                 935                 940

Arg Glu Val Tyr Thr Gln Leu Cys Asp His Arg Leu Met Ser Ala Ala
945                 950                 955                 960

Val Lys Asp Glu Arg Ala Val His Ala Asp Met Gly Tyr Trp Ile Glu
                965                 970                 975

Ser Gln Lys Asn Gly Ser Trp Lys Leu Glu Lys Ala Ser Phe Ile Glu
                980                 985                 990

Val Lys Thr Cys Thr Trp Pro Lys Ser His Thr Leu Trp Ser Asn Gly
                995                 1000                1005

Val Leu Glu Ser Asp Met Ile Ile Pro Lys Ser Leu Ala Gly Pro
     1010                1015                1020

Ile Ser Gln His Asn His Arg Pro Gly Tyr His Thr Gln Thr Ala
     1025                1030                1035

Gly Pro Trp His Leu Gly Lys Leu Glu Leu Asp Phe Asn Tyr Cys
     1040                1045                1050

Glu Gly Thr Thr Val Val Ile Ser Glu Asn Cys Gly Thr Arg Gly
     1055                1060                1065

Pro Ser Leu Arg Thr Thr Thr Val Ser Gly Lys Leu Ile His Glu
     1070                1075                1080

Trp Cys Cys Arg Ser Cys Thr Leu Pro Pro Leu Arg Tyr Met Gly
     1085                1090                1095

Glu Asp Gly Cys Trp Tyr Gly Met Glu Ile Arg Pro Ile Asn Glu
     1100                1105                1110

Lys Glu Glu Asn Met Val Lys Ser Leu Ala Ser Ala Gly Ser Gly
     1115                1120                1125
```

```
Lys Val Asp Asn Phe Thr Met Gly Val Leu Cys Leu Ala Ile Leu
    1130            1135            1140

Phe Glu Glu Val Met Arg Gly Lys Phe Gly Lys Lys His Met Ile
    1145            1150            1155

Ala Gly Val Leu Phe Thr Phe Val Leu Leu Leu Ser Gly Gln Ile
    1160            1165            1170

Thr Trp Arg Asp Met Ala His Thr Leu Ile Met Ile Gly Ser Asn
    1175            1180            1185

Ala Ser Asp Arg Met Gly Met Gly Val Thr Tyr Leu Ala Leu Ile
    1190            1195            1200

Ala Thr Phe Lys Ile Gln Pro Phe Leu Ala Leu Gly Phe Phe Leu
    1205            1210            1215

Arg Lys Leu Thr Ser Arg Glu Asn Leu Leu Gly Val Gly Leu
    1220            1225            1230

Ala Met Ala Ala Thr Leu Arg Leu Pro Glu Asp Ile Glu Gln Met
    1235            1240            1245

Ala Asn Gly Ile Ala Leu Gly Leu Met Ala Leu Lys Leu Ile Thr
    1250            1255            1260

Gln Phe Glu Thr Tyr Gln Leu Trp Thr Ala Leu Val Ser Leu Thr
    1265            1270            1275

Cys Ser Asn Thr Ile Phe Thr Leu Thr Val Ala Trp Arg Thr Ala
    1280            1285            1290

Thr Leu Ile Leu Ala Gly Ile Ser Leu Leu Pro Val Cys Gln Ser
    1295            1300            1305

Ser Ser Met Arg Lys Thr Asp Trp Leu Pro Met Thr Val Ala Ala
    1310            1315            1320

Met Gly Ala Gln Pro Leu Pro Leu Phe Ile Phe Ser Leu Lys Asp
    1325            1330            1335

Thr Leu Lys Arg Arg Ser Trp Pro Leu Asn Glu Gly Val Met Ala
    1340            1345            1350

Val Gly Leu Val Ser Ile Leu Ala Ser Ser Leu Leu Arg Asn Asp
    1355            1360            1365

Val Pro Met Ala Gly Pro Leu Val Ala Gly Gly Leu Leu Ile Ala
    1370            1375            1380

Cys Tyr Val Ile Thr Gly Thr Ser Ala Asp Leu Thr Val Glu Lys
    1385            1390            1395

Ala Ala Asp Val Thr Trp Glu Glu Ala Glu Gln Thr Gly Val
    1400            1405            1410

Ser His Asn Leu Met Val Thr Val Asp Asp Gly Thr Met Arg
    1415            1420            1425

Ile Lys Asp Asp Glu Thr Glu Asn Ile Leu Thr Val Leu Leu Lys
    1430            1435            1440

Thr Ala Leu Leu Ile Val Ser Gly Ile Phe Pro Tyr Ser Ile Pro
    1445            1450            1455

Ala Thr Leu Leu Val Trp His Thr Trp Gln Lys Gln Thr Gln Arg
    1460            1465            1470

Ser Gly Val Leu Trp Asp Val Pro Ser Pro Glu Thr Gln Lys
    1475            1480            1485

Ala Glu Leu Glu Glu Gly Val Tyr Arg Ile Lys Gln Gln Gly Ile
    1490            1495            1500

Phe Gly Lys Thr Gln Val Gly Val Gly Val Gln Lys Glu Gly Val
    1505            1510            1515
```

```
Phe His Thr Met Trp His Val Thr Arg Gly Ala Val Leu Thr His
1520                     1525                1530

Asn Gly Lys Arg Leu Glu Pro Asn Trp Ala Ser Val Lys Lys Asp
1535                     1540                1545

Leu Ile Ser Tyr Gly Gly Gly Trp Arg Leu Ser Ala Gln Trp Gln
1550                     1555                1560

Lys Gly Glu Glu Val Gln Val Ile Ala Val Glu Pro Gly Lys Asn
1565                     1570                1575

Pro Lys Asn Phe Gln Thr Met Pro Gly Ile Phe Gln Thr Thr Thr
1580                     1585                1590

Gly Glu Ile Gly Ala Ile Ala Leu Asp Phe Lys Pro Gly Thr Ser
1595                     1600                1605

Gly Ser Pro Ile Ile Asn Arg Glu Gly Lys Val Val Gly Leu Tyr
1610                     1615                1620

Gly Asn Gly Val Val Thr Lys Asn Gly Gly Tyr Val Ser Gly Ile
1625                     1630                1635

Ala Gln Thr Asn Ala Glu Pro Asp Gly Pro Thr Pro Glu Leu Glu
1640                     1645                1650

Glu Glu Met Phe Lys Lys Arg Asn Leu Thr Ile Met Asp Leu His
1655                     1660                1665

Pro Gly Ser Gly Lys Thr Arg Lys Tyr Leu Pro Ala Ile Val Arg
1670                     1675                1680

Glu Ala Ile Lys Arg Arg Leu Arg Thr Leu Ile Leu Ala Pro Thr
1685                     1690                1695

Arg Val Val Ala Ala Glu Met Glu Glu Ala Leu Lys Gly Leu Pro
1700                     1705                1710

Ile Arg Tyr Gln Thr Thr Ala Thr Lys Ser Glu His Thr Gly Arg
1715                     1720                1725

Glu Ile Val Asp Leu Met Cys His Ala Thr Phe Thr Met Arg Leu
1730                     1735                1740

Leu Ser Pro Val Arg Val Pro Asn Tyr Asn Leu Ile Ile Met Asp
1745                     1750                1755

Glu Ala His Phe Thr Asp Pro Ala Ser Ile Ala Ala Arg Gly Tyr
1760                     1765                1770

Ile Ser Thr Arg Val Gly Met Gly Glu Ala Ala Ala Ile Phe Met
1775                     1780                1785

Thr Ala Thr Pro Pro Gly Thr Ala Asp Ala Phe Pro Gln Ser Asn
1790                     1795                1800

Ala Pro Ile Gln Asp Glu Glu Arg Asp Ile Pro Glu Arg Ser Trp
1805                     1810                1815

Asn Ser Gly Asn Glu Trp Ile Thr Asp Phe Val Gly Lys Thr Val
1820                     1825                1830

Trp Phe Val Pro Ser Ile Lys Ala Gly Asn Asp Ile Ala Asn Cys
1835                     1840                1845

Leu Arg Lys Asn Gly Lys Lys Val Ile Gln Leu Ser Arg Lys Thr
1850                     1855                1860

Phe Asp Thr Glu Tyr Gln Lys Thr Lys Leu Asn Asp Trp Asp Phe
1865                     1870                1875

Val Val Thr Thr Asp Ile Ser Glu Met Gly Ala Asn Phe Lys Ala
1880                     1885                1890

Asp Arg Val Ile Asp Pro Arg Arg Cys Leu Lys Pro Val Ile Leu
1895                     1900                1905

Thr Asp Gly Pro Glu Arg Val Ile Leu Ala Gly Pro Met Pro Val
```

-continued

```
            1910                1915                1920
Thr Val Ala Ser Ala Ala Gln Arg Arg Gly Arg Val Gly Arg Asn
            1925                1930                1935

Pro Gln Lys Glu Asn Asp Gln Tyr Ile Phe Met Gly Gln Pro Leu
            1940                1945                1950

Asn Asn Asp Glu Asp His Ala His Trp Thr Glu Ala Lys Met Leu
            1955                1960                1965

Leu Asp Asn Ile Asn Thr Pro Glu Gly Ile Ile Pro Ala Leu Phe
            1970                1975                1980

Glu Pro Glu Arg Glu Lys Ser Ala Ala Ile Asp Gly Glu Tyr Arg
            1985                1990                1995

Leu Lys Gly Glu Ser Arg Lys Thr Phe Val Glu Leu Met Arg Arg
            2000                2005                2010

Gly Asp Leu Pro Val Trp Leu Ala His Lys Val Ala Ser Glu Gly
            2015                2020                2025

Ile Lys Tyr Thr Asp Arg Lys Trp Cys Phe Asp Gly Glu Arg Asn
            2030                2035                2040

Asn Gln Ile Leu Glu Glu Asn Met Asp Val Glu Ile Trp Thr Lys
            2045                2050                2055

Glu Gly Glu Lys Lys Lys Leu Arg Pro Arg Trp Leu Asp Ala Arg
            2060                2065                2070

Thr Tyr Ser Asp Pro Leu Ala Leu Lys Glu Phe Lys Asp Phe Ala
            2075                2080                2085

Ala Gly Arg Lys Ser Ile Ala Leu Asp Leu Val Thr Glu Ile Gly
            2090                2095                2100

Arg Val Pro Ser His Leu Ala His Arg Thr Arg Asn Ala Leu Asp
            2105                2110                2115

Asn Leu Val Met Leu His Thr Ser Glu His Gly Gly Arg Ala Tyr
            2120                2125                2130

Arg His Ala Val Glu Glu Leu Pro Glu Thr Met Glu Thr Leu Leu
            2135                2140                2145

Leu Leu Gly Leu Met Ile Leu Leu Thr Gly Gly Ala Met Leu Phe
            2150                2155                2160

Leu Ile Ser Gly Lys Gly Ile Gly Lys Thr Ser Ile Gly Leu Ile
            2165                2170                2175

Cys Val Ile Ala Ser Ser Gly Met Leu Trp Met Ala Asp Val Pro
            2180                2185                2190

Leu Gln Trp Ile Ala Ser Ala Ile Val Leu Glu Phe Phe Met Met
            2195                2200                2205

Val Leu Leu Ile Pro Glu Pro Glu Lys Gln Arg Thr Pro Gln Asp
            2210                2215                2220

Asn Gln Leu Ala Tyr Val Val Ile Gly Ile Leu Thr Leu Ala Ala
            2225                2230                2235

Ile Val Ala Ala Asn Glu Met Gly Leu Leu Glu Thr Thr Lys Arg
            2240                2245                2250

Asp Leu Gly Met Ser Lys Glu Pro Gly Val Val Ser Pro Thr Ser
            2255                2260                2265

Tyr Leu Asp Val Asp Leu His Pro Ala Ser Ala Trp Thr Leu Tyr
            2270                2275                2280

Ala Val Ala Thr Thr Val Ile Thr Pro Met Leu Arg His Thr Ile
            2285                2290                2295

Glu Asn Ser Thr Ala Asn Val Ser Leu Ala Ala Ile Ala Asn Gln
            2300                2305                2310
```

```
Ala Val Val Leu Met Gly Leu Asp Lys Gly Trp Pro Ile Ser Lys
2315             2320                 2325

Met Asp Leu Gly Val Pro Leu Leu Ala Leu Gly Cys Tyr Ser Gln
2330             2335                 2340

Val Asn Pro Leu Thr Leu Ala Ala Ala Val Leu Leu Leu Val Thr
2345             2350                 2355

His Tyr Ala Ile Ile Gly Pro Gly Leu Gln Ala Lys Ala Thr Arg
2360             2365                 2370

Glu Ala Gln Lys Arg Thr Ala Ala Gly Ile Met Lys Asn Pro Thr
2375             2380                 2385

Val Asp Gly Ile Met Thr Ile Asp Leu Asp Pro Val Ile Tyr Asp
2390             2395                 2400

Ser Lys Phe Glu Lys Gln Leu Gly Gln Val Met Leu Leu Val Leu
2405             2410                 2415

Cys Ala Val Gln Leu Leu Leu Met Arg Thr Ser Trp Ala Leu Cys
2420             2425                 2430

Glu Val Leu Thr Leu Ala Thr Gly Pro Ile Thr Thr Leu Trp Glu
2435             2440                 2445

Gly Ser Pro Gly Lys Phe Trp Asn Thr Thr Ile Ala Val Ser Met
2450             2455                 2460

Ala Asn Ile Phe Arg Gly Ser Tyr Leu Ala Gly Ala Gly Leu Ala
2465             2470                 2475

Phe Ser Ile Met Lys Ser Val Gly Thr Gly Lys Arg Gly Thr Gly
2480             2485                 2490

Ser Gln Gly Glu Thr Leu Gly Glu Lys Trp Lys Lys Lys Leu Asn
2495             2500                 2505

Gln Leu Ser Arg Lys Glu Phe Asp Leu Tyr Lys Lys Ser Gly Ile
2510             2515                 2520

Thr Glu Val Asp Arg Thr Glu Ala Lys Glu Gly Leu Lys Arg Gly
2525             2530                 2535

Glu Ile Thr His His Ala Val Ser Arg Gly Ser Ala Lys Leu Gln
2540             2545                 2550

Trp Phe Val Glu Arg Asn Met Val Ile Pro Glu Gly Arg Val Ile
2555             2560                 2565

Asp Leu Gly Cys Gly Arg Gly Gly Trp Ser Tyr Tyr Cys Ala Gly
2570             2575                 2580

Leu Lys Lys Val Thr Glu Val Arg Gly Tyr Thr Lys Gly Gly Pro
2585             2590                 2595

Gly His Glu Glu Pro Val Pro Met Ser Thr Tyr Gly Trp Asn Ile
2600             2605                 2610

Val Lys Leu Met Ser Gly Lys Asp Val Phe Tyr Leu Pro Pro Glu
2615             2620                 2625

Lys Cys Asp Thr Leu Leu Cys Asp Ile Gly Glu Ser Ser Pro Ser
2630             2635                 2640

Pro Thr Val Glu Glu Ser Arg Thr Ile Arg Val Leu Lys Met Val
2645             2650                 2655

Glu Pro Trp Leu Lys Asn Asn Gln Phe Cys Ile Lys Val Leu Asn
2660             2665                 2670

Pro Tyr Met Pro Thr Val Ile Glu His Leu Glu Arg Leu Gln Arg
2675             2680                 2685

Lys His Gly Gly Met Leu Val Arg Asn Pro Leu Ser Arg Asn Ser
2690             2695                 2700
```

| | | | | | | | | | | |
|---|---|---|---|---|---|---|---|---|---|---|
|Thr|His|Glu|Met|Tyr|Trp|Ile|Ser|Asn|Gly|Thr|Gly|Asn|Ile|Val|
|2705| | | | |2710| | | | |2715| | | | |

Thr His Glu Met Tyr Trp Ile Ser Asn Gly Thr Gly Asn Ile Val
2705                2710                2715

Ser Ser Val Asn Met Val Ser Arg Leu Leu Leu Asn Arg Phe Thr
2720                2725                2730

Met Thr His Arg Arg Pro Thr Ile Glu Lys Asp Val Asp Leu Gly
2735                2740                2745

Ala Gly Thr Arg His Val Asn Ala Glu Pro Glu Thr Pro Asn Met
2750                2755                2760

Asp Val Ile Gly Glu Arg Ile Lys Arg Ile Lys Glu Glu His Ser
2765                2770                2775

Ser Thr Trp His Tyr Asp Asp Glu Asn Pro Tyr Lys Thr Trp Ala
2780                2785                2790

Tyr His Gly Ser Tyr Glu Val Lys Ala Thr Gly Ser Ala Ser Ser
2795                2800                2805

Met Ile Asn Gly Val Val Lys Leu Leu Thr Lys Pro Trp Asp Val
2810                2815                2820

Val Pro Met Val Thr Gln Met Ala Met Thr Asp Thr Thr Pro Phe
2825                2830                2835

Gly Gln Gln Arg Val Phe Lys Glu Lys Val Asp Thr Arg Thr Pro
2840                2845                2850

Arg Pro Met Pro Gly Thr Arg Lys Val Met Glu Ile Thr Ala Glu
2855                2860                2865

Trp Leu Trp Arg Thr Leu Gly Arg Asn Lys Arg Pro Arg Leu Cys
2870                2875                2880

Thr Arg Glu Glu Phe Thr Lys Lys Val Arg Thr Asn Ala Ala Met
2885                2890                2895

Gly Ala Val Phe Thr Glu Glu Asn Gln Trp Asp Ser Ala Arg Ala
2900                2905                2910

Ala Val Glu Asp Glu Glu Phe Trp Lys Leu Val Asp Arg Glu Arg
2915                2920                2925

Glu Leu His Lys Leu Gly Lys Cys Gly Ser Cys Val Tyr Asn Met
2930                2935                2940

Met Gly Lys Arg Glu Lys Lys Leu Gly Glu Phe Gly Lys Ala Lys
2945                2950                2955

Gly Ser Arg Ala Ile Trp Tyr Met Trp Leu Gly Ala Arg Tyr Leu
2960                2965                2970

Glu Phe Glu Ala Leu Gly Phe Leu Asn Glu Asp His Trp Phe Ser
2975                2980                2985

Arg Glu Asn Ser Tyr Ser Gly Val Glu Gly Glu Gly Leu His Lys
2990                2995                3000

Leu Gly Tyr Ile Leu Arg Asp Ile Ser Lys Ile Pro Gly Gly Ala
3005                3010                3015

Met Tyr Ala Asp Asp Thr Ala Gly Trp Asp Thr Arg Ile Thr Glu
3020                3025                3030

Asp Asp Leu His Asn Glu Glu Lys Ile Thr Gln Gln Met Asp Pro
3035                3040                3045

Glu His Arg Gln Leu Ala Asn Ala Ile Phe Lys Leu Thr Tyr Gln
3050                3055                3060

Asn Lys Val Val Lys Val Gln Arg Pro Thr Pro Lys Gly Thr Val
3065                3070                3075

Met Asp Ile Ile Ser Arg Lys Asp Gln Arg Gly Ser Gly Gln Val
3080                3085                3090

Gly Thr Tyr Gly Leu Asn Thr Phe Thr Asn Met Glu Ala Gln Leu

```
    3095                3100                3105

Ile Arg  Gln Met Glu Gly Glu  Gly Val Leu Ser Lys  Ala Asp Leu
    3110                3115                3120

Glu Asn  Pro His Pro Leu Glu  Lys Lys Ile Thr Gln  Trp Leu Glu
    3125                3130                3135

Thr Lys  Gly Val Glu Arg Leu  Lys Arg Met Ala Ile  Ser Gly Asp
    3140                3145                3150

Asp Cys  Val Val Lys Pro Ile  Asp Asp Arg Phe Ala  Asn Ala Leu
    3155                3160                3165

Leu Ala  Leu Asn Asp Met Gly  Lys Val Arg Lys Asp  Ile Pro Gln
    3170                3175                3180

Trp Gln  Pro Ser Lys Gly Trp  His Asp Trp Gln Gln  Val Pro Phe
    3185                3190                3195

Cys Ser  His His Phe His Glu  Leu Ile Met Lys Asp  Gly Arg Lys
    3200                3205                3210

Leu Val  Val Pro Cys Arg Pro  Gln Asp Glu Leu Ile  Gly Arg Ala
    3215                3220                3225

Arg Ile  Ser Gln Gly Ala Gly  Trp Ser Leu Arg Glu  Thr Ala Cys
    3230                3235                3240

Leu Gly  Lys Ala Tyr Ala Gln  Met Trp Ala Leu Met  Tyr Phe His
    3245                3250                3255

Arg Arg  Asp Leu Arg Leu Ala  Ser Asn Ala Ile Cys  Ser Ala Val
    3260                3265                3270

Pro Val  His Trp Val Pro Thr  Ser Arg Thr Thr Trp  Ser Ile His
    3275                3280                3285

Ala His  His Gln Trp Met Thr  Thr Glu Asp Met Leu  Thr Val Trp
    3290                3295                3300

Asn Arg  Val Trp Ile Glu Asp  Asn Pro Trp Met Glu  Asp Lys Thr
    3305                3310                3315

Pro Val  Thr Thr Trp Glu Asp  Val Pro Tyr Leu Gly  Lys Arg Glu
    3320                3325                3330

Asp Gln  Trp Cys Gly Ser Leu  Ile Gly Leu Thr Ser  Arg Ala Thr
    3335                3340                3345

Trp Ala  Gln Asn Ile Leu Thr  Ala Ile Gln Gln Val  Arg Ser Leu
    3350                3355                3360

Ile Gly  Asn Glu Glu Phe Leu  Asp Tyr Met Pro Ser  Met Lys Arg
    3365                3370                3375

Phe Arg  Lys Glu Glu Glu Ser  Glu Gly Ala Ile Trp
    3380                3385                3390
```

<210> SEQ ID NO 15
<211> LENGTH: 10648
<212> TYPE: DNA
<213> ORGANISM: Dengue virus

<400> SEQUENCE: 15

```
agttgttagt ctgtgtggac cgacaaggac agttccaaat cggaagcttg cttaacacag     60
ttctaacagt ttgtttgaat agagagcaga tctctggaaa aatgaaccaa cgaaaaaagg    120
tggttagacc acctttcaat atgctgaaac gcgagagaaa ccgcgtatca acccctcaag    180
ggttggtgaa gagattctca accggacttt tttctgggaa aggaccctta cggatggtgc    240
tagcattcat cacgtttttg cgagtccttt ccatcccacc aacagcaggg attctgaaaa    300
gatggggaca gttgaagaaa aataaggcca tcaggatact gattggattc aggaaggaga    360
```

| | | | | | |
|---|---|---|---|---|---|
| taggccgcat | gctgaacatc | ttgaacggga | gaaaaaggtc | aacgataaca | ttgctgtgct | 420 |
| tgattcccac | cgtaatggcg | tttcacttgt | caacaagaga | tggcgaaccc | ctcatgatag | 480 |
| tggcaaaaca | tgaaaggggg | agacctctct | tgtttaagac | aacagagggg | atcaacaaat | 540 |
| gcactctcat | tgccatggac | ttgggtgaaa | tgtgtgagga | cactgtcacg | tataaatgcc | 600 |
| ccttactggt | caataccgaa | cctgaagaca | ttgattgctg | gtgcaatctc | acgtctacct | 660 |
| gggtcatgta | tggacatgc | acccagagcg | gagaacggag | acgagagaag | cgctcagtag | 720 |
| ctttaacacc | acattcagga | atgggattgg | aaacaagagc | tgagacatgg | atgtcatcgg | 780 |
| aaggggcttg | gaagcatgct | cagagagtag | agagctggat | actcagaaac | ccaggattcg | 840 |
| cgctcttggc | aggatttatg | gcttatatga | ttgggcaaac | aggaatccag | cgaactgtct | 900 |
| tctttgtcct | aatgatgctg | gtcgccccat | cctacggaat | gcgatgcgta | ggagtaggaa | 960 |
| acagagactt | tgtggaagga | gtctcaggtg | gagcatgggt | cgatctggtg | ctagaacatg | 1020 |
| gaggatgcgt | cacaaccatg | gcccagggaa | accaaccctt | ggattttgaa | ctgactaaga | 1080 |
| caacagccaa | ggaagtggct | ctgttaagaa | cctattgcat | tgaagcctca | atatcaaaca | 1140 |
| taaccacggc | aacaagatgt | ccaacgcaag | gagagcctta | tctaaaagag | gaacaagacc | 1200 |
| aacagtacat | ttgccggaga | gatgtggtag | acagagggtg | gggcaatggc | tgtggcttgt | 1260 |
| ttggaaaagg | aggagttgtg | acatgtgcga | agttttcatg | ttcggggaag | ataacaggca | 1320 |
| atttggtcca | aattgagaac | cttgaataca | cagtggttgt | aacagtccac | aatggagaca | 1380 |
| cccatgcagt | aggaaatgac | acatccaatc | atggagttac | agccacgata | actcccaggt | 1440 |
| caccatcggt | ggaagtcaaa | ttgccggact | atggagaact | aacactcgat | tgtgaaccca | 1500 |
| ggtctggaat | tgactttaat | gagatgattc | tgatgaaaat | gaaaagaaa | acatggcttg | 1560 |
| tgcataagca | atggttttg | gatctacctc | taccatggac | agcaggagca | gacacatcag | 1620 |
| aggttcactg | gaattacaaa | gagagaatgg | tgacatttaa | ggttcctcat | gccaagagac | 1680 |
| aggatgtgac | agtgctggga | tctcaggaag | gagccatgca | ttctgccctc | gctggagcca | 1740 |
| cagaagtgga | ctccggtgat | ggaaatcaca | tgtttgcagg | acatctcaag | tgcaaagtcc | 1800 |
| gtatggagaa | attgagaatc | aagggaatgt | catacacgat | gtgttcagga | aagttctcaa | 1860 |
| ttgacaaaga | gatggcagaa | acacagcatg | gacaacagt | ggtgaaagtc | aagtatgaag | 1920 |
| gtgctggagc | tccgtgtaaa | gtccccatag | agataagaga | tgtgaacaag | gaaaagtgg | 1980 |
| ttgggcgtat | catctcatcc | accccttggg | ctgagaatac | caacagtgca | accaacatag | 2040 |
| agttagaacc | ccccttggg | gacagctaca | tagtgatagg | tgttggaaac | agtgcattaa | 2100 |
| cactccattg | gttcaggaaa | gggagttcca | ttggcaagat | gtttgagtcc | acatacagag | 2160 |
| gtgcaaaacg | aatggccatt | ctaggtgaaa | cagcttggga | ttttggttcc | gttggtggac | 2220 |
| tgttcacatc | attgggaaag | gctgtgcacc | aggttttgg | aagtgtgtat | acaaccatgt | 2280 |
| ttggaggagt | ctcatggatg | attagaatcc | taattgggtt | cctagtgttg | tggattggca | 2340 |
| cgaactcaag | gaacacttca | atggctatga | cgtgcatagc | tgttggagga | atcactctgt | 2400 |
| ttctgggctt | cacagttcaa | gcagacatgg | gttgtgtggt | gtcatggagt | gggaaagaat | 2460 |
| tgaagtgtgg | aagcggaatt | tttgtggttg | acaacgtgca | cacttggaca | gaacagtaca | 2520 |
| aatttcaacc | ggagtcccca | gcgagactag | cgtctgcaat | attgaatgcc | cacaaagatg | 2580 |
| gggtctgtgg | aattagatca | accacgaggc | tggaaaatgt | catgtggaag | caaataacca | 2640 |
| acgagctaaa | ttatgttctc | tgggaaggag | gacatgacct | cactgtagtg | gctggggatg | 2700 |
| tgaaggggt | gttgaccaaa | ggcaagagag | cactcacacc | cccagtgaat | gatctgaaat | 2760 |

```
attcatggaa gacatgggga aaagcaaaaa tcttcacccc agaagcaaga aatagcacat   2820
ttttaataga cggaccagac acctccgaat gccccaatga acgaagagca tggaactttc   2880
ttgaggtgga agactatgga tttggcatgt tcacgaccaa catatggatg aaattccgag   2940
aaggaagttc agaagtgtgt gaccacaggt taatgtcagc ggcaattaaa gatcagaaag   3000
ctgtgcatgc tgacatgggt tattggatag agagctcaaa aaaccagacc tggcagatag   3060
agaaagcatc tcttattgaa gtgaaaacat gtctgtggcc aagacccac acattgtgga    3120
gcaatggagt gctggaaagc cagatgctca ttccaaaatc atatgcgggc cttttttcac   3180
agcacaatta ccgccagggc tatgccacgc aaaccgtggg cccatggcac ttaggcaaat   3240
tagagataga ctttggagaa tgccccggaa caacagtcgc aattcaggag gattgtgacc   3300
atagaggccc atctttgagg accaccactg catctggaaa actagtcacg caatggtgct   3360
gccgctcctg cacgatgcct cccttaaggt tcttgggaga agatgggtgc tggtatggga   3420
tggagattag gcccttgagt gaaaaagaag agaacatggt caaatcacag gtaacggccg   3480
gacagggcac atcagaaact ttttctatgg gtctgttgtg cctgaccttg tttgtggaag   3540
aatgcttgag gagaagagtc actaggaaac acatgatatt ggttgtggtg atcactcttt   3600
gtgccatcat cctaggaggc ctcacatgga tggacttact acgagccctc atcatgttgg   3660
gggacactat gtctggtaga ataggaggac agatccacct agccatcatg gcagtgttca   3720
agatgtcacc aggatacgtg ctgggtgtgt ttttaaggaa actcacttca agagagacag   3780
cactaatggt aataggaatg gccatgacaa cggtgctttc aattccacat gaccttatgg   3840
aactcattga tggaatatca ctggggctaa ttttgctaaa aatagtgaca cattttgaca   3900
acacccaagt gggaaccta gcccttttcct tgaccttcat aagatcaaca atgccattgg   3960
tcatggcttg gaggaccatt atggctgtgt tgtttgtggt cacactcatt cctttgtgca   4020
ggacaagctg tcttcaaaaa cagtctcatt gggtagaaat aacagcactc atcctaggag   4080
cccaagctct gccagtgtac ctaatgactc ttatgaaagg agcctcaaga agatcttggc   4140
ctcttaacga gggcataatg gctgtggggtt tggttagtct cttaggaagc gctcttttaa   4200
agaatgatgt ccctttagct ggcccaatgg tggcaggagc cttacttctg gcggcttacg   4260
tgatgagtgg tagctcagca gatctgtcac tagagaaggc cgccaatgtg cagtgggatg   4320
aaatggcaga cataacaggc tcaagcccaa tcatagaagt gaagcaggat gaagatggct   4380
cttttctccat acgggacgtc gaggaaacca atatgataac ccttttggtg aaactggcac   4440
tgataacagt gtcaggtctc taccccttgg caattccagt cacaatgacc ttatggtaca   4500
tgtggcaagt gaaaacacaa agatcaggag ccctgtggga cgtcccctca cccgctgcca   4560
ctcaaaaagc cgcactgtct gaaggagtgt acaggatcat gcaaagaggg ttatttggga   4620
aaactcaggt tggagtaggg atacacatgg aaggtgtatt tcacacaatg tggcatgtaa   4680
caagaggatc agtgatctgc catgagactg ggagattgga gccatcttgg gctgacgtca   4740
ggaatgacat gatatcatac ggtgggggat ggagacttgg agacaaatgg gacaagaag    4800
aagatgttca ggtcctcgcc atagaaccag gaaaaaatcc taaacatgtc caaacgaaac   4860
ccggcctttt caagacccta actggagaaa ttggagcagt aacattagat ttcaaacccg   4920
gaacgtctgg ttctcccatc atcaacagga aggaaaagt catcggactc tatggaaatg   4980
gagtagttac caaatcaggt gattacgtca gtgccataac gcaagccgaa agaattggag   5040
agccagatta tgaagtggat gaggacattt ttcgaaagaa aagattaact ataatggact   5100
```

```
tacaccccgg agctggaaag acaaaaagaa ttcttccatc aatagtgaga gaagccttaa    5160
aaaggaggct gcgaaccttg attttggctc ccacgagagt ggtggcggcc gagatggaag    5220
aggccctacg tggactgcca atccgttatc agaccccagc tgtgaaatca gaacacacag    5280
gaagagagat tgtagacctc atgtgtcatg caaccttcac aacaagactt ttgtcatcaa    5340
ccagagttcc aaattacaac ctcatagtga tggatgaagc acatttcacc gatccttcta    5400
gtgtcgcggc tagaggatac atctcgacca gggtggaaat gggagaggca gcagccatct    5460
tcatgaccgc aacccctccc ggagcgacag atcccttttcc ccagagcaac agcccaatag    5520
aagacatcga gagggaaatt ccggaaaggt catggaacac agggttcgac tggataacag    5580
actaccaagg gaaaactgtg tggtttgttc ccagcataaa agctggaaat gacattgcaa    5640
attgtttgag aaagtcggga agaaagtta tccagttgag taggaaaacc tttgatacag    5700
agtatccaaa aacgaaactc acggactggg attttgtggt cactacagac atatctgaaa    5760 tggggggccaa ttttagagct gggagagtga tagaccctag gagatgcctc aagccagtta    5820
tcctaacaga tgggccagag agagtcattt tagcaggtcc tattccagtg actccagcaa    5880
gcgctgctca gagaagaggg cgaataggaa ggaacccagc acaagaagac gaccaatacg    5940
ttttctccgg agacccacta aaaaatgatg aagatcatgc ccactggaca gaagcaaaga    6000
tgctgcttga caatatctac acccccagaag ggatcattcc aacattgttt ggtccggaaa    6060
gggaaaaaac ccaagccatt gatggagagt ttcgcctcag aggggaacaa aggaagactt    6120
ttgtggaatt aatgaggaga ggagaccttc cggtgtggct gagctataag gtagcttctg    6180
ctggcatttc ttacaaagat cgggaatggt gcttcacagg ggaaaggaat aaccaaattt    6240
tagaagaaaa catggaggtt gaaatttgga ctagagaggg agaaaagaaa agctaaggc    6300 caagatggtt agatgcacgt gtatacgctg accccatggc tttgaaggat tttaaggagt    6360
ttgctagtgg aaggaagagc ataactctcg acatcctaac agagattgcc agtttgccaa    6420
cttacctttc ctctagggcc aagctcgccc ttgataacat agtcatgctc cacacaacag    6480
aaagaggagg gagggcctac caacacgccc tgaacgaact cccggagtca ctggaaacac    6540
ttatgcttgt agctttacta ggtgctatga cagcaggtat cttcctgttt ttcatgcaag    6600 ggaaggaat agggaaattg tcaatggggtt tgataaccat tgcggtggct agtggcttgc    6660
tctgggtagc agaaattcaa ccccagtgga tagcggcctc aatcatacta gagttttttc    6720
tcatggtact gttgataccg gaaccagaaa aacaaaggac cccacaagac aatcaattga    6780
tctacgtcat attgaccatt ctcaccatta ttggtctcat agcagccaac gagatggggc    6840
tgattgaaaa aacaaaaacg gattttgggt tttaccaggt aaaaacagaa accaccatcc    6900
tcgatgtgga cttgagacca gcttcagcat ggacgctcta tgcagtagcc accacaattc    6960
tgactcccat gctgagacac accatagaaa acacgtcggc caacctatct ctagcagcca    7020
ttgccaacca gcggccgtc ctaatggggc ttggaaaagg atggccgctc cacagaatgg    7080
acctcggtgt gccgctgtta gcaatgggat gctattctca agtgaaccca acaactttga    7140
cagcatcctt agtcatgctt ttagtccatt atgcaataat aggtccagga ttgcaggcaa    7200
aagccacaag agaggcccag aaaaggacag ctgctgggat catgaaaaac cccacggtgg    7260
acgggataac agtaatagat ctagaaccaa tatcctatga cccaaaattt gaaaagcaat    7320
tagggcaggt catgctactc gtcttgtgtg ctggacaact actcttgatg agaacaacat    7380 gggcttttctg tgaagtcttg actttggcca caggaccaat cttgacctg tgggagggca    7440 acccgggaag gttttggaac acgaccatag ccgtatccac cgccaacatt tcaggggaa    7500
```

```
gttacctggc gggagctgga ctggctttt cactcataaa gaatgtacaa acccctagga   7560
ggggaactgg gaccacagga gagacactgg gagagaagtg gaagagacag ctaaactcat   7620
tagacagaaa agagtttgaa gagtataaaa gaagtggaat actagaagtg gacaggactg   7680
aagccaagtc tgccctgaaa gatgggtcta aaatcaagca tgcagtatct agagggtcca   7740
gtaagattag atggattgtt gagagaggga tggtaaagcc aaaagggaaa gttgtagatc   7800
ttggctgtgg gagaggagga tggtcttatt acatggcgac gctcaagaac gtgactgaag   7860
tgaaagggta tacaaaagga ggtccaggac atgaagaacc gattcccatg gctacttatg   7920
gctggaattt ggtcaaactc cattcagggg ttgacgtgtt ctacaaaccc acagagcaag   7980
tggacaccct gctctgtgat attggggagt catcttctaa tccaacaata gaggaaggaa   8040
gaacattaag agttttgaag atggtggagc catggctctc ttcaaaacct gaattctgca   8100
tcaaagtcct taaccccctac atgccaacag tcatagaaga gctggagaaa ctgcagagaa   8160
aacatggtgg gaaccttgtc agatgcccgc tgtccaggaa ctccacccat gagatgtatt   8220
gggtgtcagg agcgtcggga acattgtga gctctgtgaa cacaacatca agatgttgt   8280
tgaacaggtt cacaacaagg ataggaaac ccacttatga aaggacgta gatcttgggg   8340
caggaacgag aagtgtctcc actgaaacag aaaaaccaga catgacaatt attgggagaa   8400
ggcttcagcg attgcaagag gagcacaaag aaacctggca ttatgatcag gaaaacccat   8460
acagaacctg gcgtatcat ggaagctatg aagctccttc gacaggctct gcatcctcca   8520
tggtgaacgg ggtagtaaaa ctgctaacaa acccttggga tgtggttcca atggtgaccc   8580
agttagccat gacagacaca acccctttg ggcaacaaag agtgttcaaa gagaaggtgg   8640
ataccgagaac accacaacca aaacccggta cacgaatggt tatgaccacg acagccaatt   8700
ggctgtgggc cctccttggg aagaagaaaa atcccagact gtgcacaagg gaagagttca   8760
tctcaaaagt tagatcaaac gcagccatag gcgcagtctt tcaggaagaa cagggatgga   8820
catcagccag tgaagctgtg aatgacagcc ggttttggga actggttgac aaagaaaggg   8880
ccctacacca ggaagggaaa tgtgaatcgt gtgtctacaa catgatggga aaacgtgaga   8940
aaaagttagg agagtttggc agagccaagg gaagccgagc aatctggtac atgtggctgg   9000
gagcgcggtt tctggaattt gaagcctggg gttttttgaa tgaagatcac tggtttggca   9060
gagaaaattc atggagtgga gtggaagggg aaggtctgca cagattggga tatatcctgg   9120
aggagataga caagaaggat ggagacctaa tgtatgctga tgacacagca ggctgggaca   9180
caagaatcac tgaggatgac cttcaaaatg aagaactgat cacggaacag atggcccccc   9240
accacaagat cctagccaaa gccatttca aactaaccta tcaaacaaa gtggtgaaag   9300
tcctcagacc cacaccgaga ggagcggtga tggatatcat atccaggaaa gaccaaagag   9360
gtagtggaca agttggaaca tatggtttga acacattcac caacatggaa gttcaactca   9420
tccgccaaat ggaagctgaa ggagtcatca cacaagatga catgcagaac ccaaaagggt   9480
tgaaagaaag agttgagaaa tggctgaaag agtgtgtgt cgacaggtta aagaggatgg   9540
caatcagtgg agacgattgc gtggtgaagc ccctggatga gaggtttgc acttccctcc   9600
tcttcttgaa cgacatggga aaggtgagga agacattcc gcagtgggaa ccatctaagg   9660
gatggaaaaa ctgcaagag gttccttttt gctcccacca ctttcacaag atcttcatga   9720
aggatggccg ctcactagtt gttccatgta gaaaccagga tgaactgata gggagagcca   9780
gaatctcgca gggggctgga tggagcttaa gagaaacagc ctgcctgggc aaagcttacg   9840
```

```
cccagatgtg gtcgctcatg tacttccaca gaagggatct gcgtttagcc tccatggcca   9900
tatgctcagc agttccaacg gaatggtttc caacaagcag aacaacatgg tcaatccacg   9960
ctcatcatca gtggatgacc actgaagata tgctcaaagt gtggaacaga gtgtggatag  10020
aagacaaccc taatatgact gacaagactc cagtccattc gtgggaagat ataccttacc  10080
tagggaaaag agaggatttg tggtgtggat ccctgattgg actttcttcc agagccacct  10140
gggcgaagaa cattcacacg gccataaccc aggtcagaaa cctgatcgga aaagaggaat  10200
acgtggatta catgccagta atgaaaagat acagcgctcc ttcagagagt gaaggagttc  10260
tgtaattacc aacaacaaac accaaaggct attgaagtca ggccacttgt gccacggctt  10320
gagcaaaccg tgctgcctgt agctccgcca ataatgggag gcgtgaaatc cctagggagg  10380
ccatgcgcca cggaagctgt acgcgtggca tattggacta gcggttagag gagacccctc  10440
ccatcactga caaaacgcag caaaagggg cccgaagcca ggaggaagct gtactcctgg  10500
tggaaggact agaggttaga ggagacccc ccaacacaaa aacagcatat tgacgctggg  10560
aaagaccaga gatcctgctg tctctgcaac atcaatccag gcacagagcg ccgcaagatg  10620
gattggtgtt gttgatccaa caggttct                                     10648
```

<210> SEQ ID NO 16
<211> LENGTH: 3387
<212> TYPE: PRT
<213> ORGANISM: Dengue virus

<400> SEQUENCE: 16

```
Met Asn Gln Arg Lys Lys Val Val Arg Pro Pro Phe Asn Met Leu Lys
1               5                   10                  15

Arg Glu Arg Asn Arg Val Ser Thr Pro Gln Gly Leu Val Lys Arg Phe
            20                  25                  30

Ser Thr Gly Leu Phe Ser Gly Lys Gly Pro Leu Arg Met Val Leu Ala
        35                  40                  45

Phe Ile Thr Phe Leu Arg Val Leu Ser Ile Pro Pro Thr Ala Gly Ile
    50                  55                  60

Leu Lys Arg Trp Gly Gln Leu Lys Lys Asn Lys Ala Ile Arg Ile Leu
65                  70                  75                  80

Ile Gly Phe Arg Lys Glu Ile Gly Arg Met Leu Asn Ile Leu Asn Gly
                85                  90                  95

Arg Lys Arg Ser Thr Ile Thr Leu Leu Cys Leu Ile Pro Thr Val Met
            100                 105                 110

Ala Phe His Leu Ser Thr Arg Asp Gly Glu Pro Leu Met Ile Val Ala
        115                 120                 125

Lys His Glu Arg Gly Arg Pro Leu Leu Phe Lys Thr Thr Glu Gly Ile
    130                 135                 140

Asn Lys Cys Thr Leu Ile Ala Met Asp Leu Gly Glu Met Cys Glu Asp
145                 150                 155                 160

Thr Val Thr Tyr Lys Cys Pro Leu Leu Val Asn Thr Glu Pro Glu Asp
                165                 170                 175

Ile Asp Cys Trp Cys Asn Leu Thr Ser Thr Trp Val Met Tyr Gly Thr
            180                 185                 190

Cys Thr Gln Ser Gly Glu Arg Arg Arg Glu Lys Arg Ser Val Ala Leu
        195                 200                 205

Thr Pro His Ser Gly Met Gly Leu Glu Thr Arg Ala Glu Thr Trp Met
    210                 215                 220

Ser Ser Glu Gly Ala Trp Lys His Ala Gln Arg Val Glu Ser Trp Ile
```

-continued

```
               225                 230                 235                 240
Leu Arg Asn Pro Gly Phe Ala Leu Leu Ala Gly Phe Met Ala Tyr Met
                245                 250                 255
Ile Gly Gln Thr Gly Ile Gln Arg Thr Val Phe Phe Val Leu Met Met
                260                 265                 270
Leu Val Ala Pro Ser Tyr Gly Met Arg Cys Val Gly Val Gly Asn Arg
                275                 280                 285
Asp Phe Val Glu Gly Val Ser Gly Gly Ala Trp Val Asp Leu Val Leu
                290                 295                 300
Glu His Gly Gly Cys Val Thr Thr Met Ala Gln Gly Lys Pro Thr Leu
305                 310                 315                 320
Asp Phe Glu Leu Thr Lys Thr Ala Lys Glu Val Ala Leu Leu Arg
                325                 330                 335
Thr Tyr Cys Ile Glu Ala Ser Ile Ser Asn Ile Thr Thr Ala Thr Arg
                340                 345                 350
Cys Pro Thr Gln Gly Glu Pro Tyr Leu Lys Glu Glu Gln Asp Gln Gln
                355                 360                 365
Tyr Ile Cys Arg Arg Asp Val Val Asp Arg Gly Trp Gly Asn Gly Cys
370                 375                 380
Gly Leu Phe Gly Lys Gly Gly Val Val Thr Cys Ala Lys Phe Ser Cys
385                 390                 395                 400
Ser Gly Lys Ile Thr Gly Asn Leu Val Gln Ile Glu Asn Leu Glu Tyr
                405                 410                 415
Thr Val Val Val Thr Val His Asn Gly Asp Thr His Ala Val Gly Asn
                420                 425                 430
Asp Thr Ser Asn His Gly Val Thr Ala Thr Ile Thr Pro Arg Ser Pro
                435                 440                 445
Ser Val Glu Val Lys Leu Pro Asp Tyr Gly Glu Leu Thr Leu Asp Cys
                450                 455                 460
Glu Pro Arg Ser Gly Ile Asp Phe Asn Glu Met Ile Leu Met Lys Met
465                 470                 475                 480
Lys Lys Lys Thr Trp Leu Val His Lys Gln Trp Phe Leu Asp Leu Pro
                485                 490                 495
Leu Pro Trp Thr Ala Gly Ala Asp Thr Ser Glu Val His Trp Asn Tyr
                500                 505                 510
Lys Glu Arg Met Val Thr Phe Lys Val Pro His Ala Lys Arg Gln Asp
                515                 520                 525
Val Thr Val Leu Gly Ser Gln Glu Gly Ala Met His Ser Ala Leu Ala
530                 535                 540
Gly Ala Thr Glu Val Asp Ser Gly Asp Gly Asn His Met Phe Ala Gly
545                 550                 555                 560
His Leu Lys Cys Lys Val Arg Met Glu Lys Leu Arg Ile Lys Gly Met
                565                 570                 575
Ser Tyr Thr Met Cys Ser Gly Lys Phe Ser Ile Asp Lys Glu Met Ala
                580                 585                 590
Glu Thr Gln His Gly Thr Thr Val Val Lys Val Lys Tyr Glu Gly Ala
                595                 600                 605
Gly Ala Pro Cys Lys Val Pro Ile Glu Ile Arg Asp Val Asn Lys Glu
610                 615                 620
Lys Val Val Gly Arg Ile Ile Ser Ser Thr Pro Leu Ala Glu Asn Thr
625                 630                 635                 640
Asn Ser Ala Thr Asn Ile Glu Leu Glu Pro Pro Phe Gly Asp Ser Tyr
                645                 650                 655
```

```
Ile Val Ile Gly Val Gly Asn Ser Ala Leu Thr Leu His Trp Phe Arg
            660                 665                 670

Lys Gly Ser Ser Ile Gly Lys Met Phe Glu Ser Thr Tyr Arg Gly Ala
            675                 680                 685

Lys Arg Met Ala Ile Leu Gly Glu Thr Ala Trp Asp Phe Gly Ser Val
    690                 695                 700

Gly Gly Leu Phe Thr Ser Leu Gly Lys Ala Val His Gln Val Phe Gly
705                 710                 715                 720

Ser Val Tyr Thr Thr Met Phe Gly Gly Val Ser Trp Met Ile Arg Ile
                725                 730                 735

Leu Ile Gly Phe Leu Val Leu Trp Ile Gly Thr Asn Ser Arg Asn Thr
        740                 745                 750

Ser Met Ala Met Thr Cys Ile Ala Val Gly Gly Ile Thr Leu Phe Leu
        755                 760                 765

Gly Phe Thr Val Gln Ala Asp Met Gly Cys Val Val Ser Trp Ser Gly
    770                 775                 780

Lys Glu Leu Lys Cys Gly Ser Gly Ile Phe Val Val Asp Asn Val His
785                 790                 795                 800

Thr Trp Thr Glu Gln Tyr Lys Phe Gln Pro Glu Ser Pro Ala Arg Leu
                805                 810                 815

Ala Ser Ala Ile Leu Asn Ala His Lys Asp Gly Val Cys Gly Ile Arg
        820                 825                 830

Ser Thr Thr Arg Leu Glu Asn Val Met Trp Lys Gln Ile Thr Asn Glu
        835                 840                 845

Leu Asn Tyr Val Leu Trp Glu Gly Gly His Asp Leu Thr Val Val Ala
        850                 855                 860

Gly Asp Val Lys Gly Val Leu Thr Lys Gly Lys Arg Ala Leu Thr Pro
865                 870                 875                 880

Pro Val Asn Asp Leu Lys Tyr Ser Trp Lys Thr Trp Gly Lys Ala Lys
                885                 890                 895

Ile Phe Thr Pro Glu Ala Arg Asn Ser Thr Phe Leu Ile Asp Gly Pro
        900                 905                 910

Asp Thr Ser Glu Cys Pro Asn Glu Arg Arg Ala Trp Asn Phe Leu Glu
        915                 920                 925

Val Glu Asp Tyr Gly Phe Gly Met Phe Thr Thr Asn Ile Trp Met Lys
    930                 935                 940

Phe Arg Glu Gly Ser Ser Glu Val Cys Asp His Arg Leu Met Ser Ala
945                 950                 955                 960

Ala Ile Lys Asp Gln Lys Ala Val His Ala Asp Met Gly Tyr Trp Ile
                965                 970                 975

Glu Ser Ser Lys Asn Gln Thr Trp Gln Ile Glu Lys Ala Ser Leu Ile
        980                 985                 990

Glu Val Lys Thr Cys Leu Trp Pro Lys Thr His Thr Leu Trp Ser Asn
        995                 1000                1005

Gly Val Leu Glu Ser Gln Met Leu Ile Pro Lys Ser Tyr Ala Gly
    1010                1015                1020

Pro Phe Ser Gln His Asn Tyr Arg Gln Gly Tyr Ala Thr Gln Thr
    1025                1030                1035

Val Gly Pro Trp His Leu Gly Lys Leu Glu Ile Asp Phe Gly Glu
    1040                1045                1050

Cys Pro Gly Thr Thr Val Ala Ile Gln Glu Asp Cys Asp His Arg
    1055                1060                1065
```

-continued

```
Gly Pro Ser Leu Arg Thr Thr Ala Ser Gly Lys Leu Val Thr
    1070            1075            1080

Gln Trp Cys Cys Arg Ser Cys Thr Met Pro Pro Leu Arg Phe Leu
    1085            1090            1095

Gly Glu Asp Gly Cys Trp Tyr Gly Met Glu Ile Arg Pro Leu Ser
    1100            1105            1110

Glu Lys Glu Glu Asn Met Val Lys Ser Gln Val Thr Ala Gly Gln
    1115            1120            1125

Gly Thr Ser Glu Thr Phe Ser Met Gly Leu Leu Cys Leu Thr Leu
    1130            1135            1140

Phe Val Glu Glu Cys Leu Arg Arg Arg Val Thr Arg Lys His Met
    1145            1150            1155

Ile Leu Val Val Val Ile Thr Leu Cys Ala Ile Ile Leu Gly Gly
    1160            1165            1170

Leu Thr Trp Met Asp Leu Leu Arg Ala Leu Ile Met Leu Gly Asp
    1175            1180            1185

Thr Met Ser Gly Arg Ile Gly Gly Gln Ile His Leu Ala Ile Met
    1190            1195            1200

Ala Val Phe Lys Met Ser Pro Gly Tyr Val Leu Gly Val Phe Leu
    1205            1210            1215

Arg Lys Leu Thr Ser Arg Glu Thr Ala Leu Met Val Ile Gly Met
    1220            1225            1230

Ala Met Thr Thr Val Leu Ser Ile Pro His Asp Leu Met Glu Leu
    1235            1240            1245

Ile Asp Gly Ile Ser Leu Gly Leu Ile Leu Leu Lys Ile Val Thr
    1250            1255            1260

His Phe Asp Asn Thr Gln Val Gly Thr Leu Ala Leu Ser Leu Thr
    1265            1270            1275

Phe Ile Arg Ser Thr Met Pro Leu Val Met Ala Trp Arg Thr Ile
    1280            1285            1290

Met Ala Val Leu Phe Val Val Thr Leu Ile Pro Leu Cys Arg Thr
    1295            1300            1305

Ser Cys Leu Gln Lys Gln Ser His Trp Val Glu Ile Thr Ala Leu
    1310            1315            1320

Ile Leu Gly Ala Gln Ala Leu Pro Val Tyr Leu Met Thr Leu Met
    1325            1330            1335

Lys Gly Ala Ser Arg Arg Ser Trp Pro Leu Asn Glu Gly Ile Met
    1340            1345            1350

Ala Val Gly Leu Val Ser Leu Leu Gly Ser Ala Leu Leu Lys Asn
    1355            1360            1365

Asp Val Pro Leu Ala Gly Pro Met Val Ala Gly Gly Leu Leu Leu
    1370            1375            1380

Ala Ala Tyr Val Met Ser Gly Ser Ser Ala Asp Leu Ser Leu Glu
    1385            1390            1395

Lys Ala Ala Asn Val Gln Trp Asp Glu Met Ala Asp Ile Thr Gly
    1400            1405            1410

Ser Ser Pro Ile Ile Glu Val Lys Gln Asp Glu Asp Gly Ser Phe
    1415            1420            1425

Ser Ile Arg Asp Val Glu Glu Thr Asn Met Ile Thr Leu Leu Val
    1430            1435            1440

Lys Leu Ala Leu Ile Thr Val Ser Gly Leu Tyr Pro Leu Ala Ile
    1445            1450            1455

Pro Val Thr Met Thr Leu Trp Tyr Met Trp Gln Val Lys Thr Gln
```

```
            1460                 1465                 1470

Arg  Ser  Gly  Ala  Leu  Trp  Asp  Val  Pro  Ser  Pro  Ala  Ala  Thr  Gln
     1475                 1480                 1485

Lys  Ala  Ala  Leu  Ser  Glu  Gly  Val  Tyr  Arg  Ile  Met  Gln  Arg  Gly
     1490                 1495                 1500

Leu  Phe  Gly  Lys  Thr  Gln  Val  Gly  Val  Gly  Ile  His  Met  Glu  Gly
     1505                 1510                 1515

Val  Phe  His  Thr  Met  Trp  His  Val  Thr  Arg  Gly  Ser  Val  Ile  Cys
     1520                 1525                 1530

His  Glu  Thr  Gly  Arg  Leu  Glu  Pro  Ser  Trp  Ala  Asp  Val  Arg  Asn
     1535                 1540                 1545

Asp  Met  Ile  Ser  Tyr  Gly  Gly  Gly  Trp  Arg  Leu  Gly  Asp  Lys  Trp
     1550                 1555                 1560

Asp  Lys  Glu  Glu  Asp  Val  Gln  Val  Leu  Ala  Ile  Glu  Pro  Gly  Lys
     1565                 1570                 1575

Asn  Pro  Lys  His  Val  Gln  Thr  Lys  Pro  Gly  Leu  Phe  Lys  Thr  Leu
     1580                 1585                 1590

Thr  Gly  Glu  Ile  Gly  Ala  Val  Thr  Leu  Asp  Phe  Lys  Pro  Gly  Thr
     1595                 1600                 1605

Ser  Gly  Ser  Pro  Ile  Ile  Asn  Arg  Lys  Gly  Lys  Val  Ile  Gly  Leu
     1610                 1615                 1620

Tyr  Gly  Asn  Gly  Val  Val  Thr  Lys  Ser  Gly  Asp  Tyr  Val  Ser  Ala
     1625                 1630                 1635

Ile  Thr  Gln  Ala  Glu  Arg  Ile  Gly  Glu  Pro  Asp  Tyr  Glu  Val  Asp
     1640                 1645                 1650

Glu  Asp  Ile  Phe  Arg  Lys  Lys  Arg  Leu  Thr  Ile  Met  Asp  Leu  His
     1655                 1660                 1665

Pro  Gly  Ala  Gly  Lys  Thr  Lys  Arg  Ile  Leu  Pro  Ser  Ile  Val  Arg
     1670                 1675                 1680

Glu  Ala  Leu  Lys  Arg  Arg  Leu  Arg  Thr  Leu  Ile  Leu  Ala  Pro  Thr
     1685                 1690                 1695

Arg  Val  Val  Ala  Ala  Glu  Met  Glu  Glu  Ala  Leu  Arg  Gly  Leu  Pro
     1700                 1705                 1710

Ile  Arg  Tyr  Gln  Thr  Pro  Ala  Val  Lys  Ser  Glu  His  Thr  Gly  Arg
     1715                 1720                 1725

Glu  Ile  Val  Asp  Leu  Met  Cys  His  Ala  Thr  Phe  Thr  Thr  Arg  Leu
     1730                 1735                 1740

Leu  Ser  Ser  Thr  Arg  Val  Pro  Asn  Tyr  Asn  Leu  Ile  Val  Met  Asp
     1745                 1750                 1755

Glu  Ala  His  Phe  Thr  Asp  Pro  Ser  Ser  Val  Ala  Ala  Arg  Gly  Tyr
     1760                 1765                 1770

Ile  Ser  Thr  Arg  Val  Glu  Met  Gly  Glu  Ala  Ala  Ala  Ile  Phe  Met
     1775                 1780                 1785

Thr  Ala  Thr  Pro  Pro  Gly  Ala  Thr  Asp  Pro  Phe  Pro  Gln  Ser  Asn
     1790                 1795                 1800

Ser  Pro  Ile  Glu  Asp  Ile  Glu  Arg  Glu  Ile  Pro  Glu  Arg  Ser  Trp
     1805                 1810                 1815

Asn  Thr  Gly  Phe  Asp  Trp  Ile  Thr  Asp  Tyr  Gln  Gly  Lys  Thr  Val
     1820                 1825                 1830

Trp  Phe  Val  Pro  Ser  Ile  Lys  Ala  Gly  Asn  Asp  Ile  Ala  Asn  Cys
     1835                 1840                 1845

Leu  Arg  Lys  Ser  Gly  Lys  Lys  Val  Ile  Gln  Leu  Ser  Arg  Lys  Thr
     1850                 1855                 1860
```

-continued

Phe Asp Thr Glu Tyr Pro Lys Thr Lys Leu Thr Asp Trp Asp Phe
1865                1870                1875

Val Val Thr Thr Asp Ile Ser Glu Met Gly Ala Asn Phe Arg Ala
1880                1885                1890

Gly Arg Val Ile Asp Pro Arg Cys Leu Lys Pro Val Ile Leu
1895                1900                1905

Thr Asp Gly Pro Glu Arg Val Ile Leu Ala Gly Pro Ile Pro Val
1910                1915                1920

Thr Pro Ala Ser Ala Ala Gln Arg Arg Gly Arg Ile Gly Arg Asn
1925                1930                1935

Pro Ala Gln Glu Asp Asp Gln Tyr Val Phe Ser Gly Asp Pro Leu
1940                1945                1950

Lys Asn Asp Glu Asp His Ala His Trp Thr Glu Ala Lys Met Leu
1955                1960                1965

Leu Asp Asn Ile Tyr Thr Pro Glu Gly Ile Ile Pro Thr Leu Phe
1970                1975                1980

Gly Pro Glu Arg Glu Lys Thr Gln Ala Ile Asp Gly Glu Phe Arg
1985                1990                1995

Leu Arg Gly Glu Gln Arg Lys Thr Phe Val Glu Leu Met Arg Arg
2000                2005                2010

Gly Asp Leu Pro Val Trp Leu Ser Tyr Lys Val Ala Ser Ala Gly
2015                2020                2025

Ile Ser Tyr Lys Asp Arg Glu Trp Cys Phe Thr Gly Glu Arg Asn
2030                2035                2040

Asn Gln Ile Leu Glu Glu Asn Met Glu Val Glu Ile Trp Thr Arg
2045                2050                2055

Glu Gly Glu Lys Lys Lys Leu Arg Pro Arg Trp Leu Asp Ala Arg
2060                2065                2070

Val Tyr Ala Asp Pro Met Ala Leu Lys Asp Phe Lys Glu Phe Ala
2075                2080                2085

Ser Gly Arg Lys Ser Ile Thr Leu Asp Ile Leu Thr Glu Ile Ala
2090                2095                2100

Ser Leu Pro Thr Tyr Leu Ser Ser Arg Ala Lys Leu Ala Leu Asp
2105                2110                2115

Asn Ile Val Met Leu His Thr Thr Glu Arg Gly Gly Arg Ala Tyr
2120                2125                2130

Gln His Ala Leu Asn Glu Leu Pro Glu Ser Leu Glu Thr Leu Met
2135                2140                2145

Leu Val Ala Leu Leu Gly Ala Met Thr Ala Gly Ile Phe Leu Phe
2150                2155                2160

Phe Met Gln Gly Lys Gly Ile Gly Lys Leu Ser Met Gly Leu Ile
2165                2170                2175

Thr Ile Ala Val Ala Ser Gly Leu Leu Trp Val Ala Glu Ile Gln
2180                2185                2190

Pro Gln Trp Ile Ala Ala Ser Ile Ile Leu Glu Phe Phe Leu Met
2195                2200                2205

Val Leu Leu Ile Pro Glu Pro Glu Lys Gln Arg Thr Pro Gln Asp
2210                2215                2220

Asn Gln Leu Ile Tyr Val Ile Leu Thr Ile Leu Thr Ile Ile Gly
2225                2230                2235

Leu Ile Ala Ala Asn Glu Met Gly Leu Ile Glu Lys Thr Lys Thr
2240                2245                2250

```
Asp Phe Gly Phe Tyr Gln Val Lys Thr Glu Thr Thr Ile Leu Asp
2255                2260                2265

Val Asp Leu Arg Pro Ala Ser Ala Trp Thr Leu Tyr Ala Val Ala
2270                2275                2280

Thr Thr Ile Leu Thr Pro Met Leu Arg His Thr Ile Glu Asn Thr
2285                2290                2295

Ser Ala Asn Leu Ser Leu Ala Ala Ile Ala Asn Gln Ala Ala Val
2300                2305                2310

Leu Met Gly Leu Gly Lys Gly Trp Pro Leu His Arg Met Asp Leu
2315                2320                2325

Gly Val Pro Leu Leu Ala Met Gly Cys Tyr Ser Gln Val Asn Pro
2330                2335                2340

Thr Thr Leu Thr Ala Ser Leu Val Met Leu Leu Val His Tyr Ala
2345                2350                2355

Ile Ile Gly Pro Gly Leu Gln Ala Lys Ala Thr Arg Glu Ala Gln
2360                2365                2370

Lys Arg Thr Ala Ala Gly Ile Met Lys Asn Pro Thr Val Asp Gly
2375                2380                2385

Ile Thr Val Ile Asp Leu Glu Pro Ile Ser Tyr Asp Pro Lys Phe
2390                2395                2400

Glu Lys Gln Leu Gly Gln Val Met Leu Leu Val Leu Cys Ala Gly
2405                2410                2415

Gln Leu Leu Leu Met Arg Thr Thr Trp Ala Phe Cys Glu Val Leu
2420                2425                2430

Thr Leu Ala Thr Gly Pro Ile Leu Thr Leu Trp Glu Gly Asn Pro
2435                2440                2445

Gly Arg Phe Trp Asn Thr Thr Ile Ala Val Ser Thr Ala Asn Ile
2450                2455                2460

Phe Arg Gly Ser Tyr Leu Ala Gly Ala Gly Leu Ala Phe Ser Leu
2465                2470                2475

Ile Lys Asn Val Gln Thr Pro Arg Arg Gly Thr Gly Thr Thr Gly
2480                2485                2490

Glu Thr Leu Gly Glu Lys Trp Lys Arg Gln Leu Asn Ser Leu Asp
2495                2500                2505

Arg Lys Glu Phe Glu Glu Tyr Lys Arg Ser Gly Ile Leu Glu Val
2510                2515                2520

Asp Arg Thr Glu Ala Lys Ser Ala Leu Lys Asp Gly Ser Lys Ile
2525                2530                2535

Lys His Ala Val Ser Arg Gly Ser Ser Lys Ile Arg Trp Ile Val
2540                2545                2550

Glu Arg Gly Met Val Lys Pro Lys Gly Lys Val Val Asp Leu Gly
2555                2560                2565

Cys Gly Arg Gly Gly Trp Ser Tyr Tyr Met Ala Thr Leu Lys Asn
2570                2575                2580

Val Thr Glu Val Lys Gly Tyr Thr Lys Gly Gly Pro Gly His Glu
2585                2590                2595

Glu Pro Ile Pro Met Ala Thr Tyr Gly Trp Asn Leu Val Lys Leu
2600                2605                2610

His Ser Gly Val Asp Val Phe Tyr Lys Pro Thr Glu Gln Val Asp
2615                2620                2625

Thr Leu Leu Cys Asp Ile Gly Glu Ser Ser Ser Asn Pro Thr Ile
2630                2635                2640

Glu Glu Gly Arg Thr Leu Arg Val Leu Lys Met Val Glu Pro Trp
```

```
                  2645                2650                2655

Leu Ser Ser Lys Pro Glu Phe Cys Ile Lys Val Leu Asn Pro Tyr
        2660                2665                2670

Met Pro Thr Val Ile Glu Glu Leu Glu Lys Leu Gln Arg Lys His
        2675                2680                2685

Gly Gly Asn Leu Val Arg Cys Pro Leu Ser Arg Asn Ser Thr His
        2690                2695                2700

Glu Met Tyr Trp Val Ser Gly Ala Ser Gly Asn Ile Val Ser Ser
        2705                2710                2715

Val Asn Thr Thr Ser Lys Met Leu Leu Asn Arg Phe Thr Thr Arg
        2720                2725                2730

His Arg Lys Pro Thr Tyr Glu Lys Asp Val Asp Leu Gly Ala Gly
        2735                2740                2745

Thr Arg Ser Val Ser Thr Glu Thr Glu Lys Pro Asp Met Thr Ile
        2750                2755                2760

Ile Gly Arg Arg Leu Gln Arg Leu Gln Glu Glu His Lys Glu Thr
        2765                2770                2775

Trp His Tyr Asp Gln Glu Asn Pro Tyr Arg Thr Trp Ala Tyr His
        2780                2785                2790

Gly Ser Tyr Glu Ala Pro Ser Thr Gly Ser Ala Ser Ser Met Val
        2795                2800                2805

Asn Gly Val Val Lys Leu Leu Thr Lys Pro Trp Asp Val Val Pro
        2810                2815                2820

Met Val Thr Gln Leu Ala Met Thr Asp Thr Thr Pro Phe Gly Gln
        2825                2830                2835

Gln Arg Val Phe Lys Glu Lys Val Asp Thr Arg Thr Pro Gln Pro
        2840                2845                2850

Lys Pro Gly Thr Arg Met Val Met Thr Thr Thr Ala Asn Trp Leu
        2855                2860                2865

Trp Ala Leu Leu Gly Lys Lys Lys Asn Pro Arg Leu Cys Thr Arg
        2870                2875                2880

Glu Glu Phe Ile Ser Lys Val Arg Ser Asn Ala Ala Ile Gly Ala
        2885                2890                2895

Val Phe Gln Glu Glu Gln Gly Trp Thr Ser Ala Ser Glu Ala Val
        2900                2905                2910

Asn Asp Ser Arg Phe Trp Glu Leu Val Asp Lys Glu Arg Ala Leu
        2915                2920                2925

His Gln Glu Gly Lys Cys Glu Ser Cys Val Tyr Asn Met Met Gly
        2930                2935                2940

Lys Arg Glu Lys Lys Leu Gly Glu Phe Gly Arg Ala Lys Gly Ser
        2945                2950                2955

Arg Ala Ile Trp Tyr Met Trp Leu Gly Ala Arg Phe Leu Glu Phe
        2960                2965                2970

Glu Ala Leu Gly Phe Leu Asn Glu Asp His Trp Phe Gly Arg Glu
        2975                2980                2985

Asn Ser Trp Ser Gly Val Glu Gly Glu Gly Leu His Arg Leu Gly
        2990                2995                3000

Tyr Ile Leu Glu Glu Ile Asp Lys Lys Asp Gly Asp Leu Met Tyr
        3005                3010                3015

Ala Asp Asp Thr Ala Gly Trp Asp Thr Arg Ile Thr Glu Asp Asp
        3020                3025                3030

Leu Gln Asn Glu Glu Leu Ile Thr Glu Gln Met Ala Pro His His
        3035                3040                3045
```

```
Lys Ile Leu Ala Lys Ala Ile Phe Lys Leu Thr Tyr Gln Asn Lys
3050              3055              3060

Val Val Lys Val Leu Arg Pro Thr Pro Arg Gly Ala Val Met Asp
3065              3070              3075

Ile Ile Ser Arg Lys Asp Gln Arg Gly Ser Gly Gln Val Gly Thr
3080              3085              3090

Tyr Gly Leu Asn Thr Phe Thr Asn Met Glu Val Gln Leu Ile Arg
3095              3100              3105

Gln Met Glu Ala Glu Gly Val Ile Thr Gln Asp Asp Met Gln Asn
3110              3115              3120

Pro Lys Gly Leu Lys Glu Arg Val Glu Lys Trp Leu Lys Glu Cys
3125              3130              3135

Gly Val Asp Arg Leu Lys Arg Met Ala Ile Ser Gly Asp Asp Cys
3140              3145              3150

Val Val Lys Pro Leu Asp Glu Arg Phe Gly Thr Ser Leu Leu Phe
3155              3160              3165

Leu Asn Asp Met Gly Lys Val Arg Lys Asp Ile Pro Gln Trp Glu
3170              3175              3180

Pro Ser Lys Gly Trp Lys Asn Trp Gln Glu Val Pro Phe Cys Ser
3185              3190              3195

His His Phe His Lys Ile Phe Met Lys Asp Gly Arg Ser Leu Val
3200              3205              3210

Val Pro Cys Arg Asn Gln Asp Glu Leu Ile Gly Arg Ala Arg Ile
3215              3220              3225

Ser Gln Gly Ala Gly Trp Ser Leu Arg Glu Thr Ala Cys Leu Gly
3230              3235              3240

Lys Ala Tyr Ala Gln Met Trp Ser Leu Met Tyr Phe His Arg Arg
3245              3250              3255

Asp Leu Arg Leu Ala Ser Met Ala Ile Cys Ser Ala Val Pro Thr
3260              3265              3270

Glu Trp Phe Pro Thr Ser Arg Thr Thr Trp Ser Ile His Ala His
3275              3280              3285

His Gln Trp Met Thr Thr Glu Asp Met Leu Lys Val Trp Asn Arg
3290              3295              3300

Val Trp Ile Glu Asp Asn Pro Asn Met Thr Asp Lys Thr Pro Val
3305              3310              3315

His Ser Trp Glu Asp Ile Pro Tyr Leu Gly Lys Arg Glu Asp Leu
3320              3325              3330

Trp Cys Gly Ser Leu Ile Gly Leu Ser Ser Arg Ala Thr Trp Ala
3335              3340              3345

Lys Asn Ile His Thr Ala Ile Thr Gln Val Arg Asn Leu Ile Gly
3350              3355              3360

Lys Glu Glu Tyr Val Asp Tyr Met Pro Val Met Lys Arg Tyr Ser
3365              3370              3375

Ala Pro Ser Glu Ser Glu Gly Val Leu
3380              3385
```